United States Patent
Deng et al.

(10) Patent No.: US 8,999,957 B2
(45) Date of Patent: Apr. 7, 2015

(54) HETEROCYCLIC COMPOUNDS AS ERK INHIBITORS

(75) Inventors: Yongqi Deng, Newton, MA (US); Liang Zhu, Waltham, MA (US); Gerald W. Shipps, Jr., Stoneham, MA (US); Sie-Mun Lo, Revere, MA (US); Binyuan Sun, Chestnut Hill, MA (US); Xiaohua Huang, Malden, MA (US); Corey Bienstock, Natick, MA (US); Alan B. Cooper, West Caldwell, NJ (US); Xiaolei Gao, Bridgewater, NJ (US); Xin Yao, Scotch Plains, NJ (US); Hugh Y. Zhu, Warren, NJ (US); Joseph M. Kelly, Parlin, NJ (US); Sobhana Babu Boga, Scotch Plains, NJ (US); Abdul-Basit Alhassan, Scotch Plains, NJ (US); Jayaram R. Tagat, Westfield, NJ (US); Umar Faruk Mansoor, Framingham, MA (US); Kevin J. Wilson, Newton, MA (US); Brendan M. O'Boyle, Boston, MA (US); Matthew Hersh Daniels, Cambridge, MA (US); Adam Schell, Newton, MA (US); Phieng Siliphaivanh, Newton, MA (US); Christian Fischer, Natick, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 16 days.

(21) Appl. No.: 13/703,250

(22) PCT Filed: Jun. 22, 2011

(86) PCT No.: PCT/US2011/041396
§ 371 (c)(1),
(2), (4) Date: Dec. 10, 2012

(87) PCT Pub. No.: WO2011/163330
PCT Pub. Date: Dec. 29, 2011

(65) Prior Publication Data
US 2013/0096084 A1 Apr. 18, 2013

Related U.S. Application Data

(60) Provisional application No. 61/358,206, filed on Jun. 24, 2010.

(51) Int. Cl.
C07D 401/12 (2006.01)
C07D 409/14 (2006.01)
C07D 413/14 (2006.01)
C07D 417/14 (2006.01)
C07D 471/04 (2006.01)
C07D 401/14 (2006.01)
C07D 405/14 (2006.01)
A61K 31/454 (2006.01)
A61K 31/4545 (2006.01)
A61K 31/506 (2006.01)
A61K 31/5377 (2006.01)
A61K 31/55 (2006.01)
A61K 31/551 (2006.01)
A61K 31/695 (2006.01)
A61K 45/06 (2006.01)
C07F 7/18 (2006.01)

(52) U.S. Cl.
CPC ............ *C07D 401/14* (2013.01); *C07D 401/12* (2013.01); *C07D 405/14* (2013.01); *C07D 409/14* (2013.01); *C07D 413/14* (2013.01); *C07D 417/14* (2013.01); *C07D 471/04* (2013.01); *A61K 31/454* (2013.01); *A61K 31/4545* (2013.01); *A61K 31/506* (2013.01); *A61K 31/5377* (2013.01); *A61K 31/55* (2013.01); *A61K 31/551* (2013.01); *A61K 31/695* (2013.01); *A61K 45/06* (2013.01); *C07F 7/1856* (2013.01)

(58) Field of Classification Search
None
See application file for complete search history.

(56) References Cited

U.S. PATENT DOCUMENTS

| | | |
|---|---|---|
| 2004/0077877 A1 | 4/2004 | Bhagwat et al. |
| 2008/0153810 A1 | 6/2008 | Ronsheim et al. |
| 2009/0149443 A1 | 6/2009 | Munson et al. |
| 2011/0034441 A1 | 2/2011 | Hood et al. |

*Primary Examiner* — Kamal Saeed
(74) *Attorney, Agent, or Firm* — Richard S. Parr; Laura M. Ginkel

(57) ABSTRACT

The present invention provides a compound of the Formula I: (Formular I should be inserted here) or a pharmaceutically acceptable salt, solvate or ester thereof, wherein R, R1, R2 and R3 are as defined herein. The compounds are ERK inhibitors. Also disclosed are pharmaceutical compositions comprising the above compounds and methods of treating cancer using the same.

Formula I

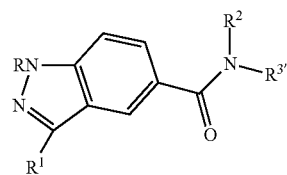

15 Claims, No Drawings

HETEROCYCLIC COMPOUNDS AS ERK INHIBITORS

REFERENCE TO RELATED APPLICATION

This application claims the benefit of U.S. Provisional Application Ser. No. 61/358,206 filed Jun. 24, 2010.

FIELD OF THE INVENTION

This invention related to compounds which can act as inhibitors of kinases, such as ERK, to uses of such compounds and to their preparation

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

PCT publications WO 2007/070398 A1 and WO 2008/153858 A1 disclose polycyclic indazole derivatives useful as ERK inhibitors for the treatment of cancer.

SUMMARY OF THE INVENTION

In its many embodiments, the present invention provides a novel class of compounds, pharmaceutical compositions comprising one or more said compounds, and methods for using said compounds for treating or preventing a disease associated with one or more kinases such as ERK1 and ERK2.

Accordingly, in one aspect, the present invention provides a compound of the Formula I:

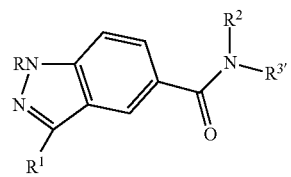

Formula I or a pharmaceutically acceptable salt, solvate or ester thereof, wherein:

R is selected from the group consisting of: H, alkyl and hydroxylalkyl;

$R^1$ is selected from the group consisting of heterocyclyl, heterocycloalkenyl, aryl and heteroaryl, wherein when said heterocyclyl, heterocycloalkenyl, aryl or heteroaryl has two substituents on adjacent ring atoms, said substituents together with the ring atoms to which they are attached, optionally form a five- or six-membered heterocyclyl, aryl or heteroaryl;

$R^2$ is H or alkyl;

$R^{3'}$ is selected from the group consisting of:

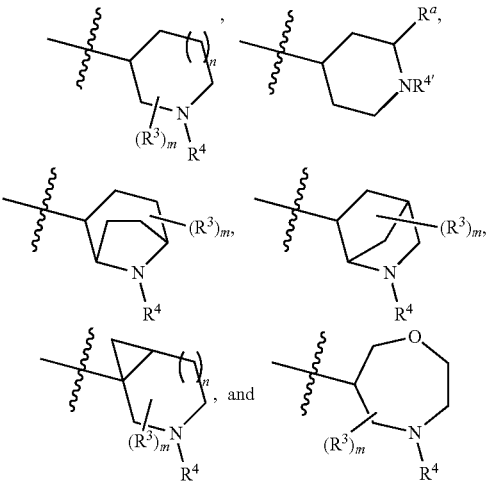

each $R^3$ independently is selected from the group consisting of —C(=O)—O-alkyl, halo, haloalkyl, —OSi(alkyl)$_3$, —C(=O)—OH, —C(O)NR$^B$R$^C$, —C(O)NH-alkyl-NR$^D$R$^E$, —C(O)NH-alkyl-O-alkyl-aryl, —C(O)R$^F$, —C(O)NH—NHR$^G$, —C(O)NH—Oalkyl, —C(O)NH—O-alkyl-cycloalkyl, alkyl, hydroxyl, alkoxy, alkenyl, cycloalkyl, cycloalkenyl, alkynyl, heterocyclyl, heterocyclenyl, aryl, and heteroaryl; or wherein two $R^3$ groups together with the carbon atom to which both $R^3$ groups are attached form —C(=O)—;

$R^B$ and $R^C$ are each independently selected from the group consisting of: H, alkyl, cycloalkyl, cycloalkylalkyl-, heteroaryl, aryl, heterocycloalkyl, benzyl, and alkoxy, wherein said alkyl, cycloalkyl, cycloalkylalkyl-, heteroaryl, aryl, heterocycloalkyl, benzyl, and alkoxy groups are optionally substituted with 1 to 3 substituents independently selected from the group consisting of: —OH, alkyl, alkoxy, hydroxyalkyl-, halo, and —C(O)Oalkyl;

$R^D$ and $R^E$ are each independently selected from the group consisting of: H, alkyl, and —C(O)Oalkyl;

$R^F$ is a heterocycloalkyl optionally substituted with 1-3 substituents independently selected from the group consisting of: —OH, halo, —C(O)Oalkyl, —C(O)NH-alkyl, —C(O)alkyl, alkyl, —C(O)Ocycloalkyl, —O—Si(alkyl)$_2$ (wherein each alkyl is independently selected), and —C(O) Oheterocycloalkyl;

$R^G$ is selected from the group consisting of: H, alkyl, and —C(=S)—NH-alkyl;

each m independently is 0, 1, 2 or 3;

each n independently is 1 or 2;

Each $R^4$ is independently selected from the group consisting of: H, alkyl, cycloalkyl, aryl, heteroaryl, —SO$_2$-aryl, —C(O)—O-alkyl, —C(O)—O-alkylaryl, and —(CR$^5$R$^6$)$_p$R$^7$, wherein p is 1 or 2; wherein when said $R^4$ cycloalkyl has two substituents on adjacent carbon atoms, said substituents together with the carbon atoms to which they are attached, optionally form a five- or six-membered ring selected from the group consisting of heterocyclyl, aryl and heteroaryl;

$R^{4'}$ is selected from the group consisting of H and alkyl;

$R^a$ is alkyl;

$R^5$ and $R^6$ independently are selected from the group consisting of H, D, halo (e.g. F), —OH, —C(O)NR$^H$R$^2$, —C(O)—O-alkyl, and alkyl; or wherein one —CR$^5$R$^6$— is —C(=O)—;

$R^H$ is selected from the group consisting of H and alkyl; and $R^7$ is selected from the group consisting of H, —O-alkylaryl, aryl and heteroaryl, wherein when said aryl or heteroaryl has two substituents on adjacent carbon atoms, said substituents together with the carbon atoms to which they are attached, optionally form a five- or six-membered ring selected from the group consisting of cycloalkylheterocyclyl, aryl or heteroaryl.

In another aspect, the compounds of Formula I, or the pharmaceutically acceptable salts, solvates, or esters thereof can be useful as protein kinase inhibitors.

In another aspect, the compounds of Formula I, or the pharmaceutically acceptable salts, solvates, or esters thereof are useful as protein kinase inhibitors that inhibit the activity of ERK1 and/or the activity of ERK2.

In another aspect, the compounds of Formula I, or the pharmaceutically acceptable salts, solvates, or esters thereof are useful as inhibitors of the phosphorylation of ERK1 and ERK2.

In another aspect, the present invention provides a pharmaceutical composition comprising at least one compound of Formula I, or a pharmaceutically acceptable salt, solvate, or ester thereof and a pharmaceutically acceptable carrier.

In another aspect, the present invention also provides a method of treating cancer in a patient in need of such treatment, said method comprising administering an effective amount of at least one compound of Formula I, or a pharmaceutically acceptable salt, solvate, or ester thereof.

DETAILED DESCRIPTION OF THE INVENTION

As used above, and throughout this disclosure, the following terms, unless otherwise indicated, shall be understood to have the following meanings:

"Patient" includes both human and animals.

"Mammal" means humans and other mammalian animals.

"At least one", as used in reference to the number of compounds of this invention means for example 1-6, generally 1-4, more generally 1, 2 or 3, and usually one or two, and more usually one;

"At least one", as used in reference to the number of chemotherapeutic agents used, means for example 1-6, generally 1-4, more generally 1, 2 or 3, and usually one or two, or one;

"one or more" means for example 1-6, generally 1-4, more generally 1, 2 or 3, and usually one or two, and more usually one;

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, heterocyclyl, heteroaryl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, heterocyclyl, heteroaryl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocycle or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thin before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core, Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system to form a carbocyclic or heterocyclic (aromatic or nonaromatic) ring. Examples of such moiety are methylene dioxy, ethylenedioxy, —C(CH$_3$)$_2$— and the like which form moieties such as, for example:

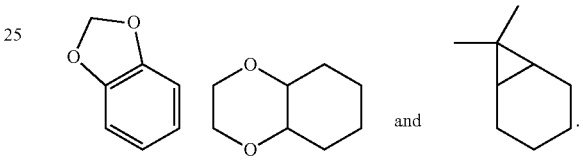

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

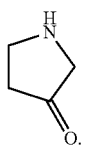

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

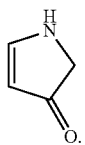

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in

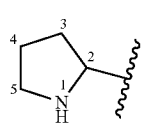

there is no —OH attached directly to carbons marked 2 and 5.

It should also be noted that tautomeric forms such as, for example, the moieties:

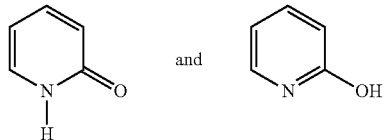 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I), or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I, or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxy-methyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)-ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of any one of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy ($C_1$-$C_6$)alkyl, amino($C_1$-$C_4$)alkyl or mono-N— or $C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt (s)" as used herein.

Pharmaceutically acceptable (i.e., non-toxic, physiologically acceptable) salts are preferred, although other salts are also useful. Salts of the compounds of Formulae I may be formed, for example, by reacting a compound of Formula I, with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula I as set forth herein may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula I (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

In one embodiment of the present invention the compounds of formula I, or a pharmaceutically acceptable salt, solvate or ester thereof, are compounds wherein:

R is H or alkyl;

R$^1$ is selected from the group consisting of heterocyclyl, aryl and heteroaryl, wherein when said heterocyclyl, aryl or heteroaryl has two substituents on adjacent ring atoms, said substituents together with the ring atoms to which they are attached, optionally form a five- or six-membered heterocyclyl, aryl or heteroaryl;

R$^2$ is H or alkyl;

R$^{3'}$ is selected from the group consisting of:

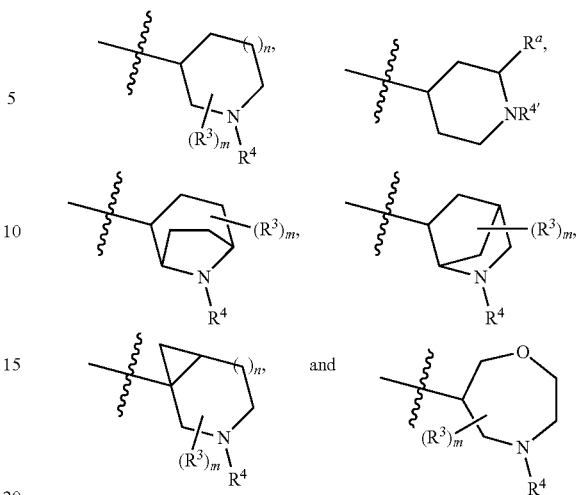

each R$^3$ independently is selected from the group consisting of —C(=O)—O-alkyl, halo, haloalkyl, —OSi(alkyl)$_3$, —C(=O)—N(alkyl)$_2$, —C(=O)—NH-alkyl, alkyl, hydroxyl, alkoxy, alkenyl, cycloalkyl, cycloalkenyl, alkynyl, heterocyclyl, heterocyclenyl, aryl, and heteroaryl; or wherein two R$^3$ groups together with the carbon atom to which both R$^3$ groups are attached form —C(=O)—;

each m independently is 0, 1, 2 or 3;

each n independently is 1 or 2;

each R$^4$ independently is H, cycloalkyl, or —(CR$^5$R$^6$)$_p$R$^7$, wherein p is 1 or 2; wherein when said R$^4$ cycloalkyl has two substituents on adjacent carbon atoms, said substituents together with the carbon atoms to which they are attached, optionally form a five- or six-membered ring selected from the group consisting of heterocyclyl, aryl and heteroaryl;

R$^{4'}$ is selected from the group consisting of H and alkyl;

R$^a$ is alkyl;

R$^5$ and R$^6$ independently are selected from the group consisting of H, D, and alkyl; or wherein one —CR$^5$R$^6$— is —C(=O)—;

R$^7$ is selected from the group consisting of H, —O-alkyl-aryl, aryl and heteroaryl, wherein when said aryl or heteroaryl has two substituents on adjacent carbon atoms, said substituents together with the carbon atoms to which they are attached, optionally form a five- or six-membered ring selected from the group consisting of cycloalkylheterocyclyl, aryl or heteroaryl.

In one embodiment of the invention, R in formula I is selected from the group consisting of: H, C$_1$-C$_4$alkyl (e.g., C$_1$-C$_2$alkyl, such as, for example, methyl), and hydroxyC$_1$-C$_4$alkyl (e.g., hydroxyC$_1$-C$_2$alkyl, such as, for example, —CH$_2$OH).

In one embodiment of the present invention, R$^1$ is selected from the group consisting of heterocyclyl, heterocycloalkenyl, aryl and heteroaryl, wherein when said heterocyclyl, heterocycloalkenyl, aryl or heteroaryl has two substituents on adjacent ring atoms, said substituents together with the ring atoms to which they are attached, optionally form a five- or six-membered heterocyclyl, aryl or heteroaryl; and said R$^1$ is optionally substituted with 1 or more (e.g., 1-3) substitutents independently selected from the group consisting of =O, —OH, alkyl (e.g., C$_1$-C$_4$alkyl, such as, for example, methyl), cycloalkyl (C$_3$-C$_5$ cycloalkyl, such as, for example, cyclopropyl), haloalkyl (e.g. (1-3)haloC$_1$-C$_4$alkyl, wherein each halo (e.g., F, Cl and Br, and in one example F) is independently selected, such as, for example, (1-3)halomethyl or (1-3)haloethyl, such as, for example, —CF$_3$), alkoxy (C$_1$-C$_4$alkoxy, such as, for example, methoxy and isopropyloxy), halo (e.g., F, Cl, and Br, and in one example F), —NH—C(=O)-alkyl (e.g., —NH—C(=O)—C$_1$-C$_4$alkyl, such as, for example, —NH—C(=O)—CH$_3$), —S(=O)$_2$—N(alkyl)$_2$ (e.g., —S(=O)$_2$N((C$_1$-C$_4$)alkyl)$_2$ wherein each alkyl is independently selected and —S(=O)$_2$N((C$_1$-C$_2$)alkyl)$_2$ wherein each alkyl is independently selected, such as, for example, —S(O)$_2$N(CH$_3$)$_2$), —C(=O)-alkyl (e.g., —C(O)—(C$_1$-C$_4$) alkyl and —C(O)—(C$_1$-C$_2$)alkyl, such as, for example, —C(O)CH$_3$), cyano, —S(=O)$_2$-alkyl (e.g., —S(O)$_2$—(C$_1$-C$_4$alkyl), and —S(O)$_2$—(C$_1$-C$_2$alkyl), such as, for example, —S(O)CH$_3$), —NH$_2$, and —OC(=O)alkyl (e.g., —OC(=O)—(C$_1$-C$_4$alkyl) and —OC(=O)—(C$_1$-C$_4$alkyl), such as, for example, —OC(O)CH$_3$). In one embodiment said R$^1$ group is substituted with 1-3 independently selected substituents. In another embodiment said R$^1$ group is substituted with 1-2 independently selected substituents. In another embodiment said R$^1$ group is substituted with 1 substituent.

In one embodiment of the present invention, in formula I, R is H.

In another embodiment, in formula I, said R$^1$ is heteroaryl, wherein said heteroaryl optionally with said five- or six-membered heterocyclyl, aryl or heteroaryl is selected from the group consisting of imidazo[1,2-a]pyridinyl, pyridyl, pyrazolyl, [1,2,4]triazolo[1,5-a]pyridinyl, and [1,2,4]-triazolo[4,3-a]pyridinyl, each of which is independently unsubstituted or substituted with at least one substituent independently selected from the group consisting of alkyl, cycloalkyl, haloalkyl, alkoxy and halo.

In another embodiment, in formula I, R$^1$ is pyridyl, wherein said pyridyl is 4-pyridyl or 3-pyridyl, each of which is independently unsubstituted or substituted with at least one substituent selected from the group consisting of alkoxy, cycloalkyl, alkyl, haloalkyl, and halo.

In another embodiment, in formula I, R$^1$ is pyridyl, which is 4-pyridyl or 3-pyridyl, each of which is independently unsubstituted or substituted with at least one substituent selected from the group consisting of methoxy, isopropyloxy, cyclopropyl, ethyl, methyl, and trifluoromethyl.

In another embodiment, in formula I, R$^1$ is aryl, wherein when said aryl has two substituents on adjacent carbon atoms, said substituents together with the carbon atoms to which they are attached, optionally form a five- or six-membered ring selected from the group consisting of heterocyclyl, aryl and heteroaryl; wherein said aryl optionally with said five- or six-membered heterocyclyl, aryl and heteroaryl is independently unsubstituted or substituted with at least one substitutent selected from the group consisting of alkyl, alkoxy, hydroxy, —NH—C(=O)-alkyl, —S(=O)$_2$—N(alkyl)$_2$, —C(=O)-alkyl, cyano, —S(=O)$_2$-alkyl, —NH$_2$, and —OC(=O)alkyl.

In another embodiment, in formula I, R$^1$ is aryl, wherein said aryl optionally with said five- or six-membered heterocyclyl, aryl and heteroaryl is selected from the group consisting of phenyl, benzo[c][1,2,5]thiadiazolyl, benzo[c][1,2,5]oxadiazolyl, 2H-indazolyl, benzotetrahydrofuranyl, benzothiophenyl, benzopyrrolyl, benzopyrazolyl, benzothiazolyl, benzofuranyl, and benzoxazolyl, each of which independently is unsubstituted or substituted with at least one substitutent selected from the group consisting of alkyl, alkoxy, hydroxy, —NH—C(=O)-alkyl, —S(=O)$_2$—N(alkyl)$_2$, —C(=O)-alkyl, cyano, —S(=O)$_2$-alkyl, —NH$_2$, and —OC(=O)alkyl.

In another embodiment, in formula I, R$^1$ is aryl, wherein said aryl optionally with said five- or six-membered heterocyclyl, aryl and heteroaryl is selected from the group consisting of phenyl,

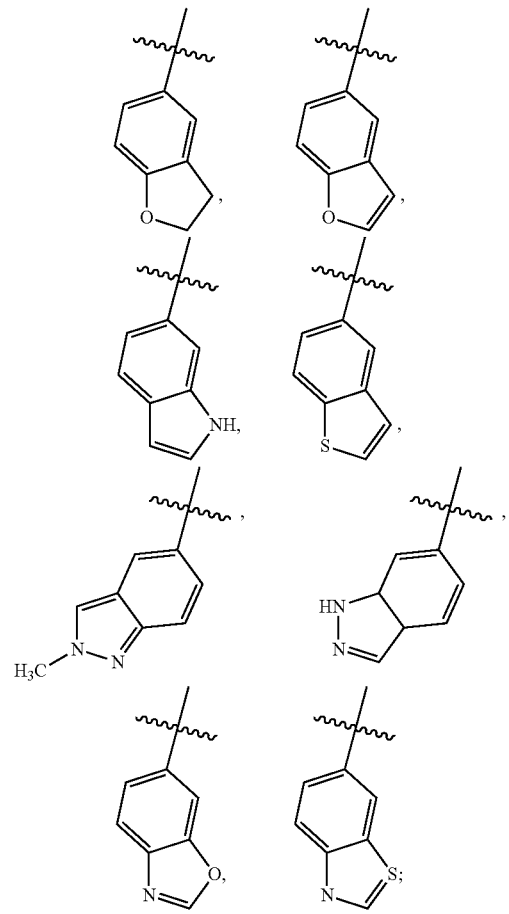

each of which independently is unsubstituted or substituted with at least one substitutent selected from the group consisting of alkyl, alkoxy, hydroxy, —NH—C(=O)-alkyl, —S(=O)$_2$—N(alkyl)$_2$, —C(=O)-alkyl, cyano, —S(=O)$_2$-alkyl, —NH$_2$, and —OC(=O)alkyl.

In another embodiment, in formula I, said R$^1$ is heterocyclyl, wherein said heterocyclyl optionally with said five- or six-membered heterocyclyl, aryl and heteroaryl is selected from the group consisting of:

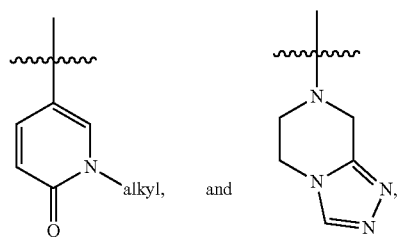

wherein the second structure is unsubstituted or substituted with a cycloalkyl group.

In another embodiment, in formula I, R$^1$ is selected from the group consisting of: phenyl, pyridyl, methylpyridyl, methylindazolyl, methylbenzothiazolyl, pyridazinyl, dihydropyran, dioxidodihydrothiopyran, dioxidotetrahydrothiopyran, imidazolyl, pyridazinyl, teterahydropyran, benzofuranyl, indazolyl, pyridazinyl, indazolyl, imidazopyridly, benzooxazolyl, benzothiadiazolyl, benzooxadiazolyl, benzothiazolyl, pyridine-one, triazolopyridinyl (e.g., [1,2,4]triazolo[1,5-a]pyridinyl, and [1,2,4]triazolo[4,3-a]pyridinyl), dihydrobenzoimidazolyl (e.g., 2,3-dihydro-1H-benzo[d]imidazolyl), benzohydrofuranyl; and wherein said $R^1$ is optionally substituted with 1 or more (e.g., 1-3) substituents independently selected from the group consisting of: =O, —OH, alkyl (e.g., $C_1$-$C_4$alkyl, such as, for example, methyl), cycloalkyl ($C_3$-$C_6$ cycloalkyl, such as, for example, cyclopropyl), haloalkyl (e.g. (1-3)halo$C_1$-$C_4$alkyl, wherein each halo (e.g., F, Cl and Br, and in one example F) is independently selected, such as, for example, (1-3)halomethyl or (1-3)haloethyl, such as, for example, —$CF_3$), alkoxy ($C_1$-$C_4$alkoxy, such as, for example, methoxy and isopropyloxy), halo (e.g., F, Cl, and Br, and in one example F), —NH—C(=O)-alkyl (e.g., —NH—C(=O)—$C_1$-$C_4$alkyl, such as, for example, —NH—C(=O)—$CH_3$), —S(=O)$_2$—N(alkyl)$_2$ (e.g., —S(=O)$_2$N(($C_1$-$C_4$)alkyl)$_2$ wherein each alkyl is independently selected and —S(=O)$_2$N(($C_1$-$C_2$)alkyl)$_2$ wherein each alkyl is independently selected, such as, for example, —S(O)$_2$N($CH_3$)$_2$), —C(=O)-alkyl (e.g., —C(O)—($C_1$-$C_4$)alkyl and —C(O)—($C_1$-$C_2$)alkyl, such as, for example, —C(O)$CH_3$), cyano, —S(=O)$_2$-alkyl (e.g., —S(O)$_2$—($C_1$-$C_4$alkyl), and —S(O)$_2$—($C_1$-$C_2$alkyl), such as, for example, —S(O)$CH_3$), —$NH_2$, and —OC(=O)alkyl (e.g., —OC(=O)—($C_1$-$C_4$alkyl) and —OC(=O)—($C_1$-$C_2$alkyl), such as, for example, —OC(O)$CH_3$). In one embodiment said $R^1$ group is substituted with 1-3 independently selected substituents. In another embodiment said $R^1$ group is substituted with 1-2 independently selected substituents. In another embodiment said $R^1$ group is substituted with 1 substituent.

In another embodiment, in formula I, $R^2$ is alkyl, which is unsubstituted or substituted with at least one (in one embodiment one, in another embodiment two) aryl.

In another embodiment, in formula I, $R^2$ is alkyl, which is unsubstituted or substituted with at least one phenyl.

In one embodiment of this invention $R^3$ is —C(O)$NR^BR^C$, wherein $R^B$ and $R^C$ are each independently selected from the group consisting of (1) H, (2) $C_1$-$C_6$ alkyl (e.g., $C_1$-$C_4$alkyl, such as, for example, methyl, ethyl, propyl, and butyl), (3) $C_3$-$C_6$ cycloalkyl (e.g., cylopropyl and cyclopentyl), (4) $C_3$-$C_6$cycloalkyl-$C_1$-$C_6$alkyl- (e.g., $C_3$-$C_6$cycloalkyl-$C_1$-$C_4$alkyl), (5) 5-6 membered heteroaryl comprising 1 to 3 (example 1, 2 or 3, and in another example 1 or 2, and in another example 2, and in another example 1) heteroatoms selected from the group consisting of N, O, and S (and in one example the heteroatoms are 1 or 2 nitrogen atoms, and in another example the heteroatoms are N and S), (6) $C_6$-$C_{10}$aryl (e.g., phenyl or naphthyl, and in one example phenyl), (7) benzyl, (8) $C_1$-$C_2$ alkoxy (e.g., methoxy); wherein each of said $R^B$ and $R^C$ is optionally substituted with 1 to 3 substitutents independently selected from the group consisting of: —OH, $C_1$-$C_4$alkyl (e.g., methyl and ethyl), —$C_1$-$C_4$alkoxy (e.g., —$OCH_3$), -hydroxy($C_1$-$C_3$)alkyl- (e.g., —$CH_2$OH), halo (e.g., F), —C(O)O$C_1$-$C_4$alkyl (e.g., wherein said alkyl is t-butyl), and the optional substitution of $R^B$ is independent of the optional substitution of $R^C$. In one embodiment one of $R^B$ and $R^C$ is H or alkyl (e.g., methyl), and the other is one of the other moieties described above.

In one embodiment of this invention $R^3$ is —C(O)NH-alkyl-$NR^DR^E$, and $R^D$ and $R^E$ are independently selected from the group consisting of: H, $C_1$-$C_4$alkyl (e.g., methyl) and —C(O)O$C_1$-$C_4$alkyl (e.g., wherein said alkyl is t-butyl).

In one embodiment of this invention $R^3$ is —C(O)NH—$C_1$-$C_2$alkyl-$NR^DR^E$.

In one embodiment of this invention $R^3$ is —C(O)NH—$C_1$-$C_2$alkyl-$NR^DR^E$ wherein $R^D$ and $R^E$ are independently selected from the group consisting of: H, $C_1$-$C_4$alkyl (e.g., methyl), and —C(O)O$C_1$-$C_4$alkyl (e.g., wherein said alkyl is t-butyl).

In one embodiment of the present invention, in formula I, $R^3$ is —C(O)NH-alkyl-O-alkyl-aryl wherein said $R^3$ group is, for example, —C(O)—NH—$C_1$-$C_2$alkyl-O—$C_1$-$C_2$alkyl-phenyl.

In one embodiment of the present invention, in formula I, $R^3$ is —C(O)$R^F$ wherein $R^F$ is a 4-7 membered heterocycloalkyl comprising 1 to 3 heteroatoms selected from the group consisting of O, N and S (e.g., pyrrolidinyl, piperidinyl, piperazinyl, azetidinyl, morpholinyl, isoxazolidinyl), said $R^F$ group is optionally substituted with 1-3 substituents independently selected from the group consisting of: —OH, halo (e.g., F), —C(O)O$C_1$-$C_4$alkyl (e.g., wherein said alkyl is methyl, ethyl, i-propyl, or t-butyl), —C(O)NH—$C_1$-$C_4$alkyl (e.g., wherein said alkyl is methyl or ethyl), —C(O)$C_1$-$C_4$alkyl (e.g., wherein said alkyl is methyl), $C_1$-$C_4$ alkyl (e.g., methyl), —C(O)O$C_3$-$C_6$cycloalkyl (e.g., wherein said cycloalkyl is propyl or pentyl), —O—Si($C_1$-$C_4$alkyl)$_2$ wherein each alkyl is independently selected (e.g., wherein each alkyl is methyl), and —C(O)Oheterocycloalkyl wherein said heterocycloalkyl moiety is a 5 to 6 membered ring comprising 1 to 3 heteroatoms selected from the group consisting of O, N and S (e.g., wherein there is one heteroatom in said heterocycloalkyl group, and in another example there is one heteroatom and said heteroatom is O, and in another example, said heterocycloalkyl is tetrahydropyran).

In one embodiment of the present invention, in formula I, $R^3$ is —C(O)—NH—$NHR^G$ wherein $R^G$ is selected from the group consisting of: H, $C_1$-$C_4$alkyl (e.g., methyl), and —C(=S)—NH—$C_1$-$C_4$alkyl (e.g., wherein said alkyl is methyl), In one embodiment of the present invention, in formula I, $R^3$ is —C(O)NH—O—$C_1$-$C_4$alkyl (e.g., wherein said alkyl is t-butyl).

In one embodiment of the present invention, in formula I, $R^3$ is —C(=O)—N(alkyl)$_2$ (that is $R^3$ is —C(O)$NR^BR^C$ wherein $R^B$ and $R^C$ are alkyl groups), wherein each alkyl group is independently selected.

In one embodiment of the present invention, in formula I, $R^3$ is —C(=O)—NHalkyl (that is $R^3$ is —C(O)$NR^BR^C$ wherein one of $R^B$ is a H and the other is alkyl group).

In one embodiment of the present invention, in formula I, $R^3$ is aryl wherein said aryl is phenyl.

In one embodiment of the present invention, in formula I, $R^3$ is —C(O)NH—O—$C_1$-$C_2$alkyl-$C_3$-$C_5$cycloalkyl (e.g., wherein said alkyl moiety is —$CH_2$ and said cycloalkyl moiety is cyclopropyl).

In other embodiments of the present invention, $R^3$ for formula I is as described in any one of the individual embodiments directed to $R^3$ above, and $R^{3'}$ is

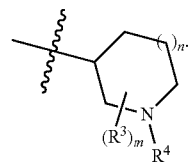

In another embodiment of the present invention R³ is selected from the group consisting of: phenyl, —C(O)—NH—O—CH₂-cyclopropyl, —C(O)—NH-cyclopropyl, —C(O)—N(CH₃)-cyclopropyl, —C(O)—NH-pyridyl, —C(O)—NH-thiazolyl, —C(O)—NH—(F-phenyl), —C(O)—NH—(F,CH₃O-phenyl), —C(O)—NH-(phenyl-(CH₃)₂), —C(O)-(piperidinyl-OH), —C(O)OH, —C(O)—NH—(CH₂)₂—NH₂, —C(O)—NH—CH₃, —C(O)—N(CH₃)₂, —C(O)—NH—CH₂-phenyl, —C(O)—NH—CH₂CH₃, —C(O)—NH₂, —C(O)-piperidinyl, —C(O)-pyrrolidinyl, —C(O)-(di-F-piperidinyl), —C(O)—N(C₂H₅), —C(O)-(di-F-azetidinyl), —C(O)-azetidinyl, —C(O)-morpholinyl, —C(O)—NH—(CH₂)₂—O—CH₂-phenyl, —C(O)—NH—(CH₂)₂—O—(CH₂)₂-phenyl, —C(O)—NH—CH(CH₃)₂, —C(O)—NH-cyclopentyl, —C(O)—NH—(CH₂)₂—OH, —C(O)—N(C₃H₇)₂, —C(O)—N(C₄H₉)₂, —C(O)—N(CH₃)(C₂H₅), —C(O)—N(CH₃)(C₃H₇), —C(O)—NH—NH₂, —C(O)NH—N(CH₃)₂, —C(O)-(piperizinyl-C(O)Otbutyl), —C(O)—NH—(CH₂)₂—CH₂Cl, —C(O)-(piperidinyl-Cl), —C(O)—N(CH₃)—OCH₃, —C(O)—NH—NH—CH₃, —C(O)-piperazinyl, —C(O)-(piperazinyl-C(O)—NH—CH₂CH₃), —C(O)—NHCH₃, —C(O)—NH—NH—C(=S)—NHCH₃, —C(O)—NH—CH₂—CH₂F, —C(O)—NH—CH₂—CF₃, —C(O)O-t-butyl, —C(O)-(piperazinyl-C(O)CH₃), —C(O)-isoxazolidinyl, —C(O)-(piperazinyl-CH₃), —C(O)-(piperazinyl-C(O)OCH₃), —C(O)-(piperazinyl-C(O)OCH₂CH₃), —C(O)—NH—CH₂—CH₂—NH—C(O)Ot-butyl, —C(O)—NH—CH₂—CH₂—CH₂—NH—C(O)Ot-butyl, —C(O)-(piperazinyl-C(O)O-(cyclopropyl-CH₃)), —C(O)-(isoxazolidinyl-O—Si(CH₃)₂), —C(O)—NH—O-t-butyl, —C(O)—N(CH₃)—(CH₂)₄—NH—C(O)Ot-butyl, —C(O)-piperazinyl-C(O)Ocyclopentyl, —C(O)-piperazinyl-C(O)Oi-propyl, —C(O)-pipeazinyl-C(O)—O-tetrahydropyran, —C(O)NHbenzyl,

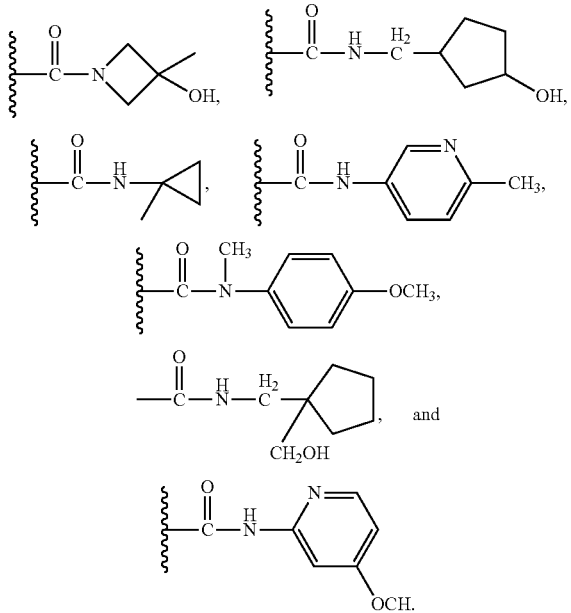

In other embodiments of the present invention, R³ for formula I is as described in any one of the individual embodiments directed to R³ above, and R³' is

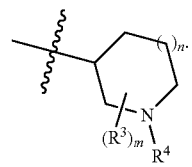

In other embodiments of the present invention, R³ for formula I is as described in any one of the individual embodiments directed to R³ above, R³' is

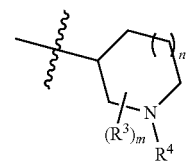

and m is 1.

In other embodiments of the present invention, R³ for formula I is as described in any one of the individual embodiments directed to R³ above, R³' is

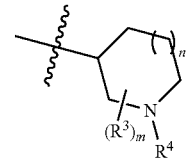

m is 1, and n is 1.

In another embodiment, in formula I, R³' is

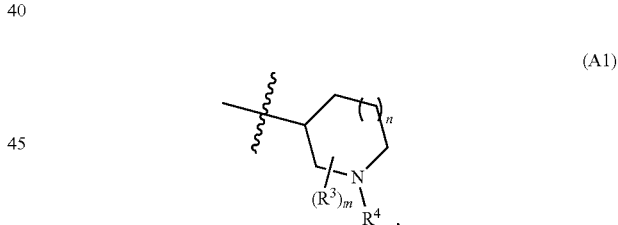

wherein n is 1 or 2.

In another embodiment, in formula I, R³' is (A1), wherein n is 1, i.e., R³' is

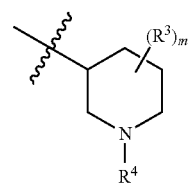

and m is 0, 1 or 2.

In another embodiment, in formula I, R³' is selected from the group consisting of:

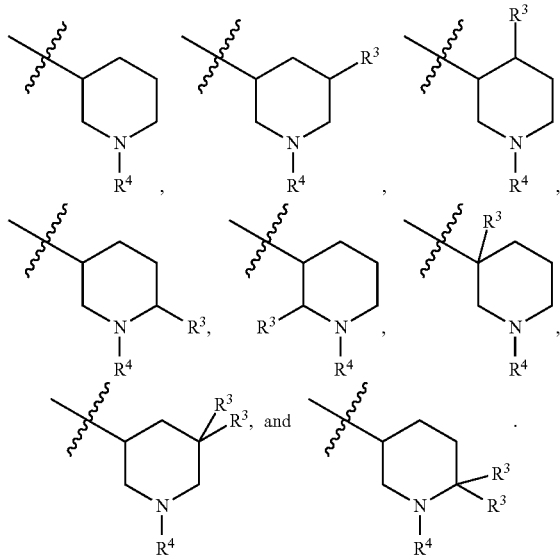

In another embodiment, in formula I, R³' is (A1), wherein n is 1, and m is 1 or 2, and R³ is selected from the group consisting of halo, haloalkyl, —OSi(alkyl)₃, hydroxyl, alkyl, cycloalkyl, alkoxy, aryl, —C(=O)OH, —C(=O)—O-alkyl, —C(=O)N(alkyl)₃, —C(=O)NH-alkyl; or wherein two R³ groups together with the carbon atom to which both R³ groups are attached form —C(=O)—.

In another embodiment, in formula I, R³' is (A1), wherein n is 1, and m is 1 or 2, wherein R³ is alkyl that is unsubstituted or substituted with at least one substituent selected from the group consisting of hydroxy, aryl, alkoxy, and —O-alkyl-O-alkyl.

In another embodiment, in formula I, R³' is (A1), wherein n is 1, and m is 1 or 2, wherein R³ is -alkyl-aryl wherein the "aryl" portion of said -alkyl-aryl is substituted with at least one fluoro substituent.

In another embodiment, in formula I, R³' is (A1), wherein n is 1, and m is 1 or 2, and R³ is aryl, wherein said aryl is phenyl which is unsubstituted or substituted with a halo.

In another embodiment, in formula I, R³' is (A1), wherein n is 1, and R⁴ is H.

In another embodiment, in formula I, R³' is (A1), wherein n is 1, and R⁴ is cycloalkyl, wherein when said R⁴ cycloalkyl has two substituents on adjacent carbon atoms, said substituents together with the carbon atoms to which they are attached, optionally form a six-membered aryl.

In another embodiment, in formula I, R³' is (A1), wherein n is 1, and R⁴ is cycloalkyl, wherein when said R⁴ cycloalkyl has two substituents on adjacent carbon atoms, said substituents together with the carbon atoms to which they are attached, optionally form a six-membered aryl; wherein said R⁴ cycloalkyl, optionally with said six-membered aryl is unsubstituted or substituted with at least one deuterium (D).

In another embodiment, in formula I, R³' is (A1), wherein n is 1, and R⁴ is cycloalkyl, wherein when said R⁴ cycloalkyl has two substituents on adjacent carbon atoms, said substituents together with the carbon atoms to which they are attached, optionally form a six-membered aryl; wherein said R⁴ cycloalkyl, optionally with said six-membered aryl is unsubstituted or substituted with at least one deuterium (D), wherein said R⁴ cycloalkyl is a benzo fused cyclopentyl that is unsubstituted or substituted with a D.

In another embodiment, in formula I, R³' is (A1), wherein n is 1, and R⁴ is —(CR⁵R⁶)₁₋₂R⁷, wherein each of R⁵ and R⁶ independently is H or alkyl, or wherein one —CR⁵R⁶— together is —C(=O)— and R⁷ is selected from the group consisting of H, cycloalkyl, heterocyclyl, —O-alkyl-aryl, aryl and heteroaryl, wherein when each of said R⁷ cycloalkyl, heterocyclyl, aryl and heteroaryl has two substituents on adjacent carbon atoms, said substituents together with the carbon atoms to which they are attached, optionally form a five- or six-membered cycloalkyl, heterocyclyl, aryl or heteroaryl.

In another embodiment, in formula I, R³' is (A1), wherein n is 1, and R⁴ is —(CR⁵R⁶)₁₋₂R⁷, wherein R⁵ and R⁶ are both H.

In another embodiment, in formula I, R³' is (A1), wherein n is 1, and R⁴ is selected from the group consisting of H, —CH₂—R⁷, —CH₂CH₂R⁷, —CH(CH₃)—R⁷, —CH₂—C(=O)₁₋₂R⁷, —C(=O)—R⁷, and —CH₂CH(OH)R⁷.

In another embodiment, in formula I, R³' is (A1), wherein n is 1, and R⁴ is —(CR⁵R⁶)₁₋₂R⁷, wherein R⁷ is aryl, wherein when said aryl has two substituents on adjacent carbon atoms, said substituents together with the carbon atoms to which they are attached, optionally form a five- or six-membered heterocyclyl or heteroaryl.

In another embodiment, in formula I, R³' is (A1), wherein n is 1, and R⁴ is —(CR⁵R⁶)₁₋₂R⁷, wherein R⁷ is aryl, wherein when said R⁷ aryl has two substituents on adjacent carbon atoms, said substituents together with the carbon atoms to which they are attached, optionally form a five- or six-membered heterocyclyl or heteroaryl; wherein said R⁷ aryl, optionally with said five- or six-membered heterocyclyl or heteroaryl is selected from the group consisting of phenyl,

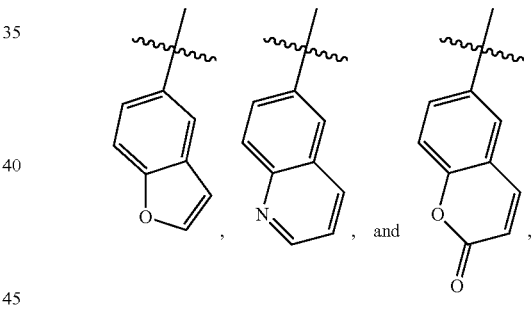

each of which is independently unsubstituted or substituted with at least one substituent independently selected from the group consisting of halo, cyano, alkoxy, haloalkyl, and —N(alkyl)₂.

In another embodiment, in formula I, R³' is (A1), wherein n is 1, and R⁴ is —(CR⁵R⁶)₁₋₂R⁷, wherein R⁷ is heteroaryl, wherein when said heteroaryl has two substituents on adjacent carbon atoms, said substituents together with the carbon atoms to which they are attached, optionally form a phenyl.

In another embodiment, in formula I, R³' is (A1), wherein n is 1, and R⁴ is —(CR⁵R⁶)₁₋₂R⁷, wherein R⁷ is heteroaryl, wherein when said heteroaryl has two substituents on adjacent carbon atoms, said substituents together with the carbon atoms to which they are attached, optionally form a phenyl; wherein said R⁷ heteroaryl optionally with said phenyl is selected from the group consisting of pyridyl, thiophenyl, pyrimidinyl, thiazolyl, benzothiophenyl, benzopyrrolyl, and benzofuranyl, each of which is independently unsubstituted or substituted with at least one substituent independently selected from the group consisting of alkyl, —C(=O)-alkyl, and alkoxy.

In another embodiment, in formula I, $R^{3'}$ is (A1), wherein n is 1, and $R^4$ is —$(CR^5R^6)_{1-2}R^7$, wherein $R^7$ is heteroaryl, wherein when said heteroaryl has two substituents on adjacent carbon atoms, said substituents together with the carbon atoms to which they are attached, optionally form a phenyl; wherein said $R^7$ heteroaryl optionally with said phenyl is selected from the group consisting of pyridyl, thiophenyl, pyrimidinyl, thiazolyl, benzothiophenyl, benzopyrrolyl, and benzofuranyl, each of which is independently unsubstituted or substituted with at least one substituent independently selected from the group consisting of alkyl, —C(=O)-alkyl, and alkoxy; wherein said $R^7$ pyridyl is selected from the group consisting of 2-pyridyl and 4-pyridyl.

In another embodiment, in formula I, $R^{3'}$ is (A1), wherein n is 1, and $R^4$ is —$(CR^5R^6)_{1-2}R^7$, wherein each of $R^5$ and $R^6$ independently is H, —C(=O)$NR^HR^2$ or alkyl, or wherein one —$CR^5R^6$— together is —C(=O)— and $R^7$ is selected from the group consisting of H, cycloalkyl, heterocyclyl, aryl and heteroaryl, wherein when each of said $R^7$ cycloalkyl, heterocyclyl, aryl and heteroaryl has two substituents on adjacent carbon atoms, said substituents together with the carbon atoms to which they are attached, optionally form a five- or six-membered cycloalkyl, heterocyclyl, aryl or heteroaryl; wherein said $R^7$ cycloalkyl is cyclohexyl.

In another embodiment, in formula I, $R^{3'}$ is (A1), wherein n is 2, i.e., $R^{3'}$ is

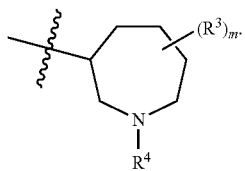

In another embodiment, in formula I, $R^{3'}$ is (A1), wherein n is 2, and m is 0, i.e., $R^{3'}$ is

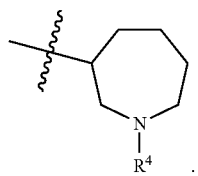

In another embodiment, in formula I, $R^{3'}$ is (A1), wherein n is 2, m is 0, and $R^4$ is —$(CR^5R^6)_{1-3}R^7$, wherein each of $R^5$ and $R^6$ independently is H or alkyl, or wherein one —$CR^5R^6$— together is —C(=O)— and $R^7$ is selected from the group consisting of cycloalkyl, aryl and heteroaryl, wherein when each of said $R^7$ cycloalkyl, aryl and heteroaryl has two substituents on adjacent carbon atoms, said substituents together with the carbon atoms to which they are attached, optionally form a five- or six-membered cycloalkyl, heterocyclyl, aryl or heteroaryl.

In another embodiment, in formula I, $R^{3'}$ is (A1), wherein n is 2, m is 0, and $R^4$ is —$(CR^5R^6)_{1-3}R^7$, $R^8$ and $R^6$ are both H, and $R^7$ is selected from the group consisting of cycloalkyl, aryl and heteroaryl, wherein when each of said $R^7$ cycloalkyl, aryl and heteroaryl has two substituents on adjacent carbon atoms, said substituents together with the carbon atoms to which they are attached, optionally form a five- or six-membered cycloalkyl, heterocyclyl, aryl or heteroaryl.

In another embodiment, in formula I, $R^{3'}$ is (A1), wherein n is 2, m is 0, $R^4$ is selected from the group consisting of H, —CH$_2$—R$^7$, —CH$_2$CH$_2$R$^7$, —CH$_2$CH$_2$CH$_2$—R$^7$, and —CH$_2$—C(=O)—R$^7$, and $R^7$ is selected from the group consisting of cycloalkyl, aryl and heteroaryl, wherein when each of said $R^7$ cycloalkyl, aryl and heteroaryl has two substituents on adjacent carbon atoms, said substituents together with the carbon atoms to which they are attached, optionally form a five- or six-membered cycloalkyl, heterocyclyl, aryl or heteroaryl.

In another embodiment, in formula I, $R^{3'}$ is (A1), wherein n is 2, m is 0, and $R^4$ is —$(CR^5R^6)_{1-3}R^7$, wherein each of $R^5$ and $R^6$ independently is H or alkyl, or wherein one —$CR^5R^6$— together is —C(=O)— and $R^7$ is selected from the group consisting of cycloalkyl, aryl and heteroaryl, wherein when each of said $R^7$ cycloalkyl, aryl and heteroaryl has two substituents on adjacent carbon atoms, said substituents together with the carbon atoms to which they are attached, optionally form a five- or six-membered cycloalkyl, heterocyclyl, aryl or heteroaryl; wherein said $R^7$ optionally with said five- or six-membered cycloalkyl, heterocyclyl, aryl or heteroaryl, is selected from the group consisting of phenyl, naphthyl, pyridyl, and

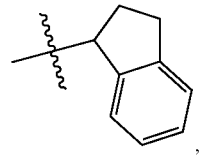 [SMILES: *C1CCc2ccccc21]

each of which is independently unsubstituted or substituted with at least one substituent independently selected from the group consisting of halo, and alkoxy.

In another embodiment, in formula I, $R^{3'}$ is (A1), wherein n is 2, m is 0, and $R^4$ is —$(CR^5R^6)_{1-3}R^7$, wherein each of $R^5$ and $R^6$ independently is H or alkyl, or wherein one —$CR^5R^6$— together is —C(=O)— and $R^7$ is selected from the group consisting of cycloalkyl, aryl and heteroaryl, wherein when each of said $R^7$ cycloalkyl, aryl and heteroaryl has two substituents on adjacent carbon atoms, said substituents together with the carbon atoms to which they are attached, optionally form a five- or six-membered cycloalkyl, heterocyclyl, aryl or heteroaryl; wherein said $R^7$ optionally with said five- or six-membered cycloalkyl, heterocyclyl, aryl or heteroaryl, is selected from the group consisting of phenyl, naphthyl, pyridyl, and

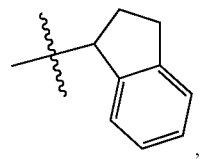

each of which is independently unsubstituted or substituted with at least one substituent independently selected from the group consisting of halo, and alkoxy, wherein said naphthyl is 1-naphthyl, and said pyridyl is 2-pyridyl.

In another embodiment, in formula I, $R^{3'}$ is

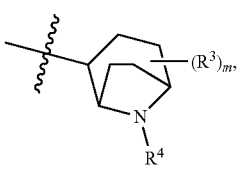 (A2)

wherein m is 0, and $R^4$ is —$CR^5R^6R^7$.

In another embodiment, in formula I, $R^{3'}$ is (A2), wherein m is 0, and $R^4$ is —$CR^5R^6R^7$; wherein $R^5$ and $R^6$ are H, and $R^7$ is aryl.

In another embodiment, in formula I, $R^{3'}$ is (A2), wherein m is 0, and $R^4$ is —$CR^5R^6R^7$; wherein $R^5$ and $R^6$ are H, and $R^7$ is phenyl which is unsubstituted or substituted with at least one substituent selected from the group consisting of halo and alkoxy.

In another embodiment, in formula I, $R^{3'}$ is

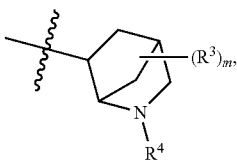 (A3)

wherein m is 0, and $R^4$ is —$CR^5R^6R^7$.

In another embodiment, in formula I, $R^{3'}$ is (A3), wherein m is 0, and $R^4$ is —$CR^5R^6R^7$, wherein $R^5$ and $R^6$ are H, and $R^7$ is aryl.

In another embodiment, in formula I, $R^{3'}$ is (A3), wherein m is 0, and $R^4$ is —$CR^5R^6R^7$, wherein $R^5$ and $R^6$ are H, and $R^7$ is aryl, wherein said aryl is phenyl which is unsubstituted or substituted with at least one substituent selected from the group consisting of halo and alkoxy.

In another embodiment, in formula I, $R^{3'}$ is

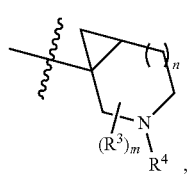 (A4)

wherein n is 1, m is 0, and $R^4$ is —$CR^5R^6R^7$.

In another embodiment, in formula I, $R^{3'}$ is (A4), wherein n is 1, m is 0, and $R^4$ is —$CR^5R^6R^7$, wherein $R^5$ and $R^6$ are H, and $R^7$ is aryl.

In another embodiment, in formula I, $R^{3'}$ is (A4), wherein n is 1, m is 0, and $R^4$ is —$CR^5R^6R^7$, wherein $R^5$ and $R^6$ are H, and $R^7$ is aryl, wherein said $R^7$ aryl is phenyl which is unsubstituted or substituted with at least one substituent selected from the group consisting of halo and alkoxy.

In another embodiment, in formula I, $R^{3'}$ is

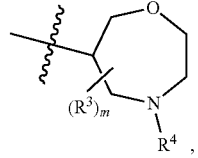 (A5)

wherein m is 0 and $R^4$ is —$CR^5R^6R^7$.

In another embodiment, in formula I, $R^{3'}$ is (A5), wherein m is 0 and $R^4$ is —$CR^5R^6R^7$, wherein $R^5$ and $R^6$ are H, and $R^7$ is aryl.

In another embodiment, in formula I, $R^{3'}$ is (A5), wherein m is 0 and $R^4$ is —$CR^5R^6R^7$, wherein $R^5$ and $R^6$ are H, and $R^7$ is aryl, wherein said $R^7$ aryl is phenyl which is unsubstituted or substituted with at least one halo substituent.

In another embodiment, in formula I, $R^{3'}$ is

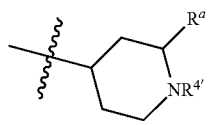 (A6)

wherein $R^{4'}$ is H, and $R^a$ is alkyl which is unsubstituted or substituted with an aryl substituent.

In another embodiment, in formula I, $R^{3'}$ is (A6) wherein $R^{4'}$ is H, and $R^a$ is benzyl.

In one embodiment, in formula I, $R^4$ is H, $C_1$-$C_4$alkyl (e.g., methyl and ethyl), $C_3$-$C_6$cycloalkyl (e.g., cyclopropyl, cyclopentyl, and cyclohexyl), $C_6$-$C_{10}$aryl (e.g. phenyl and benzocyclopentyl 2,3-dihydro-1H-indene)), 5-10 membered heteroaryl comprising 1-3 heteroatoms independently selected from the group consisting of O, N and S (e.g., a 5-6 membered heteroaryl, such as, for example, quinolinyl, thienyl), —$SO_2$-aryl (e.g., —$S(O)_2$—($C_6$-$C_{10}$)aryl and —$S(O)_2$-phenyl), —C(O)—O-alkyl (—C(O)—O—$C_1$-$C_4$alkyl), such as, for example, —C(O)—O-t-butyl), —C(O)—O-alkylaryl (e.g., —C(O)—O—$C_1$-$C_4$alkyl-$C_6$-$C_{10}$aryl, —C(O)—O—$C_1$-$C_2$alkyl-$C_6$-$C_{10}$aryl, and —C(O)—O—$C_1$-$C_2$alkyl-phenyl, such as, for example, —C(O)—O—$CH_2$-phenyl), and —$(CR^5R^6)_pR^7$ (wherein p, $R^5$, $R^6$, and $R^7$ are as defined for formula I).

In one embodiment of the invention, one of $R^5$ and $R^6$ in formula I is H, and the other is —C(O)$NR^HR^2$ wherein $R^H$ and $R^2$ are independently selected from the group consisting of H and methyl.

In one embodiment of the invention, one of $R^5$ and $R^6$ is H and the other is —C(O)—O-alkyl (e.g., —C(O)—O—$C_1$-$C_4$alkyl and —C(O)—O—$C_1$-$C_2$alkyl, such as, for example, —C(O)—O—$CH_3$).

In one embodiment of the invention, $R^7$ in formula I, is selected from the group consisting of: H, —O-alkyl-aryl (e.g., —O-$C_1$-$C_4$-$C_6$-$C_{10}$aryl, —O—$C_1$-$C_2$-$C_6$-$C_{10}$aryl, and —O—$C_1$-$C_2$-phenyl), aryl (e.g. $C_6$-$C_{10}$aryl, such as, for example, phenyl and benzocyclopentyl), and heteroaryl (e.g., 5-10 membered heteroaryl, 5-9 membered heteroaryl, and 5-6 membered heteroaryl, wherein said heteroaryl comprises 1-3 heteroatoms independently selected from the group consisting of O, N and S, and wherein examples of said heteroaryl include, for example, pyrimidinyl, pyridyl, oxadiazolyl, thiazolyl, indolyl, benzothiophenyl (i.e., benzothienyl), benzofuranyl, and thienyl), wherein when said aryl or heteroaryl has two substituents on adjacent carbon atoms, said substituents together with the carbon atoms to which they are attached, optionally form a five- or six-membered ring selected from the group consisting of cycloalkylheterocyclyl, aryl or heteroaryl; and wherein said $R^7$ group is optionally substituted with 1-3 substituents independently selected from the group consisting of CN, halo (e.g., F), —O—$C_1$-$C_4$alkyl (e.g., —O—$C_1$-$C_3$alkyl, such as, for example, —$OCH_3$ and —$O(CH_2)CH_3$), $C_1$-$C_4$alkyl (e.g., $C_1$-$C_2$alkyl, such as for example, methyl), —C(O)—$C_1$-$C_4$alkyl (e.g., —C(O)—$C_1$-$C_2$alkyl, such as, for example, —$C(O)CH_3$), —O—$C_1$-$C_4$alkyl wherein at least 1 (e.g., 1-3, 1-2, or 1) H atom is deuterium (D) (e.g., —O—$C_1$-$C_3$alkyl, such as, for example, —$OCD_3$).

In one embodiment of the invention, $R^4$ for formula I is selected from the group consisting of: phenyl, quinolinyl, —$SO_2$-phenyl, —$CH_2$-phenyl, di-F-phenyl, F-phenyl, —$CH_2$-thienyl, —$(CH_2)_2$-phenyl, —$CH_2$-($D_3$CO—, F-phenyl), —CH(C(O)$NH_2$)(F-phenyl), —CH(C(O)$NHCH_3$)(F-phenyl), —CH(C(O)$NH_2$)(di-F-phenyl), —CH(C(O)$NHCH_3$)(di-F-phenyl), —CH(C(O)N($CH_3$)$_2$)(di-F-phenyl), —CH(C(O)N($CH_3$)$_2$)(F-phenyl), and —CH(C(O)$OCH_3$)(di-F-phenyl).

In another embodiment, the compound of formula I is selected from the group consisting of:

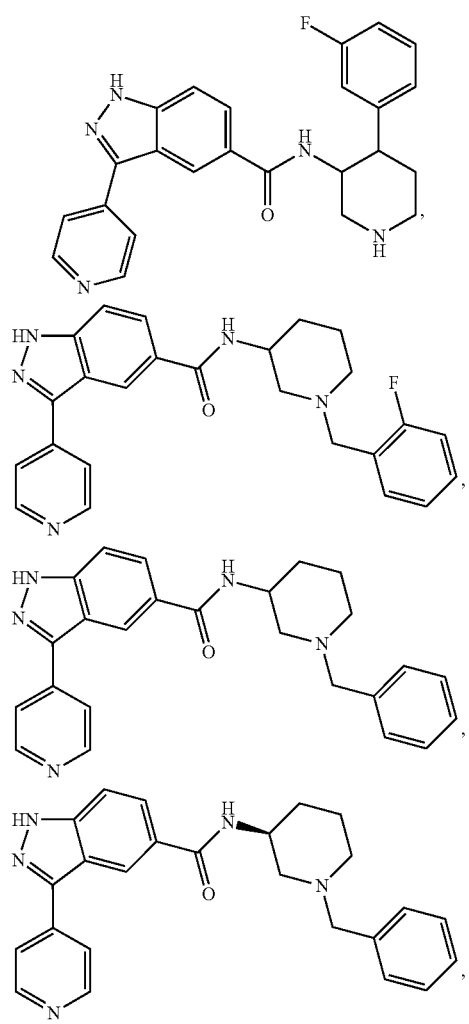

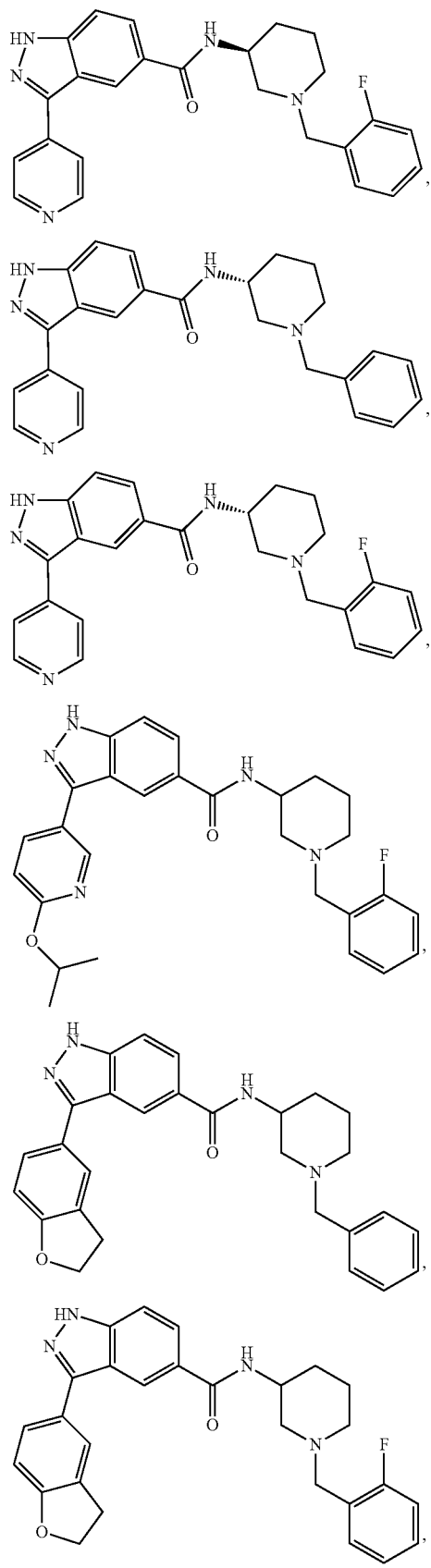

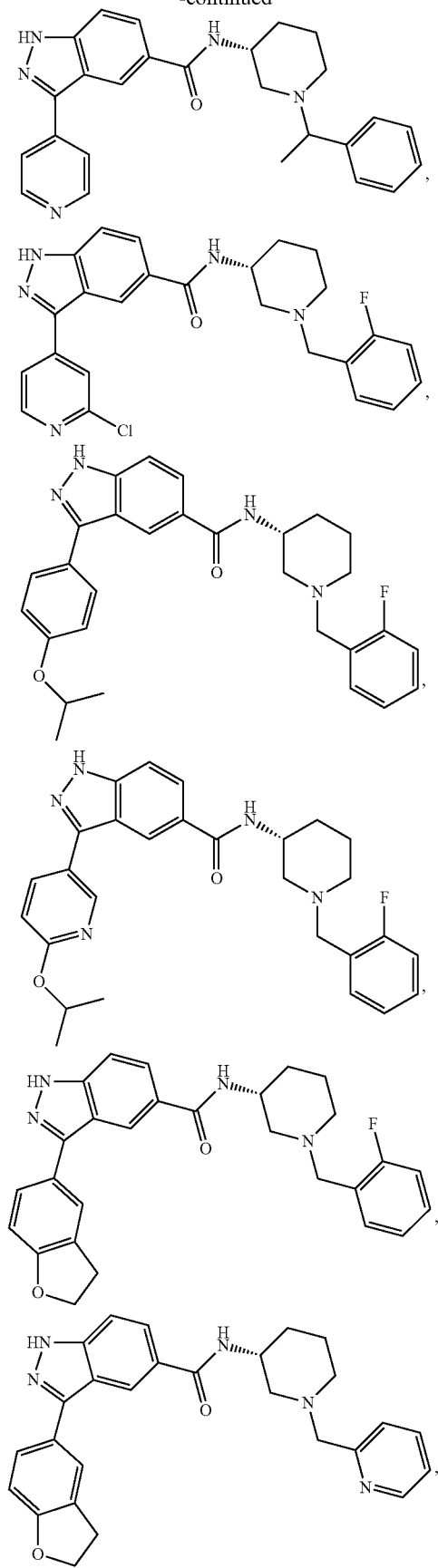
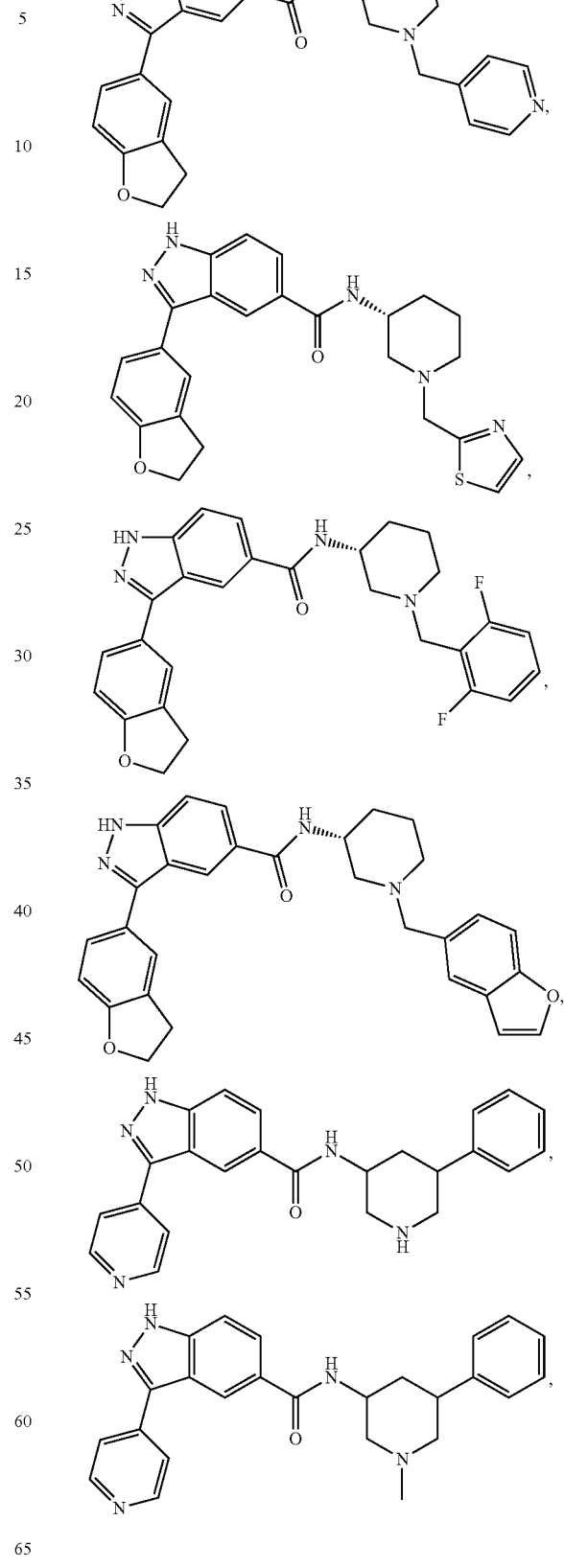

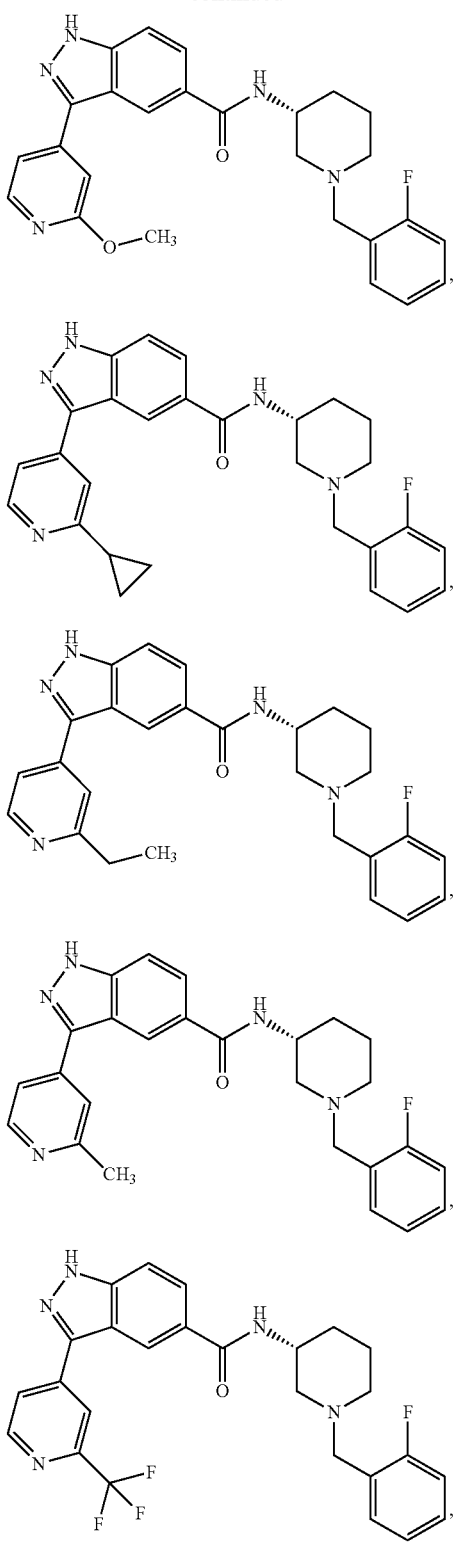
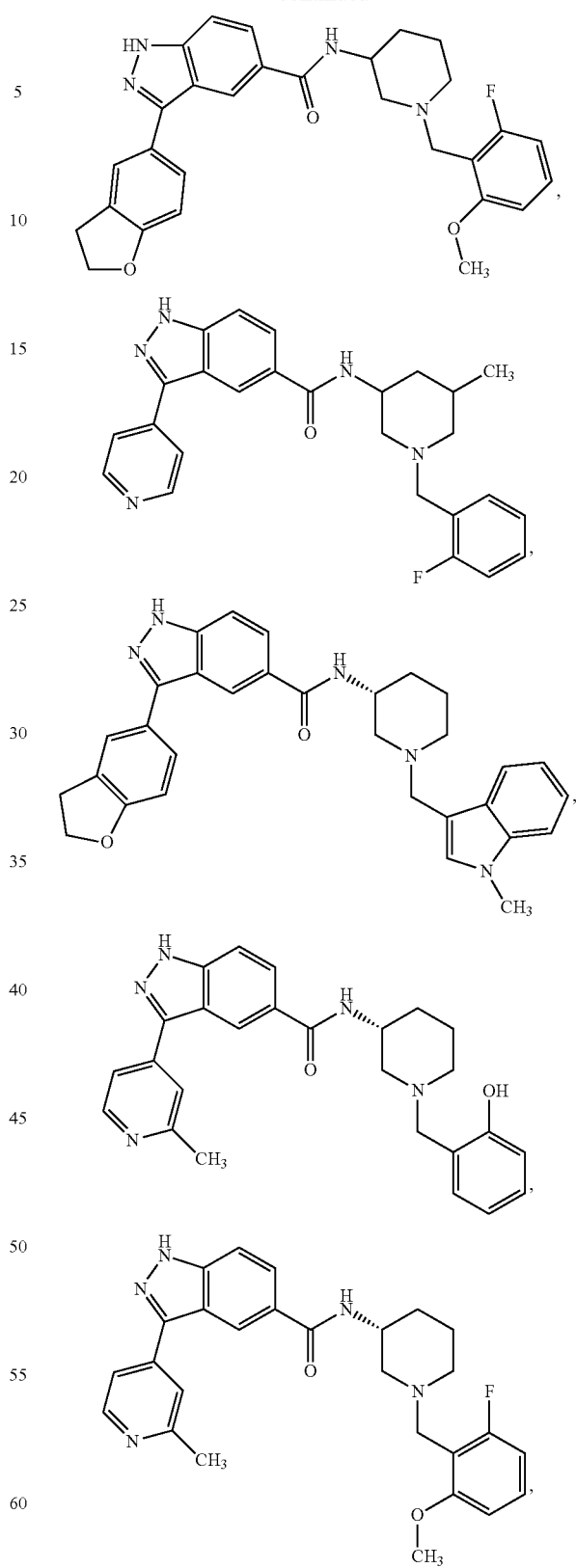

33
-continued
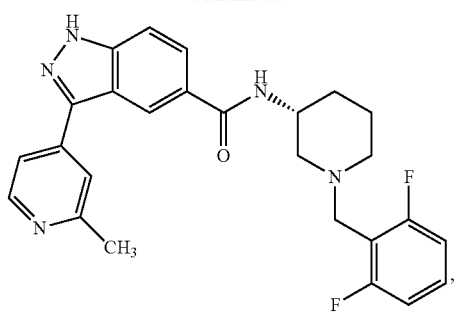
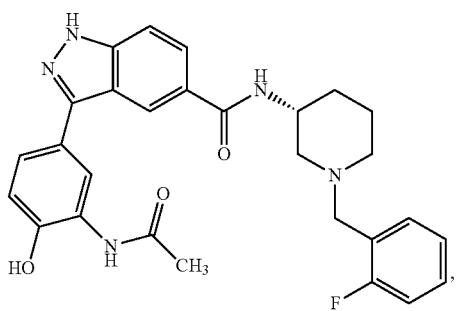
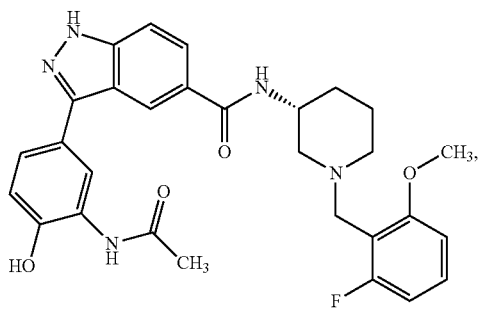
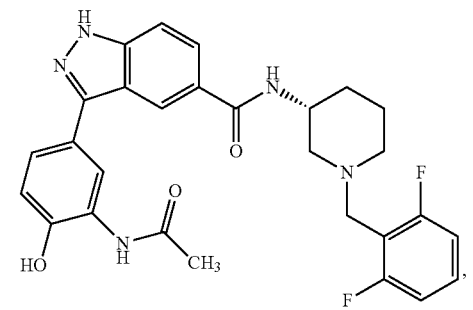
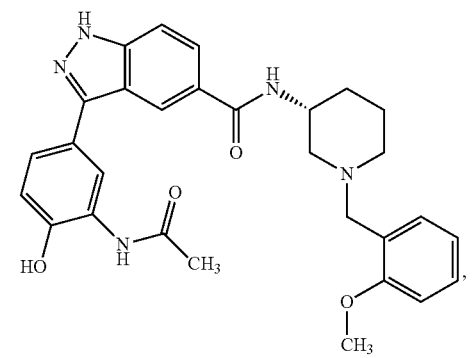
34
-continued
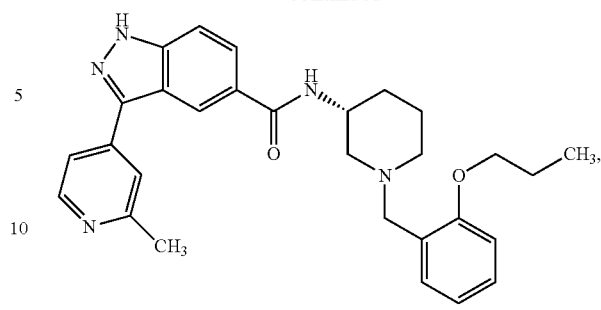
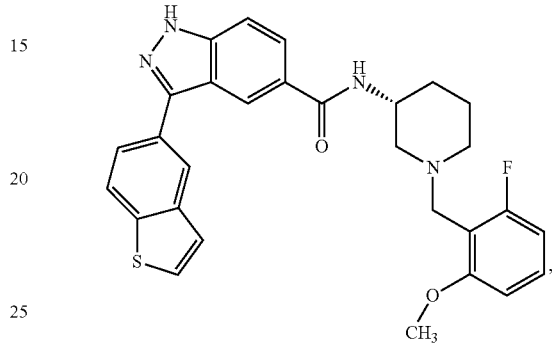
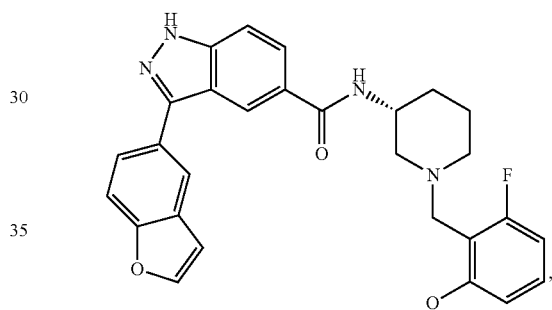
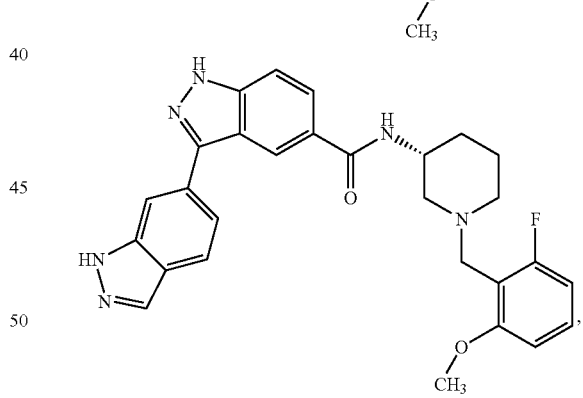
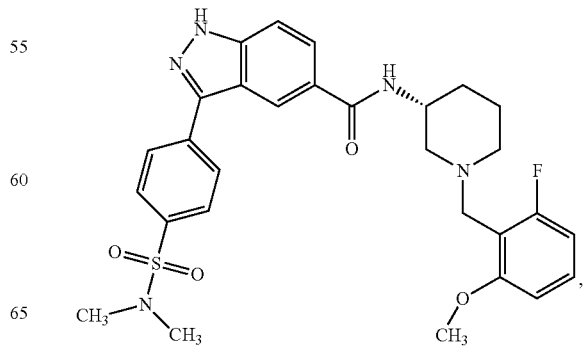

35
-continued
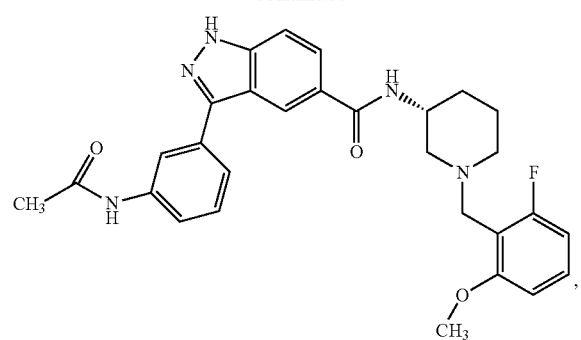
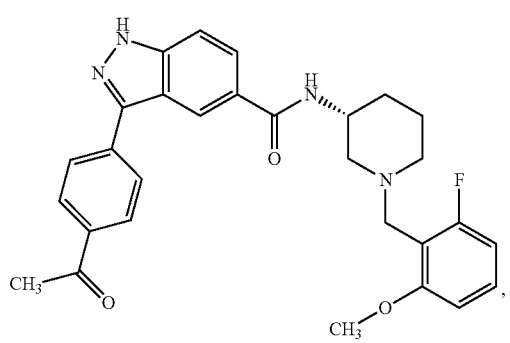
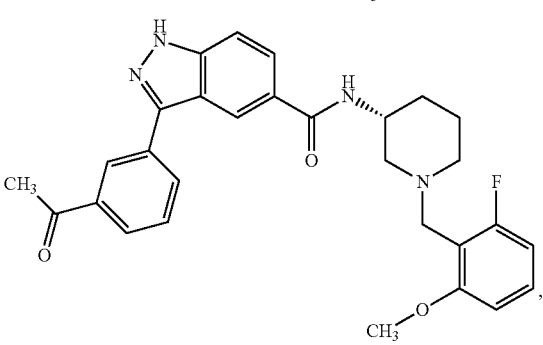
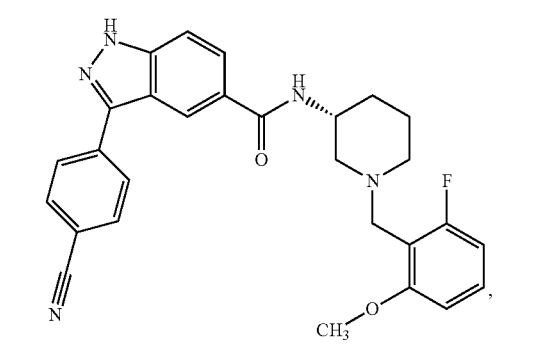
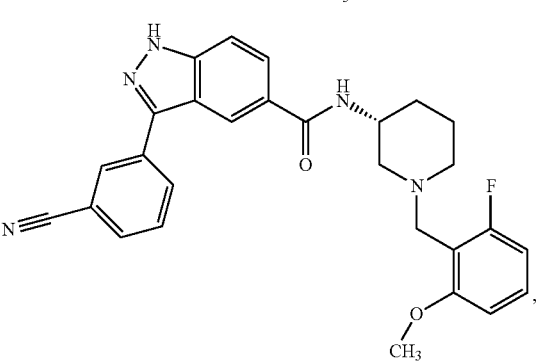
36
-continued
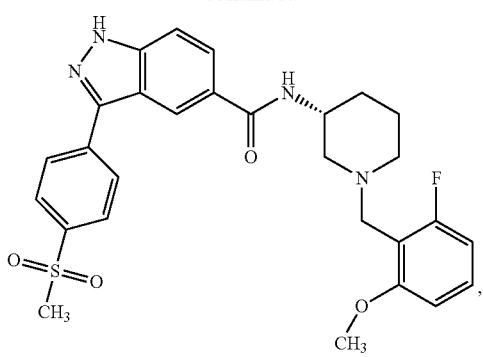
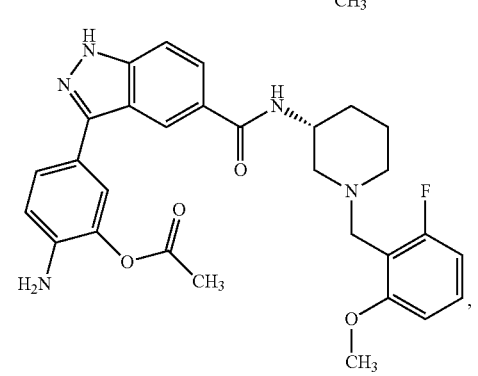
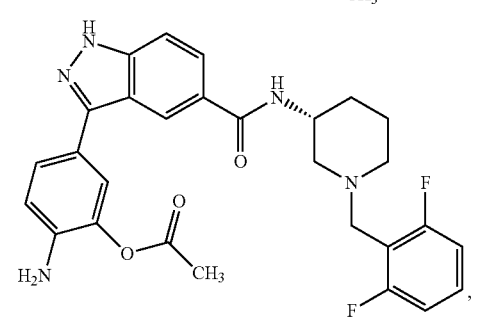
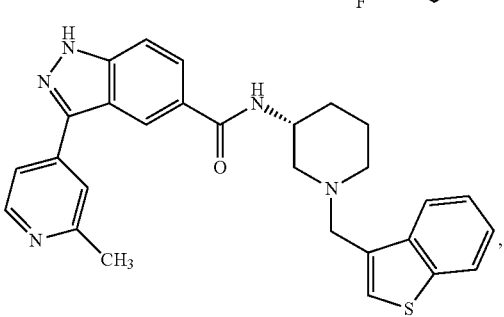
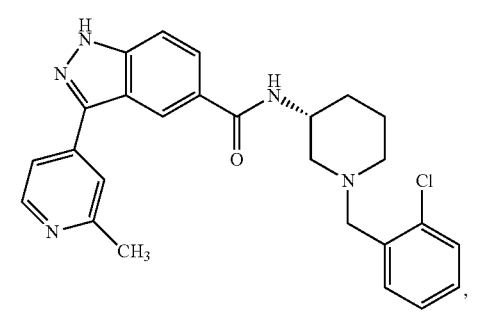

37
-continued
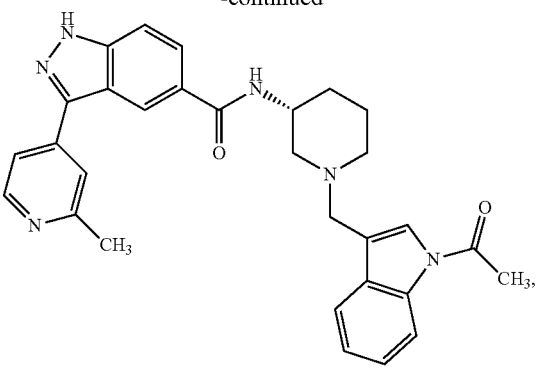
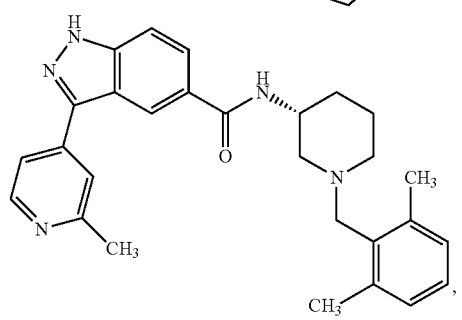
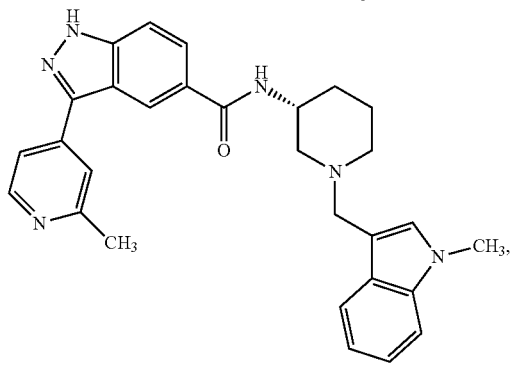
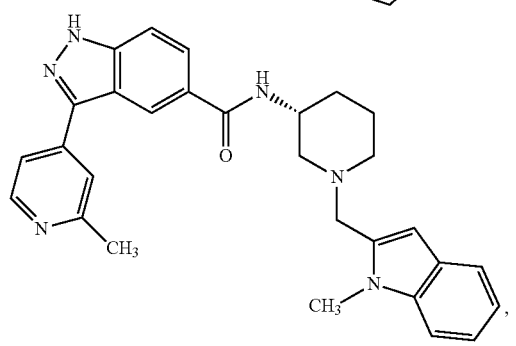
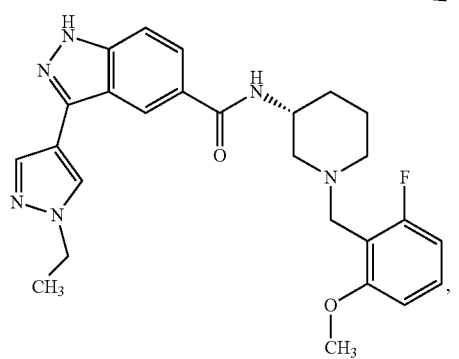
38
-continued
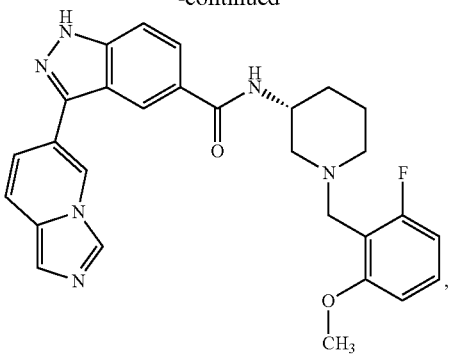
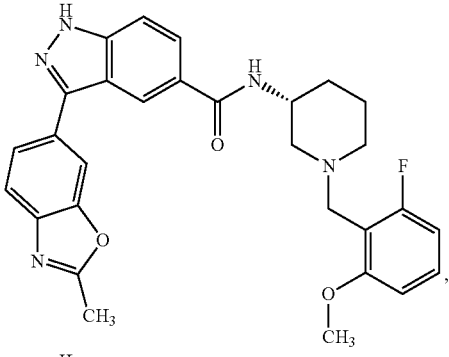
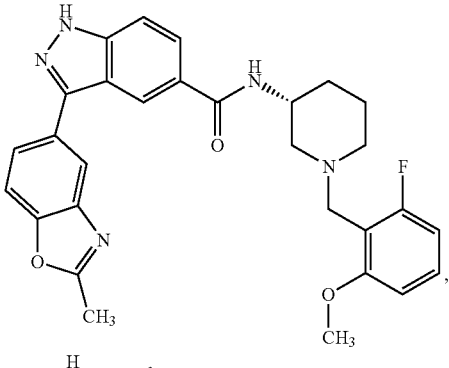
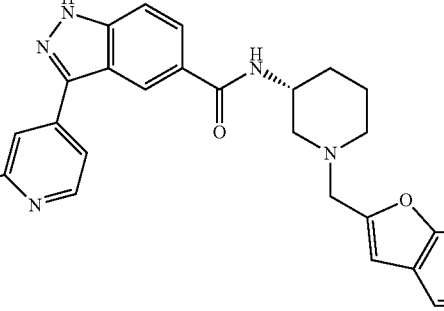
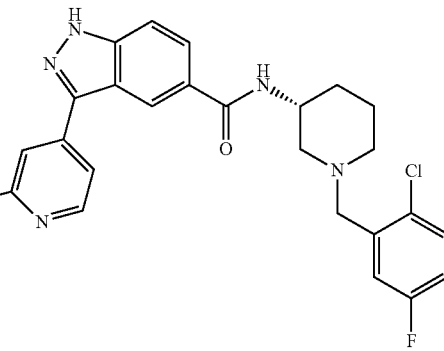

39
-continued
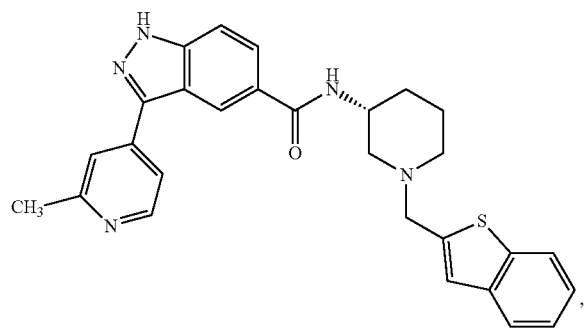
40
-continued
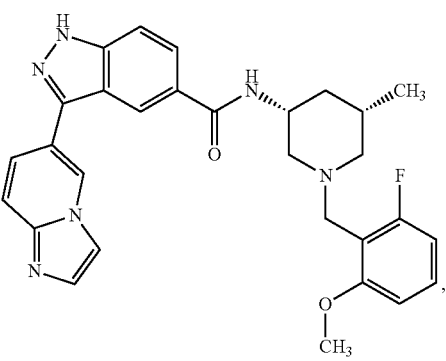

41
-continued
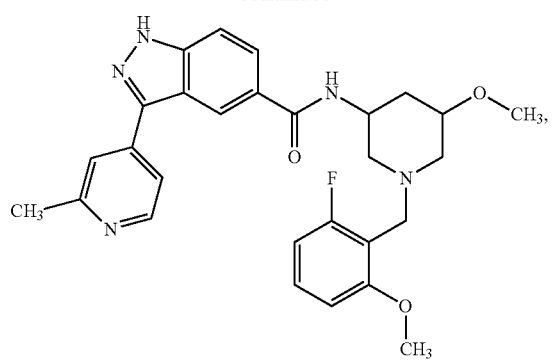
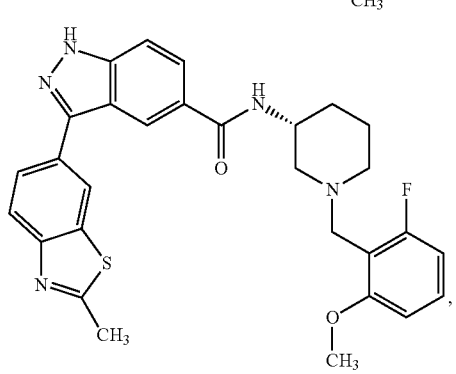
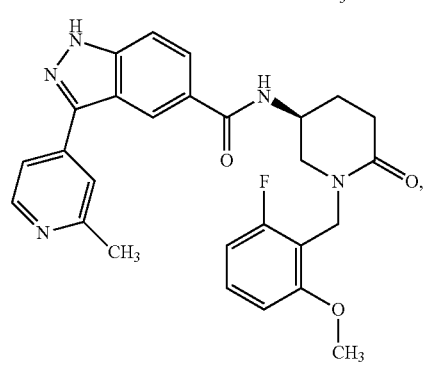
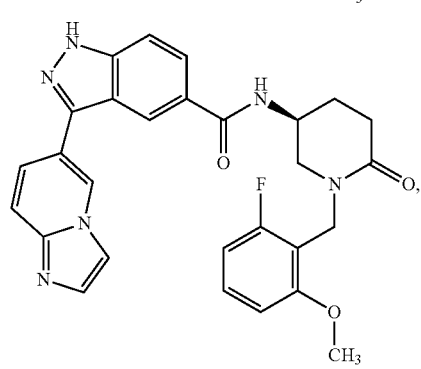
42
-continued
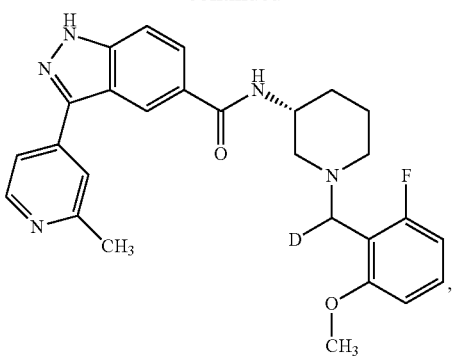
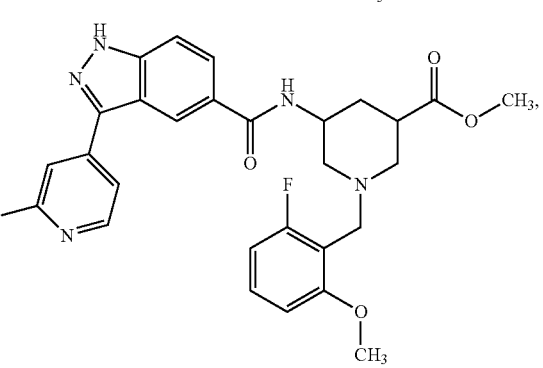
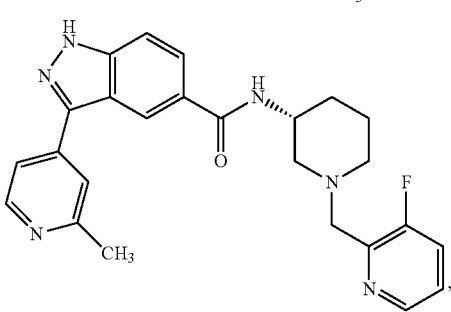
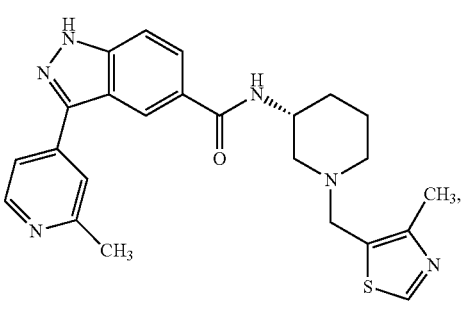
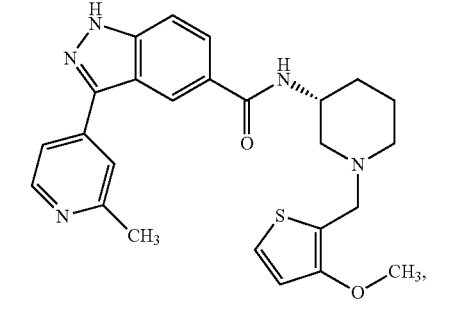

43
-continued
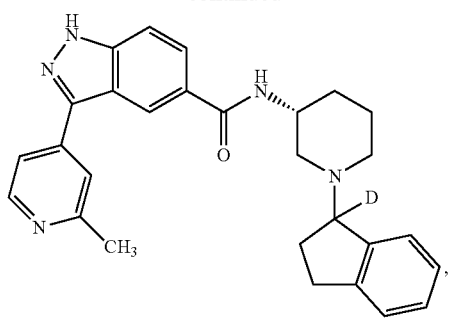
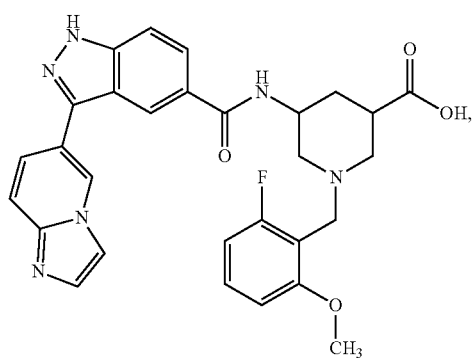
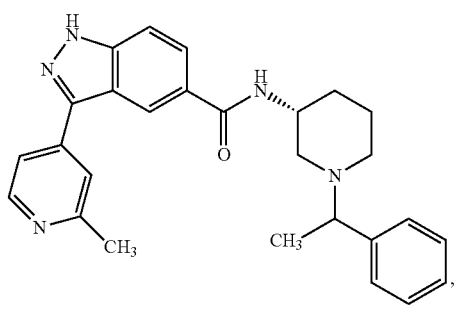
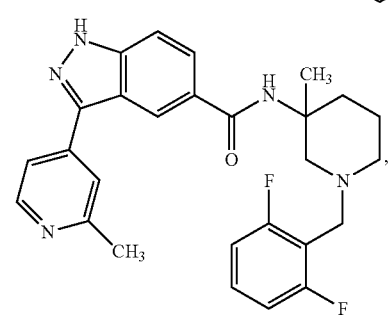
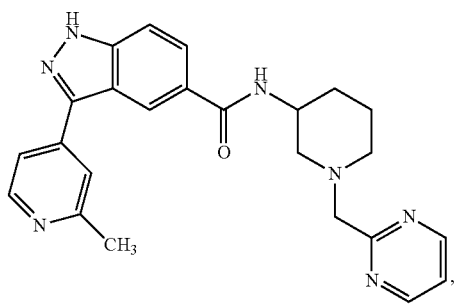
44
-continued
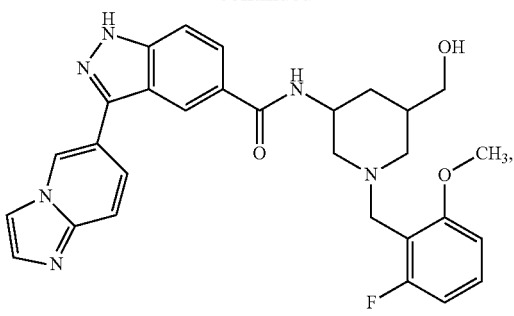
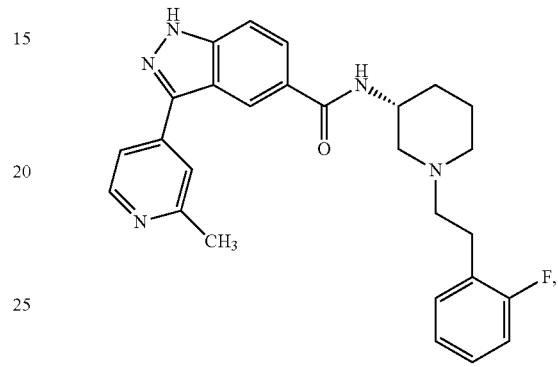
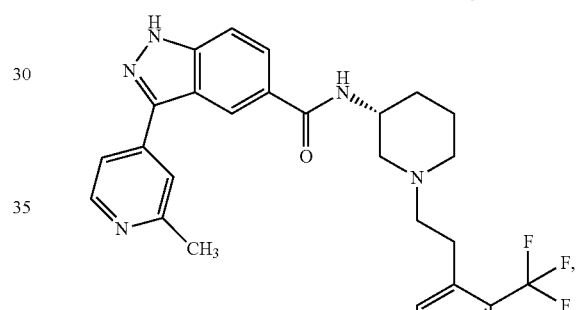
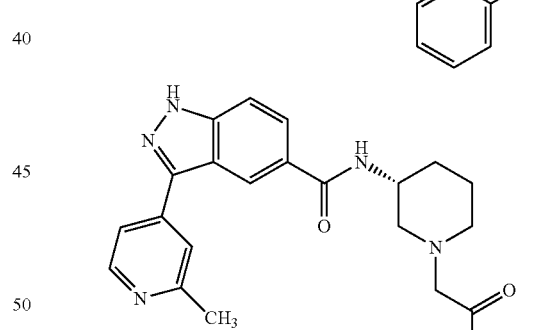

-continued
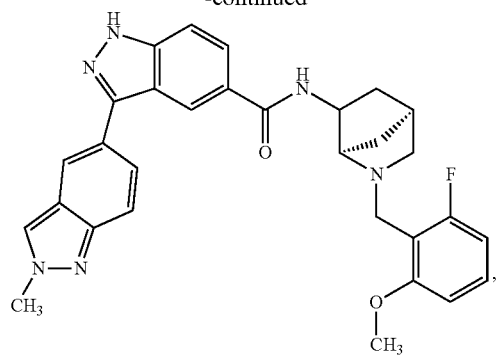
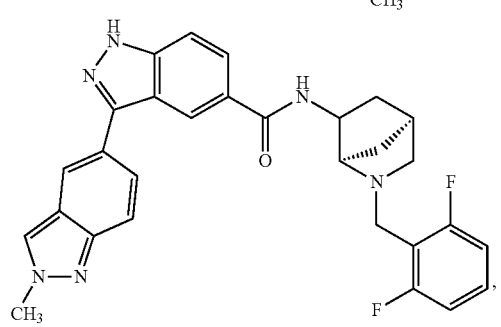
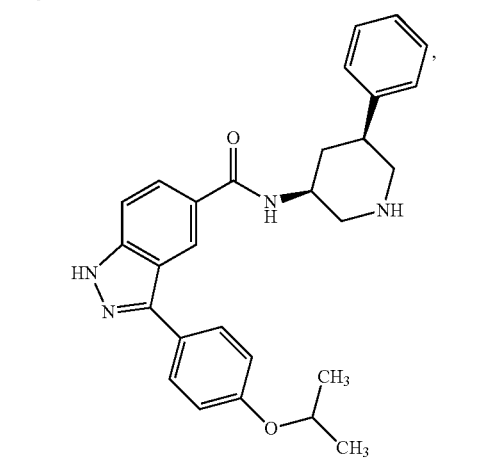
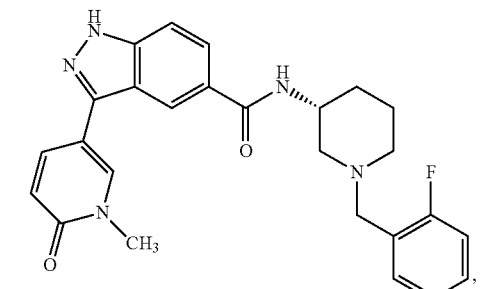
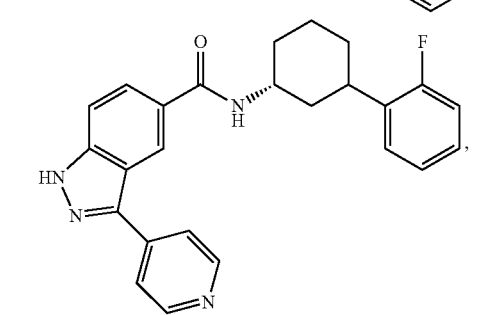
-continued
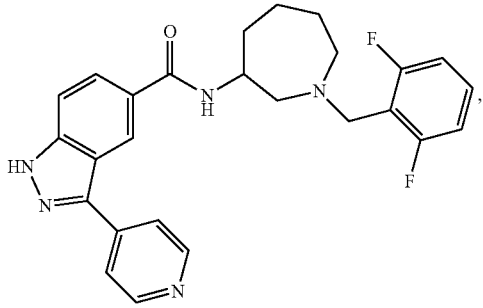
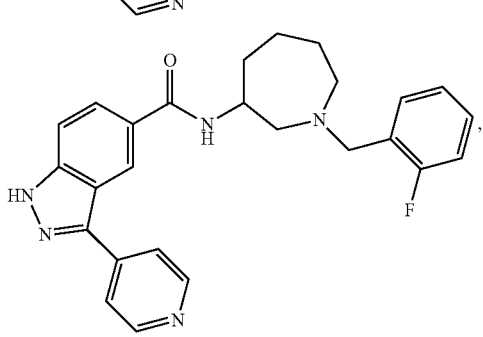
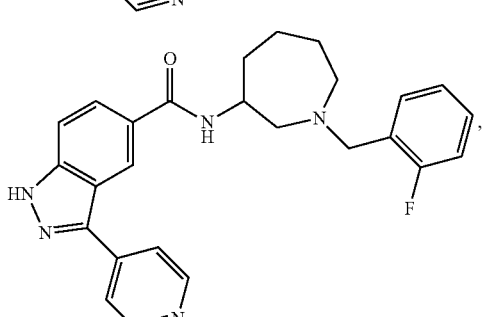
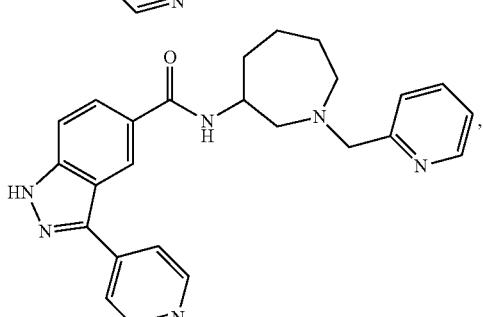
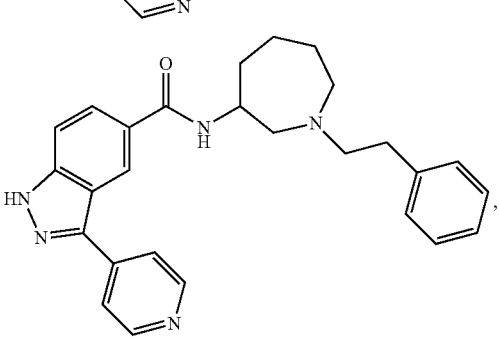

-continued
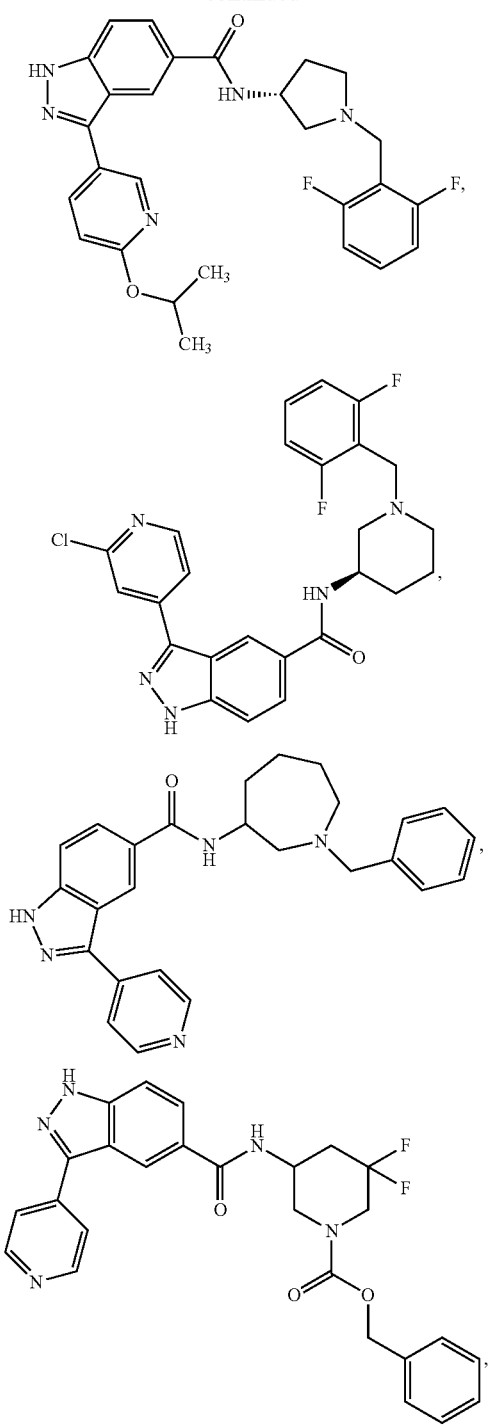
-continued
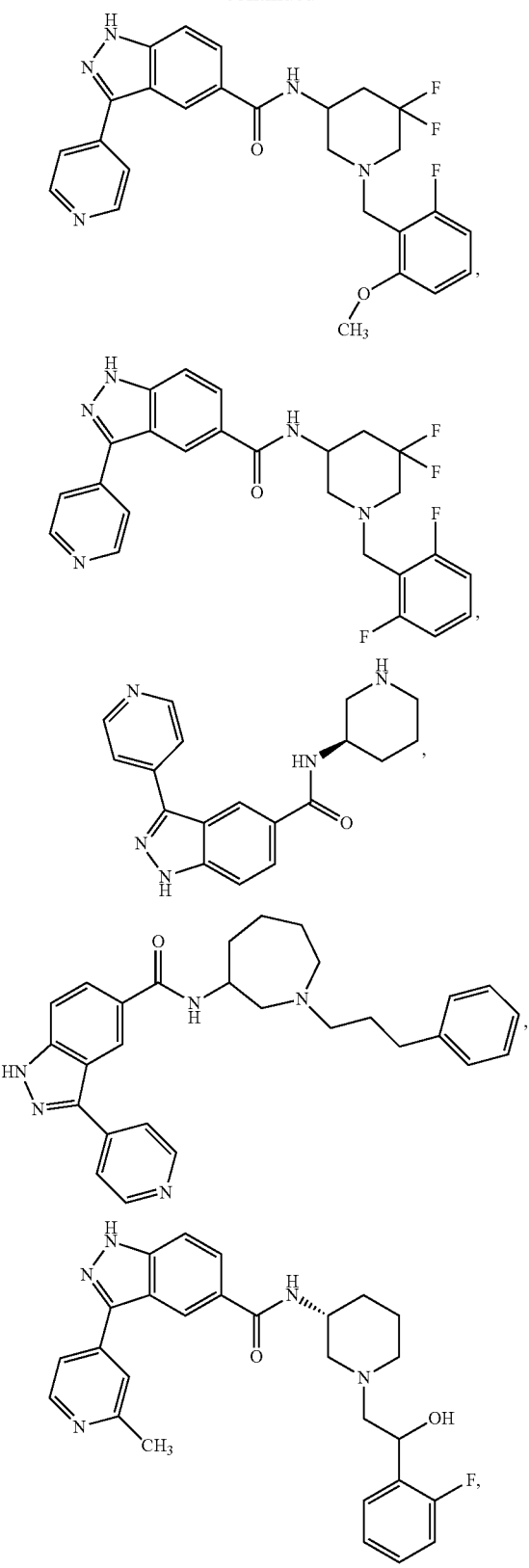

49
-continued
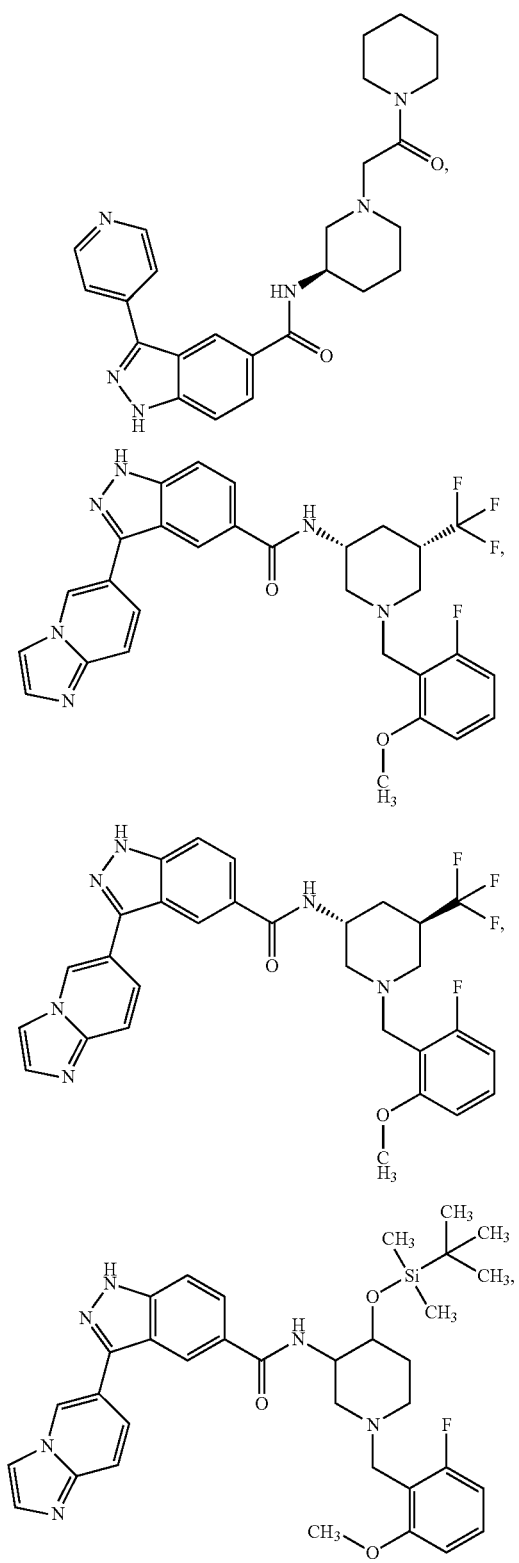
50
-continued
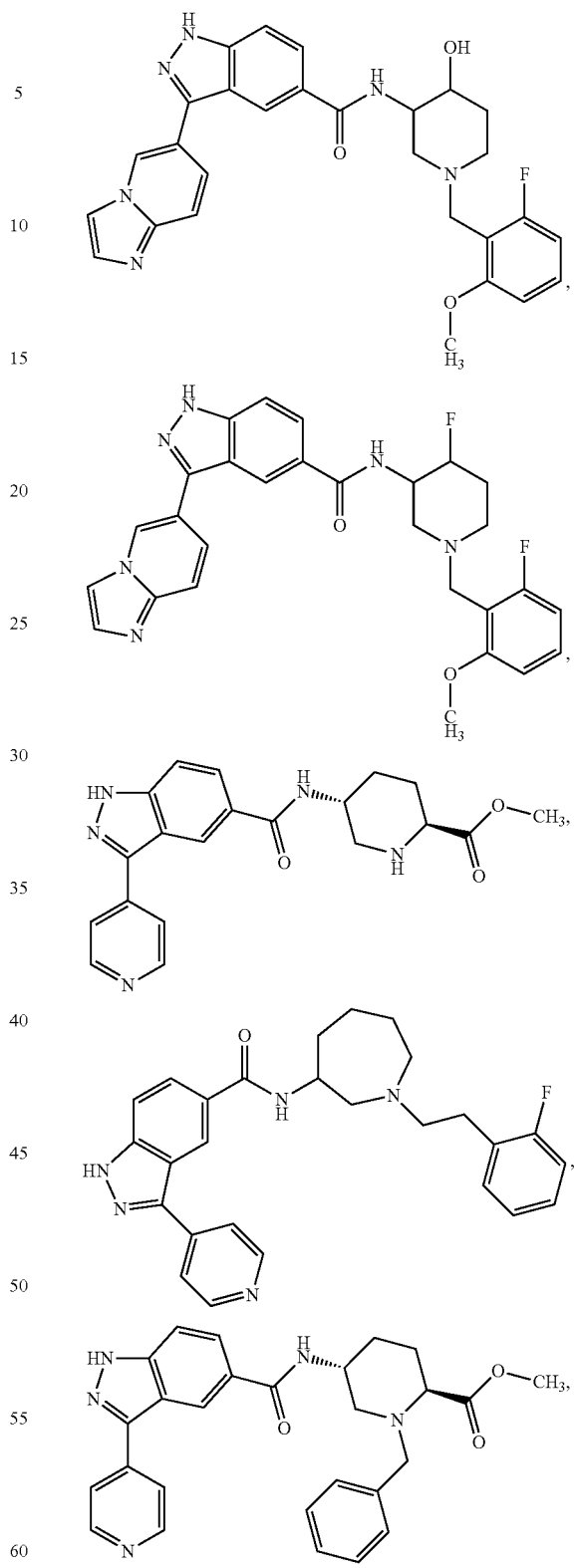

51
-continued
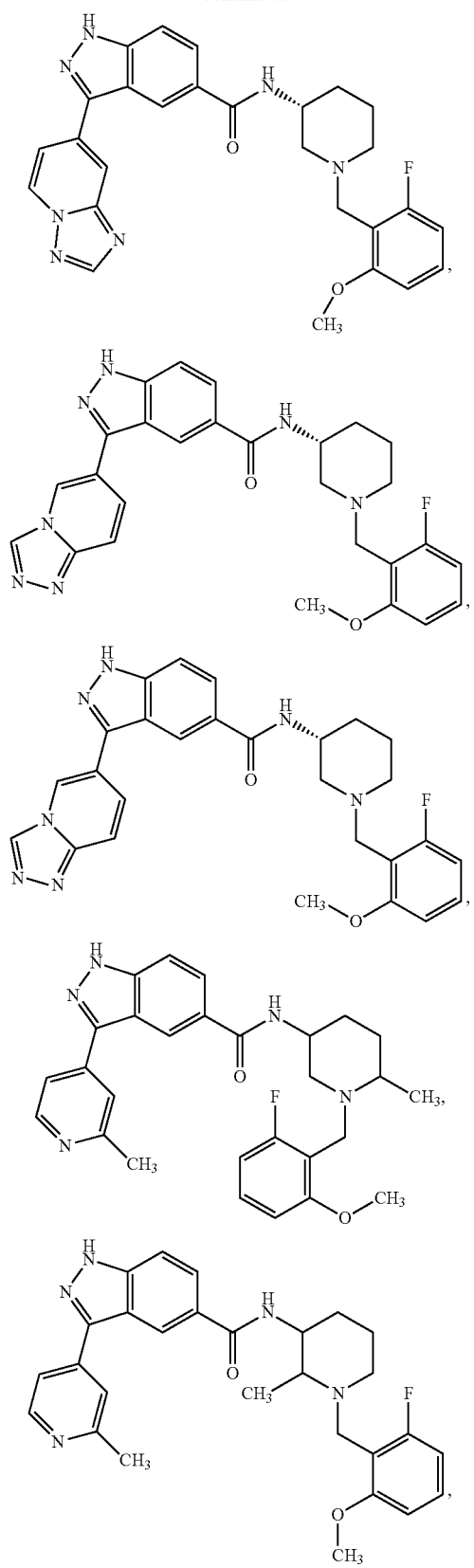
52
-continued
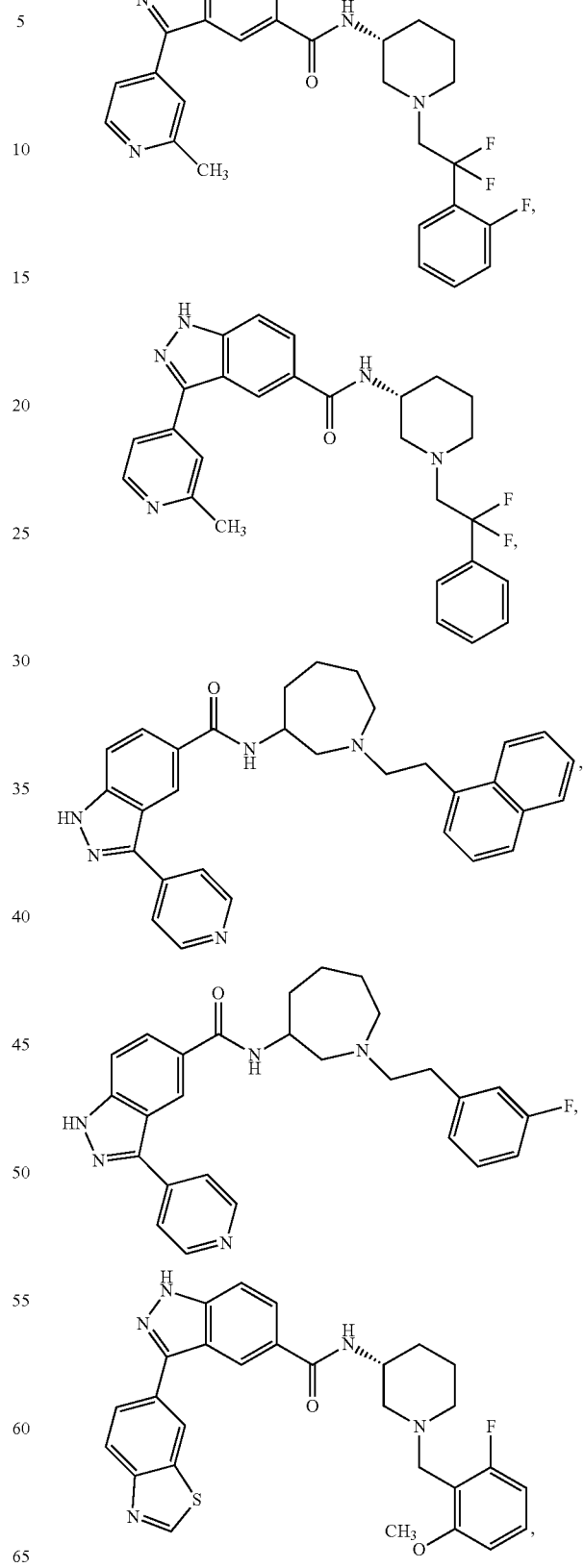

53
-continued
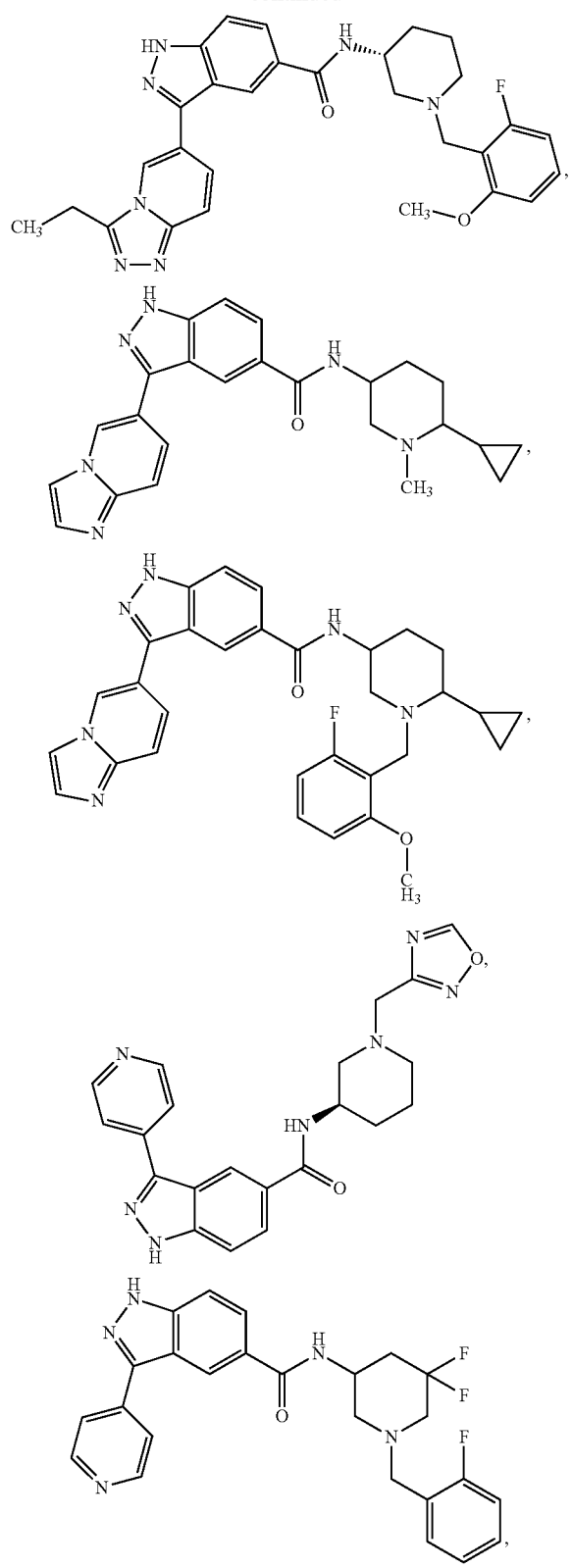
54
-continued
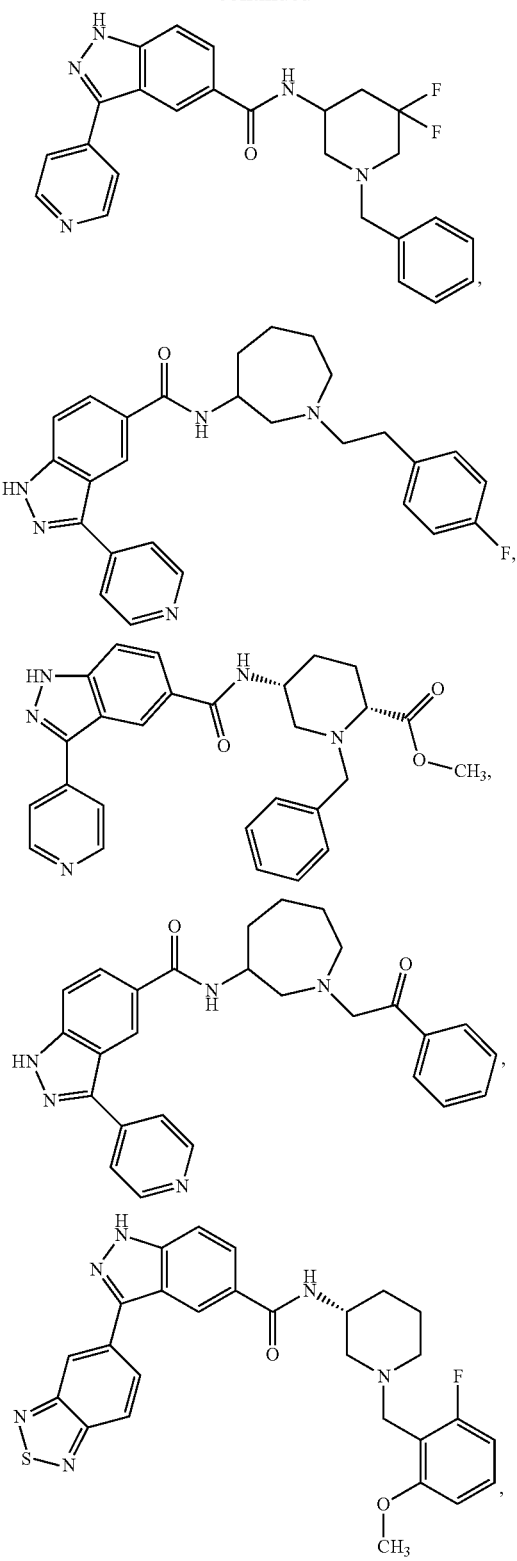

55
-continued
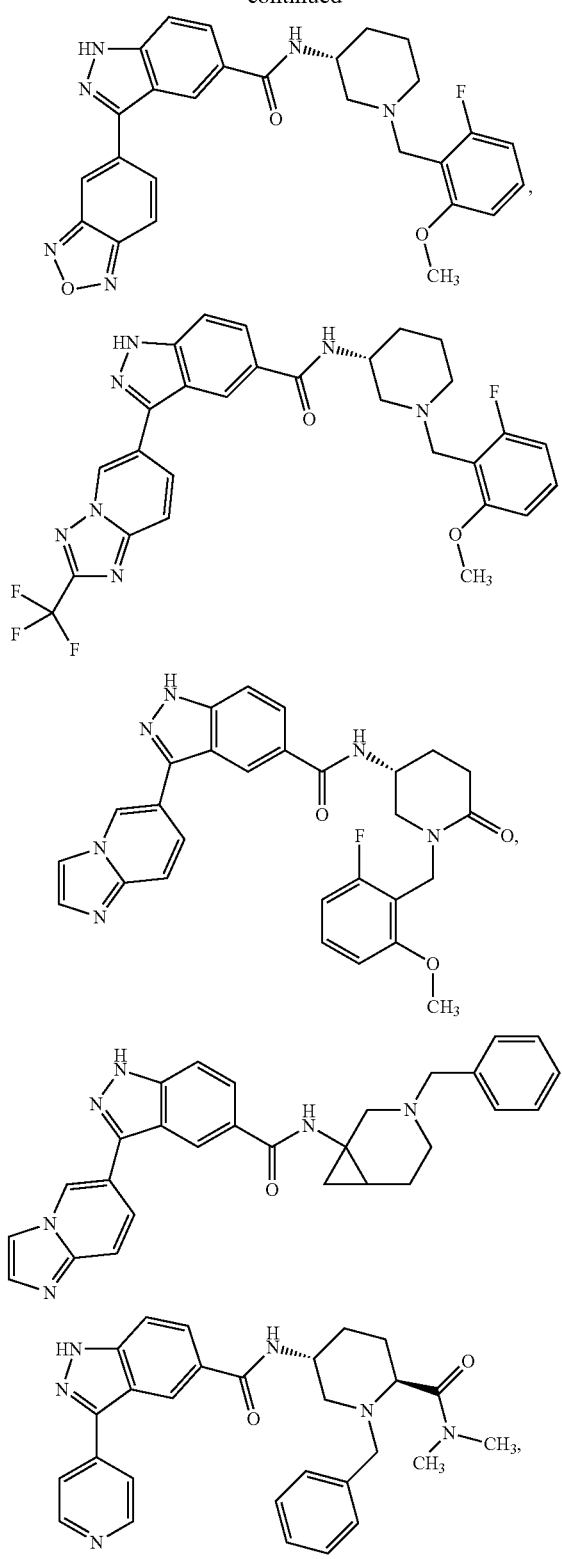
56
-continued
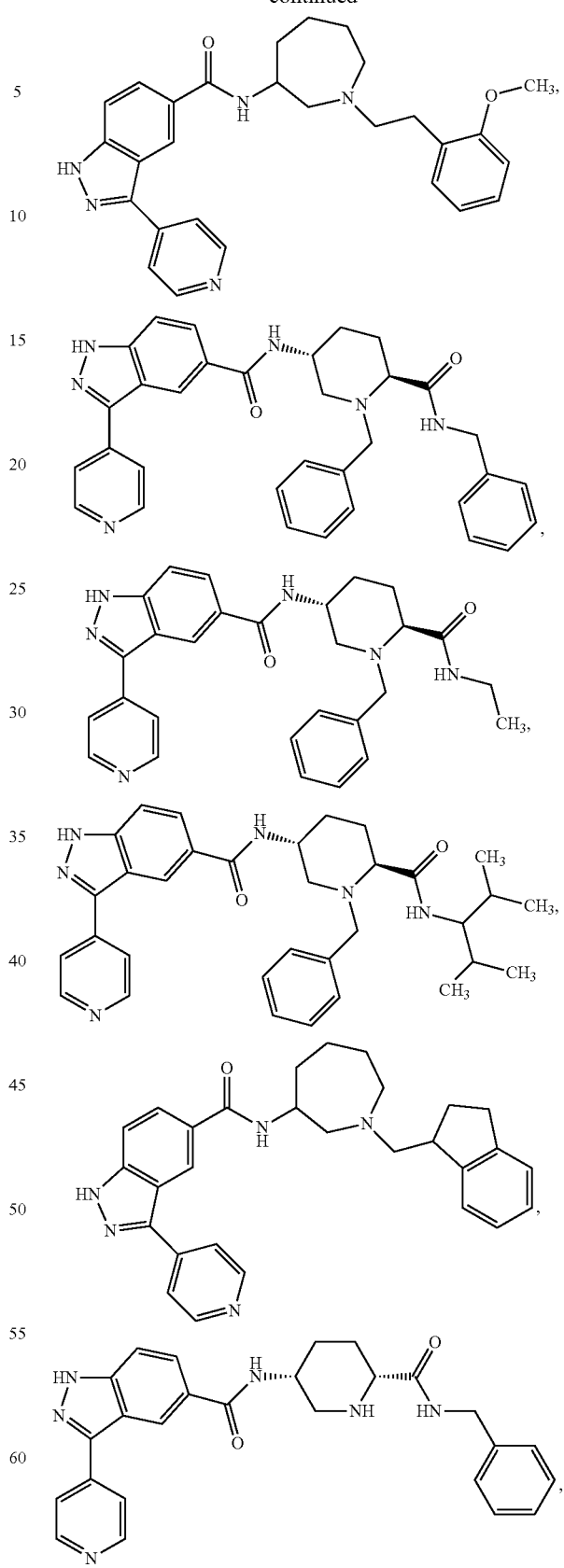

-continued
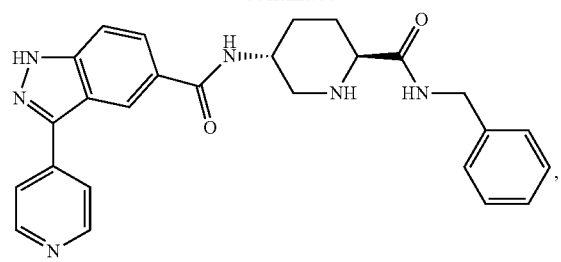
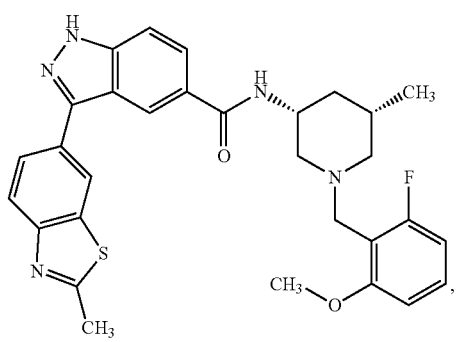
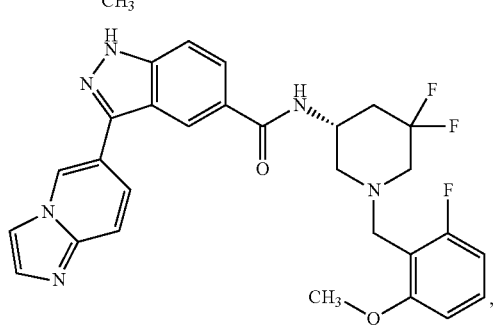
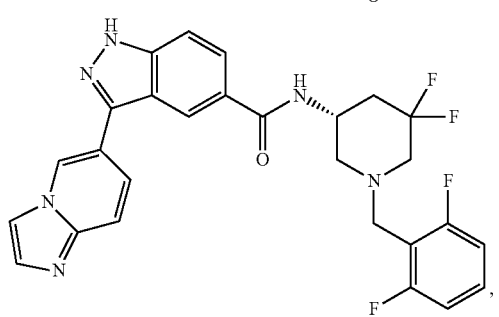
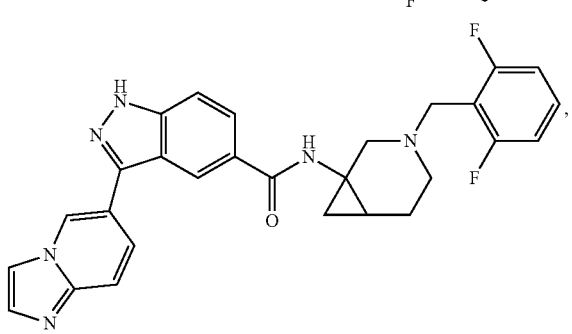
-continued
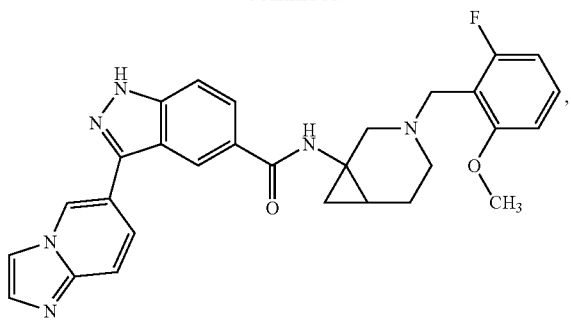
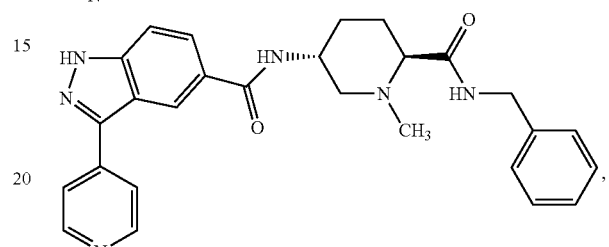
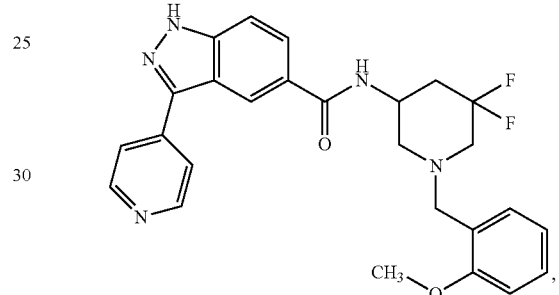
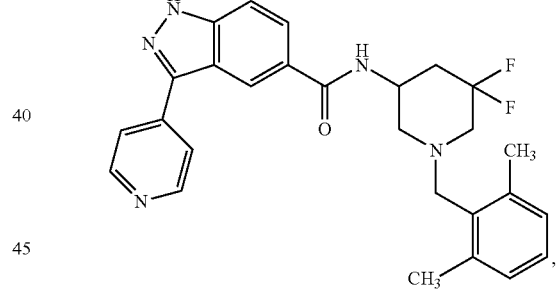
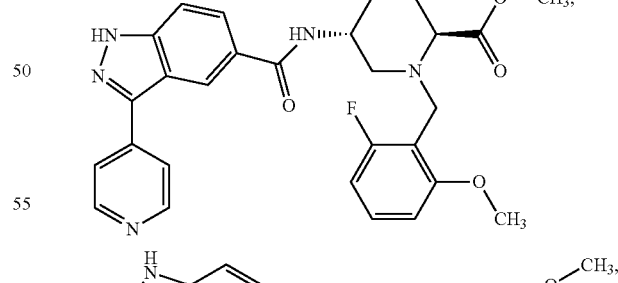
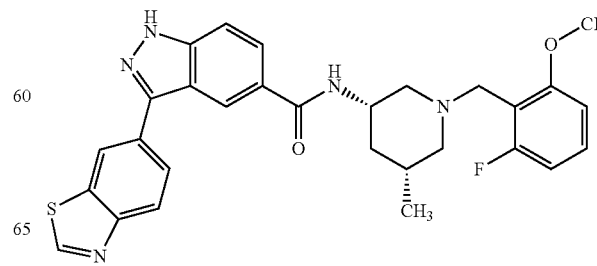

59
-continued
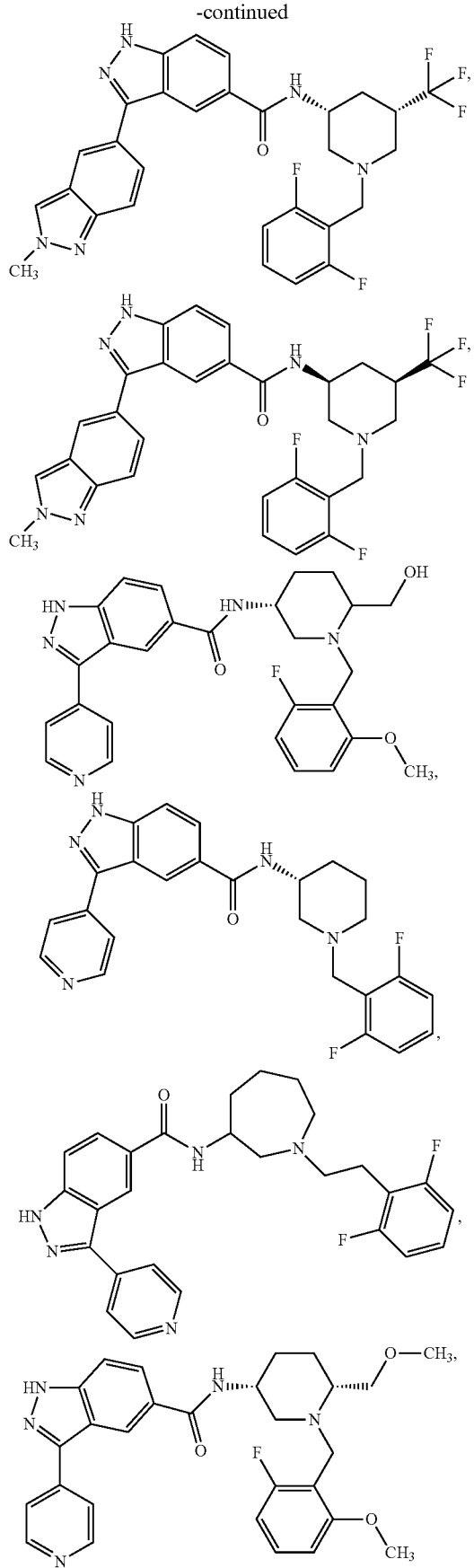
60
-continued
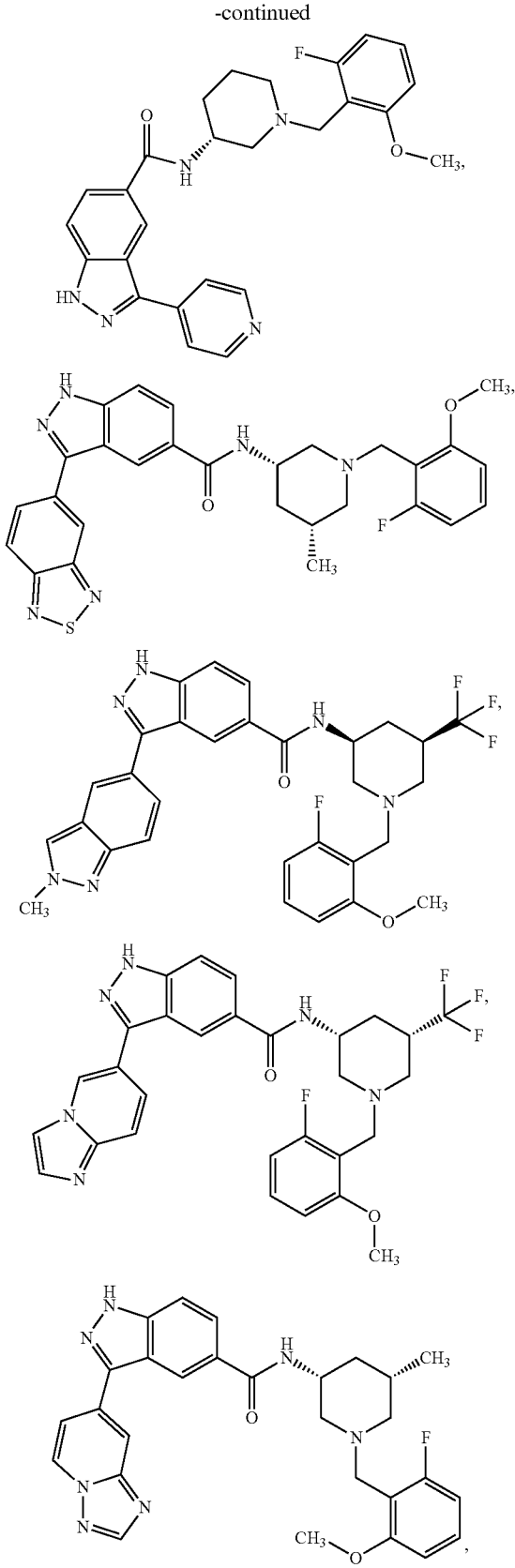

61
-continued
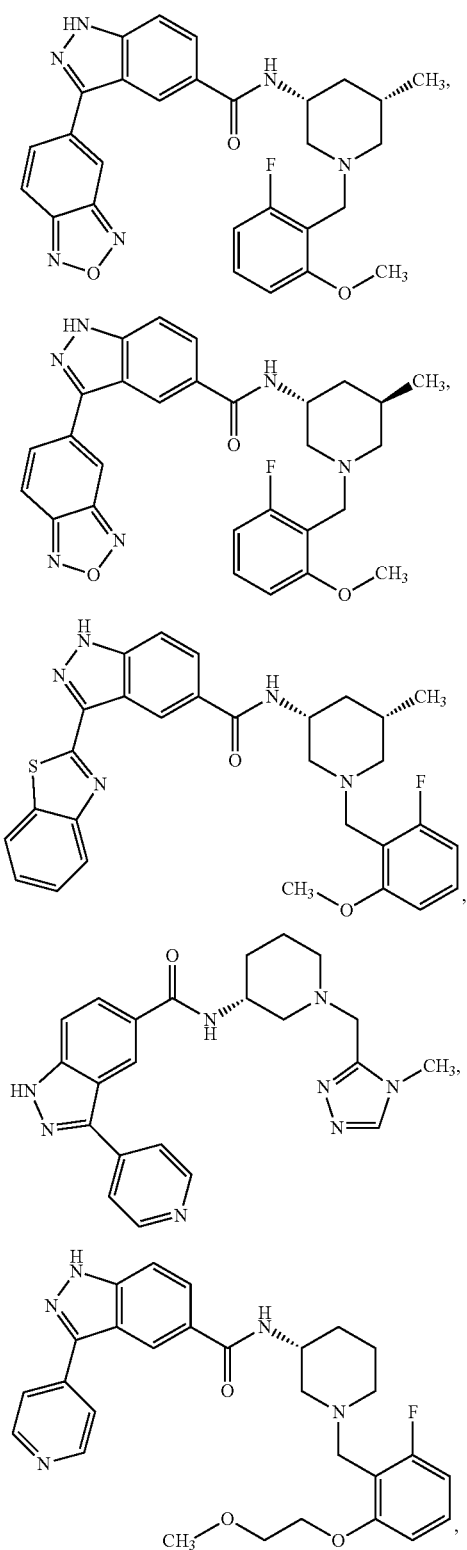
62
-continued
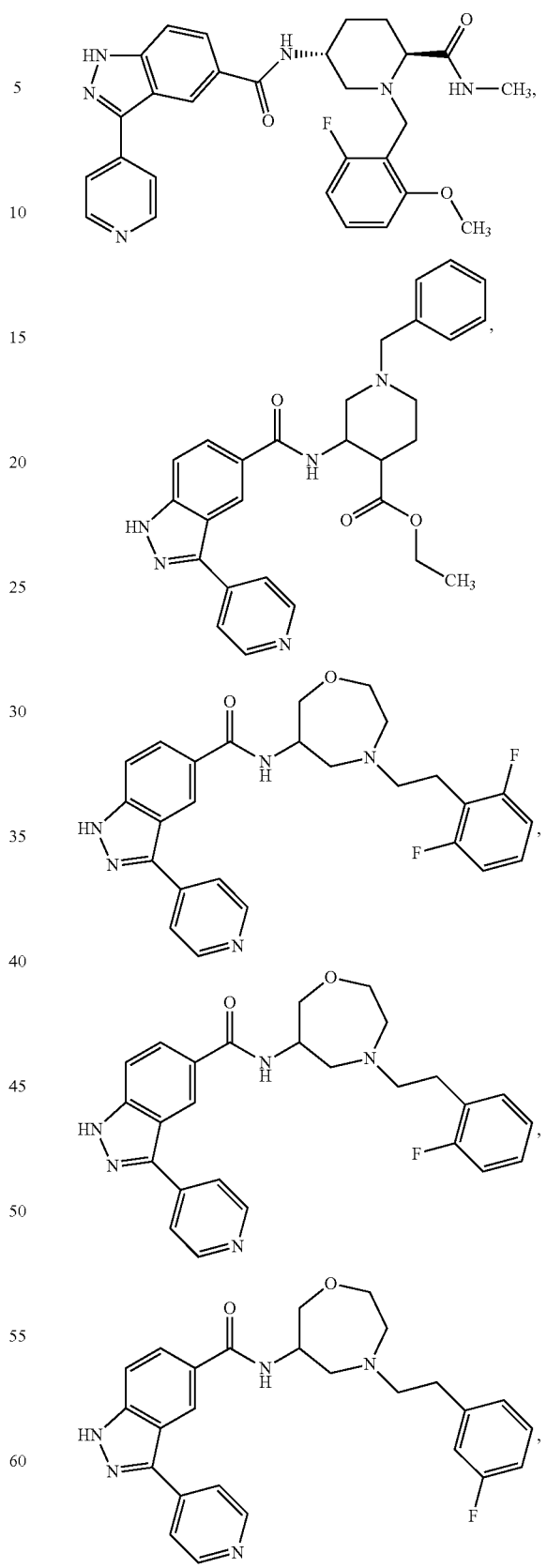

63
-continued
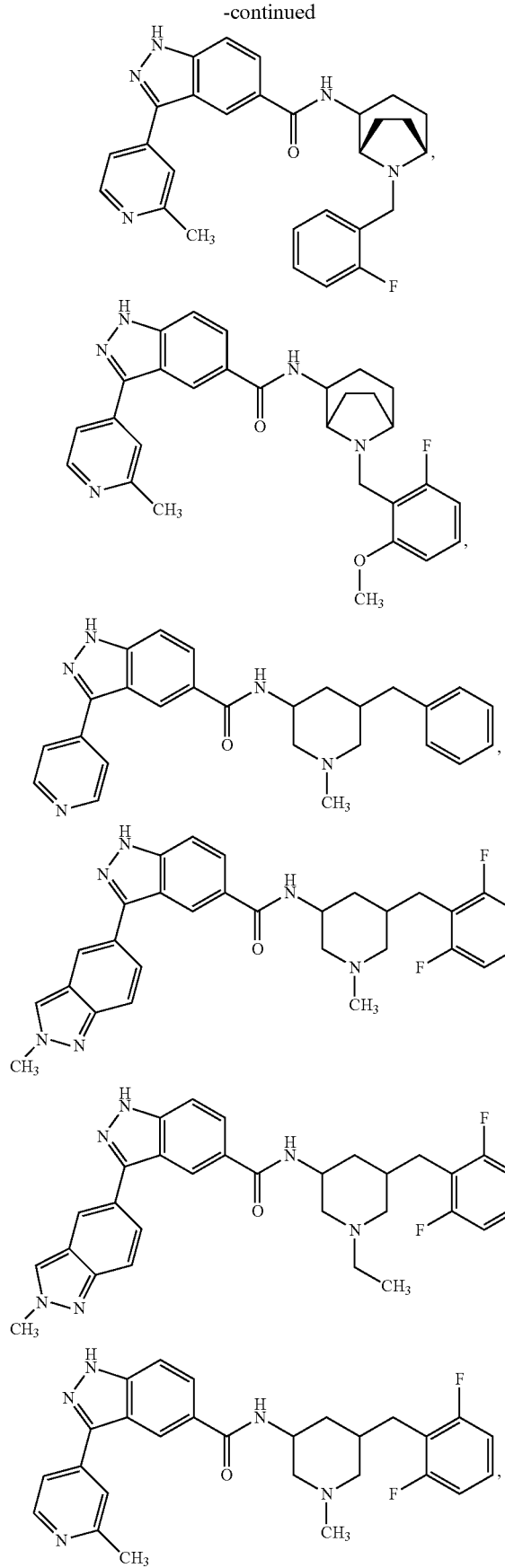
64
-continued
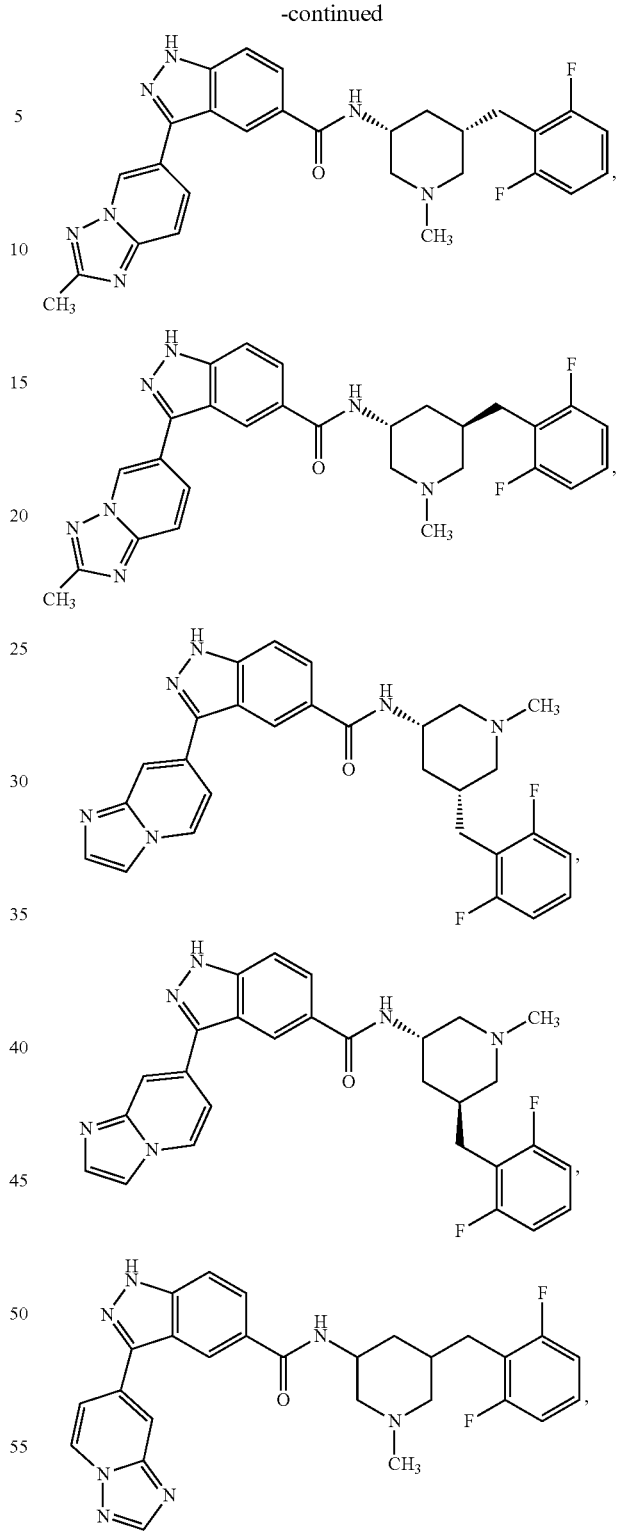

65
-continued
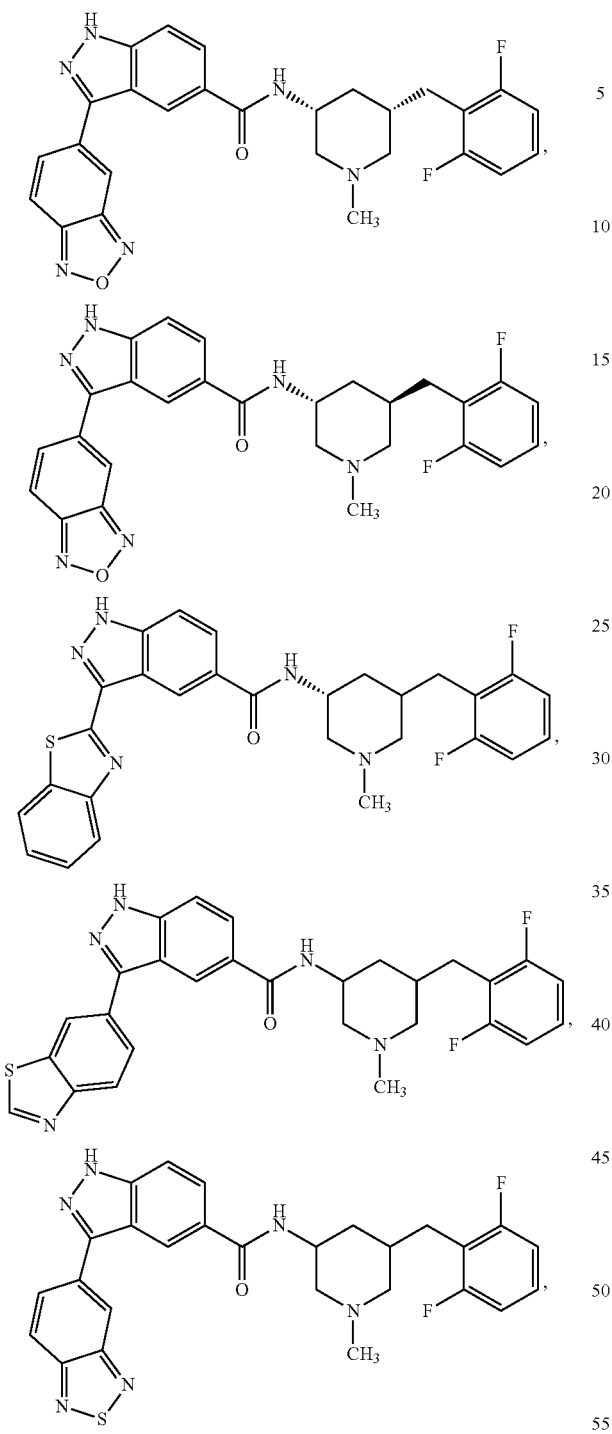
66
-continued
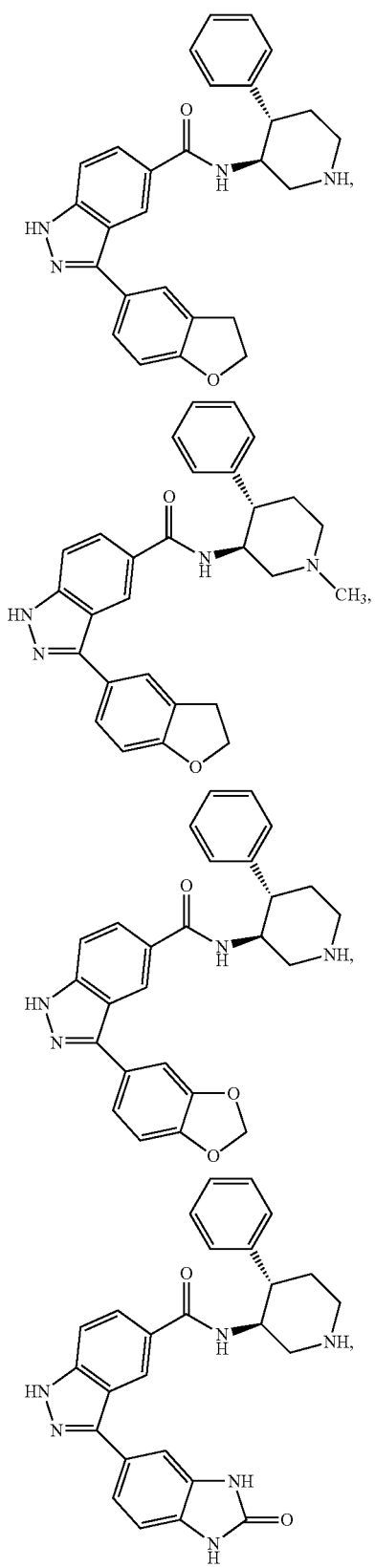

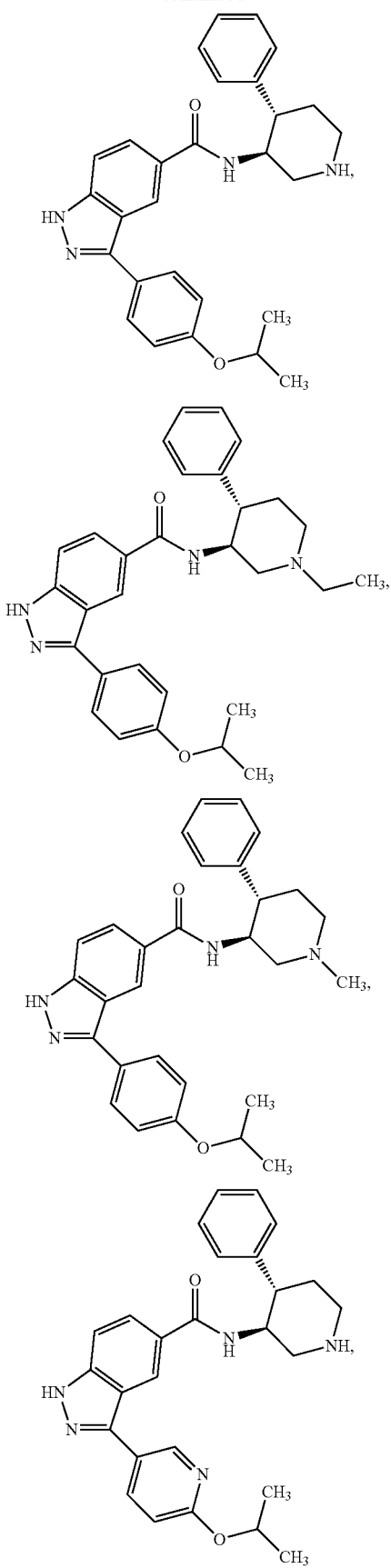
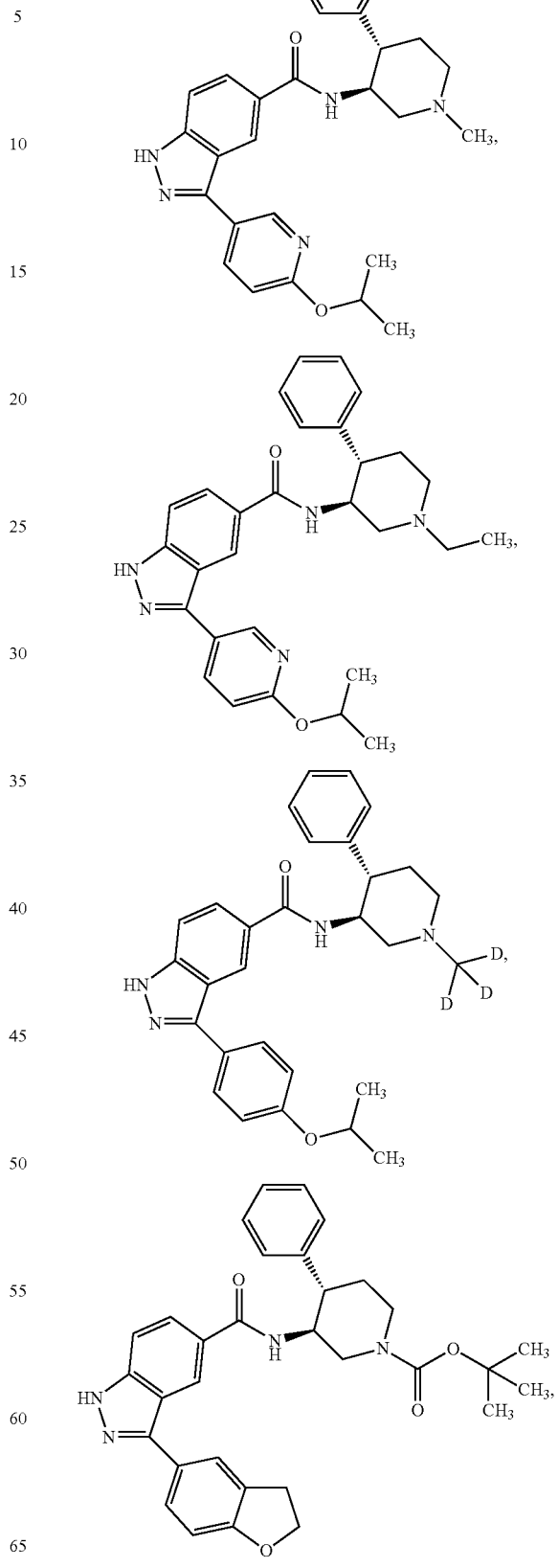

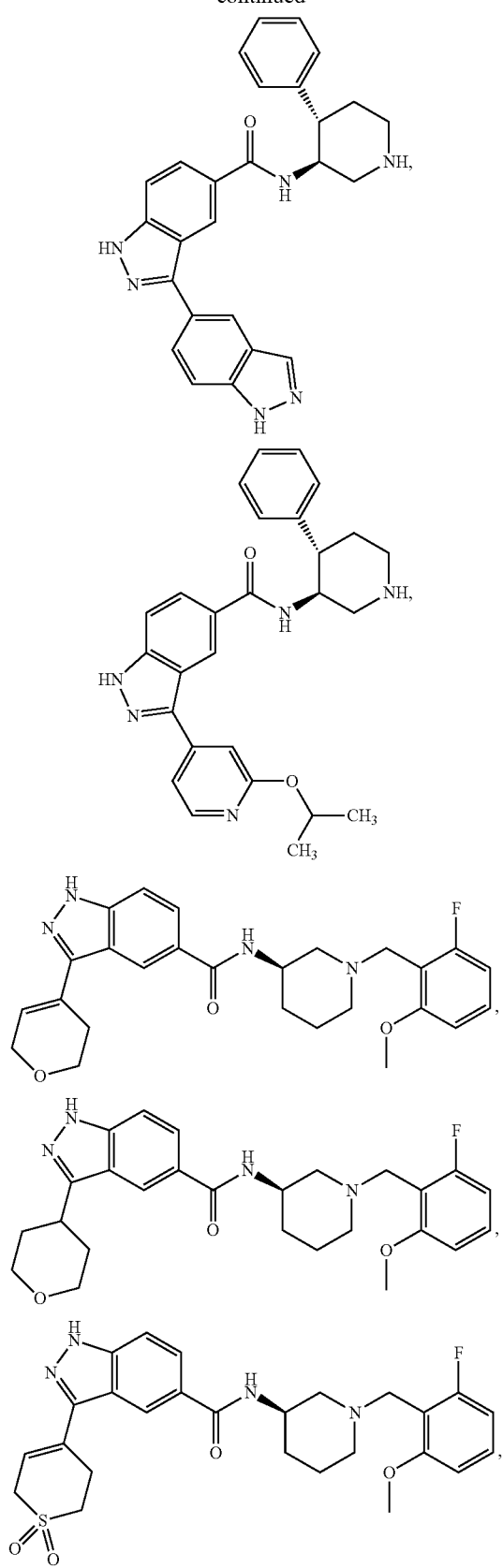
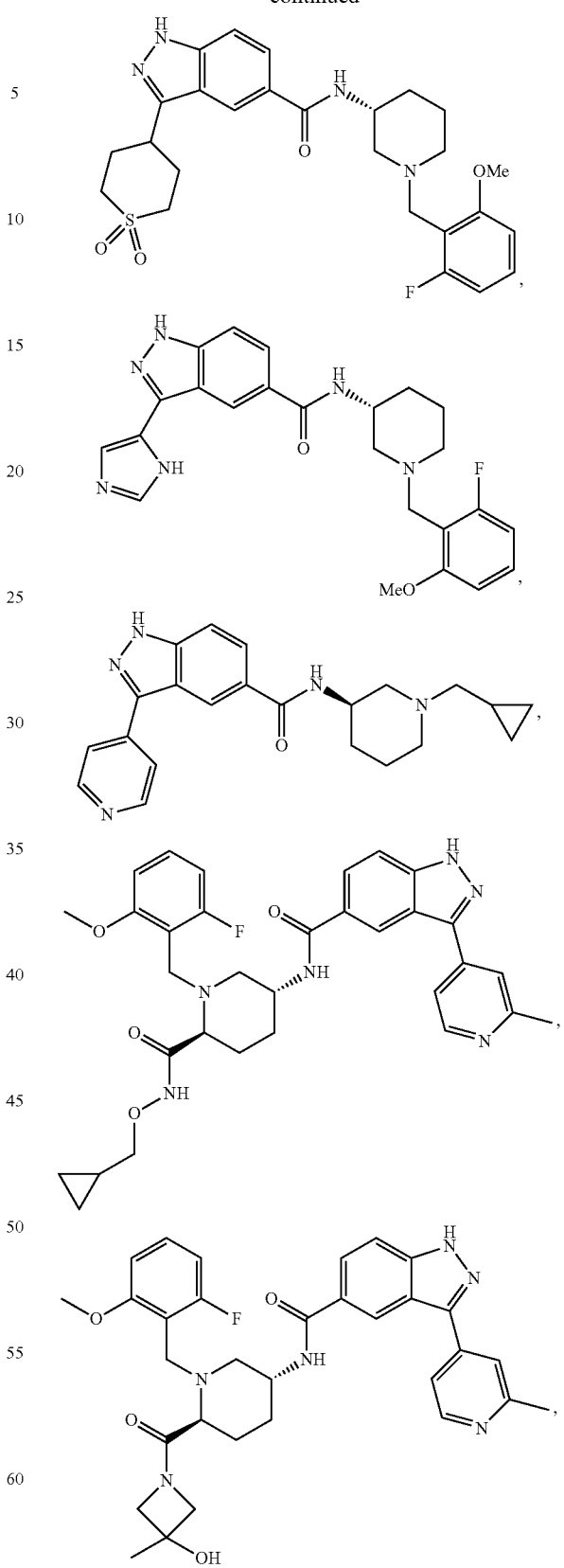

71
-continued
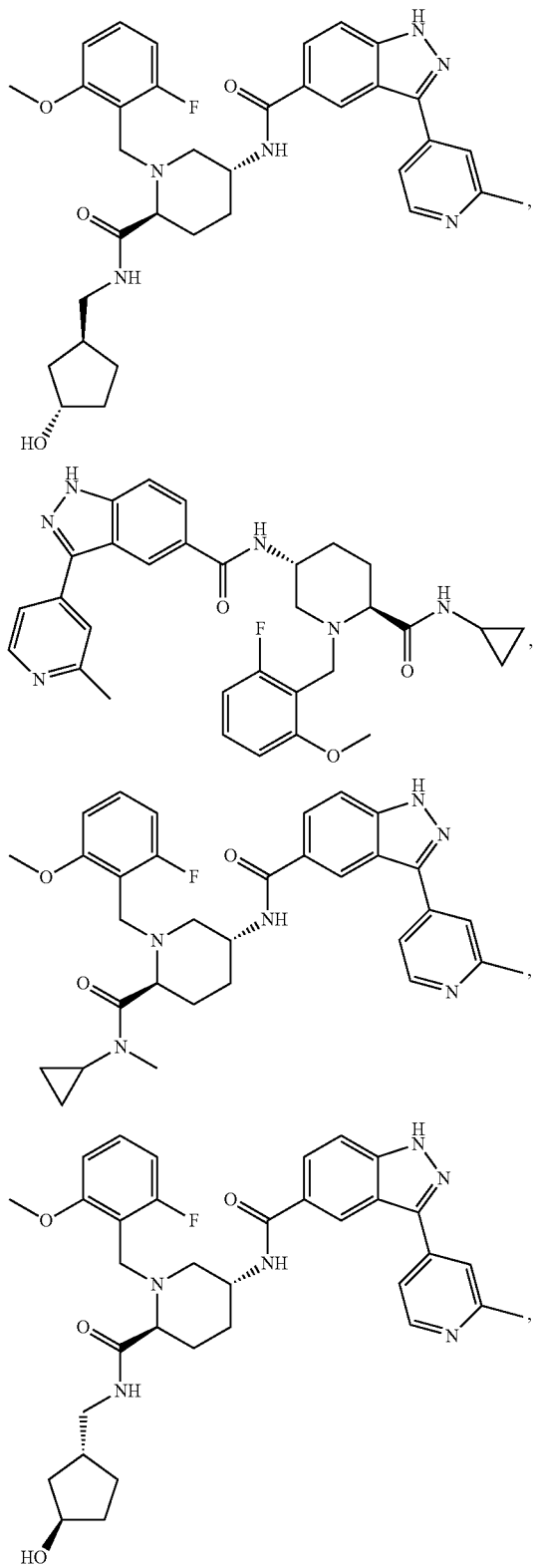
72
-continued
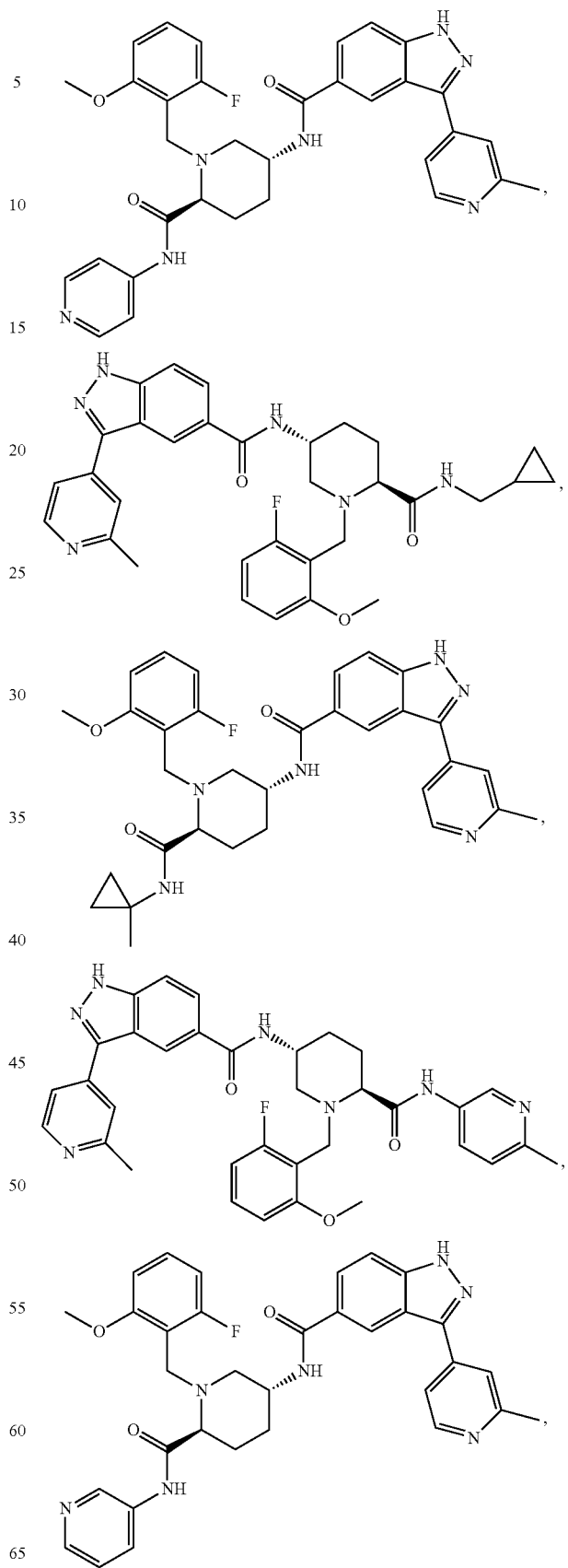

73
-continued
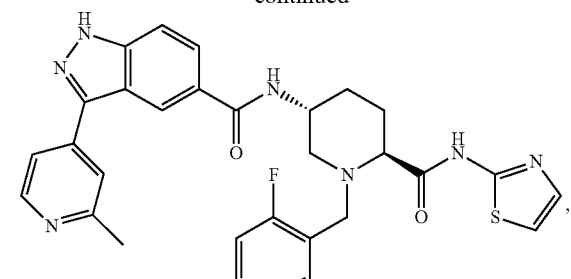
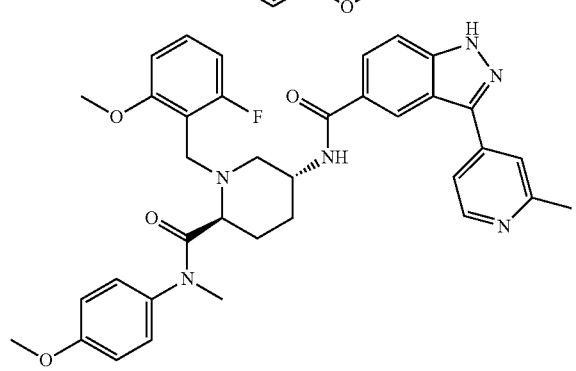
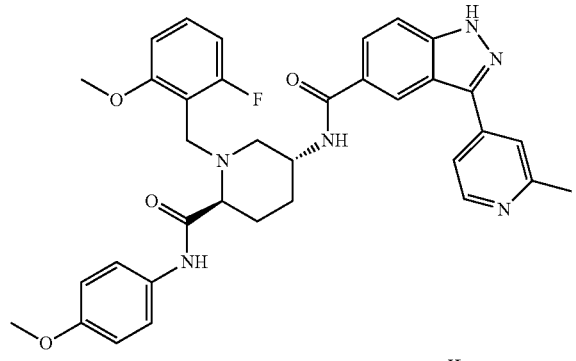
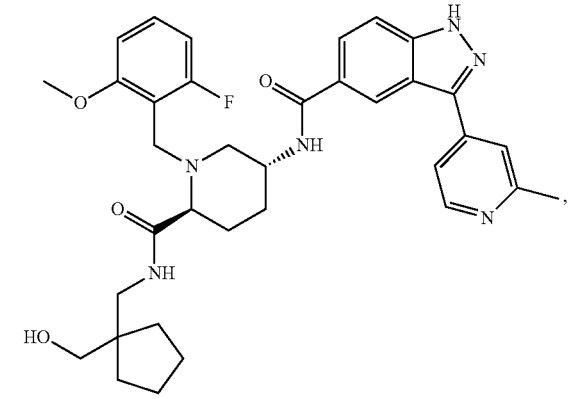
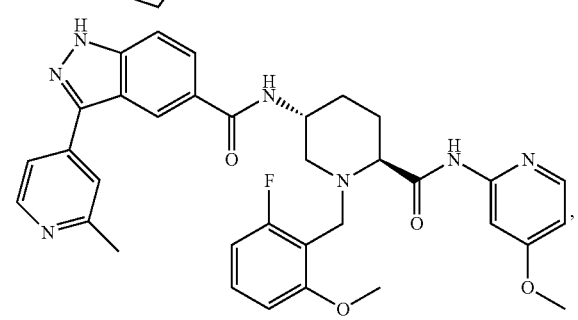
74
-continued
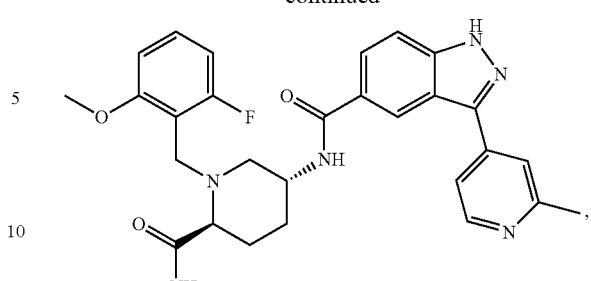
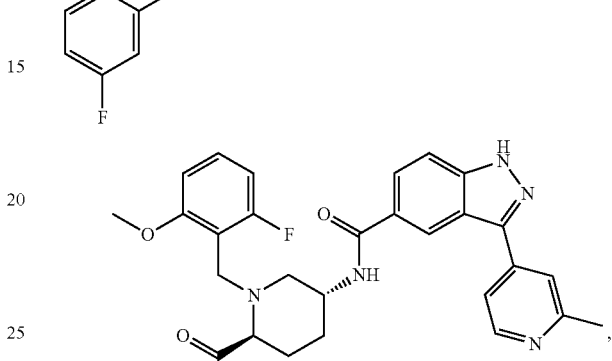
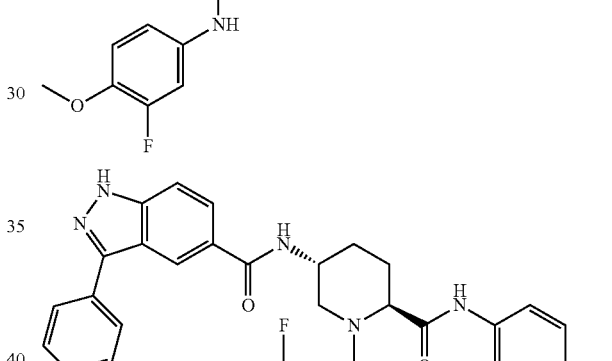
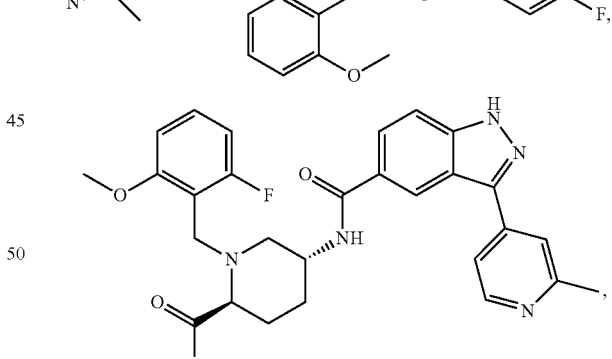

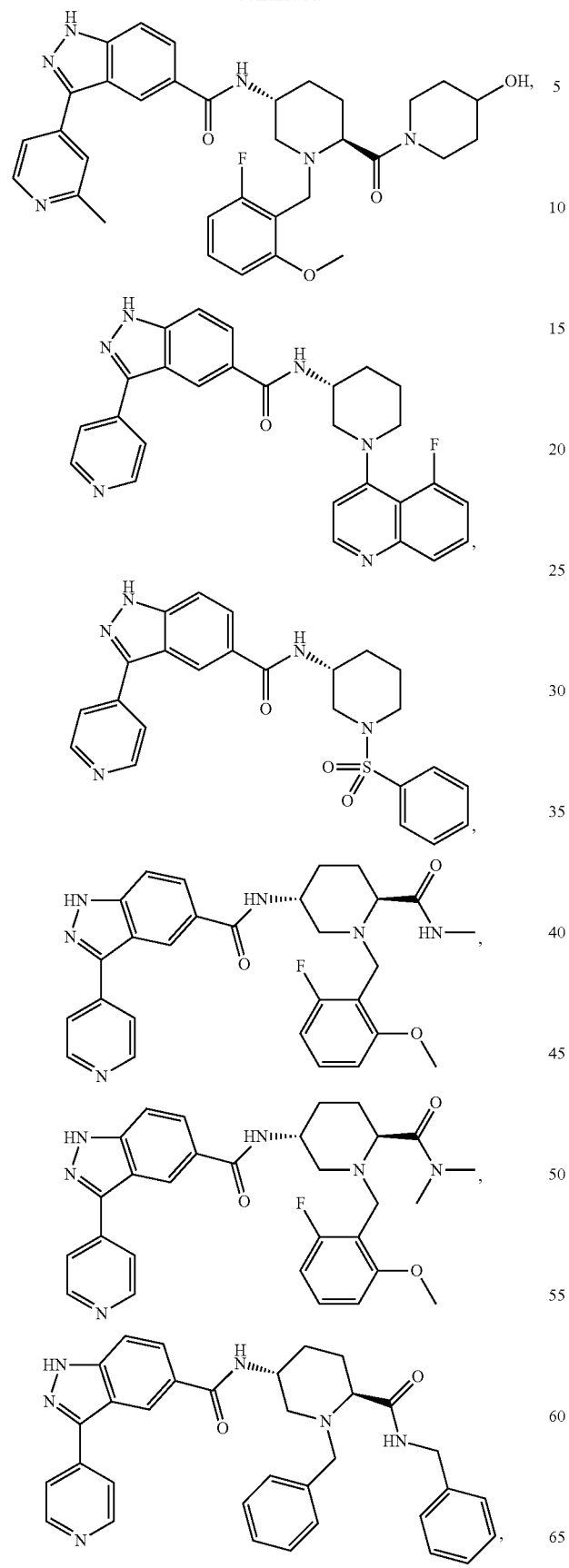
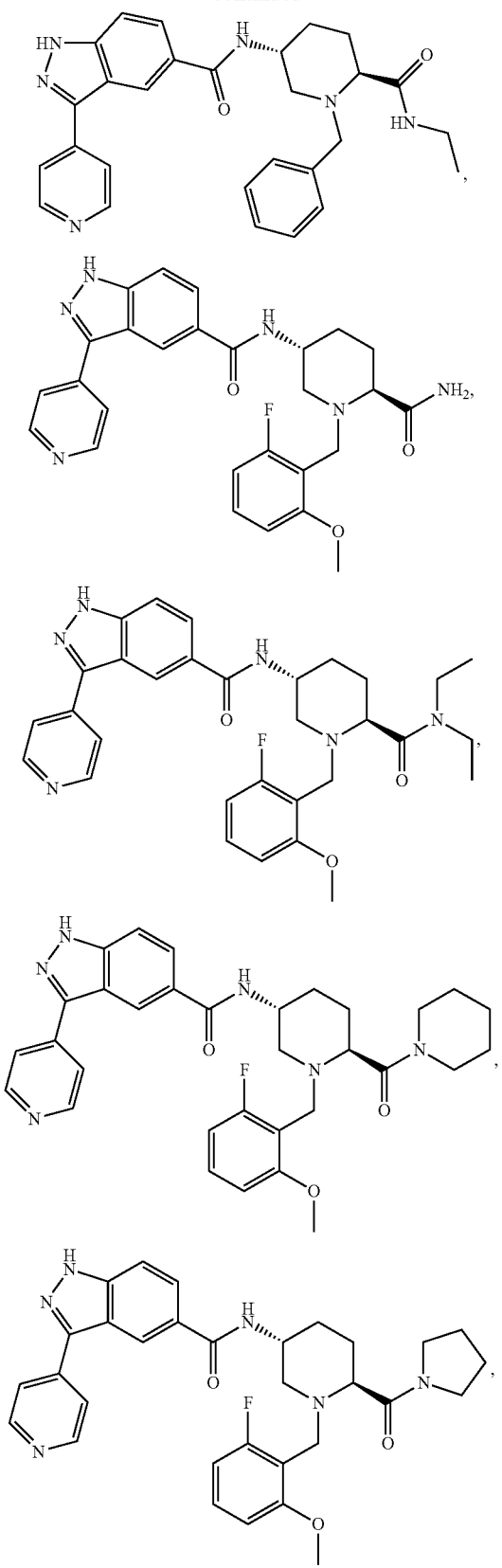

77
-continued
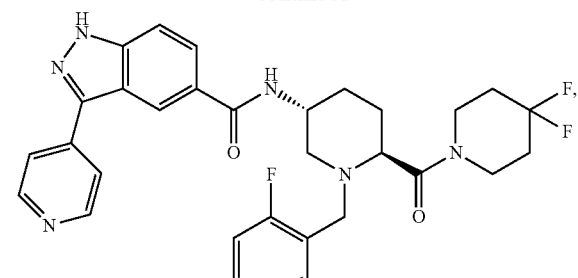
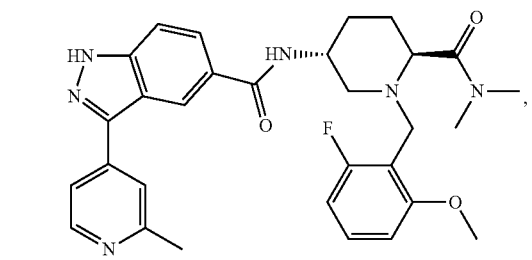
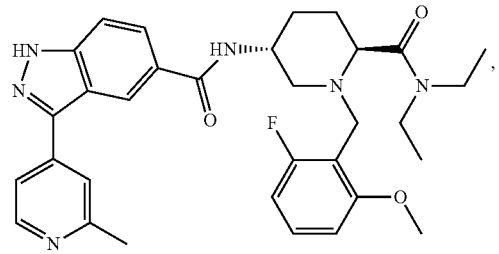
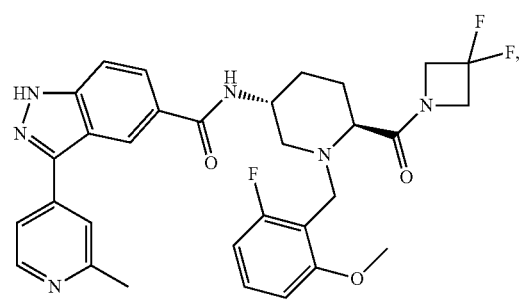
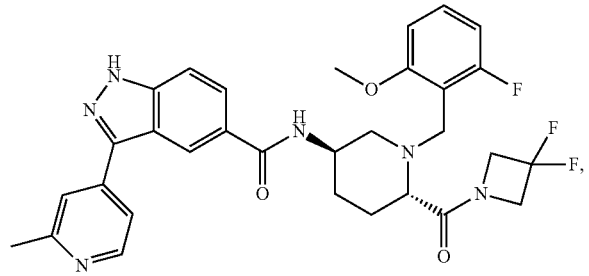
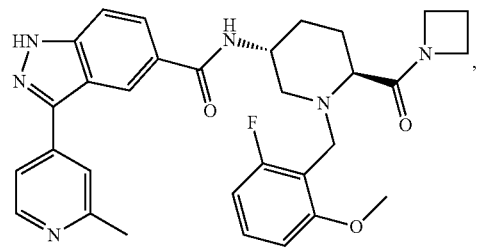
78
-continued
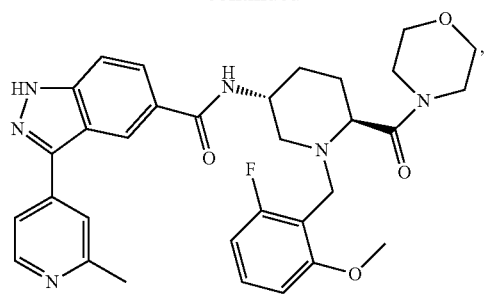
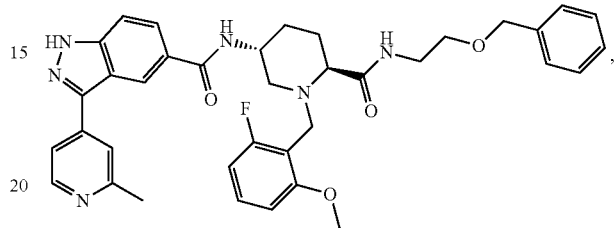
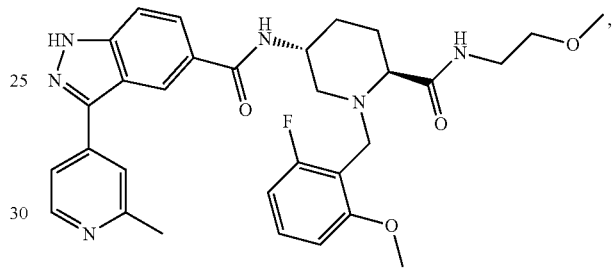
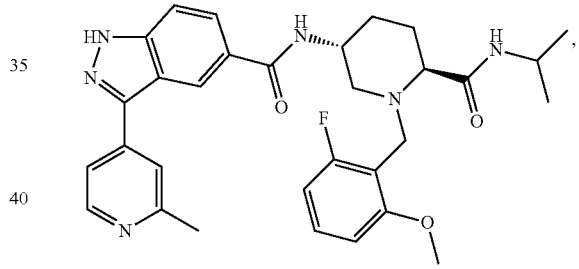
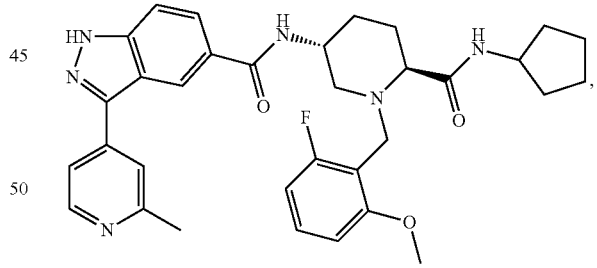
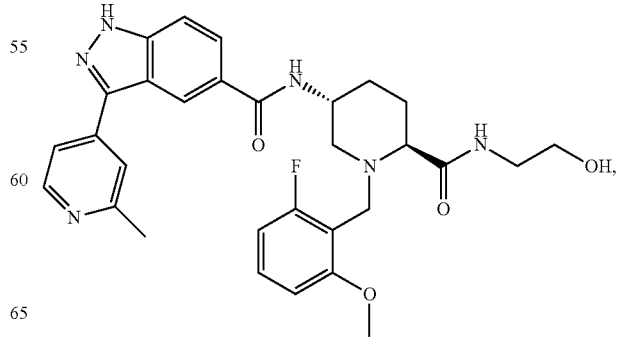

79
-continued
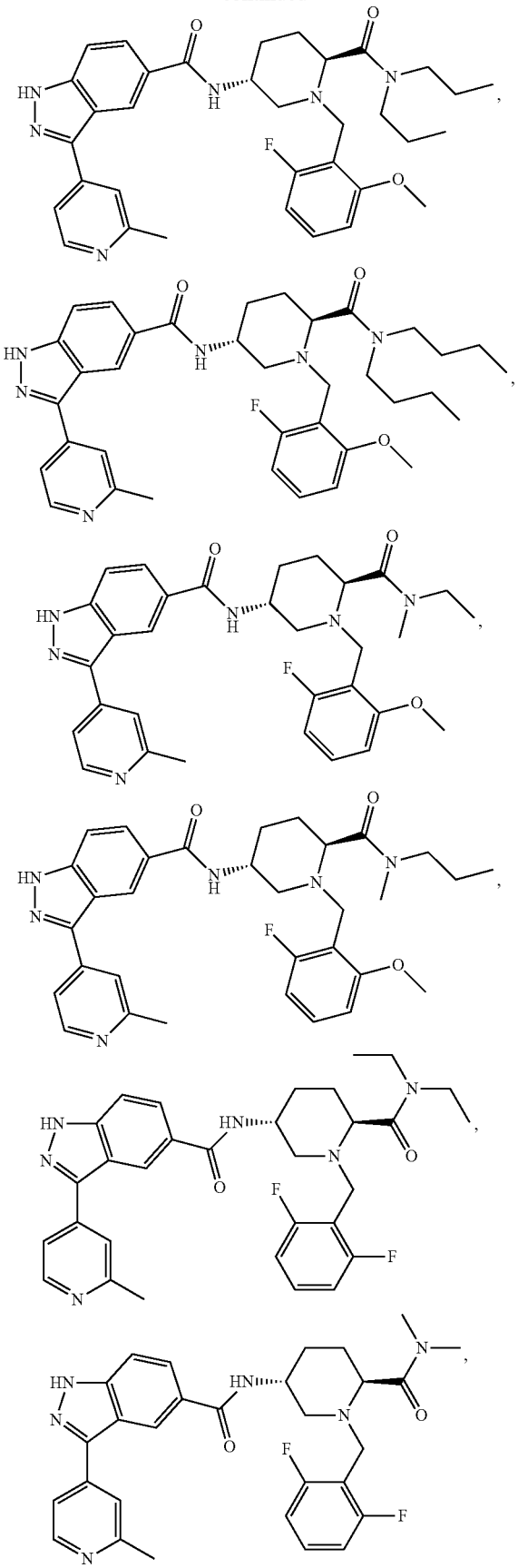
80
-continued
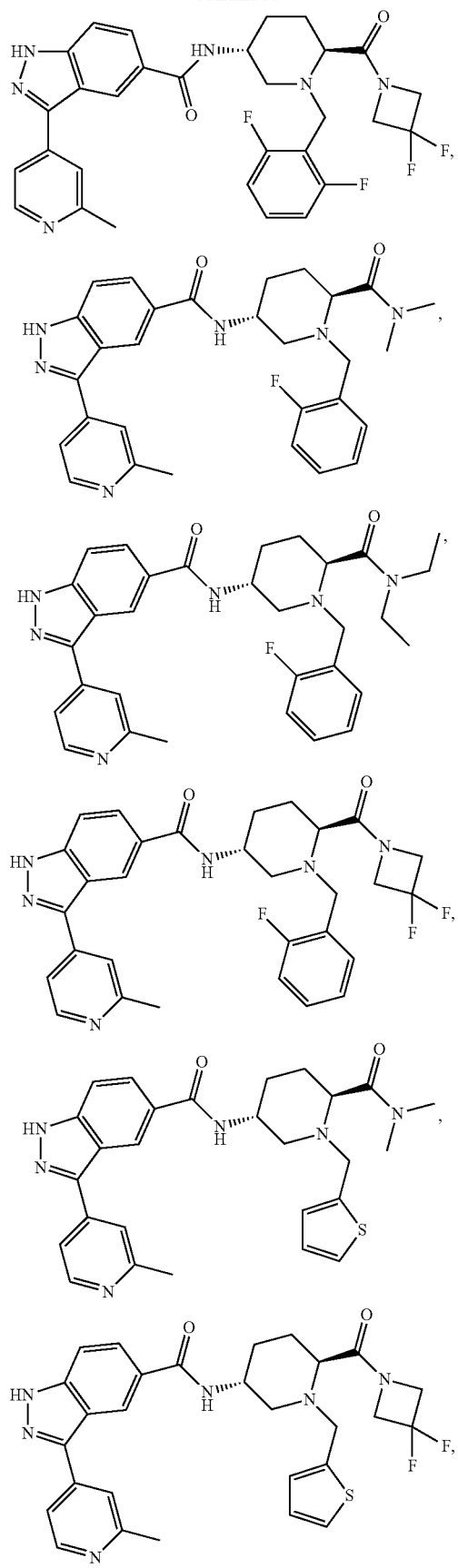

-continued
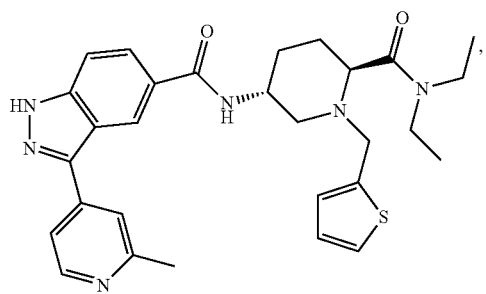
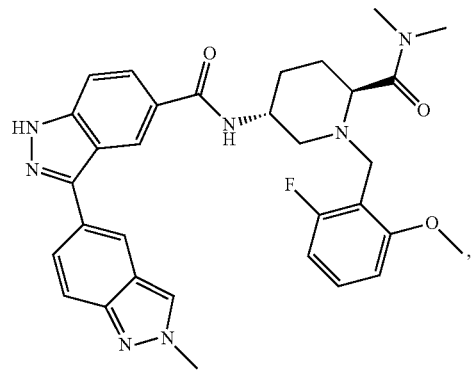
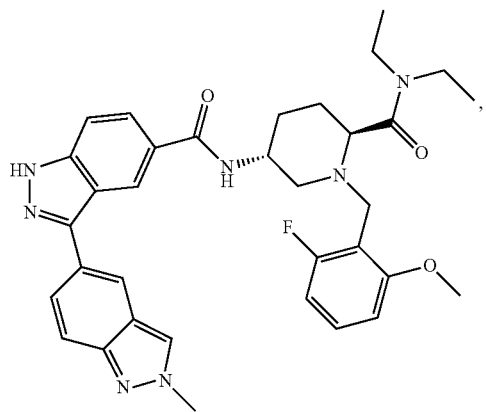
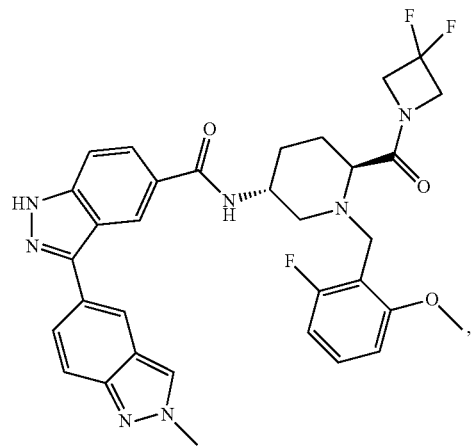
-continued
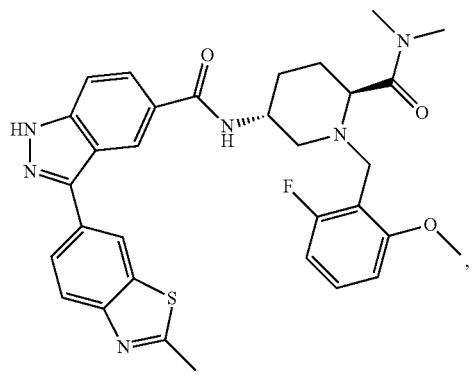
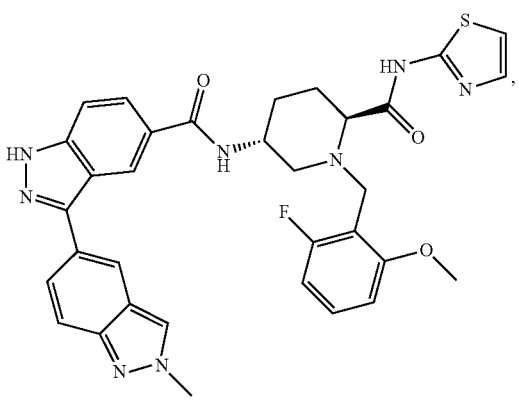
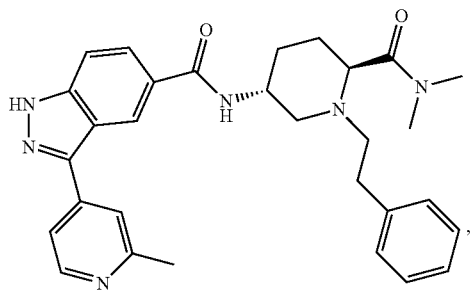
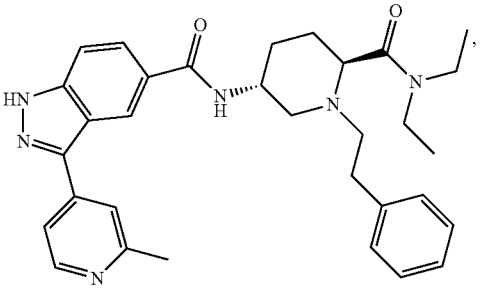
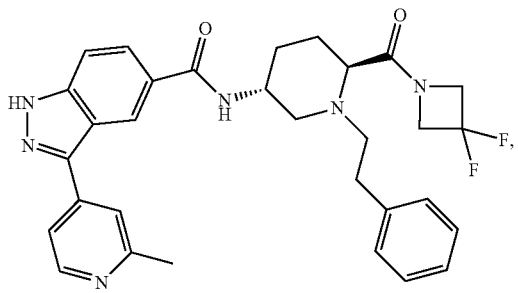

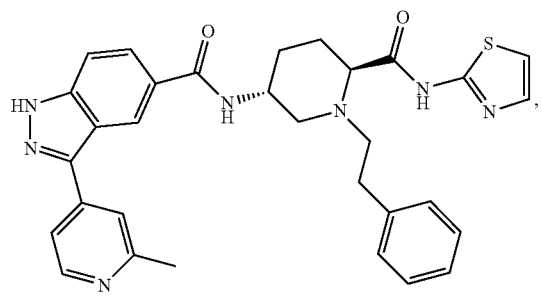
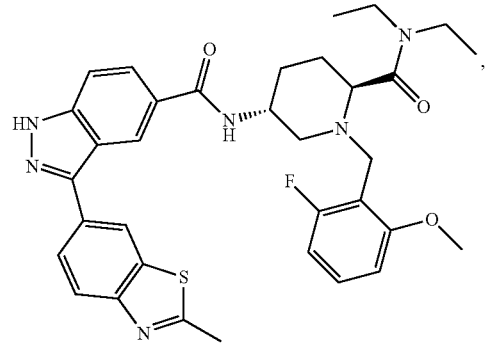
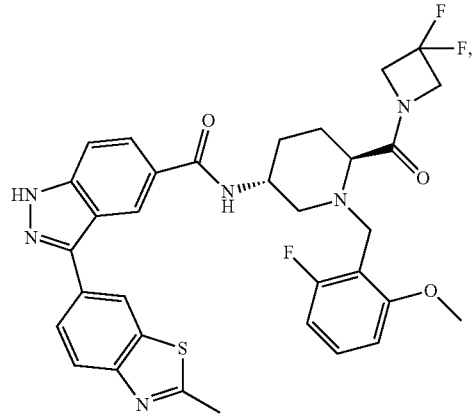
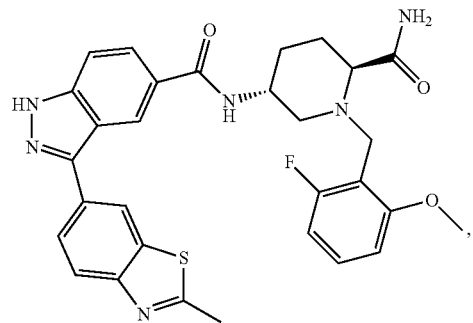
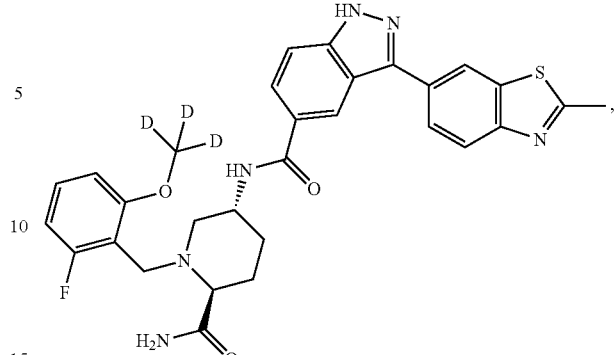
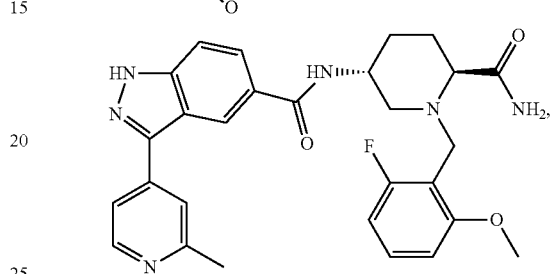
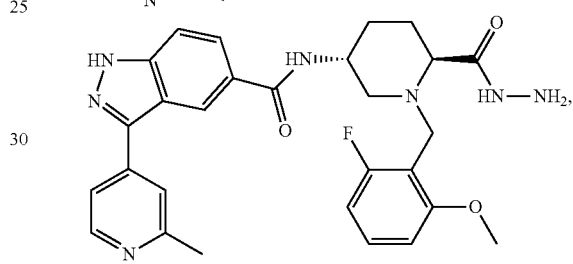
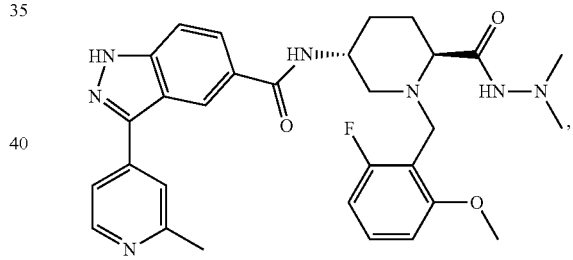
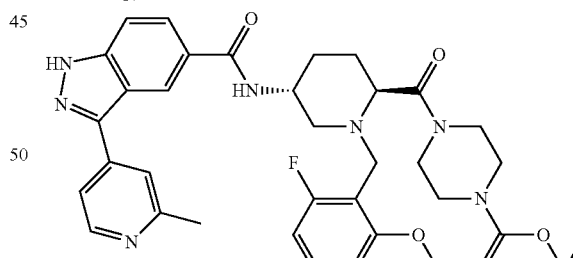
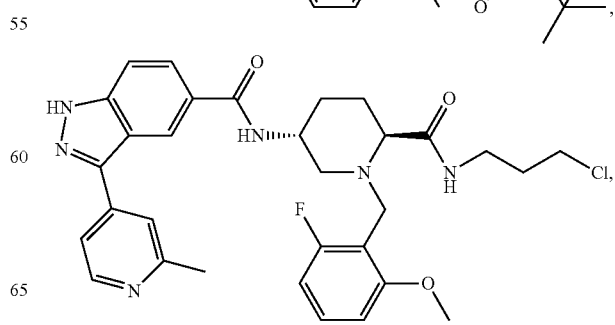

85
-continued
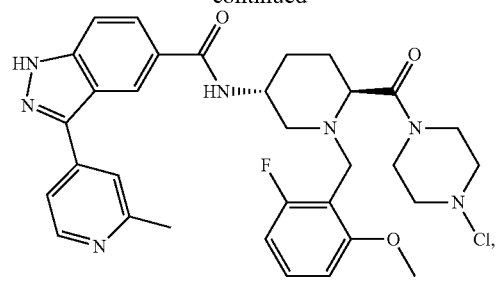
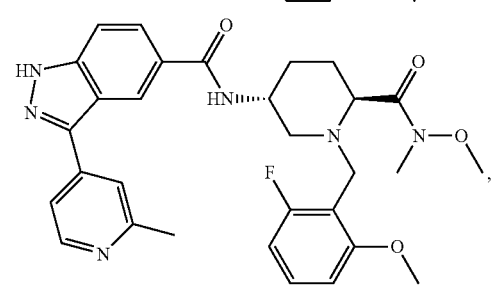
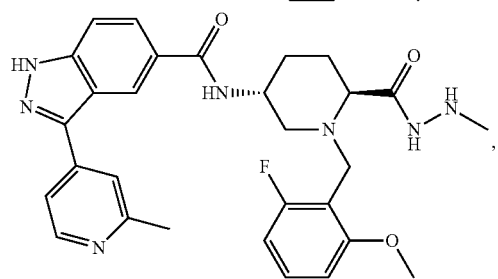
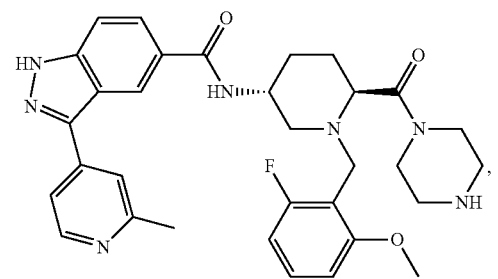
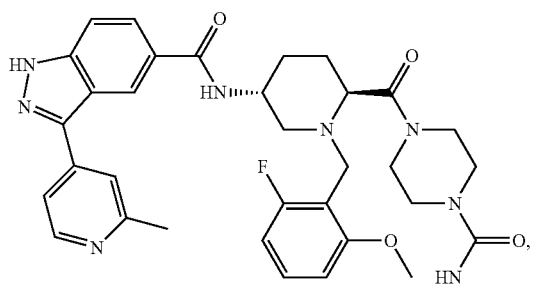
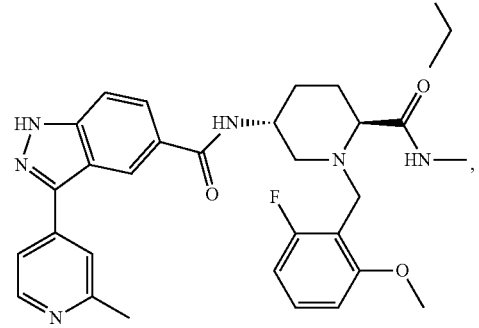
86
-continued
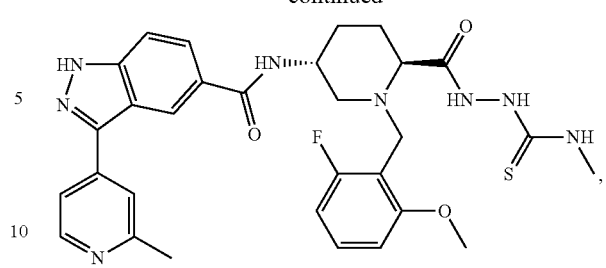
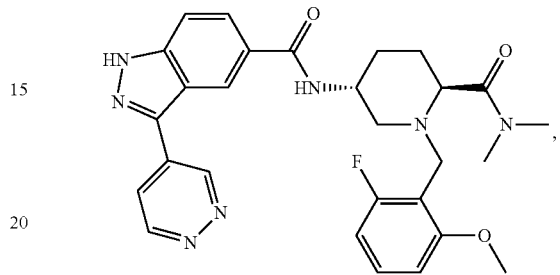
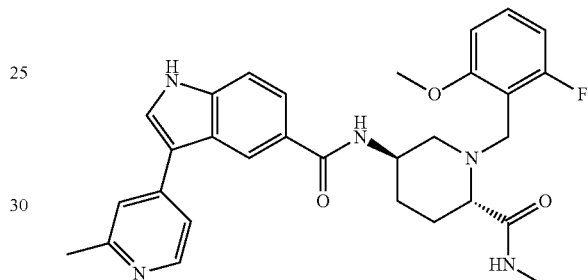
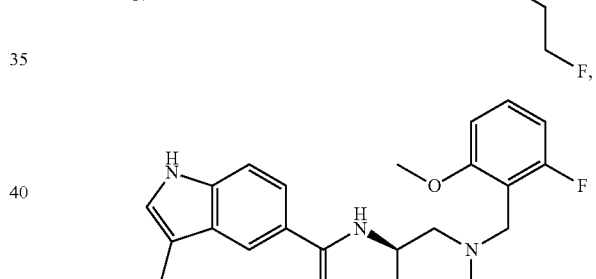

87
-continued
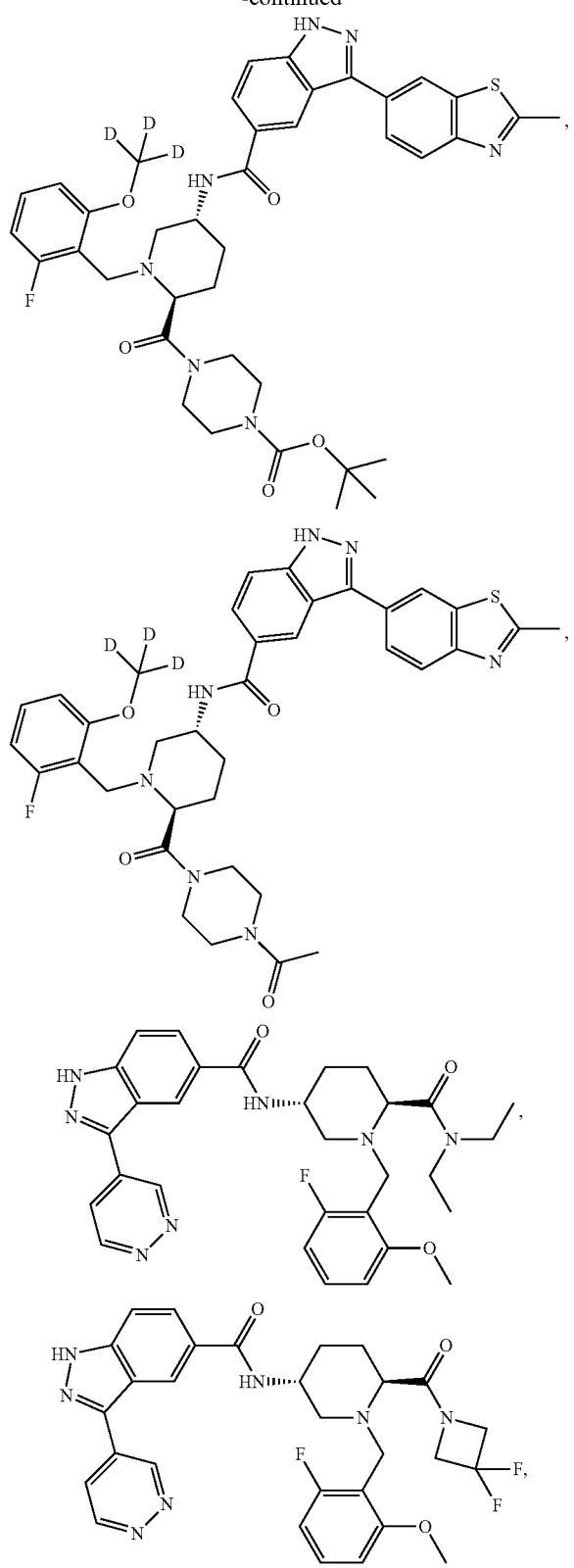
88
-continued
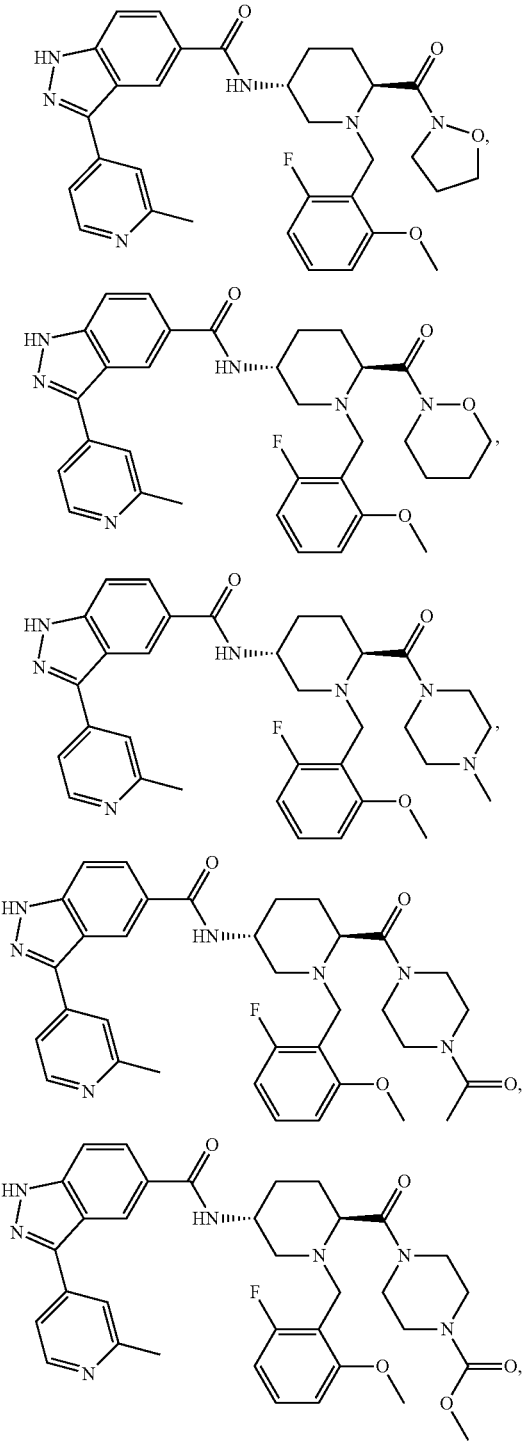

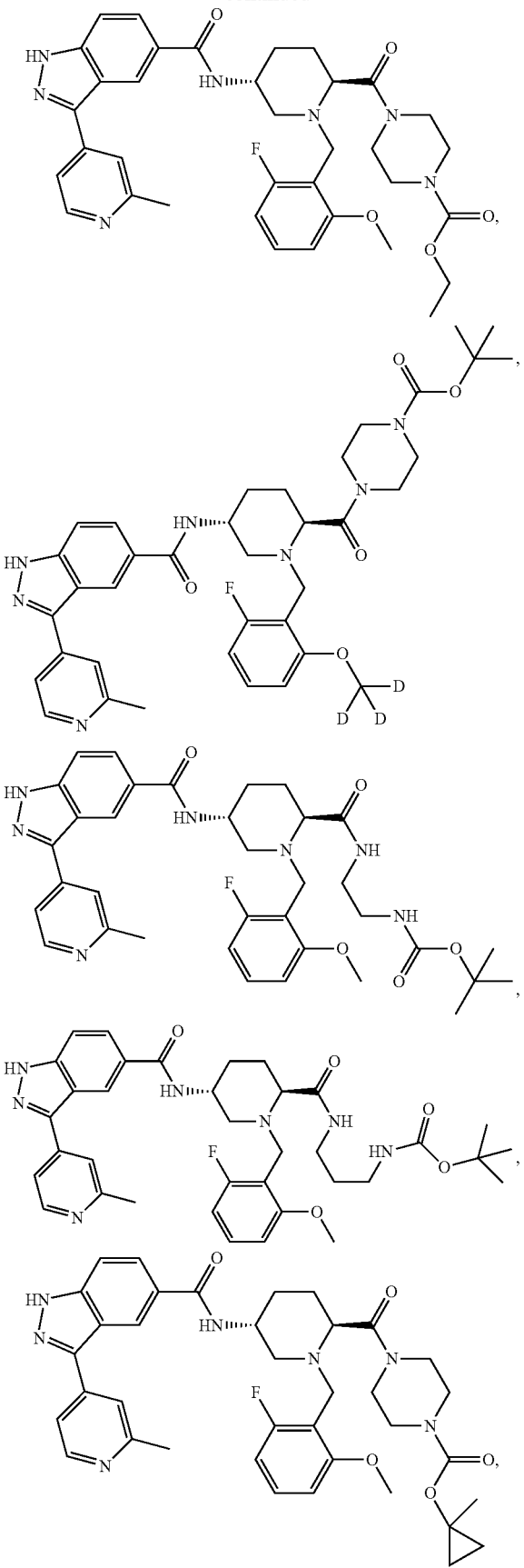
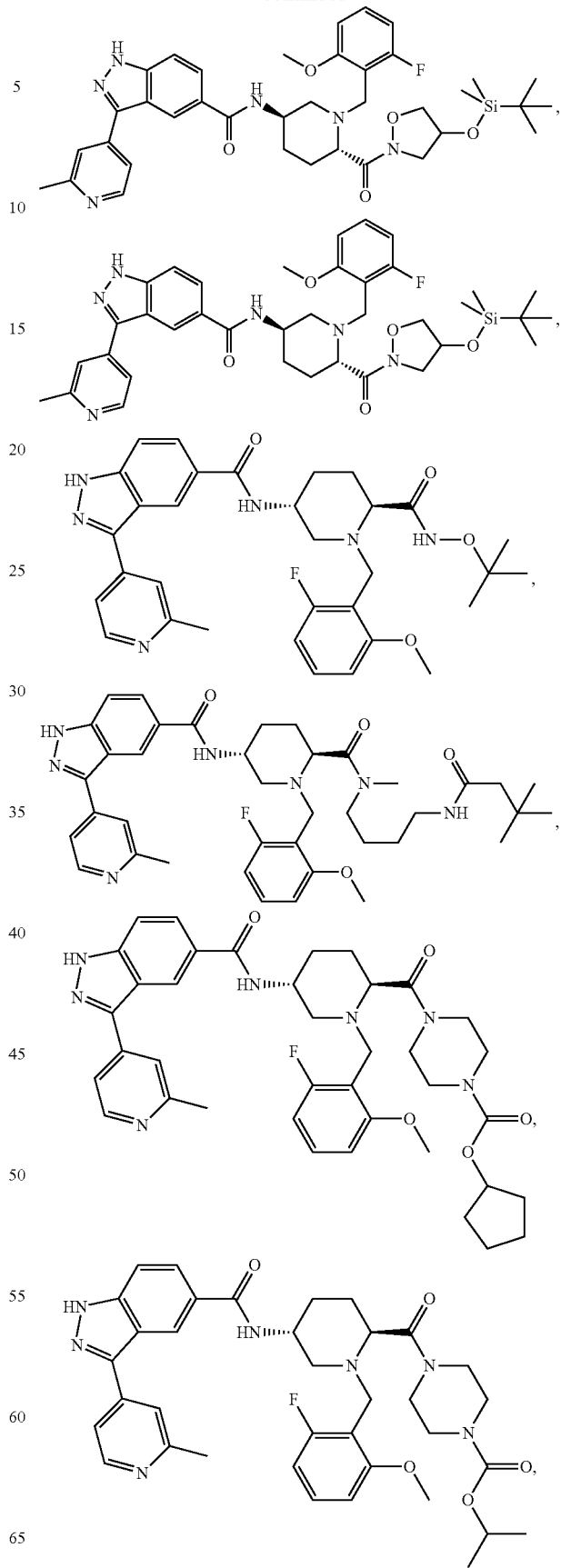

91
-continued
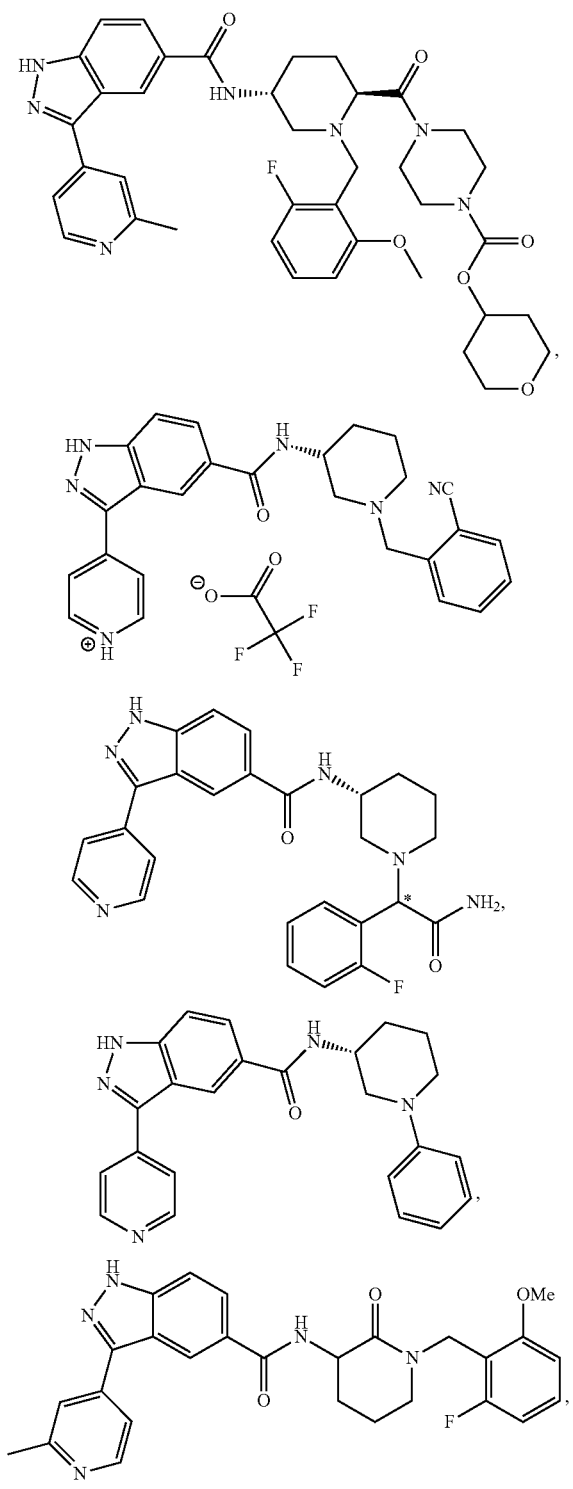
92
-continued
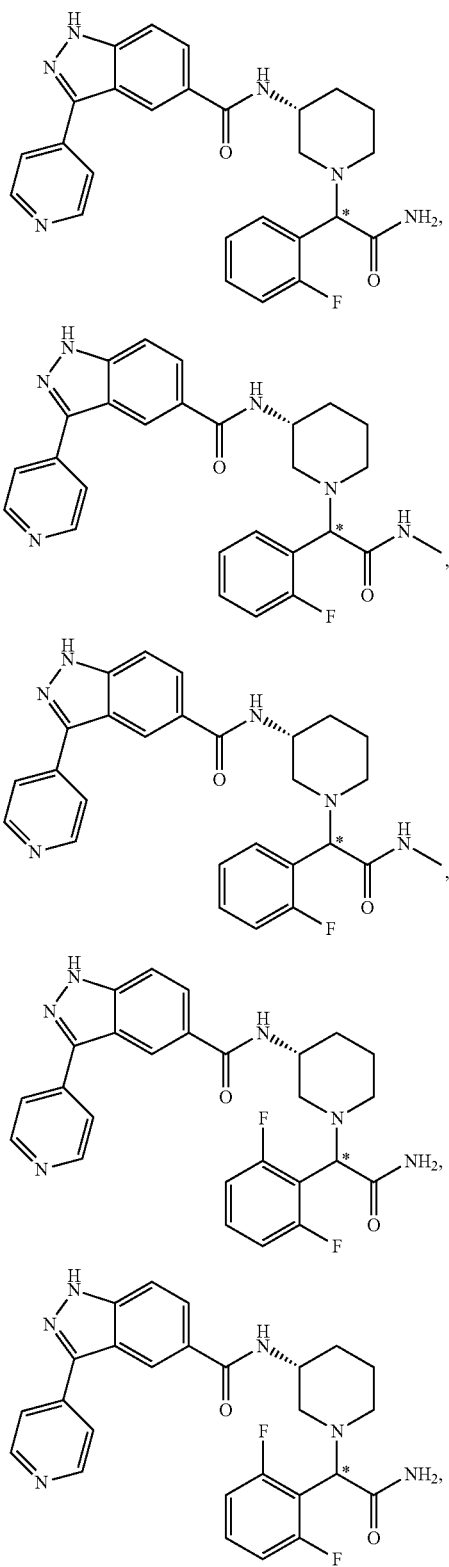

-continued

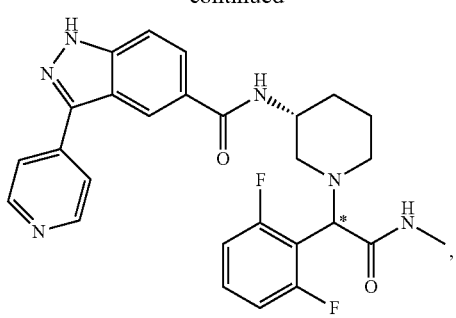

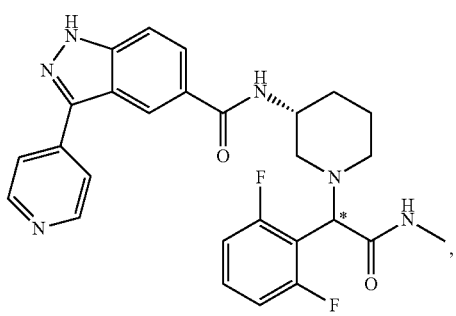

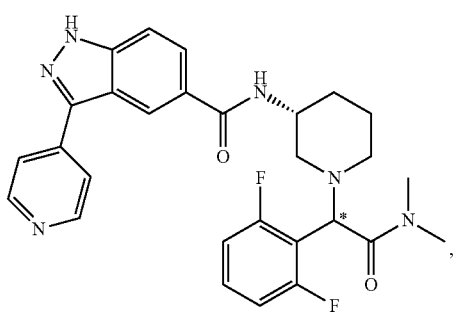

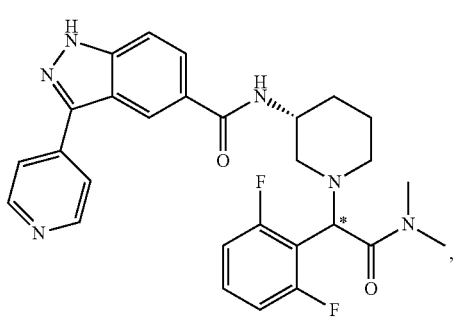

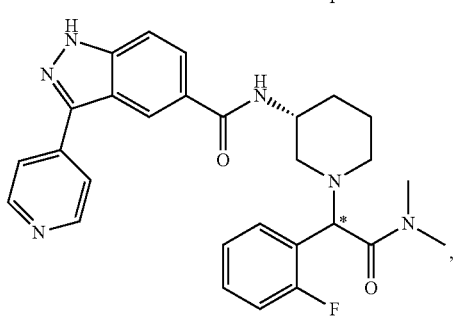

-continued

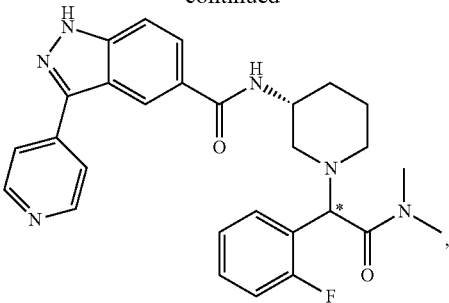

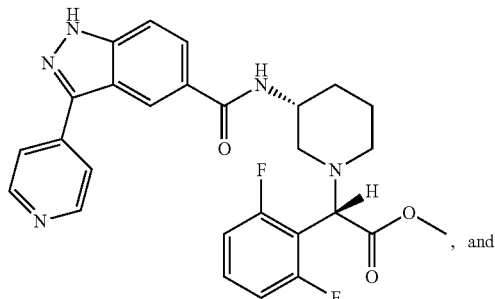

, and

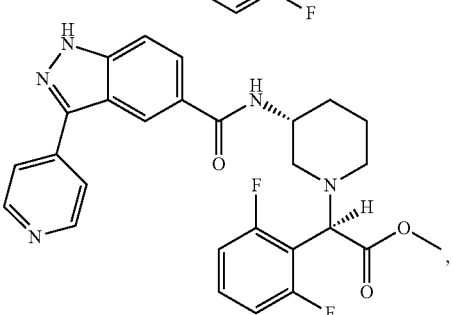

, or a pharmaceutically acceptable salt, solvate or ester thereof.

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, nuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compounds, compositions and methods of the invention include breast and prostate.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-

3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H -benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydrOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylaraino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamfiatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-1), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No.

5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS, Vol.* 89, p. 7384 (1992); *JNCI, Vol.* 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetylcarbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors, For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134, 142, 5,380,738, 5,393,790, 5,466,823, 5,633,272 and 5,932, 598, all of which are hereby incorporated by reference. Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_4\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacal.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthalmol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, HT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33434, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifedepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may be used in combination with a chemotherapeutic agent selected from the group consisting of (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

Examples of such chemotherapeutic agents include:

(1) taxanes such as paclitaxel (TAXOL®) and/or docetaxel (Taxotere®); (2) platinum coordinator compounds, such as, for example, carboplatin, cisplatin and oxaliplatin (e.g. Eloxatin); (3) EGF inhibitors that are antibodies, such as: HER2 antibodies (such as, for example trastuzumab (Herceptin®, Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA); (4) EGF inhibitors that are small molecules, such as, Tarceva™ (OSI-774, OSI Pharmaceuticals, Inc.), and Iressa (ZD 1839, Astra Zeneca); (5) VEGF inhibitors that are antibodies such as: bevacizumab (Genentech, Inc.), and IMC-1C11 (ImClone Systems), DC 101 (a KDR VEGF Receptor 2 from ImClone Systems); (6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals); (7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.); (8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda); (9) epothilones such as BMS-247550 (Bristol-Myers Squibb), and EP0906 (Novartis Pharmaceuticals); (10) topoisomerase inhibitors such as topotecan (Glaxo SmithKline), and Camptosar (Pharmacia); (11) vinca alkaloids, such as, navelbine (Anvar and Fabre, France), vincristine and vinblastine; (12) antibodies that are inhibitors of αVβ3 integrins, such as, LM-609 (see, Clinical Cancer Research, Vol. 6, page 3056-3061, August 2000, the disclosure of which is incorporated herein by reference thereto); 13) folate antagonists, such as Methotrexate (MTX), and Premetrexed (Alimta); (14) ribonucleotide reductase inhibitors, such as Hydroxyurea (HU); (15) anthracyclines, such as Daunorubicin, Doxorubicin (Adriamycin), and Idarubicin; (16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma); (16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma); (17) thalidomide (or related imid); (18) Bcr/abl kinase inhibitors, such as, for example Gleevec (STI-571), AMN-17, ON012380, SU 11248 (Sunitinib) and BMS-354825; (19) MEK1 and/or MEK2 inhibitors, such as PD0325901 and Arry-142886 (AZD6244); (20) IGF-1 and IGF-2 inhibitors that are small molecules, such as, for example, NVP-AEW541; (21) small molecule inhibitors of RAF and BRAF kinases, such as, for example, BAY 43-9006 (Sorafenib); (22) small molecule inhibitors of cell cycle dependent kinases such as CDK1, CDK2, CDK4 and CDK6, such as, for example, CYC202, BMS387032, and Flavopiridol; (23) alkylating agents, such as, for example, Temodar® brand of temozolomide; (24) farnesyl protein transferase inhibitors, such as, for example:

(a) Sarasar® brand of lonifarnib (i.e., 4-[2-[4-(3,10-dibromo-8-chloro-6,11-dihydro-5H-benzo[5,6]cyclohepta[1,2-b]byridin-1'-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto),
(b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and
(c) Bristol-Myers Squibb 214662:

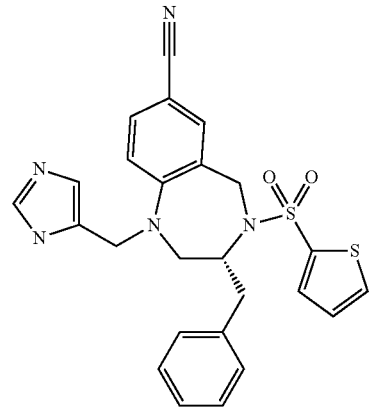 [SMILES: N#Cc1ccc2c(c1)CN(S(=O)(=O)c1cccs1)[C@H](Cc1ccccc1)CN2Cc1cnc[nH]1]

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®e); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux); chlorambucil (Leukeran®); cisplatin (Platinol®); cladribine (Leustatin®, 2-CdA); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®) idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); Ridaforolimus; romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosole); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

For example, the compounds of formula I can be administered orally (e.g., as a capsule), and the chemotherapeutic agents can be administered intravenously, usually as an intravenous (IV) solution. The use of a pharmaceutical composition comprising more than one drug is within the scope of this invention.

The compound of formula I and the chemotherapeutic agents are administered in therapeutically effective dosages to obtain clinically acceptable results, e.g., reduction or elimination of symptoms or of the tumor. Thus, the compound of formula I and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15.

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (0 about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250 mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be continuously dosed or used until releapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The FPT inhibitor Sarasar® (brand of lonifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®, for example, can be administered once per week in an amount of about 50 to about 100 mg/m$^2$ and in another example about 60 to about 80 mg/m$^2$. In another example Paclitaxel (e.g., Taxol® can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula I and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of the invention can be made according to the processes described below.

Commonly used Abbreviations

AIBN is azobisisobutyronitrile; Boc is tert-butoxycarbonyl, BBr3 is tribromo-borane, dba is dibenzylideneacetone, ACN is Acetonitrile; AcOH is Acetic acid; CBZ is benzyloxy carbonyl, CDI is carbodiimidazole, $CH_3CN$ is acetonitrile, DAST is (diethylamino)sulfur trifluoride; DCC is Dicyclohexylcarbodiimide; DCU is Dicyclo-hexylurea; DCM is Dichloromethane; DIAD is Diisopropylazodicarboxylate; DIEA is Diisopropylethylamine; DIPEA is diisopropylethylamine, DMAP is 4-Dimethylamino-pyridine; DME is Dimethoxyethane; DMF is Dimethylformamide (N,N-dimethyl-formamide); DMFDMA is N,N-Dimethylformamide dimethylacetal; DMSO is Dimethyl sulfoxide; DTT is Dithiothreitol; EDC is 1-(3-dimethylamino-propyl)-3-ethylcarbodiimide; EDCI is 1-(3-dimethylamino-propyl)-3-ethylcarbodiimide hydrochloride; EtOAc is Ethyl acetate; EtOH is Ethanol; HATU is N,N,N',N-Tetra-methyl-O-(7-Azabenzotriazol-1-yl)Uronium hexafluorophosphate (2-(1H-azabenzotriazol-1-yl-1,13,3-tetramethyl uranium hexafluorophosphate); $H_2O$ is water; Hex is hexanes; HOBt is 1-Hydroxylbenzotriazole; HPLC is High pressure liquid chromatography; LCMS is Liquid chromatography mass spectrometry; LDA is Lithium diisopropylamide; mCPBA is meta-Chloroperoxy-benzoic acid; Me is methyl; MeOH is Methanol; $Me_4Si$ is tetramethyl silane, MTT is (3-[4,5-dimethyl-thiazol-2-yl]-2,5-diphenyltetrazolium bromide, Thiazolyl blue); NaH is Sodium hydride; NBS is N-bromosuccinimide; NMR is Nuclear magnetic resonance; PBS is phosphate buffered saline, $PdCl_2(dppf)$ is [1,1-Bis(diphenylphosphino)ferrocene]dichloropalladium(II); PFP is Pentafluorophenol; PMB is p-methoxybenzyl; Pyr is Pyridine; RT is Room temperature; SEMCl is 2-(Trimethylsily)ethoxy methyl chloride; SOC is silicagel column, $SiO_2$ is silica, SPA is scintillation proximity assay, TBSOTf t-butyldimethyl-silyltrifluoromethane sulfonate; TEA is Triethylamine; TES is triethylsilane, Tf is triflate, Tr is Triphenyl methane; TrCl is Triphenyl methane chloride; TFA is Trifluoro-acetic acid; THF is Tetrahydrofuran; TLC is Thin layer chromatography; TMS is Trimethylsilyl, $TMSCHN_2$ is trimethylsilyl diazomethane, Tos is p-toluene sulfonyl, and Xantphos is 9,9-Dimethyl-4,5-bis(diphenylphosphino)xanthene.

Analytical Method

The LCMS conditions are: (1) column: C-18 reverse phase, 5 um, 4.6×50 mm, (2) MS:PE Sciex API-150EX, (3) HPLC: Shimadzu LC-10ADvp, 1 ml/min, linear gradient 10% acetonitirle in water to 95% acetonitrile in water, both contain 0.05% TFA, (4) Ascentis Express Column: C18, 75 mm×3.0 mm ID, 2.7 micron column; 2 µL injection; 10% to 98% $MeCN/H_2O+0.1\%$ TFA gradient over 3.5 minutes; 1 mL/min flow; ESI; positive ion mode; UV detection at 254 nM, Bw8) and (5) Sunfire C18, 30 mm×2.1 mm ID, 3.0 micron column; 2 µl, injection; 3% to 98% $MeCN/H_2O+0.1\%$ TFA gradient over 1.9 minutes; 0.9 mL/min flow; ESI; positive ion mode; UV detection at 254 nM, Bw8.

Compound Synthesis

The compounds of this invention can be made according to the according to the synthetic schemes described below. As used herein, unless indicated otherwise, "Ar" represents aryl.

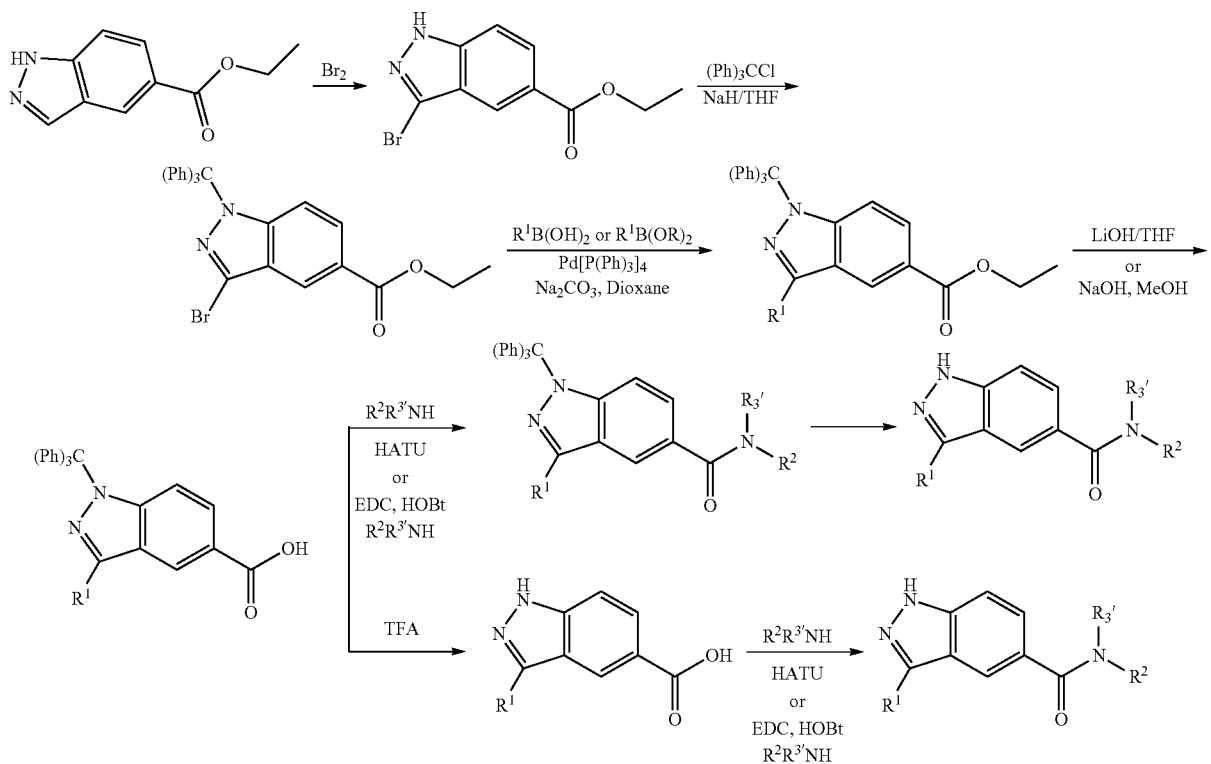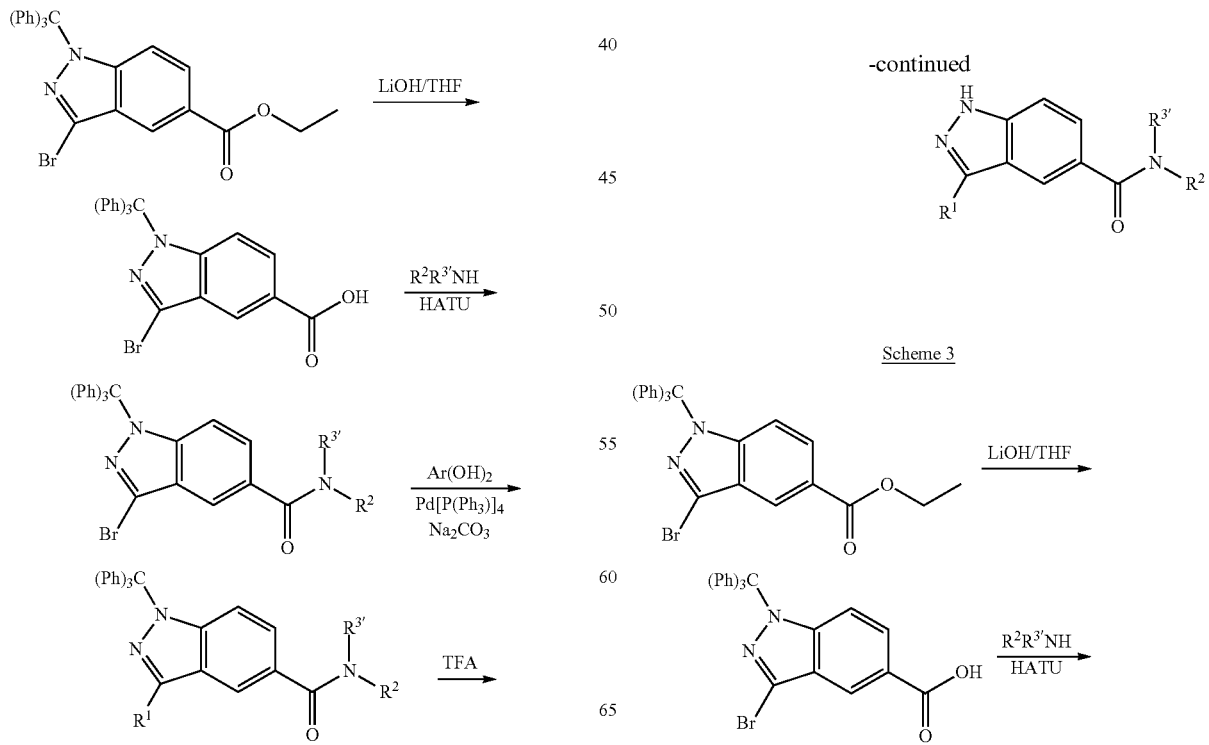

117
-continued
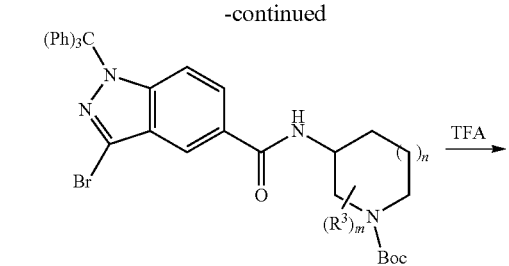
TFA →
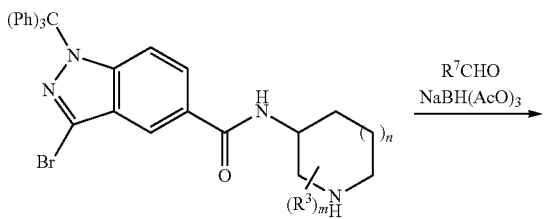
R⁷CHO
NaBH(AcO)₃ →
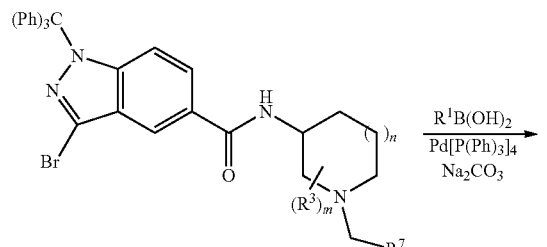
R¹B(OH)₂
Pd[P(Ph)₃]₄
Na₂CO₃ →
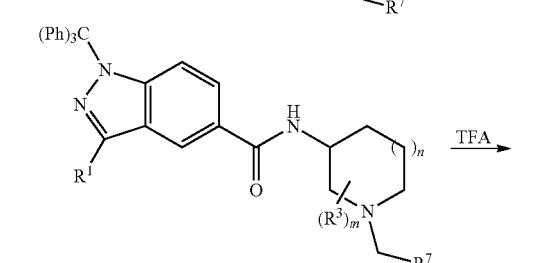
TFA →
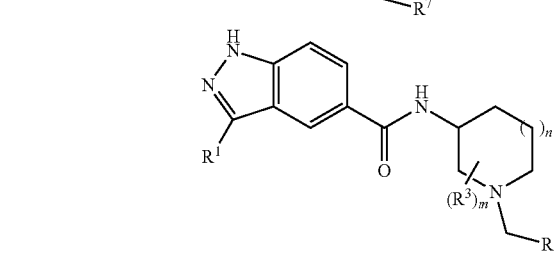
118
-continued
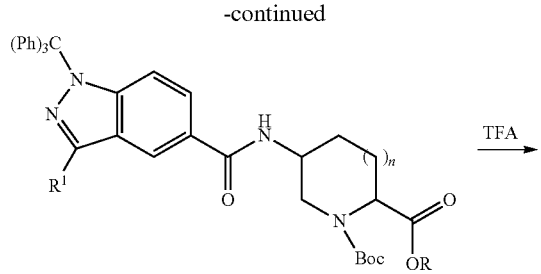
TFA →
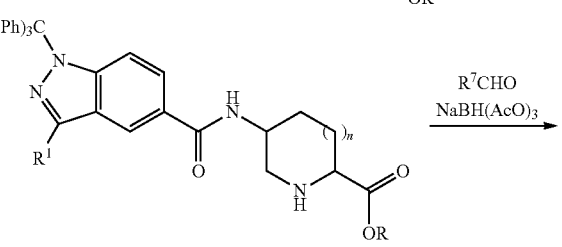
R⁷CHO
NaBH(AcO)₃ →
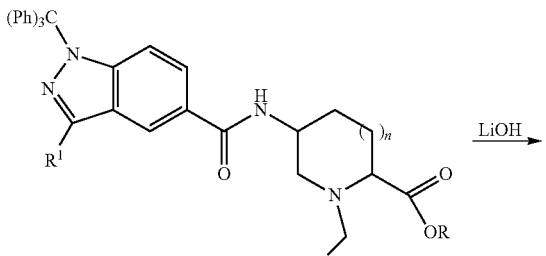
LiOH →
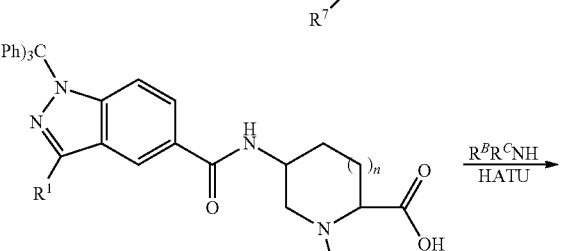
R^B R^C NH
HATU →
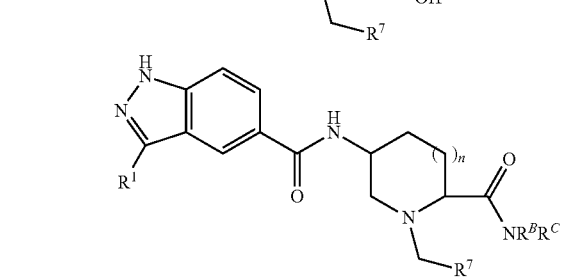
Scheme 4
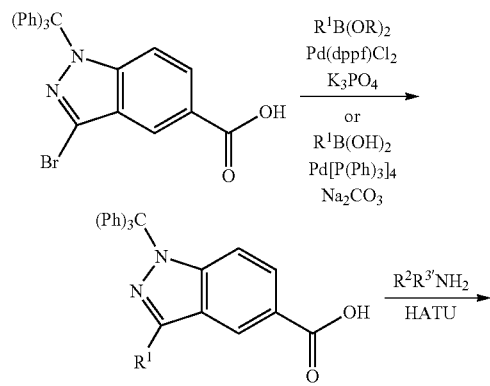
Scheme 5
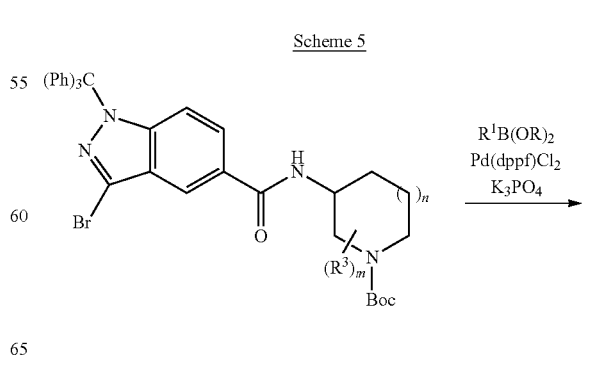

119
-continued
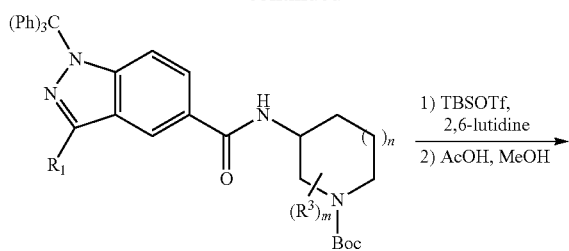
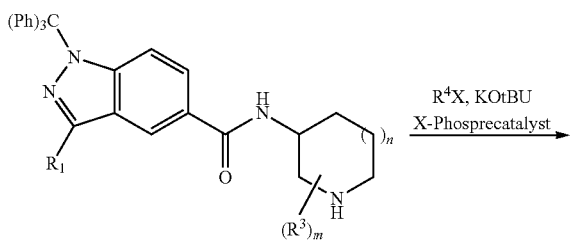
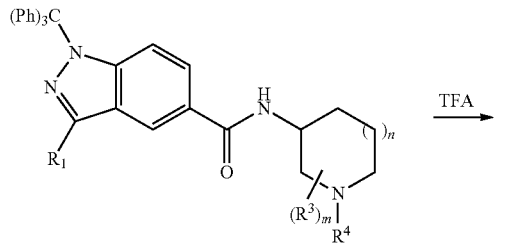
120
-continued
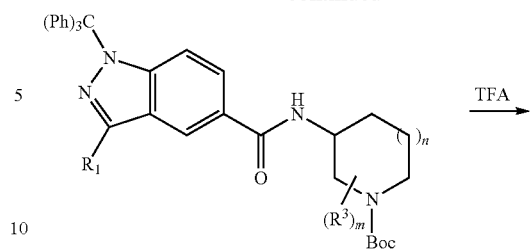
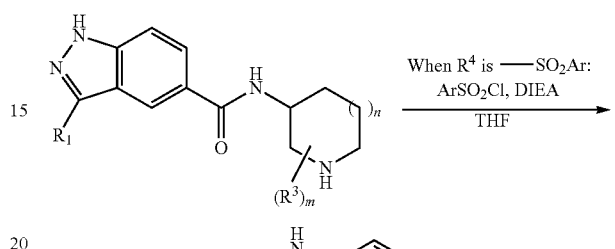
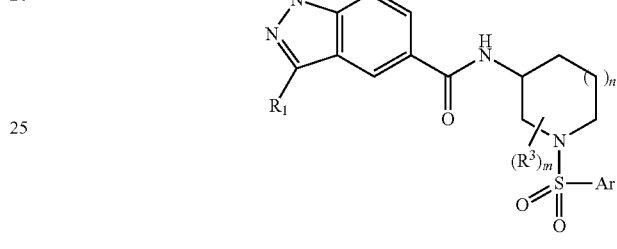
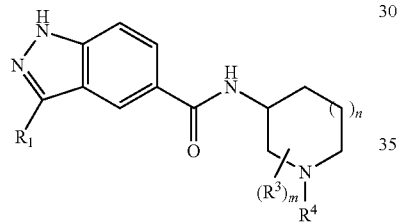
Scheme 6
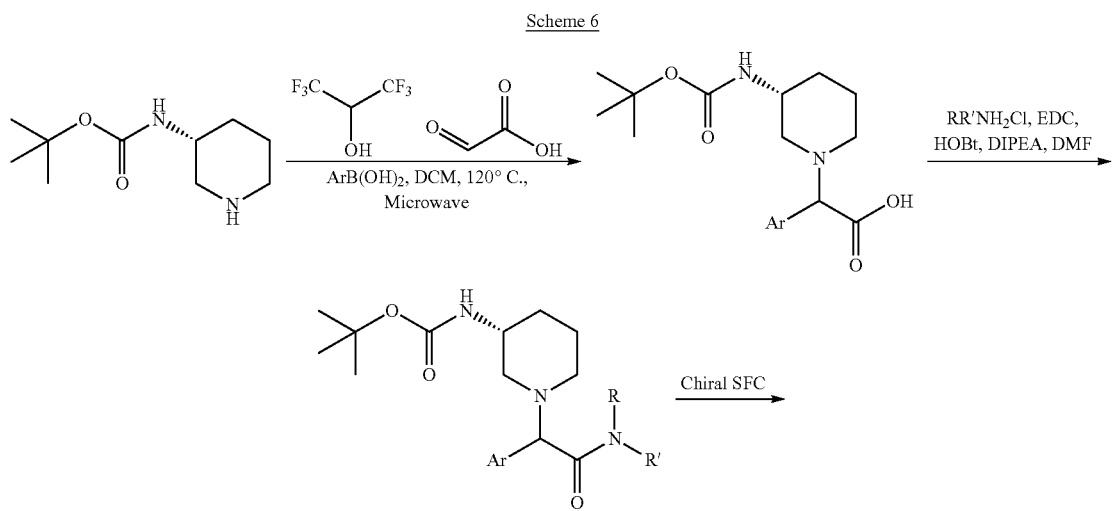

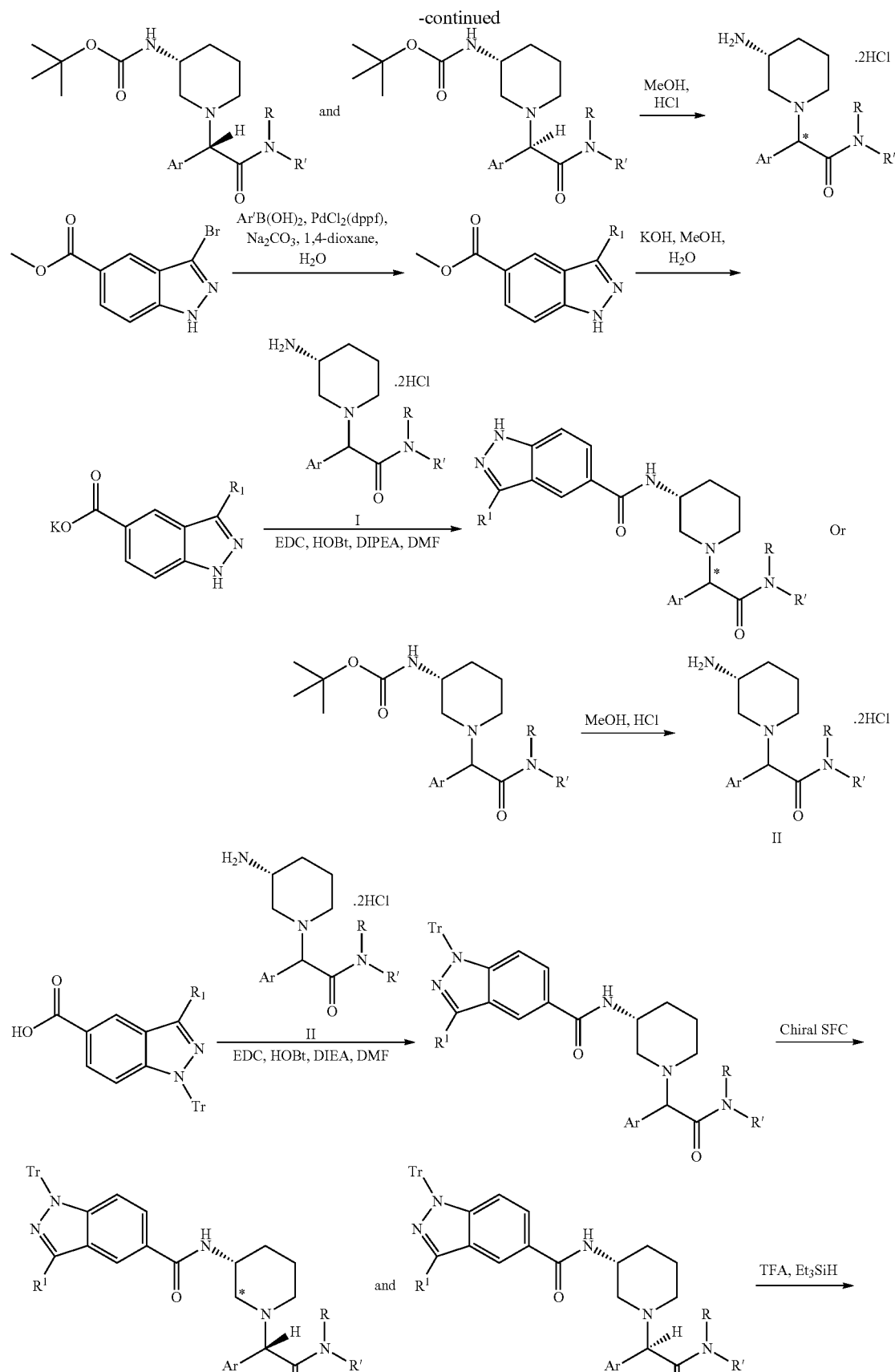

Scheme 7

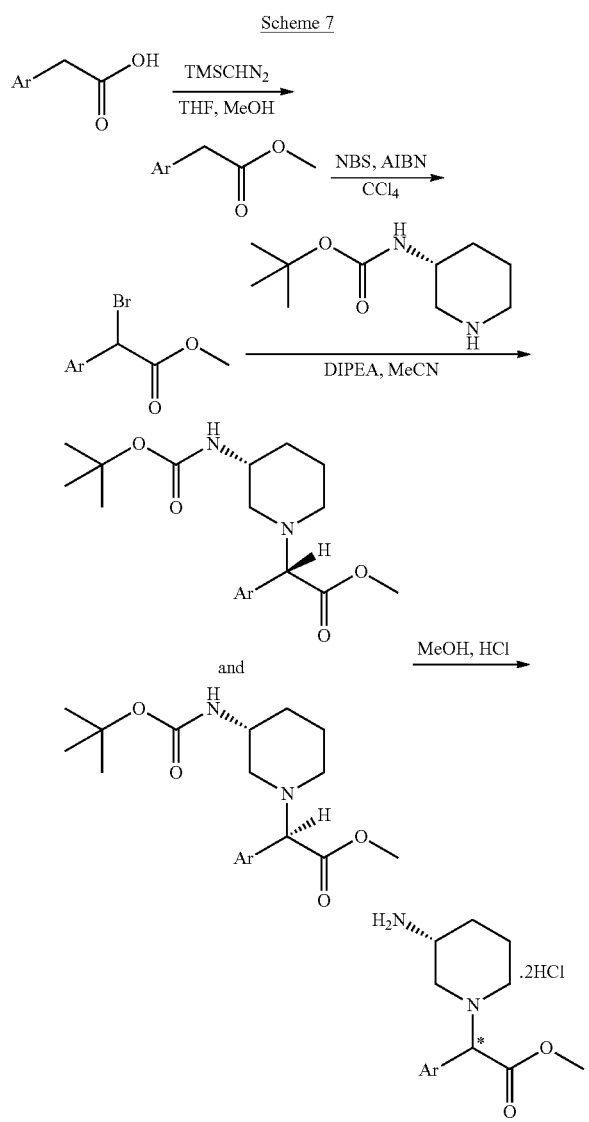

Further details for the preparation of synthetic intermediates and specific compounds are described hereinbelow.

ethyl 3-bromo-1H-indazole-5-carboxylate

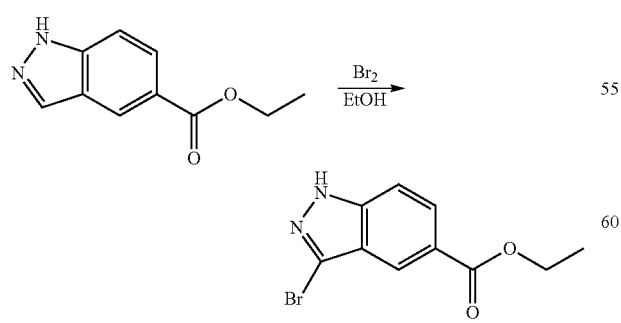

ethyl 1H-indazole-5-carboxylate hydrochloride (146 g, 0.645 mol) was dissolved in ethanol (4 L, anhydrous). Bromine (113.3 g, 0.709 mol) in 200 ethanol was added at room temperature. The reaction mixture was allowed to stir for 17 hours at toom temperature. TLC (30% ethyl acetate/hexane) indicated thate starting material was left. Bromine (40 g in 100 mL of ethanol) was added at room temperature. After 1 hour, TLC indicated no starting material was left. Ethanol was evaporated (2 L removed) and the mixture was poured into ice-water (8 L). The purple solide was stirred and 750 mL of saturated $Na_2S_2O_3$ and NaOH solution was added to adjust the pH to 10-11. Total volume was 10 L. The mixture was stirred for 30 minutes and the solid were filtered and washed with 1.5 L of water and dried in a vacuum oven to obtain 170 gram of product as yellow solid.

ethyl 3-bromo-1-trityl-1H-indazole-5-carboxylate

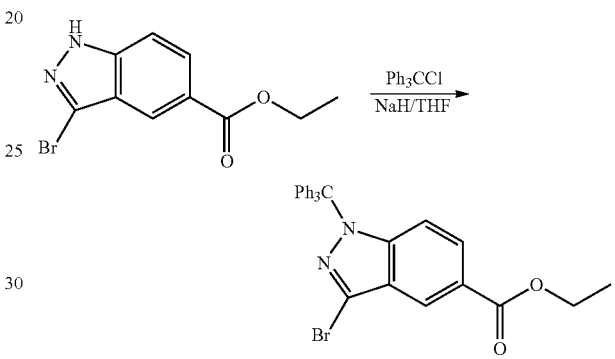

To a suspension of ethyl 3-bromo-1H-indazole-5-carboxylate (1032 g, 0.04 mol) in 160 mL of THF was added NaH (2.8 g, 0.068 mol) portion wise at 5-10 C under ice/water bath. The solution was stirred for 15 minutes further until no more bubling. Tritylchloride (14 g, 0.05 mol) was added in several portions. After the addition, the cooling bath was removed and the orange suspension was stirred at room temperature for overnight. The reaction mixture was poured slowly into 100 mL of saturated NH4Cl with stirring and 100 mL EtOAc. The layers were separated and the aqueous phase extracted with Ethyl acetate (2 Lx2). The combined organic layers were washed with water (100 mL), brine (100 mL), dried over $Na_2SO_4$, filter and concentrated. The solid was triturated with hexane (100 mL), filtered and washed with hexane and dried under vacuum to give 20 gram product as light yellow solid.

Ethyl 3-pyridin-4-yl-1-trityl-1H-indazole-5-carboxylate

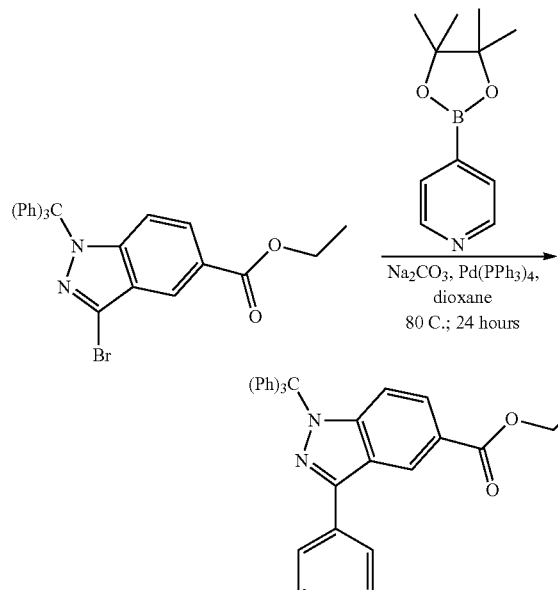

To a 5 ml microwave vial equipped with a stir bar was added ethyl 3-bromo-1-trityl-1H-indazole-5-carboxylate (1095.3 mg, 2.142 mmol), pyridine-4-boronic acid pinacol ester (679 mg, 3.21 mmol), sodium carbonate (2142 µl, 4.28 mmol), dioxane (1.07E+04 µl), and PalladiumTetrakis (247 mg, 0.214 mmol). The vial was purged with nitrogen, and was then sealed and heated to 80° C. for 24 h. LCMS taken after 24 hours indicates formation of the desired product. The crude reaction mixture was filtered through a column pre-packed with celite. The combined organics were concentrated under reduced pressure and the material was dry loaded onto a 100 g column. A column was run from 100% hexanes to 100% ethyl acetate. The desired product eluted; fractions were collected and concentrated in vacuo 3-pyridin-4-yl-1-trityl-1H-indazole-5-carboxylic acid

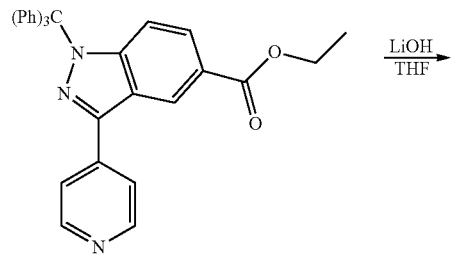

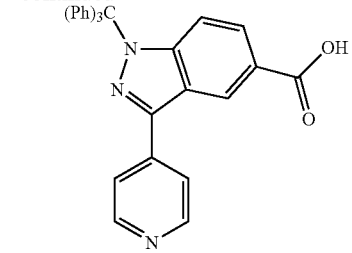

To a 5 ml microwave vial equipped with a stir bar was added ethyl 3-pyridin-4-yl-1-trityl-1H-indazole-5-carboxylate (816 mg, 1.601 mmol), LOH (2402 µl, 2.402 mmol), and THF (8006 µl). The vial was sealed and heated to 50° C. for 19 hours, after which the LCMS indicates formation of the desired product. Crude was quenched with HCl (2402 µl, 2.402 mmol) and the reaction was concentrated in vacuo. Material was dry loaded onto a 100 g column; was run from 100% dichloromethane to 25% methanol. Desired product eluted; fractions were collected and concentrated in vacuo to a white solid.

2-{[(3R)-3-aminopiperidin-1-yl]methyl}benzonitrile

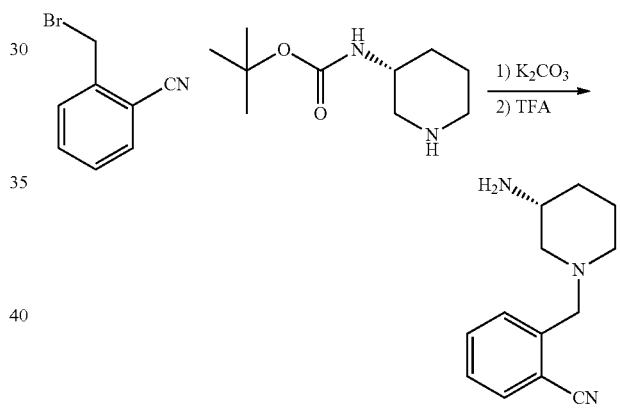

Intermediate tert-butyl [(3R)-1-(2-cyanobenzyl)piperidin-3-yl]carbamate

To a microwave vial equipped with a stir bar was added tert-butyl (3R)-piperidin-3-ylcarbamate (3000 mg, 14.98 mmol), Potassium Carbonate (6211 mg, 44.9 mmol), and 2-(bromomethyl)benzonitrile (3230 mg, 16.48 mmol). The vial was sealed and stirred at room temperature. The LCMS taken after 2.5 hours indicates the formation of the desired product. The crude reaction mixture was filtered and concentrated in vacuo. The material was dry loaded onto a 50 g column. The column was run from 100% dichloromethane to 15% methanol. The desired product eluted and the fractions were collected and concentrated in vacuo.

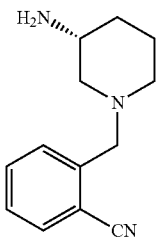

2-{[(3R)-3-aminopiperidin-1-yl]methyl}benzonitrile

To a microwave vial equipped with a stir bar was added tert-butyl [(3R)-1-(2-cyanobenzyl)piperidin-3-yl]carbamate (1000 mg, 3.17 mmol) and TFA (1000 µl, 12.98 mmol). The reaction was stirred at room temperature for 30 minutes. The LCMS taken after 30 minutes indicates formation of the desired product. The crude reaction mixture was concentrated in vacuo, and was then dissolved in ethyl acetate and filtered through a sodium bicarbonate filter. The combined organics were concentrated under reduced pressure. The material was dissolved in acetonitrile and water, and was dried on the lyophilizer overnight.

N-[(3R)-1-(2-cyanobenzyl)piperidin-3-yl]-3-pyridin-4-yl-1-trityl-1H-indazole-5-carboxamide

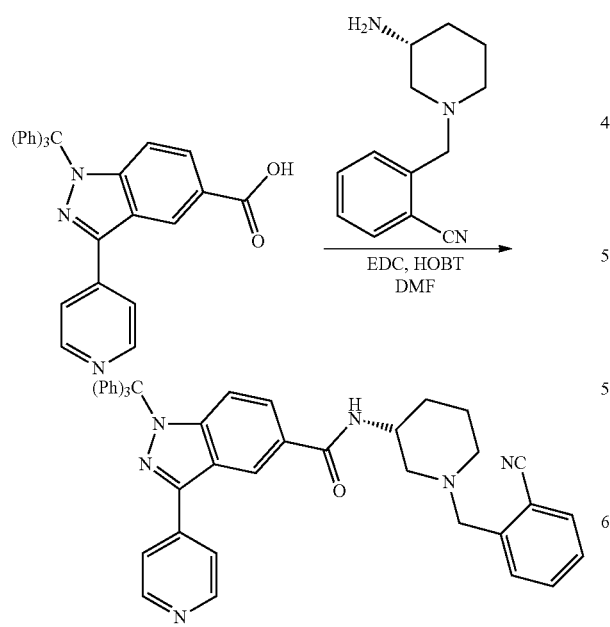

To a microwave vial equipped with a stir bar was added 3-(pyridin-4-yl)-1-trityl-1H-indazole-5-carboxylic acid (50 mg, 0.104 mmol), HOBT (23.85 mg, 0.156 mmol), EDC (29.9 mg, 0.156 mmol), DIPEA (54.4 µl, 0.311 mmol), 2-{[(3R)-3-aminopiperidin-1-yl]methyl}benzonitrile (22.35 mg, 0.104 mmol), and DMF (1038 µl). The vial was sealed and heated to 40° C. The LCMS taken after 23 hours indicates formation of the desired product. The crude reaction mixture was filtered through a column pre-packed with celite. The material was dry loaded onto 2×10 g columns. The desired product eluted and fractions were collected and concentrated in vacuo.

4-[5-({[(3R)-1-(2-cyanobenzyl)piperidin-3-yl]amino}carbonyl)-1H-indazol-3-yl]pyridinium trifluoroacetate

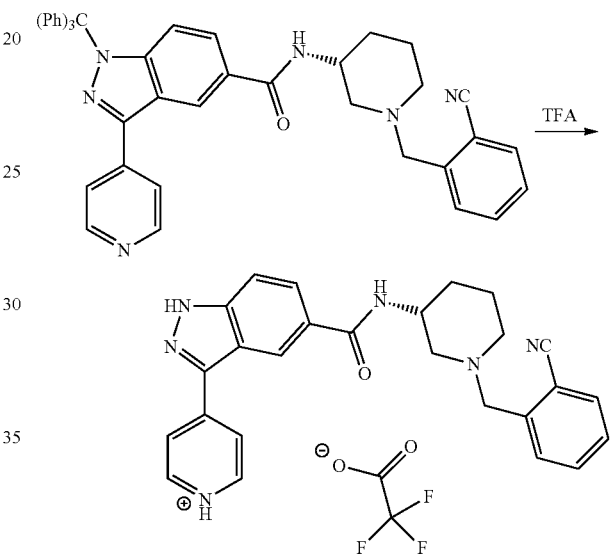

To a microwave vial equipped with a stir bar was added N-[(3R)-1-(2-cyanobenzyl)piperidin-3-yl]-3-pyridin-4-yl-1-trityl-1H-indazole-5-carboxamide (41.7 mg, 0.061 mmol) and TFA (1000 µl, 12.98 mmol). The reaction was stirred at room temperature for 20 minutes. After 20 minutes the LCMS indicates formation of the desired product. Triethylsilane (19.62 µl, 0.123 mmol) was addes, and the crude reaction was concentrated in vacuo. The crude was dissolved in 1 ml DMSO, filtered, and purified by reverse phase chromatography. The material was concentrated, and was then dissolved in acetonitrile and water. The compound was dried on the lyophilizer over 2 days to provide fluffy white solid. LCMS calc'd for $C_{26}H_{25}N_6O$ $[M+H]^+$=437; found 437 $^1$H NMR (600 MHz, $CD_3OD$) δ 8.9 (d, 2H), 8.9 (s, 1H), 8.7 (d, 2H), 8.0 (d, 1H), 7.9 (d, 1H), 7.8 (s, 2H), 7.8 (d, 1H), 7.7 (m, 1H), 4.6

(s, 2H), 4.4 (m, 1H), 3.7 (m, 1H), 3.6 (m, 1H), 3.2 (m, 2H), 2.2 (m, 2H), 2.0 (m, 1H), 1.8 (m, 1H).

tert-butyl 3-phenyl-5-{[(3-pyridin-4-yl-1-trityl-1H-indazol-5-yl)carbonyl]amino}piperidine-1-carboxylate

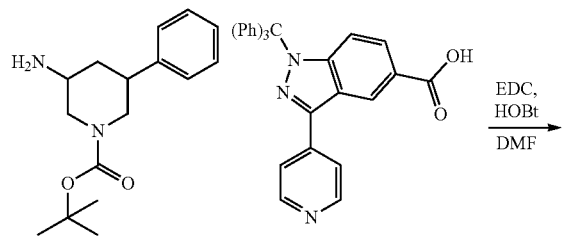

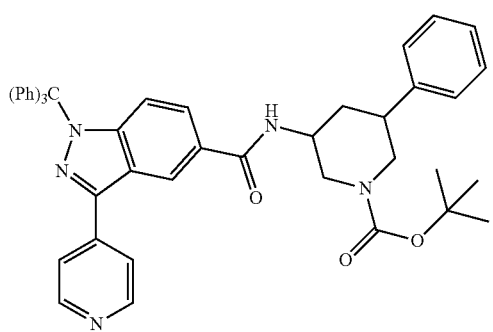

To a microwave vial equipped with a stir bar was added 3-pyridin-4-yl-1-trityl-1H indazole-5-carboxylic acid (155.4 mg, 0.323 mmol), HOBT (74.1 mg, 0.484 mmol), EDC (93 mg, 0.484 mmol), DIPEA (225 µl, 1.291 mmol), tert-butyl 3-amino-5-phenylpiperidine-1-carboxylate (89 mg, 0.323 mmol), and DMF (3227 µl). The vial was sealed and heated to 45° C. The LCMS taken after 4 hours indicates formation of the desired product. The material was filtered through a column pre-packed with celite and was concentrated under reduced pressure. A column was run from 100% hexanes to 100% ethyl acetate. The desired product eluted and fractions were collected and concentrated in vacuo. The material was dissolved in acetonitrile and water and was dried on the lyophilizer.

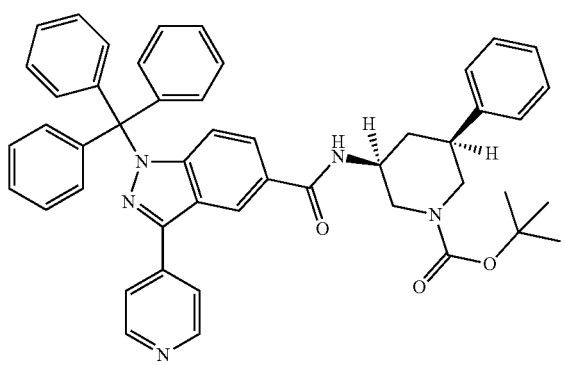

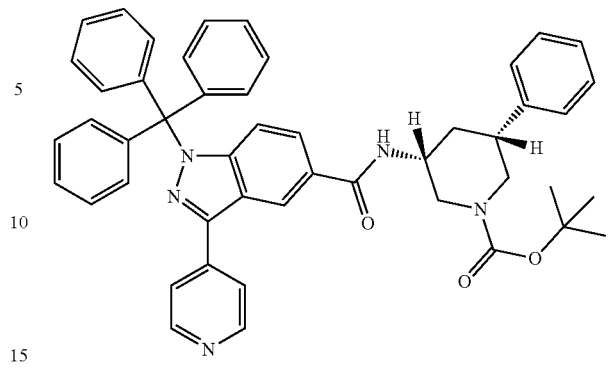

tert-butyl (3S,5S)-3-phenyl-5-{[(3-pyridin-4-yl-1-trityl-1H-indazol-5-yl)carbonyl]amino}piperidine-1-carboxylate and tert-butyl (3R,5R)-3-phenyl-5-{[(3-pyridin-4-yl-1-trityl-1H-indazol-5-yl)carbonyl]amino}piperidine-1-carboxylate Conditions for chiral separation using Supercritical Fluid Chromatography (SFC)

Column: Chiral Technology IB-H 2.1×25 cm, 5 uM.

MP: 45%/55% Methanol/CO2 (no other modifiers).

Flow rate: 70 mL/Min, 5 min run time.

WL: 220 nm.

tert-butyl 3-phenyl-5-{[(3-pyridin-4-yl-1-trityl-1H-indazol-5-yl)carbonyl]amino}-piperidine-1-carboxylate (175 mg) was dissolved up in 5 ml methanol/DMF with the use of heat and then subjected to SFC purification. Injections of 1.0 ml were performed on the Berger Multigram II SFC in 3-201. Compound precipitated out and required re-heating. Elution was observed at 3.1 minutes and 4.27 minutes. Compound also showed separation on the OD column.

N-[(3S,5S)-5-phenylpiperidin-3-yl]-3-pyridin-4-yl-1H-indazole-5-carboxamide

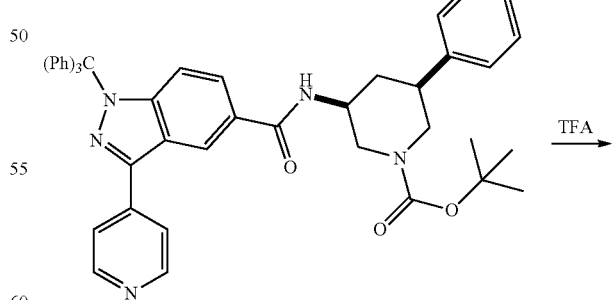

131

-continued

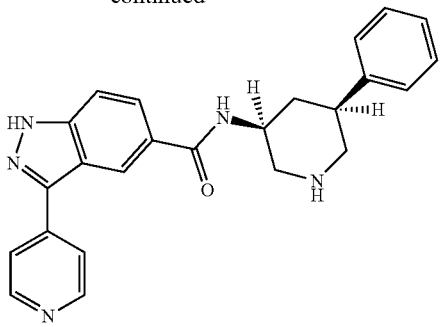

To a microwave vial equipped with a stir bar was added tert-butyl (3S,5S)-3-phenyl-5-{[(3-pyridin-4-yl-1-trityl-1H-indazol-5-yl)carbonyl]amino}piperidine-1-carboxylate (61.9 mg, 0.084 mmol) and TPA (1000 µl). The reaction was stirred for 20 minutes, after which the LCMS indicates formation of the desired product. Crude reaction mixture was concentrated in vacuo. The residue was dissolved in 1 ml DMSO and subjected to reverse phase chromatography. LCMS calc'd for $C_{24}H_{23}N_{5O}$ [M+H]$^+$=398

N-[(3R)-1-Phenylpiperidin-3-yl]-3-(pyridin-4-yl)-1H-indazole-5-carboxamide

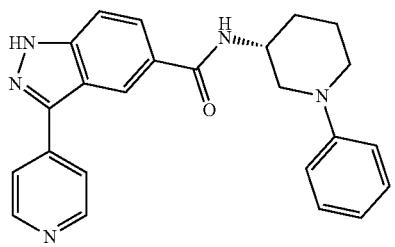 [SMILES: O=C(N[C@@H]1CCCN(c2ccccc2)C1)c1ccc2[nH]nc(-c3ccncc3)c2c1]

Step 1. tert-Butyl [(3R)-1-phenylpiperidin-3-yl]carbamate

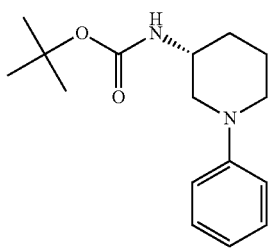 [SMILES: CC(C)(C)OC(=O)N[C@@H]1CCCN(c2ccccc2)C1]

A solution of (R)-3-(tert-butoxycarbonylamino)piperidine (0.10 g, 0.50 mmol), phenylboronic acid (0.13 g, 1.1 mmol) and copper (II) acetate (0.10 g, 0.551 mmol) in DCM (2 ml) under air was charged with triethylamine (0.14 ml, 1.0 mmol), sealed and stirred at RT for 18 hours followed by stirring at 60° C. for 72 hours. The reaction mixture was filtered through celite and eluted with DCM/MeOH. The filtrate was concentrated in vacuo and purified by flash chromatography (Biotage, 0-20% MeOH/DCM) to provide tert-butyl [(3R)-1-phenylpiperidin-3-yl]carbamate.

Step 2. (3R)-1-Phenylpiperidin-3-amine

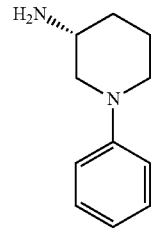 [SMILES: N[C@@H]1CCCN(c2ccccc2)C1]

A solution of tert-butyl [(3R)-1-phenylpiperidin-3-yl]carbamate (133 mg, 0.483 mmol) in 3 M HCl in MeOH (3 ml) was heated to 70° C. for 3 hr. The reaction mixture was concentrated in vacuo to provide crude (3R)-1-phenylpiperidin-3-amine as the bis HCl salt, which was used as-is without further purification.

LCMS calcd for $C_{11}H_{17}N_2$ [M+H]$^+$=177; found 177.

Step 3. N-[(3R)-1-Phenylpiperidin-3-yl]-3-(pyridin-4-yl)-1-trityl-1H-indazole-5-carboxamide

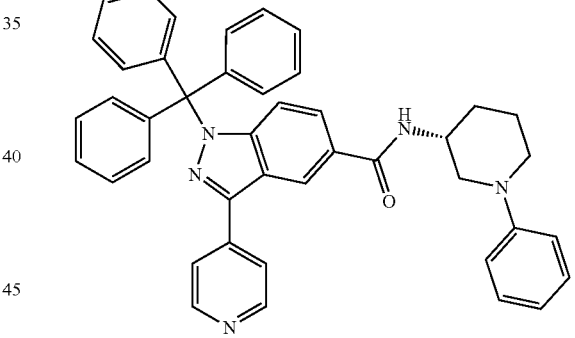

A solution of 3-(pyridin-4-yl)-1-trityl-1H-indazole-5-carboxylic acid (97 mg, 0.20 mmol), (3R)-1-phenylpiperidin-3-amine (120 mg, 0.48 mmol), EDC (0.08 g, 0.4 mmol), HOBt (0.07 g, 0.5 mmol) and DIPEA (400 µl, 2.3 mmol) in DMF (2 ml) was stirred at room temperature for 1.5 hours. The reaction mixture was concentrated in vacuo to provide crude N-[(3R)-1-phenylpiperidin-3-yl]-3-(pyridin-4-yl)-1-trityl- 1H-indazole-5-carboxamide, which was used as-is without further purification. LCMS calc'd for $C_{43}H_{38}N_5O$ [M+H]$^+$ =640; found 640.

Step 4. N-[(3R)-1-Phenylpiperidin-3-yl]-3-(pyridin-4-yl)-1H-indazole-5-carboxamide

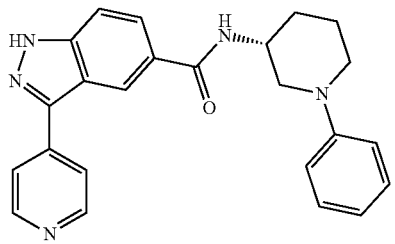 [SMILES: O=C(N[C@@H]1CCCN(c2ccccc2)C1)c1ccc2[nH]nc(-c3ccncc3)c2c1]

Crude N-[(3R)-1-phenylpiperidin-3-yl]-3-(pyridin-4-yl)-1-trityl-1H-indazole-5-carboxamide (129 mg, 0.202 mmol) was stirred with TFA (0.5 ml) at room temperature for 45 minutes. Addition TFA (1 ml) was added and the reaction mixture was stirred at room temperature for 1.5 hours. Triethylsilane (100 µl, 0.626 mmol) was added and then the reaction mixture diluted with DMSO purified by mass-triggered reverse-phase HPLC to provide N-[(3R)-1-phenylpiperidin-3-yl]-3-(pyridin-4-yl)-1H-indazole-5-carboxamide.

LCMS calc'd for $C_{24}H_{24}N_5O$ [M+H]$^+$=398; found 398.

$^1$H NMR: δ 8.87 (d, J=5.4 Hz, 2 H), 8.69 (s, 1 H), 8.52 (d, J=7.6 Hz, 1 H), 8.37 (d, J=6.1 Hz, 2 H), 8.00 (dd, J=1.5 Hz, 8.8 Hz, 1 H), 7.39 (d, J=8.9 Hz, 1 H), 7.20 (m, 2 H), 6.99 (d, J=6.6 Hz, 2 H), 6.75 (t, J=7.3 Hz, 1 H), 4.06 (m, 1 H), 3.82 (d, J=11.7, 1 H), 3.68 (d, J=11.2 Hz, 1 H), 2.68-2.76 (m, 2 H), 1.99 (m, 1 H), 1.81 (m, 1 H), 1.63 (m, 2 H).

Synthesis of 3-(2-methylpyridin-4-yl)-1H-indazole-5-carboxylic acid

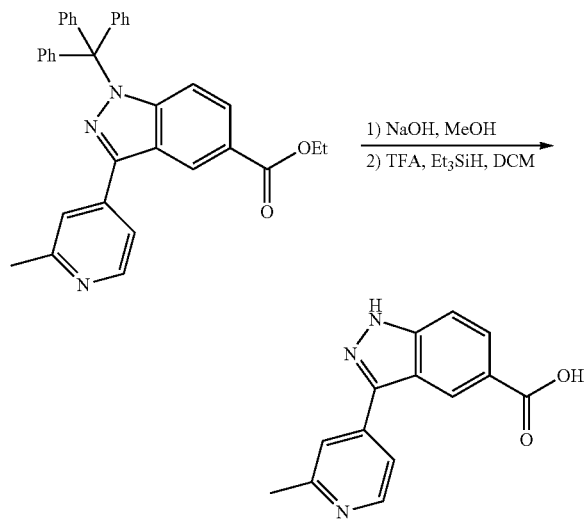

Step 1: In a sealed flask was added ethyl 3-(2-methylpyridin-4-yl)-1-trityl-1H-indazole-5-carboxylate (420 mg, 0.802 mmol), MeOH (6 ml), and sodium hydroxide (1N in water, 4 ml, 4.00 mmol). The resulting mixture was then heated for 60 min at a temperature of 80° C. with stirring. The mixture was then neutralized with HCl (2N in water), diluted with 10% isopropanol in chloroform, washed with water, dried with sodium sulfate, filtered, and concentrated to afford 3-(2-methylpyridin-4-yl)-1-trityl-1H-indazole-5-carboxylic acid (392 mg, 0.791 mmol) as a light yellow solid. The crude product was progressed to the next step without purification.

Step 2: The synthetic intermediate from Step 1 (392 mg, 0.791 mmol), dichloromethane (2 ml), and trifluoroacetic acid (2 ml) were combined in an open vial. Triethylsilane (1.011 ml, 6.33 mmol) was then added, and the resulting mixture was stirred at a temperature of 23° C. for 50 minutes. The reaction mixture was then diluted with dichloromethane, and 2N HCl was added drop-wise until the pH of the mixture was between 4 and 5. This resulting precipitate was collected via filtration and rinsed with water, methanol and dichloromethane to afford 3-(2-methylpyridin-4-yl)-1H-indazole-5-carboxylic acid (220 mg, 0.674 mmol, 85% yield) as a green solid. The crude product was progressed to the next step without purification.

Synthesis of 3-amino-1-(2-fluoro-6-methoxybenzyl) piperidin-2-one

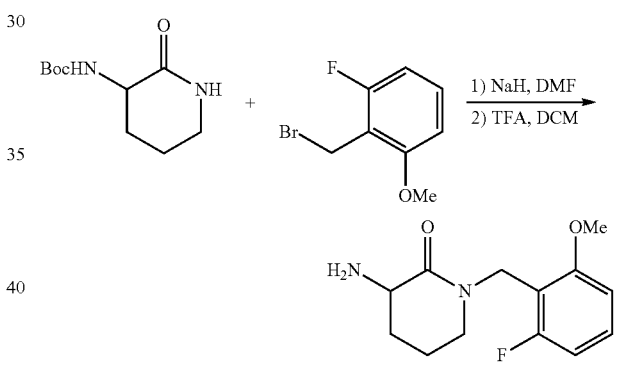

Step 1: Sodium hydride (82 mg, 2.054 mmol) was added to a solution of tert-butyl 2-oxopiperidin-3-ylcarbamate (200 mg, 0.933 mmol) in dimethylformamide (2 ml) at 23° C. and the resulting mixture was allowed to stir for 30 minutes. The mixture was then cooled to 0° C., and a solution of 2-(bromomethyl)-1-fluoro-3-methoxybenzene (214 mg, 0.977 mmol) in dimethylformamide (1.2 ml) added to the reaction mixture drop-wise. The resulting solution was allowed to stir for 90 minutes and was quenched with methanol. The mixture was then diluted with EtOAc, washed with water and brine, dried with magnesium sulfate, filtered and concentrated to afford tert-butyl 1-(2-fluoro-6-methoxybenzyl)-2-oxopiperidin-3-ylcarbamate. The crude product was progressed to the next step without purification.

Step 2: The synthetic intermediate from Step 1 (329 mg, 0.934 mmol), dichloromethane (1 ml), and trifluoroacetic acid (1 ml) were combined in an open vial, and the mixture was allowed to stir for 1 hour. The mixture was then diluted with toluene (3 ml) and subsequently concentrated to dryness. Crude (3-amino-1-(2-fluoro-6-methoxybenzyl)piperidin-2-one so obtained was used in the next synthetic transformation without additional purification.

Synthesis of N-(1-(2-fluoro-6-methoxybenzyl)-2-oxopiperidin-3-yl)-3-(2-methylpyridin-4-yl)-1H-indazole-5-carboxamide

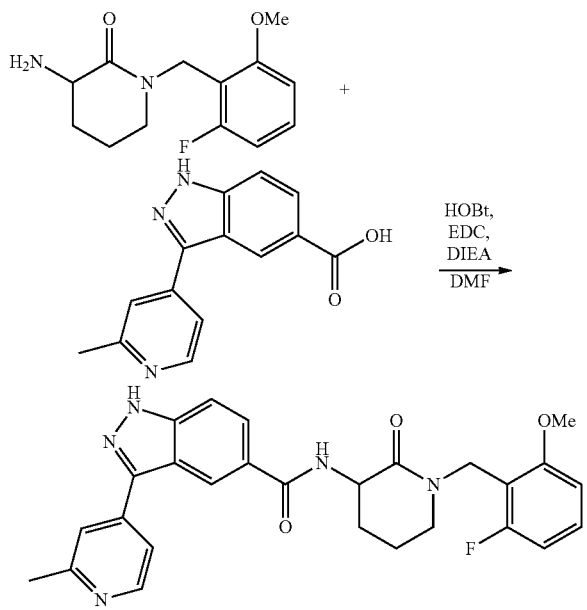

3-(2-methylpyridin-4-yl)-1H-indazole-5-carboxylic acid (50 mg, 0.154 mmol), 3-amino-1-(2-fluoro-6-methoxybenzyl)piperidin-2-one (148 mg, 0.308 mmol), 1-ethyl-3-(3-dimethylaminopropyl)carbodiimide (44.4 mg, 0.231 mmol) and hydroxybenzo-triazole (23.62 mg, 0.154 mmol) were combined in a sealed vial. DMF (0.8 ml) and N,N-diisopropylethylamine (0.269 ml, 1.542 mmol) were added and the reaction mixture stirred for 16 hours at a temperature of 23° C. The residue was then purified by preparative HPLC Normal phase, eluting with dichloromethane/MeOH (0-20%) to give N-(1-(2-fluoro-6-methoxybenzyl)-2-oxopiperidin-3-yl)-3-(2-methylpyridin-4-yl)-1H-indazole-5-carboxamide as a colorless solid. MS ESI calc'd. for $C_{27}H_{26}FN_5O_3$ [M+H]$^+$ 488, found 488. $^1$H NMR (600 MHz, CDCl$_3$) δ 10.80-10.49 (m, 1H), 8.60 (d, J=5.1 Hz, 1H), 8.53 (s, 1H), 7.85 (d, J=8.8 Hz, 1H), 7.73 (s, 1H), 7.67 (d, J=4.9 Hz, 1H), 7.52 (d, J=8.7 Hz, 1H), 7.46 (s, 1H), 6.75-6.65 (m, 3H), 5.00 (d, J=14.1 Hz, 1H), 4.51 (d, J=14.2 Hz, 1H), 4.49-4.42 (m, 1H), 3.84 (s, 3H), 3.35-3.21 (m, 2H), 2.65 (s, 3H), 1.95-1.82 (m, 2H), 1.65-1.55 (s, 2H).

3-bromo-1-trityl-1H-indazole-5-carboxylic acid

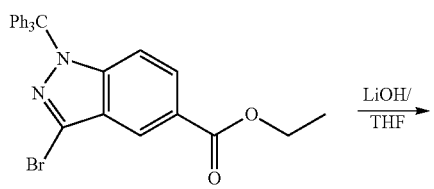

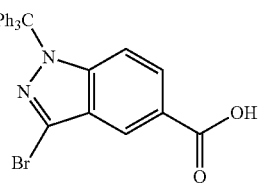

To a solution of ethyl 3-bromo-1-trityl-1H-indazole-5-carboxylate (5.3 g, 20 mmol) in THF (80 mL), was added LiOH (30 mL, 1 N) and the reaction mixture was stirred at 50° C. for overnight. HCl (1 N) was added to adjust the pH~4. Then ethyl acetated (100 mL) was added. The organic layer was separated and the aqueous layer was extract three times with ethyl acetate (20 mL each). The combined organic was washed with water (30 mL×3). Dry over Na$_2$SO$_4$ and concentrated on vacuum to give desired product as light yellow solid (4.8 g).

(R)-benzyl 3-(3-bromo-1-trityl-1H-indazole-5-carboxamido)piperidine-1-carboxylate

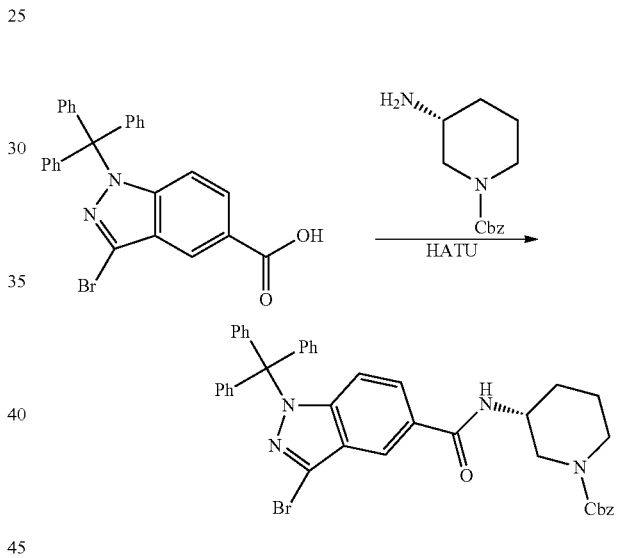

2-(7-Aza-1H-benzotriazole-1-yl)-1,1,3,3-tetramethyluronium hexafluorophosphate (HATU) (3.1 mmol) was added to a suspension of 3-bromo-1-trityl-1H-indazole-5-carboxylic acid (1 g, 2.07 mmol) in DMF (5 mL) and was stirred at room temperature for 15 minutes. A solution of (R)-benzyl 3-aminopiperidine-1-carboxylate (500 mg, 2.13 mmol) in DMF (5 mL) was added to the reaction and followed by diisopropyl ethyl amine (DIEA) (0.72 mL). The mixture was stirred at room temperature for an additional 30 minutes. The reaction was quenched with water (50 mL) and extracted with ethyl acetate (3×100 mL). The extracts were combined, dried using Benzyl 3-(3-(2,3-dihydrobenzofuran-5-yl)-1-trityl-1H-indazole-5-carboxamido)piperidine-1-carboxylate

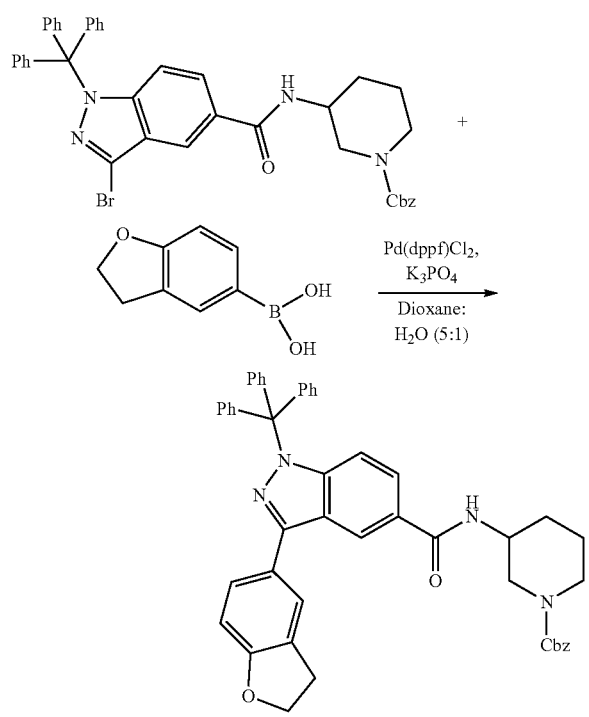

Benzyl 3-(3-bromo-1-trityl-1'-1-indazole-5-carboxamido)piperidine-1-carboxylate (0.050 g, 0.0716 mmol), [1,1'-Bis(diphenylphosphino)ferrocene]dichloro-palladium(II) (0.0052 g, 0.00716 mmol), Potassium phosphate tribasic (0.046 g, 0.215 mmol) and 2,3-dihydrobenzofuran-5-ylboronic acid (0.0129 g, 0.0788 mmol) was added into a flask. After purging the reaction vessel with nitrogen gas, dioxane (0.215 mL) and water (0.043 mL) was added. The reaction was allowed to stir at 80° C. for 16 hrs. The reaction was quenched with water (1 mL) and extracted with dichloromethane (3×1 mL). The extracts were combined, dried using sodium sulfate, filtered through celite, and concentrated under vacuo. The crude product was progressed to the next step without further purification.

3-(2,3-Dihydrobenzefuran-5-yl)-N-(piperidin-3-yl)-1-trityl-1H-indazole-5-carboxamide

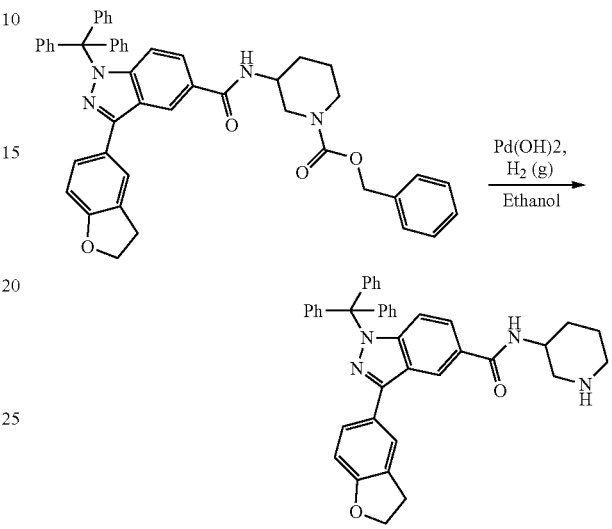

In a flask, ethanol (5.66 mL) was added to Benzyl 3-(3-(2,3-dihydrobenzofuran-5-yl)-1-trityl-1H-indazole-5-carboxamido)piperidine-1-carboxylate (0.53 g, 0.0718 mmol). The reaction vessel was purged with argon$_{(g)}$ and palladium hydroxide (0.053 g) was added. Hydrogen gas was bubbled through the solution for 15 minutes, and the reaction was allowed to stir for 1 hr at room temperature under hydrogen atmosphere. The reaction was filtered through celite, concentrated, and columned using hexane and ethyl acetate gradient from 0% to 100%. The reaction yielded 97% of pure product.

Synthesis of tert-butyl 3-(3-bromo-1-trityl-1H-indazole-5-carboxamido)-4-(3-fluorophenyl)piperidine-1-carboxylate

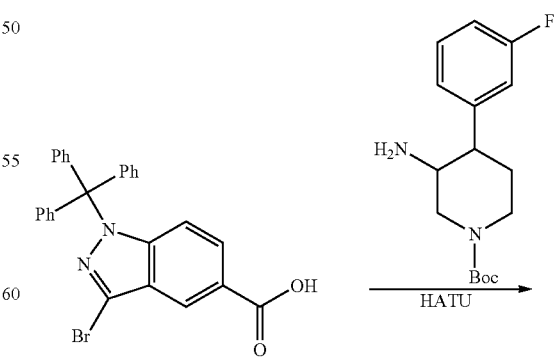

-continued

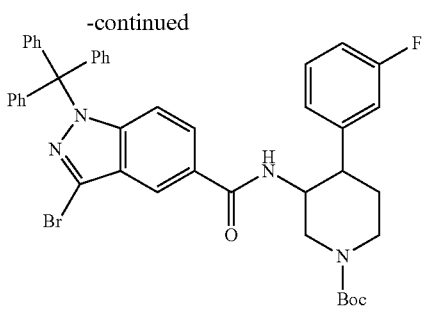

2-(7-Aza-1H-benzotriazole-1-yl)-1,1,3,3-tetramethyluronium hexafluoro-phosphate (HATU) (88 mg, 0.231 mmol) was added to a suspension of 3-bromo-1-trityl-1H-indazole-5-carboxylic acid (100 mg, 0.21 mmol) in DMF (0.5 mL) and was stirred at room temperature for 15 minutes. A solution of tert-butyl 3-amino-4-(3-fluorophenyl)piperidine-1-carboxylate (62 mg, 0.21 mmol) in DMF (0.5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

Synthesis of tert-butyl 4-(3-fluorophenyl)-3-(3-(pyridin-4-yl)-1-trityl-1H-indazole-5-carboxamido)piperidine-1-carboxylate

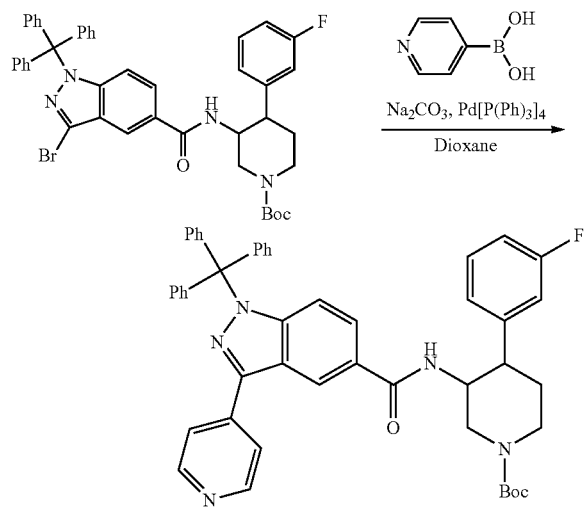

tert-butyl 3-(3-bromo-1-trityl-1H-indazole-5-carboxamido)-4-(3-fluorophenyl)-piperidine-1-carboxylate (80 mg, 0.105 mmol) was added to a vial containing pyridin-4-ylboronic acid (13 mg, 0.105 mmol) and tetrakis(triphenylphosphine)palladium (13 mg, 0.0105 mmol). After purging the vial with nitrogen gas, dioxane (0.5 mL) and 2M sodium carbonate (0.5 mL) was added to the vial respectively. The reaction mixture was stirred and was heated to 80° C. for overnight. Upon completion, the mixture was concentrated under vacuo. Water (3 mL) was added and was extracted using dichloromethane (3×5 mL). The extracts were combined and dried using anhydrous sodium sulfate. The resulting suspension was filtered and concentrated. The crude product was progressed to the next step without purification.

Synthesis of N-(4-(3-fluorophenyl)piperidin-3-yl)-3-(pyridin-4-yl)-1H-indazole-5-carboxamide

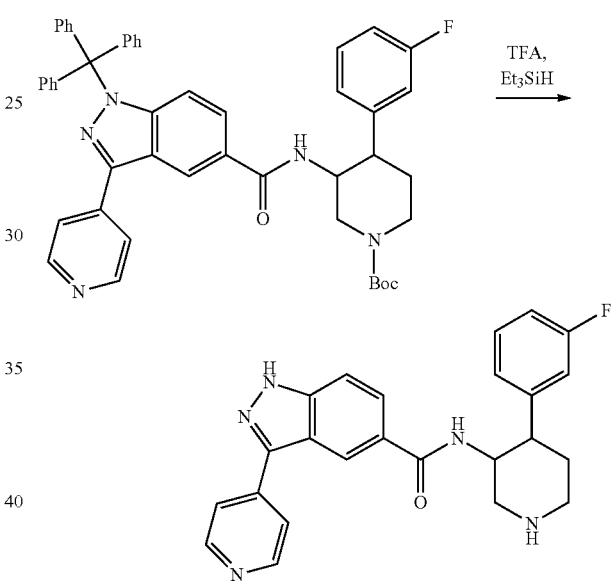

Trifluoroacetic acid (1 mL) was added to tert-butyl 4-(3-fluorophenyl)-3-(3-(pyridin-4-yl)-1-trityl-1H-indazole-5-carboxamido)piperidine-1-carboxylate (0.105 mmol). The reaction was stirred at room temperature for 30 minutes. Triethylsilane (1 drop) was added to the reaction and stirred for an additional 5 minutes. The reaction was concentrated in vacuo and purified using prep LC/MS.

Similar compounds with varying right-hand-side substitutions were made using the procedure above with slight modifications.

| Structure | Kd TdF (nM) | cERK IC50 (nM) | aERK IC50 (nM) | M + H Calcd. | M + H Obs. | Retention Time minutes |
|---|---|---|---|---|---|---|
| 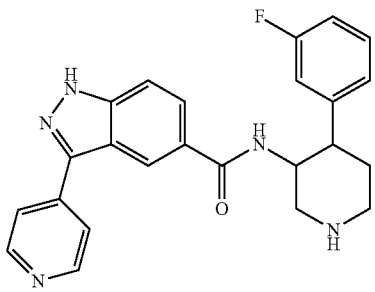 [SMILES: O=C(NC1CNCCC1c1cccc(F)c1)c1ccc2[nH]nc(-c3ccncc3)c2c1] | 106 | | | 416.2 | 416.1 | 2.4 |
| 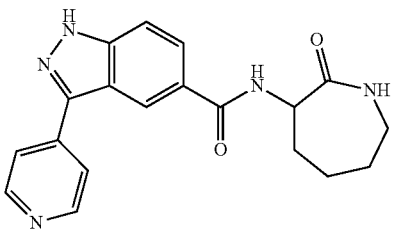 [SMILES: O=C(NC1CCCCNC1=O)c1ccc2[nH]nc(-c3ccncc3)c2c1] | 73 | | | 350.2 | 350.2 | 2.2 |
| 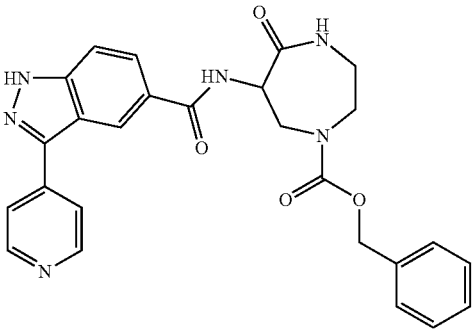 [SMILES: O=C(NC1CN(C(=O)OCc2ccccc2)CCNC1=O)c1ccc2[nH]nc(-c3ccncc3)c2c1] | 290 | | | 485.2 | 485.1 | 2.9 |
| 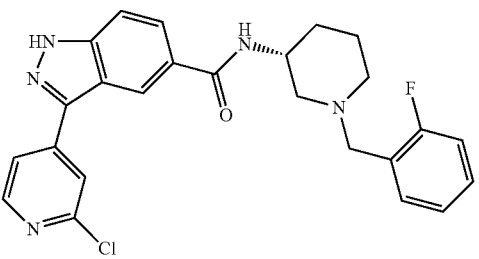 [SMILES: O=C(N[C@@H]1CCCN(Cc2ccccc2F)C1)c1ccc2[nH]nc(-c3ccnc(Cl)c3)c2c1] | 0.58 | 25.0 | 26.1 | 464.2 | 464.6 | 3.1 |
| 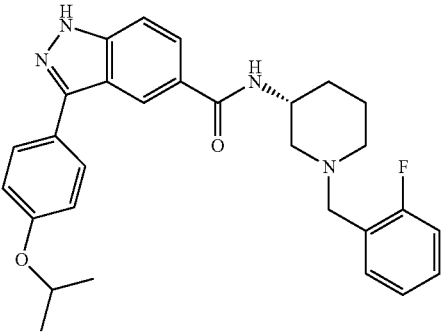 [SMILES: CC(C)Oc1ccc(-c2n[nH]c3ccc(C(=O)N[C@@H]4CCCN(Cc5ccccc5F)C4)cc23)cc1] | 1.2 | 442.6 | 275.1 | 487.2 | 487.7 | 3.7 |
| 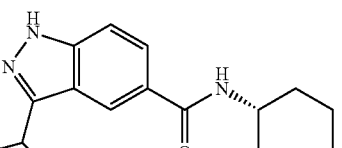 | 2 | 124.1 | 77.9 | 488.2 | 488.7 | 3.5 |

The following compounds were made by procedures similar to those described above.

| Structure | IUPAC Name | Exact Mass [M + H]+ | aERK IC$_{50}$ (nM)[b] |
|---|---|---|---|
| (Abs) | 3-(3,6-dihydro-2H-pyran-4-yl)-N-[(3R)-1-(2-fluoro-6-methoxybenzyl)piperidin-3-yl]-1H-indazole-5-carboxamide | Calc'd 465, found 465 | 1.3 |
| (Abs) | 3-(1,1-dioxido-3,6-dihydro-2H-thiopyran-4-yl)-N-[(3R)-1-(2-fluoro-6-methoxybenzyl)piperidin-3-yl]-1H-indazole-5-carboxamide | Calc'd 513, found 513 | 8.4 |

[b]aERK assay condition 2

3-(1,1-dioxidotetrahydro-2H-thiopyran-4-yl)-N-[(3R)-1-(2-fluoro-6-methoxybenzyl)piperidin-3-yl]-1H-indazole-5-carboxamide

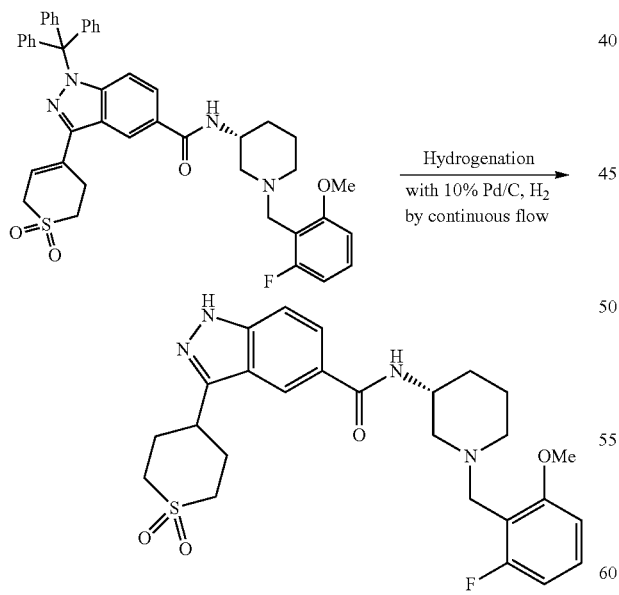

A vial containing 3-(1,1-dioxido-3,6-dihydro-2H-thiopyran-4-yl)-N-[(3R)-1-(2-fluoro-6-methoxybenzyl)piperidin-3-yl]-1-trityl-1H-indazole-5-carboxamide (100 mg, 0.132 mmol) was charged with ethyl acetate (20 mL) to yield a homogenous solution. The resulting volume was continuously recycled through a 30 mm 10% Pd/C cartridge on a CatCart Thalesnano instrument (flow rate: 1 mL/min; temperature: 60° C.; pressure: 60 bar).

Within 4 hours the reaction was judged to be complete by LC/MS analysis. The solution was concentrated and the residue was dissolved in 3:1 acetonitrile/dimethyl-sulfoxide (1 mL). The solution was filtered and the filtrate was purified by reversed phase mass triggered chromatography with a formic acid buffer. The active fraction was concentrated to dryness yielding a white powder. The white solid was analyzed by $^1$H NMR and LC/MS. These confirmed isolation of the monoformic acid salt in good purity (24.0 mg, 32%). MS ESI calc'd for $C_{26}H_{32}FN_4O_4S$ [M+H]$^+$515, found 515. $^1$H NMR (500 MHz, d$_6$DMSO) δ 13.02 (s, 1H), 8.28 (s, 1H), 8.17 (s, 1H), 8.13 (d, J=8.2, 1H), 7.82 (d, J=8.8, 1H), 7.50 (d, J=8.7, 1H), 7.30 (dd, J=8.3, 15.3, 1H), 6.87 (d, J=8.4, 1H), 6.78 (t, J=8.7, 1H), 4.02-3.85 (m, 1H), 3.80-3.70 (m, 4H), 3.56-3.50 (m, 3H), 3.25-3.20 (m, 2H), 2.87-2.80 (m, 1H), 2.72-2.65 (m, 1H), 2.34-2.30 (m, 4H), 1.94 (d, J=10.3, 2H), 1.87-1.70 (m, 1H), 1.65-1.60 (m, 1H), 1.53-1.39 (m, 1H), 133 (s, 1H) ppm.

| Structure | IUPAC Name | Exact Mass [M + H]+ | aERK IC$_{50}$ (nM)[b] |
|---|---|---|---|
| (Abs) | N-[(3R)-1-(2-fluoro-6-methoxybenzyl)piperidin-3-yl]-3-(tetrahydro-2H-pyran-4-yl)-1H-indazole-5-carboxamide | Calc'd 467, found 467 | 195 |

[b]aERK assay condition 2

N-[(3R)-1-(2-fluoro-6-methoxybenzyl)piperidin-3-yl]-3-(1H-imidazol-5-yl)-1H-indazole-5-carboxamide

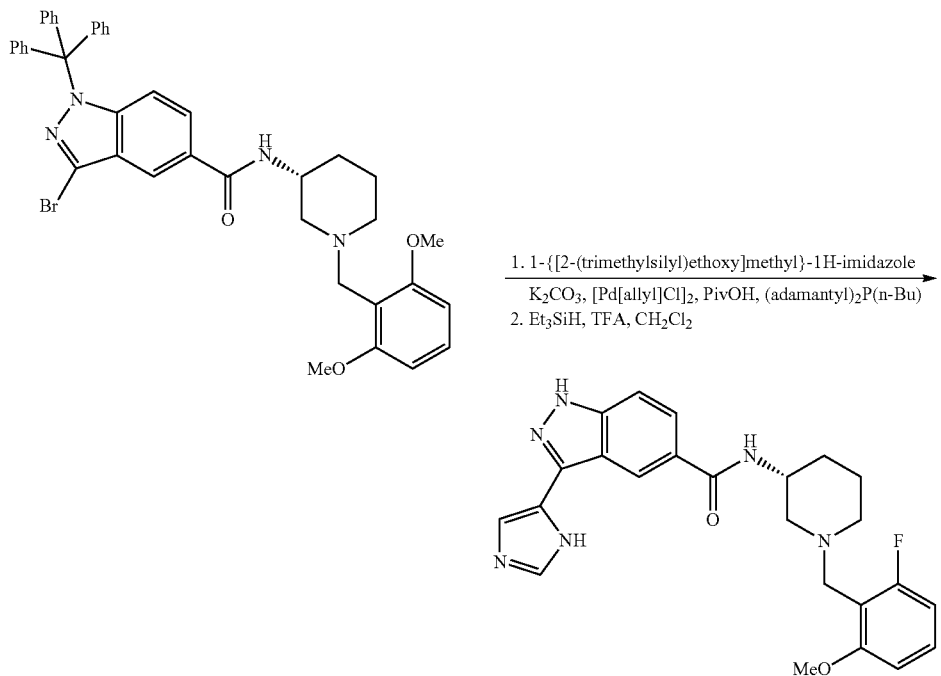

A conical vial was charged with 3-bromo-N-[(3R)-1-(2-fluoro-6 methoxybenzyl)piperidin-3-yl]-1-trityl-1H-indazole-5-carboxamide (100 mg, 0.142 mmoles), 1-{[2-(trimethylsilyl)ethoxy]methyl}-1H-imidazole (42.3 mg, 0.213 mmoles), potassium carbonate (58.9 mg, 0.426 mmoles), butyldi-1-adamantylphosphine (10.2 mg, 0.028 mmoles), pivalic acid (21.8 mg, 0.213 mmoles) and allylpalladium(II) chloride dimer (2.6 mg, 0.0071 mmoles). The reaction vessel was put under an atmosphere of argon and dimethylacetamide (0.50 mL) was injected. The reaction was heated to 105° C. for a period of 16 hours.

The reaction was allowed to cool and was poured into ethyl acetate and saturated sodium bicarbonate. The organic phase was separated, dried over sodium sulfate, filtered and concentrated. The resulting residue was dissolved in dichloromethane (2 mL) and the solution was treated with trimethylsilane (0.56 mL, 3.5 mmoles) and trifluoroacetic acid (0.054 mL, 0.70 mmoles).

The solution was heated to 40° C. for 4 hours and then allowed to cool. The solvent was removed under reduced pressure and the residue was dissolved in acetonitrile, filtered and purified by reversed phase HPLC. The active fraction was concentrated to dryness and the residue was filtered through a Varian sodium bicarbonate cartridge.

The resulting solution was concentrated to dryness yielding the title compound (2.1 mg, 3.2%) as yellow oil. Data fully matched the expected product, although the proton NMR displayed somewhat broad peaks. MS EST calc'd for $C_{24}H_{26}FN_6O_2$ [M+H]$^+$449. found 449. $^1$H NMR (500 MHz, d$_6$DMSO) δ 8.30-8.04 (m, 2H), 7.99-7.90 (m, 4H), 7.60-7.43 (m, 1H), 7.38 (d, J=7.2, 2H), 6.85 (d, J=8.4, 1H), 6.77 (t, J=8.9, 1H), 3.98-3.93 (m, 1H), 3.83 (s, 3H), 2.91-2.80 (m, 1H), 2.76-2.65 (m, 1H), 2.01-1.95 (m, 2H), 1.82-1.70 (m, 1H), 1.70-1.58 (m, 1H), 1.54-1.38 (m, 1H), 1.38-1.26 (m, 1H) ppm.

Synthesis of tert-butyl 3-phenyl-5-(3-(pyridin-4-yl)-1-trityl-1H-indazol-5-ylcarbamoyl)piperidine-1-carboxylate

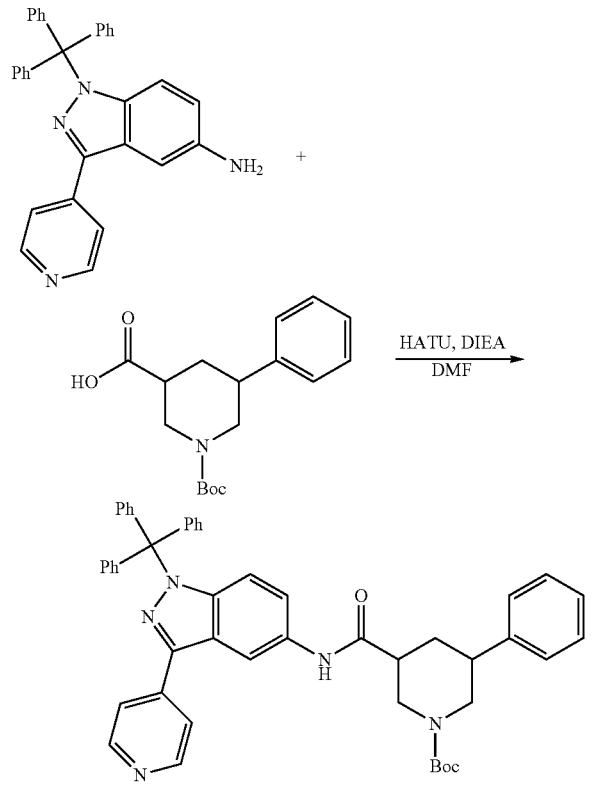

2-(7-Aza-1H-benzotriazole-1-yl)-1,1,3,3-tetramethyluronium hexafluorophosphate (HATU) (49 mg, 0.129 mmol) was added to a suspension of 1-(tert-butoxycarbonyl)-5-phenylpiperidine-3-carboxylic acid (36 mg, 0.117 mmol) in DMF (0.5 mL) and was stirred at room temperature for 15 minutes. A solution of 3-(pyridin-4-yl)-1-trityl-1H-indazol-5-amine (0.117 mmol) in DMF (0.5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

Synthesis of 5-phenyl-N-(3-(pyridin-4-yl)-1H-indazol-5-yl)piperidine-3-carboxamide

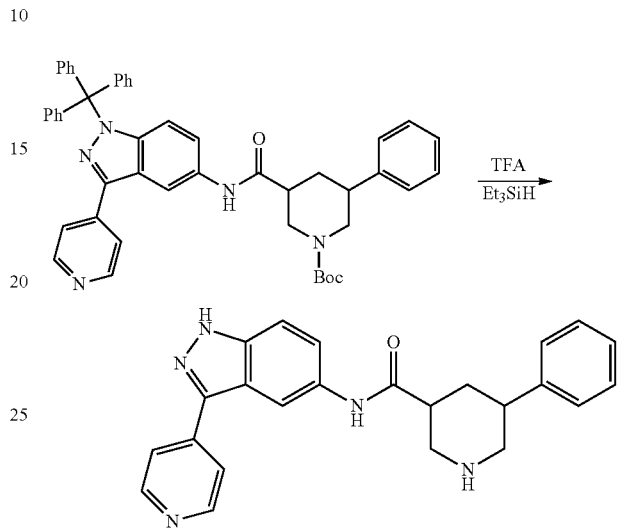

Trifluoroacetic acid (1 mL) was added to tert-butyl 3-phenyl-5-(3-(pyridin-4-yl)-1-trityl-1H-indazol-5-ylcarbamoyl)piperidine-1-carboxylate (0.117 mmol). The reaction was stirred at room temperature for 30 minutes. Triethylsilane (1 drop) was added to the reaction and stirred for an additional 5 minutes. The reaction was concentrated in vacuo and purified using prep LC/MS.

| Structure | Kd TdF (nM) | cERK IC50 (nM) | aERK IC50 (nM) | M + H Calcd. | M + H Obs. | Retention Time minutes |
|---|---|---|---|---|---|---|
| 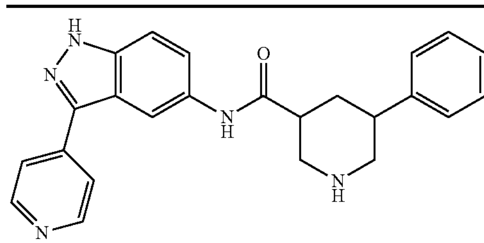 | 8 | 69.4 | 123.7 | 398.2 | 398.2 | 2.2 |

149

Synthesis of 3-(pyridin-4-yl)-1-trityl-1H-indazole-5-carboxylic acid

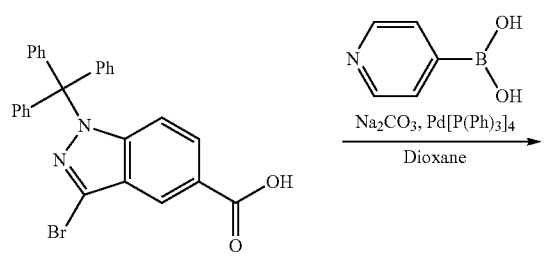

3-bromo-1-trityl-1H-indazole-5-carboxylic acid (500 mg, 1.04 mol) was added to a vial containing pyridin-4-ylboronic acid (128 mg, 1.04 mol) and tetrakis(triphenyl-phosphine) palladium (120 mg, 0.104 mol). After purging the vial with nitrogen gas, dioxane (5 mL) and 2M sodium carbonate (5 mL) was added to the vial respectively. The reaction mixture was stirred and was heated to 80° C. for overnight. Upon completion, the mixture was concentrated under vacuo. Water (30 mL) was added and pH was adjusted to 7 by HCl. The mixture was extracted using dichloromethane (3×100 mL). The extracts were combined and dried using anhydrous sodium sulfate. The resulting suspension was filtered and concentrated. The crude product was purified using prep LC/MS.

Synthesis of tert-butyl 3-phenyl-5-(3-(pyridin-4-yl)-1-trityl-1H-indazole-5-carboxamido)piperidine-1-carboxylate

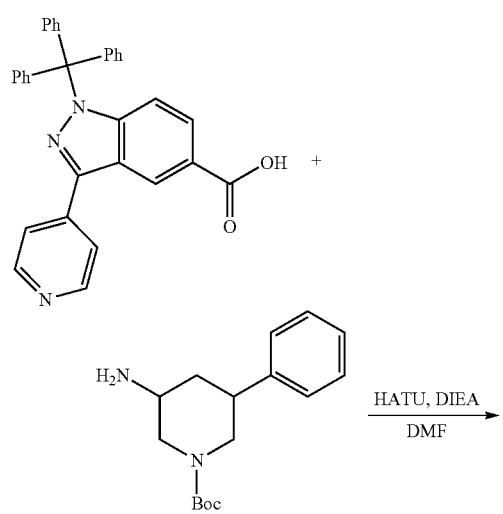

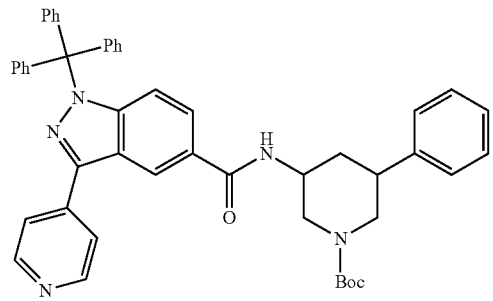

2-(7-Aza-1H-benzotriazole-1-yl)-1,1,3,3-tetramethyluronium hexafluorophosphate (HATU) (44 mg, 0.114 mmol) was added to a suspension of 3-(pyridin-4-yl)-1-trityl-1H-indazole-5-carboxylic acid (50 mg, 0.104 mmol) in DMF (0.5 mL) and was stirred at room temperature for 15 minutes. A solution of tert-butyl 3-amino-5-phenyl-piperidine-1-carboxylate (29 mg, 0.104 mmol) in DMF (0.5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

N-(5-phenylpiperidin-3-yl)-3-(pyridin-4-yl)-1H-indazole-5-carboxamide

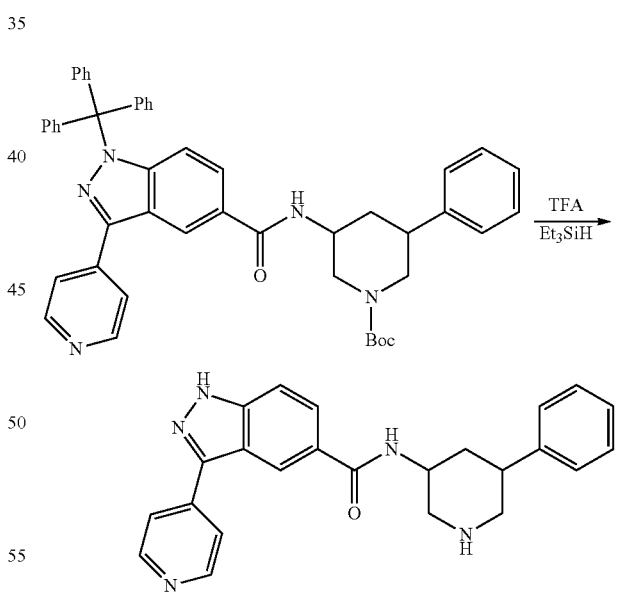

Trifluoroacetic acid (1 mL) was added to tort-butyl 3-phenyl-5-(3-(pyridin-4-yl)-1-trityl-1H-indazole-5-carboxamido)piperidine-1-carboxylate (0.104 mmol). The reaction was stirred at room temperature for 30 minutes. Triethylsilane (1 drop) was added to the reaction and stirred for an additional 5 minutes. The reaction was concentrated in vacuo and purified using prep LC/MS.

Synthesis of (S)-tert-butyl 1-benzylpiperidin-3-ylcarbamate

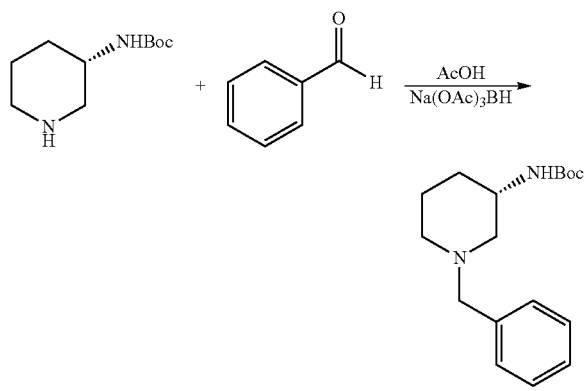 [SMILES: "AcOH" ; CC(C)(C)OC(=O)N[C@H]1CCCNC1 ; O=Cc1ccccc1 ; CC(C)(C)OC(=O)N[C@H]1CCCN(Cc2ccccc2)C1 ; "Na(OAc)3BH"]

In a flask, dichloromethane (2 mL) and acetic acid (2 drops) was added to (S)-tert-butyl piperidin-3-ylcarbamate (100 mg, 0.5 mmol) and benzaldehyde (1 mmol). The reaction was stirred for 15 minutes. Sodium triacetoxyborohydride (422 mg, 2 mmol) was added in one portion. The reaction was stirred overnight. Saturated sodium bicarbarbonate (5 mL) was added. The reaction was stirred for an additional 5 minutes and was extracted with dichloromethane (3×10 mL). The extracts were combined, dried with anhydrous sodium sulfate, filtered, and concentrated in vacuo. The crude product was progressed to the next step without purification.

Synthesis of (S)-1-benzylpiperidin-3-amine

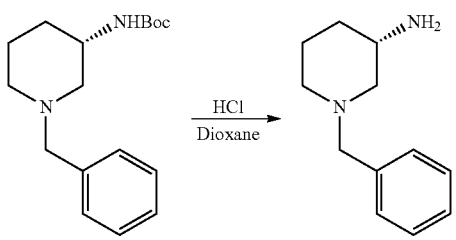 [SMILES: CC(C)(C)OC(=O)N[C@H]1CCCN(Cc2ccccc2)C1 ; Cl ; N[C@H]1CCCN(Cc2ccccc2)C1]

4N HCl in dioxane (1 mL) was added to (S)-tert-butyl 1-benzylpiperidin-3-ylcarbamate (0.5 mmol). The reaction was stirred at room temperature for 30 minutes. The solvent was removed by vacuo. The crude product was progressed to the next step without purification.

Similar compounds) with varying right-hand-side substitutions were made using the procedure above with slight modifications.

| Structure | Kd TdF (nM) | cERK IC50 (nM) | aERK IC50 (nM) | M + H Calcd. | M + H Obs. | Retention Time minutes |
|---|---|---|---|---|---|---|
| 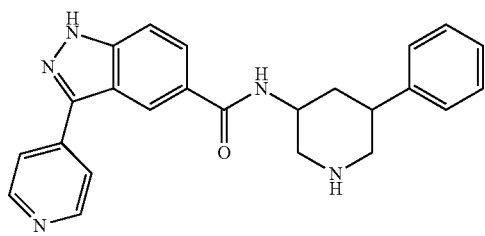 [SMILES: O=C(NC1CNCC(c2ccccc2)C1)c1ccc2[nH]nc(-c3ccncc3)c2c1] | 0.8 | | | 398.2 | 398.0 | 2.2 |
| 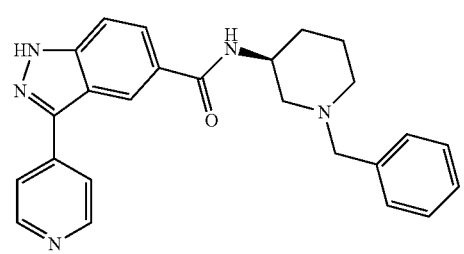 [SMILES: O=C(N[C@H]1CCCN(Cc2ccccc2)C1)c1ccc2[nH]nc(-c3ccncc3)c2c1] | 118 | 303.5 | 485.1 | 412.2 | 412.0 | 2.0 |

| Structure | Kd TdF (nM) | cERK IC50 (nM) | aERK IC50 (nM) | M + H Calcd. | M + H Obs. | Retention Time minutes |
|---|---|---|---|---|---|---|
| 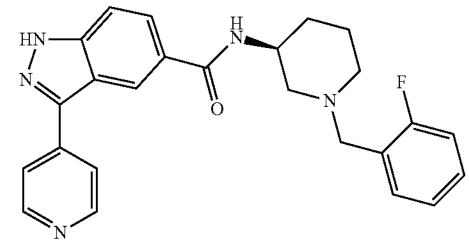 [SMILES: O=C(N[C@H]1CCCN(Cc2ccccc2F)C1)c1ccc2[nH]nc(-c3ccncc3)c2c1] | 38 | 165.6 | 224.0 | 430.2 | 430.6 | 2.0 |
| 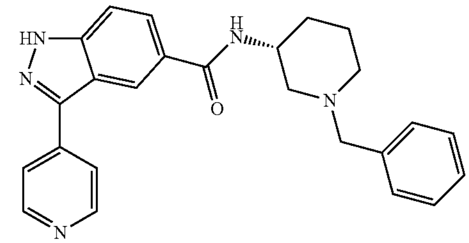 [SMILES: O=C(N[C@@H]1CCCN(Cc2ccccc2)C1)c1ccc2[nH]nc(-c3ccncc3)c2c1] | 0.3 | 2.9 | 5.8 | 412.2 | 412.6 | 2.0 |
| 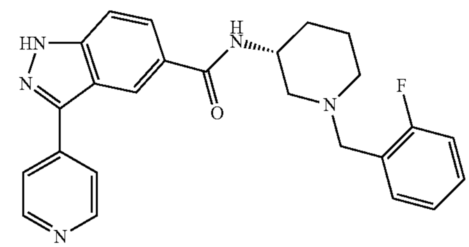 [SMILES: O=C(N[C@@H]1CCCN(Cc2ccccc2F)C1)c1ccc2[nH]nc(-c3ccncc3)c2c1] | 0.6 | 1.1 | 5.5 | 430.2 | 430.6 | 2.0 |

Synthesis of N-(1-methyl-5-phenylpiperidin-3-yl)-3-(pyridin-4-yl)-1H-indazole-5-carboxamide

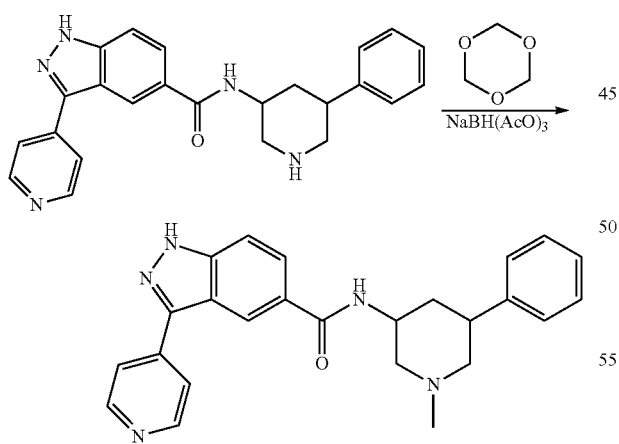

In a flask, dichloromethane (1 mL) and acetic acid (1 drop) was added to N-(5-phenylpiperidin-3-yl)-3-(pyridin-4-yl)-1H-indazole-5-carboxamide (0.05 mmol) and 1,3,5-trioxane (0.2 mmol). The reaction was stirred for 60 minutes. Sodium triacetoxyborohydride (1 mmol) was added in one portion. The reaction was stirred for 1 h. The reaction was concentrated in vacuo and purified using prep LC/MS.

| Structure | Kd TdF (nM) | cERK IC50 (nM) | aERK IC50 (nM) | M + H Calcd. | M + H Obs. | Retention Time minutes |
|---|---|---|---|---|---|---|
| 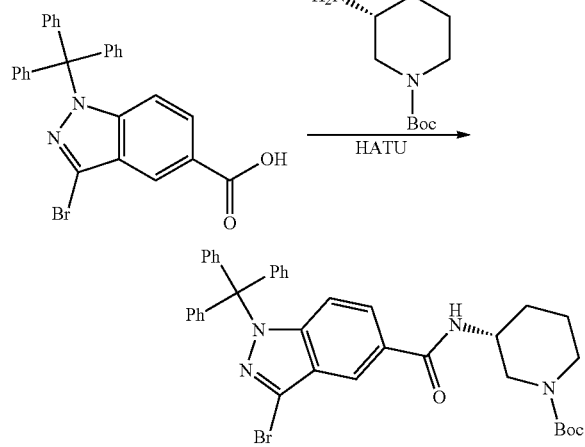 | 1.4 | 7.4 | 2.6 | 412.2 | 412.6 | 2.3 | sulfate, filtered, and concentrated in vacuo. The crude product was progressed to the next step without purification.

Synthesis of (R)-tert-butyl 3-(3-(2,3-dihydrobenzofuran-5-yl)-1-trityl-1H-indazole-5-carboxamido)piperidine-1-carboxylate Synthesis of (R)-tert-butyl 3-(3-bromo-1-trityl-1H-indazole-5-carboxamido)piperidine-1-carboxylate

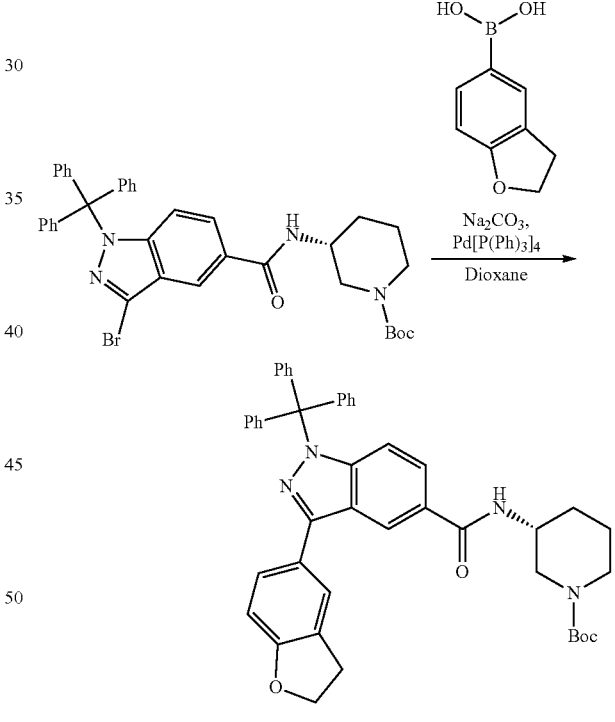

2-(7-Aza-1H-benzotriazole-1-yl)-1,1,3,3-tetramethyluronium hexafluorophosphate (HATU) (3.1 mmol) was added to a suspension of 3-bromo-1-trityl-1H-indazole-5-carboxylic acid (1 g) in DMF (5 mL) and was stirred at room temperature for 15 minutes. A solution of (R)-tert-butyl 3-aminopiperidine-1-carboxylate (415 mg) in DMF (5 mL) was added to the reaction and followed by diisopropyl ethyl amine (DIEA) (0.72 mL). The mixture was stirred at room temperature for an additional 30 minutes. The reaction was quenched with water (50 mL) and extracted with ethyl acetate (3×100 mL). The extracts were combined, dried using anhydrous sodium (R)-tert-butyl 3-(3-bromo-1-trityl-1H-indazole-5-carboxamido)piperidine-1-carboxylate (650 mg, 1 mmol) was added to a vial containing 2,3-dihydrobenzofuran-5-ylboronic acid (180 mg, 1.1 mmol) and tetrakis(triphenylphosphine)palladium (58 mg, 0.05 mmol). After purging the vial with nitrogen gas, dioxane (3 mL) and 2M sodium carbonate (1.5 mL) was added to the vial respectively. The reaction mixture was stirred and was heated to 80° C. for overnight. Upon completion, the mixture was concentrated under vacuo. Water (10 mL) was added and was extracted using dichloromethane (3×25 mL). The extracts were combined and dried using anhydrous sodium sulfate. The resulting suspension was filtered and concentrated. The crude product was purified using flash chromatography.

Synthesis of (R)-3-(2,3-dihydrobenzofuran-5-yl)-N-(piperidin-3-yl)-1H-indazole-5-carboxamide

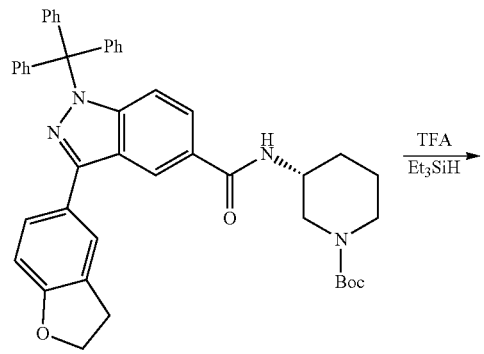

Trifluoroacetic acid (10 mL) was added to (R)-tert-butyl 3-(3-(2,3-dihydrobenzofuran-5-yl)-1-trityl-1'-1-indazole-5-carboxamido)piperidine-1-carboxylate (1 mmol). The reaction was stirred at room temperature for 30 minutes. Triethylsilane (0.3 mL) was added to the reaction and stirred for an additional 5 minutes. The crude product was progressed to the next step without purification.

Synthesis of (R)-3-(2,3-dihydrobenzofuran-5-yl)-N-(1-(pyridin-2-ylmethyl)-piperidin-3-yl)-1H-indazole-5-carboxamide

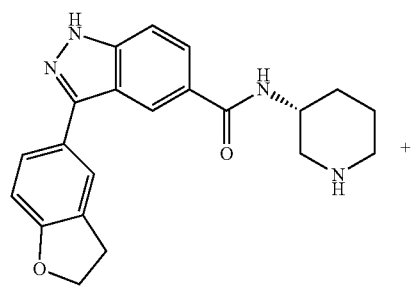

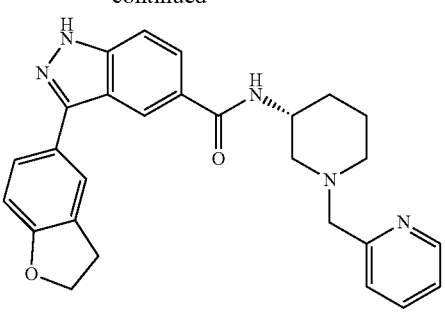

In a flask, dichloromethane (1 mL) and acetic acid (2 drops) was added to (R)-3-(2,3-dihydrobenzofuran-5-yl)-N-(piperidin-3-yl)-1H-indazole-5-carboxamide (12 mg) and picolinaldehyde (7 mg). The reaction was stirred for 15 minutes. Sodium triacetoxyborohydride (28 mg) was added in one portion. The reaction was stirred overnight. The reaction was concentrated in vacuo and purified using prep LC/MS.

Synthesis of (2S,5R)-1-tert-butyl 2-methyl 5-(3-(2-methylpyridin-4-yl)-1-trityl-1H-indazole-5-carboxamido)piperidine-1,2-dicarboxylate

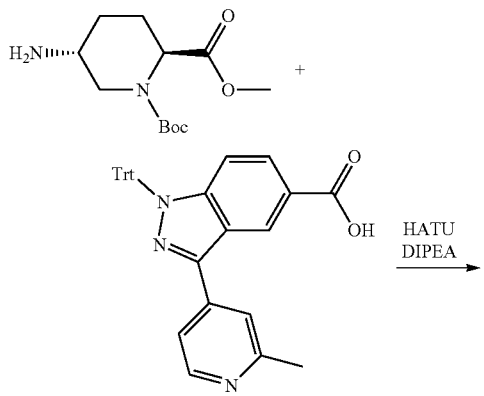

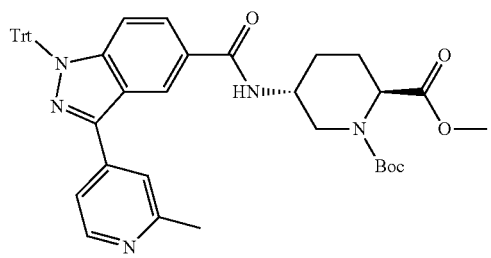

1 (167 g, 14.21 mmol) was added to a stirred mixture of 2 (6.4 g, 12.91 mmol), HATU (6.14 g, 16.14 mmol), DIPEA (11.28 ml, 64.6 mmol) in dimethylformamide and the mixture was stirred at room temperature for overnight. The reaction LCMS gave M+H at 736. The reaction was partioned between $H_2O$/EA, the EA layer was dried and rotovap to dryness and the residue was purified by column chromatography on silica gel Biotage 40M, eluting with 5% MeOH/NH₃ (2M) CH₂Cl₂ to give desired product as a white solid (7 g, 73.7% yield).

Synthesis of (2S,5R)-methyl 5-(3-(2-methylpyridin-4-yl)-1H-indazole-5-carboxamido)piperidine-2-carboxylate

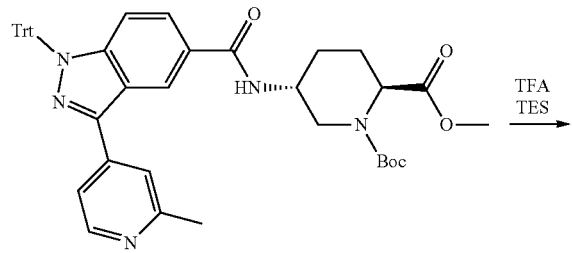

TFA (25 ml, 324 mmol) was added to a stirred mixture of (2S,5R)-1-tert-butyl 2-methyl 5-(3-(2-methylpyridin-4-yl)-1-trityl-1H-indazole-5-carboxamido) piperidine-1,2-dicarboxylate (5 g, 6.79 mmol) and TRIETHYLSILANE (1.085 ml, 6.79 mmol) in dichloromethane and the mixture was stirred at room temperature for overnight. The reaction LCMS gave M+H at 394. The reaction was rotovap to dryness and the residue was purified by column chromatography on silica gel Biotage 40M, eluting with 10% MeOH/NH₃(2M) CH₂Cl₂ to give desired product as a brown solid (4.3 g, 100% yield).

Synthesis of (2S,5R)-methyl 1-(2-fluoro-6-methoxybenzyl)-5-(3-(2-methylpyridin-4-yl)-1H-indazole-5-carboxamido)piperidine-2-carboxylate

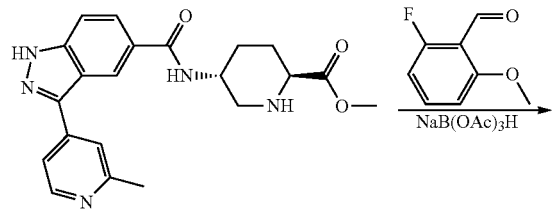

SODIUM TRIACETOXYBOROHYDRIDE (6.46 g, 30.5 mmol) was added to a stirred mixture of (2S,5R)-methyl 5-(3-(2-methylpyridin-4-yl)-1H-indazole-5-carboxamido)-piperidine-2-carboxylate (2 g, 5 mmol) and 2-Fluoro-6-Methoxy-Benzaldehyde (4.70 g, 30.5 mmol) in MeOH (100 ml) and the mixture was stirred at room temperature for overnight. The reaction LCMS gave M+H at 532. The reaction was rotovap to dryness and the residue was purified by column chromatography on silica gel Biotage 40M, eluting with 5% MeOH/NH₃(2M)CH₂Cl₂ to give desired product as a brown solid (2 g, 3.76 mmol, 74.0% yield).

Synthesis of (2S,5R)-1-(2-fluoro-6-methoxybenzyl)-5-(3-(2-methylpyridin-4-yl)-1H-indazole-5-carboxamido)piperidine-2-carboxylic acid

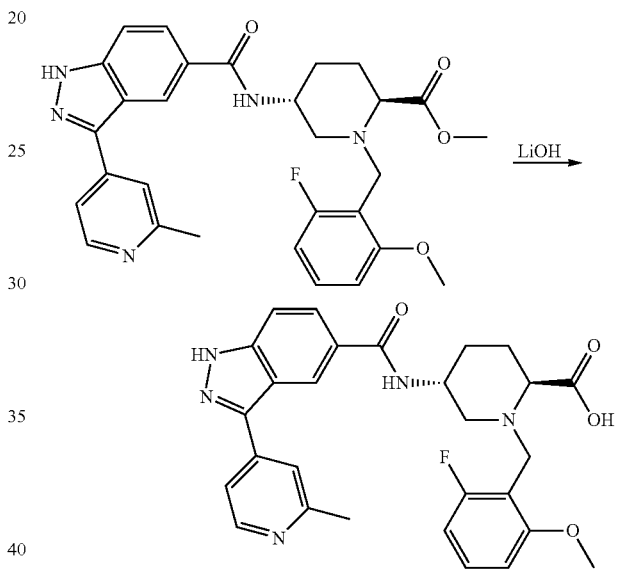

LiOH (1M, aqueous) (3.0 ml, 3.00 mmol) was added to a stirred mixture of (2S,5R)-methyl 1-(2-fluoro-6-methoxybenzyl)-5-(3-(2-methylpyridin-4-yl)-1H-indazole-5-carboxamido)piperidine-2-carboxylate (1 g, 1.881 mmol) in THF (30 ml) & MeOH (10 ml) and the mixture was stirred at room temperature for Overnight. The reaction LCMS showed most starting material (M+1=532), but tlc showed product, another 3 ml of LiOH was added to the rxn, stirred for one day, LCMS gave M+H at 518, tlc showed completion. The reaction was treated 1 N HCl in ether, 6 ml, 1 eq, and rotovap to dryness and the residue was purified by column chromatography on silica gel Biotage 40M, eluting with 20% MeOH/ CH₂Cl₂ to give the titled compound as a off-white (0.67 g, 68.8% yield).

Synthesis of N-((3R,6S)-6-(2-aminoethylcarbamoyl)-1-(2-fluoro-6-methoxybenzyl)-piperidin-3-yl)-3-(2-methylpyridin-4-yl)-1H-indazole-5-carboxamide

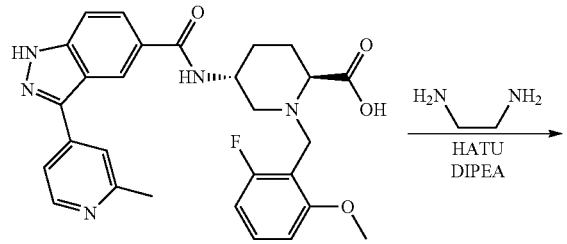

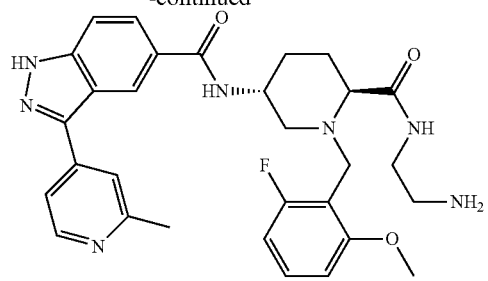

ethane-1,2-diamine (18 mg, 0.290 mmol) was added to a stirred mixture of (2S,5R)-1-(2-fluoro-6-methoxybenzyl)-5-(3-(2-methylpyridin-4-yl)-1H-indazole-5-carboxamido)-piperidine-2-carboxylic acid (50 mg, 0.097 mmol), N,N-DIISOPROPYLETHYL-AMINE (0.084 ml, 0.483 mmol), HATU (73.5 mg, 0.193 mmol) in dimethylformamide and the mixture was stirred at room temperature for Overnight. The reaction was rotovap to dryness and the residue was purified by column chromatography on silica gel Isolute Flash Si; 50 g prepacked, eluting with 5% MeOH/NH₃(2M)CH₂Cl₂ to give the desired (48.1 mg, 0.085 mmol, 88% yield) as a white solid.

Similar compounds with varying right-hand-side substitutions were made using the procedure above with slight modifications.

| Structure | Kd TdF (nM) | aERK IC50 (nM) | M + H Calcd. | M + H Obs. | Retention Time minutes |
|---|---|---|---|---|---|
| 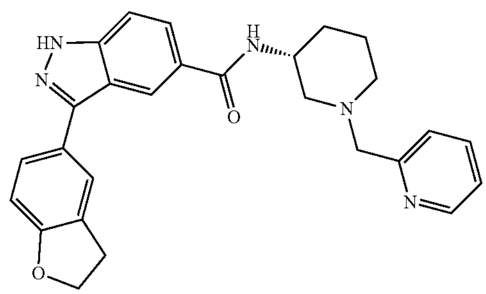 [SMILES: O=C(N[C@@H]1CCCN(Cc2ccccn2)C1)c1ccc2[nH]nc(-c3ccc4c(c3)CCO4)c2c1] | 9.2 | 591 | 454.2 | 454.6 | 2.93 |
| | 1000 | | 521.2 | 521.7 | 3.57 |

-continued
| Structure | Kd TdF (nM) | aERK IC50 (nM) | M + H Calcd. | M + H Obs. | Retention Time minutes |
|---|---|---|---|---|---|
| 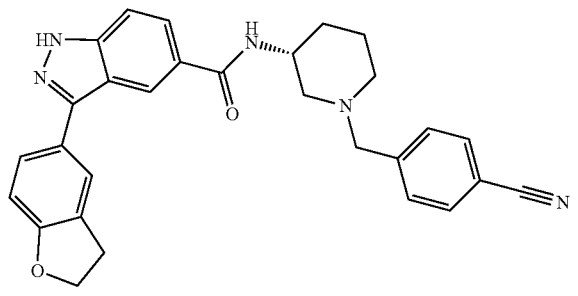 [SMILES: N#Cc1ccc(CN2CCC[C@@H](NC(=O)c3ccc4[nH]nc(-c5ccc6c(c5)CCO6)c4c3)C2)cc1] | 82 | 1000 | 478.2 | 478.6 | 3.07 |
| 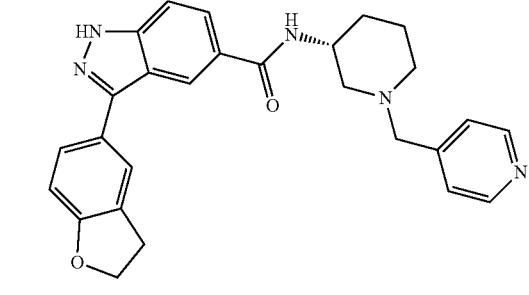 [SMILES: O=C(N[C@@H]1CCCN(Cc2ccncc2)C1)c1ccc2[nH]nc(-c3ccc4c(c3)CCO4)c2c1] | 76 | 626 | 454.2 | 454.6 | 2.44 |
| 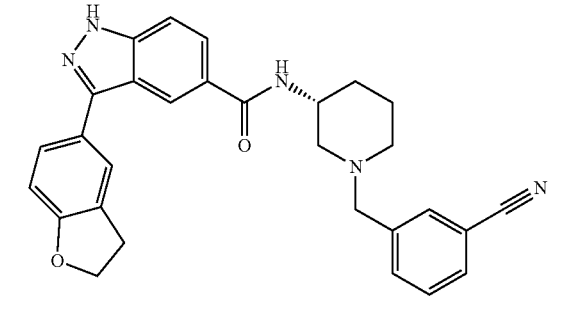 [SMILES: N#Cc1cccc(CN2CCC[C@@H](NC(=O)c3ccc4[nH]nc(-c5ccc6c(c5)CCO6)c4c3)C2)c1] |  | 999 | 478.2 | 478.6 | 3.09 |
| 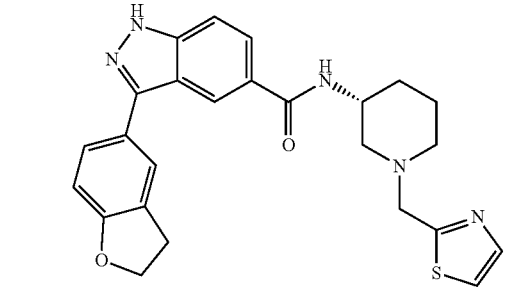 [SMILES: O=C(N[C@@H]1CCCN(Cc2nccs2)C1)c1ccc2[nH]nc(-c3ccc4c(c3)CCO4)c2c1] | 10.5 | 251 | 460.2 | 460.6 | 2.84 |
| 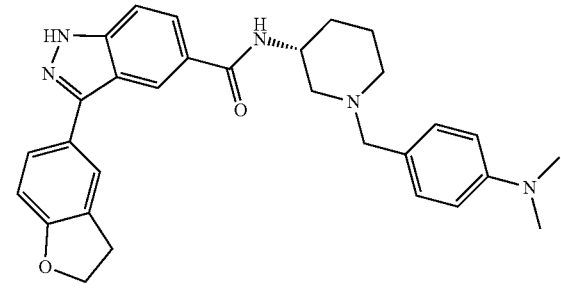 [SMILES: CN(C)c1ccc(CN2CCC[C@@H](NC(=O)c3ccc4[nH]nc(-c5ccc6c(c5)CCO6)c4c3)C2)cc1] | 1000 | 1000 | 496.3 | 496.7 | 2.81 |
| 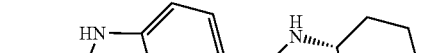 |  | 173 | 489.2 | 489.6 | 3.16 |

The following compounds were made by procedures similar to those described above.

| Structure | IUPAC Name | Exact Mass [M + H]+ | aERK IC$_{50}$ (nM)[b] |
|---|---|---|---|
| 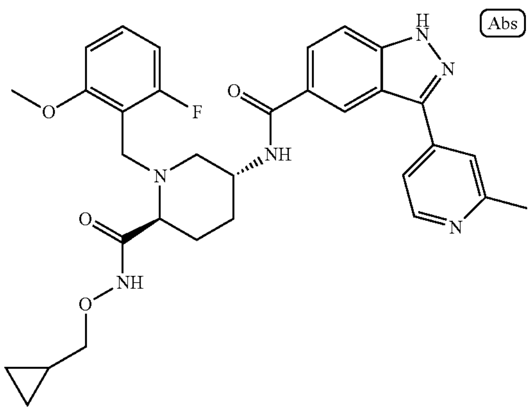 [SMILES: COc1cccc(F)c1CN1C[C@H](NC(=O)c2ccc3[nH]nc(-c4ccnc(C)c4)c3c2)CC[C@H]1C(=O)NOCC1CC1] | N-[(3R,6S)-6-[(cyclopropylmethoxy)carbamoyl]-1-(2-fluoro-6-methoxybenzyl)piperidin-3-yl]-3-(2-methylpyridin-4-yl)-1H-indazole-5-carboxamide | Calc'd 587, found 587 | 0.6 |
| 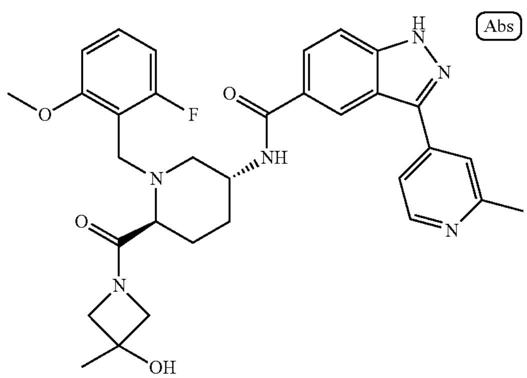 | N-{(3R,6S)-1-(2-fluoro-6-methoxybenzyl)-6-[(3-hydroxy-3-methylazetidin-1-yl)carbonyl]piperidin-3-yl}-3-(2-methylpyridin-4-yl)-1H-indazole-5-carboxamide | Calc'd 587, found 587 | 1.1 |
| 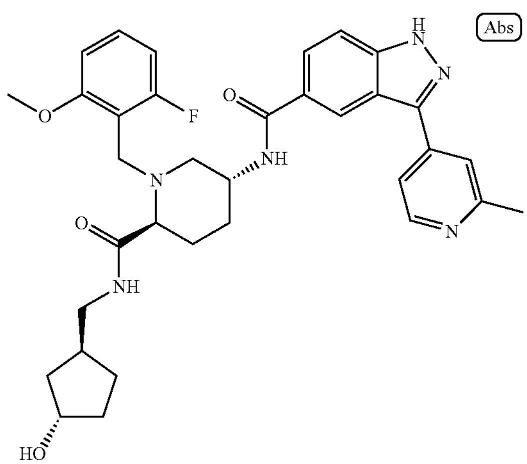 | N-[(3R,6S)-1-(2-fluoro-6-methoxybenzyl)-6-({[(1S,3S)-3-hydroxycyclopentyl]methyl}carbamoyl)piperidin-3-yl]-3-(2-methylpyridin-4-yl)-1H-indazole-5-carboxamide | Calc'd 615, found 615 | 1.3 |

-continued

| Structure | IUPAC Name | Exact Mass [M + H]+ | aERK IC50 (nM)[b] |
|---|---|---|---|
| 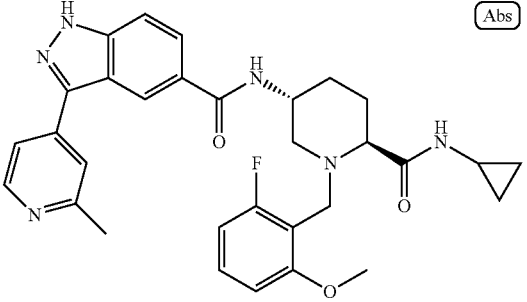 [SMILES: COc1cccc(F)c1CN1C[C@H](NC(=O)c2ccc3[nH]nc(-c4ccnc(C)c4)c3c2)CC[C@H]1C(=O)NC1CC1] | N-[(3R,6S)-6-(cyclopropylcarbamoyl)-1-(2-fluoro-6-methoxybenzyl)piperidin-3-yl]-3-(2-methylpyridin-4-yl)-1H-indazole-5-carboxamide | Calc'd 557, found 557 | 3.4 |
| 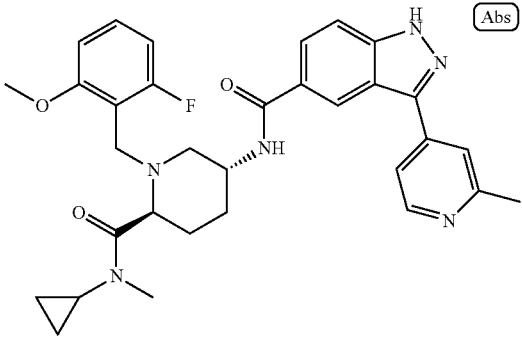 | N-[(3R,6S)-6-[cyclopropyl(methyl)carbamoyl]-1-(2-fluoro-6-methoxybenzyl)piperidin-3-yl]-3-(2-methylpyridin-4-yl)-1H-indazole-5-carboxamide | Calc'd 571, found 571 | 2.5 |
| 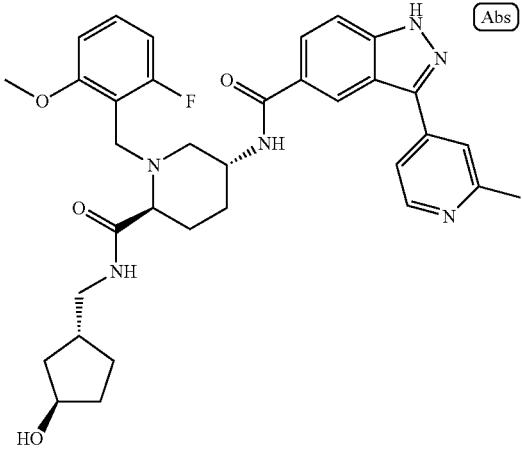 | N-[(3R,6S)-1-(2-fluoro-6-methoxybenzyl)-6-({[(1R,3R)-3-hydroxycyclopentyl]methyl}carbamoyl)piperidin-3-yl]-3-(2-methylpyridin-4-yl)-1H-indazole-5-carboxamide | Calc'd 615, found 615 | 1.5 |
| 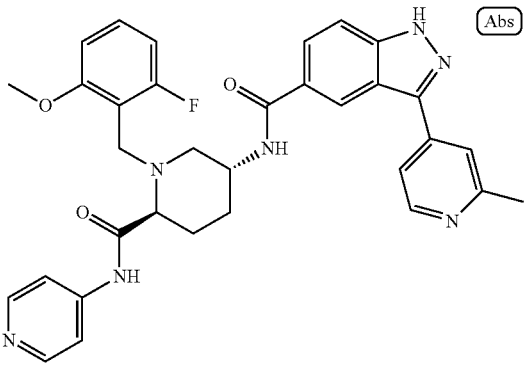 | N-[(3R,6S)-1-(2-fluoro-6-methoxybenzyl)-6-(pyridin-4-ylcarbamoyl)piperidin-3-yl]-3-(2-methylpyridin-4-yl)-1H-indazole-5-carboxamide | Calc'd 594, found 594 | 3.0 |
| 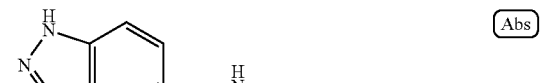 | N-[(3R,6S)-6-[(cyclopropylmethyl)carbamoyl]-1-(2-fluoro-6-methoxybenzyl)piperidin-3-yl]- | Calc'd 571, found 571 | 4.9 |

N-[(3R)-1-(5-fluoroquinolin-4-yl)piperidin-3-yl]-3-(pyridin-4-yl)-1H-indazole-5-carboxamide

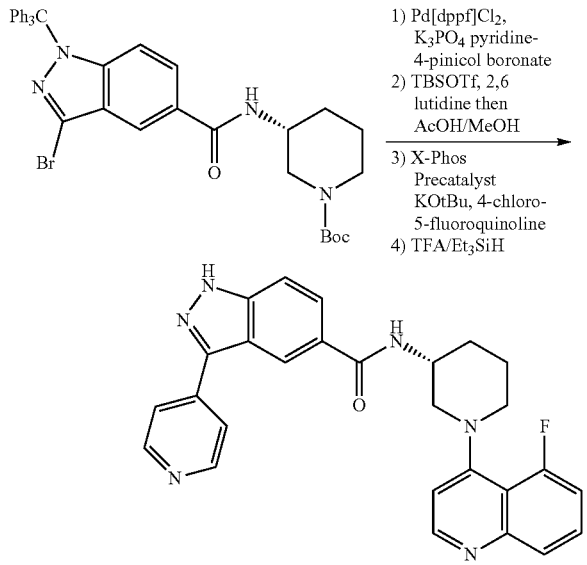

1) Pd[dppf]Cl$_2$, K$_3$PO$_4$ pyridine-4-pinicol boronate
2) TBSOTf, 2,6 lutidine then AcOH/MeOH
3) X-Phos Precatalyst KOtBu, 4-chloro-5-fluoroquinoline
4) TFA/Et$_3$SiH A flask was charged with tert-butyl (3R)-3-{[(3-bromo-1-trityl-1H-indazol-5-yl)carbonyl]amino}piperidine-1-carboxylate (4.00 g, 6.01 mmoles), potassium phosphate (2.05 g, 9.66 mmoles) and 1,1'-Bis(diphenylphosphino)ferrocene]-dichloropalladium(II) (160.0 mg, 0.219 mmoles). The flask was put under an atmosphere of argon (3× vacuum/argon cycle) and degassed dioxane (20 mL) and water (5 mL) were injected. The reaction was heated to 80° C. for 16 hours and was then allowed to cool to ambient temperature. The resulting solution was poured into water (100 mL) and the aqueous emulsion was washed three times with chloroform/isopropanol (4:1, 50 mL portions). The combined organic washings were dried over sodium sulfate, filtered and concentrated to dryness. Flash chromatography (gradient 0-15% dichloromethane/methanol) to yield tert-butyl (3R)-3-({[3-(pyridin-4-yl)-1-trityl-1H-indazol-5-yl]carbonyl}amino)piperidine-1-carboxylate as a white solid (3.79 g, 95%).

A round bottomed flask was charged with the product above and dichloromethane (30 mL) was injected under argon to yield a clear solution. 2,6-lutidine (2.4 mL, 21 mmoles) and tert-butyl-dimethylsilyl triflate (2.9 mL, 13 mmoles) were injected. The reaction mixture was warmed to 40° C. for a period of 2 hours and was then allowed to cool. The resulting solution was concentrated on the rotary evaporator and the residue was dissolved in methanol and 2-methyl tetrahydrofuran (3:1, 40 mL total volume). Acetic acid was added (5.0 mL, 87 mmoles) and the reaction was heated to 40° C. for an additional 4 hours. The reaction was then allowed to cool and was poured into sodium hydroxide (100 mL, 1N) to give a roughly neutral solution. The biphasic mixture was further diluted with sodium bicarbonate (50 mL) and ethyl acetate (300 mL). The organic phase was separated, dried over sodium sulfate and concentrated to dryness. The crude residue was purified by silica gel chromatography (gradient 0-30% dichloromethane/methanol) to yield N-[(3R)-piperidin-3-yl]-3-(pyridin-4-yl)-1-trityl-1H-indazole-5-carboxamide as a white solid (2.60 g, 79%).

A conical vial was charged with 4-chloro-5-fluoro-quinoline (24.2 mg, 0.133 mmol) and chloro(2-dicyclohexylphosphino-2',4',6'-tri-i-propyl-1,1'-biphenyl)[2-(2 minoethyl)phenyl]palladium(II) methyl-t-butyl ether adduct (1.0 mg, 1.2 μmol). The reaction was put under an atmosphere of argon and a solution of N-[(3R)-piperidin-3-yl]-3-(pyridin-4-yl)-1-trityl-1H-indazole-5-carboxamide (50.0 mg, 0.089 mmol) in THF (300 μl) was injected. potassium tert-butoxide –1M in THF (177 μl, 0.177 mmol) was injected and the reaction was heated to 60° C. under an atmosphere of argon for 16 hours.

After cooling to room temperature the reaction was filtered through a pad of celite and the filter cake was washed with ethyl acetate. The solvent was concentrated under reduced pressure and the residue was dissolved in dichloromethane (2 mL) and treated with triethylsilane (0.032 ml, 0.201 mmol) and TFA (0.309 ml, 4.01 mmol).

Within two hours the reaction was judged to be complete by LC/MS analysis. The solvent was removed under reduced pressure and the residue was dissolved in acetonitrile/dimethylsulfoxide (4:1, 1 mL). The solution was filtered and the filtrate was purified by reversed phase mass triggered chromatography. The active fraction was returned and concentrated to dryness.

The resulting white solid was dissolved in acetonitrile/methanol (1:1, ~2 mL) and filtered through a Varian bicarbonate filter. The filter was washed with methanol (~4 mL) to yield the free-base. The solvent was removed under reduced pressure to yield the product (53.4 mg, 85%). Proton NMR and LC/MS analysis confirmed isolation of the desired product. MS ESI calc'd for C$_{27}$H$_{24}$FN$_6$O [M+H]$^+$467, found 467. $^1$H NMR (500 MHz, d$_6$DMSO) δ 8.70 (d, J=6.0, 2H), 8.66-8.57 (m, 2H), 8.48 (d, J=7.5, 1H), 8.02 (d, J=6.1, 2H), 7.91 (d, J=8.8, 1H), 7.75 (d, J=8.5, 1H), 7.65 (t, J=8.1, 2H), 7.28 (s, 1H), 7.05 (s, 1H), 4.32-4.14 (m, 1H), 3.63-3.60 (m, 1H), 3.45-3.40 (m, 2H), 2.87-2.65 (m, 2H), 2.12-1.98 (m, 1H), 1.98-1.92 (m, 2H), 1.72-1.56 (m, 1H) ppm.

(R)—N-(1-(Phenylsulfonyl)piperidin-3-yl)-3-(pyridin-4-yl)-1H-indazole-5-carboxamide

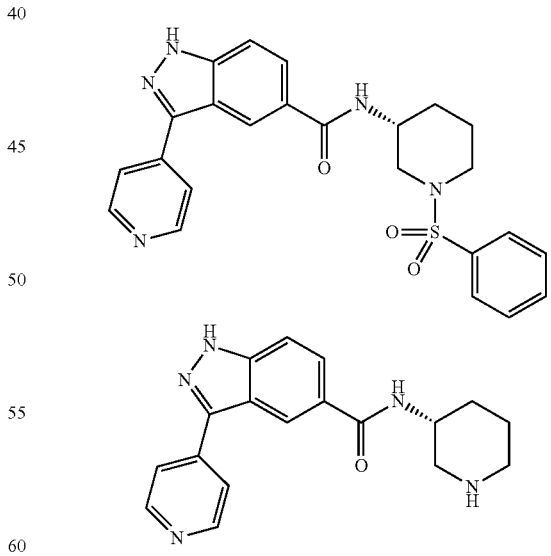

Step 1. (R) —N-(1-(Phenylsulfonyl)piperidin-3-yl)-3-(pyridin-4-yl)-1H-indazole-5-carboxamide (R)-tent-Butyl 3-(3-(pyridin-4-yl)-1-trityl-1H-indazole-5-carboxamido)piperidine-1-carboxylate (1.422 g, 2.142 mmol) and triethylsilane (0.685 mL, 4.29 mmol) were stirred in TFA (10 mL) at room temperature for 1 hour. The solvent was removed in vacuo and the residue triturated in Et$_2$O to give the bis TFA salt of (R)—N-(piperidin-3-yl)-3-(pyridin-4-yl)-1H-indazole-5-carboxamide as a beige solid. MS (APCI) calculated for C$_{18}$H$_{20}$N$_5$O [M+H]$^+$, 322; found 322 (0.85 mins).

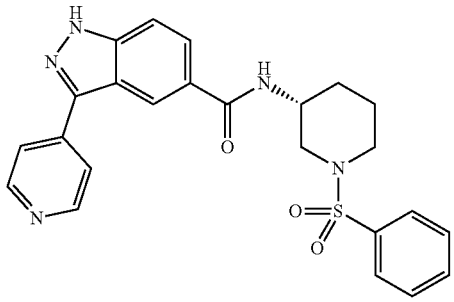 [SMILES: O=C(N[C@@H]1CCCN(S(=O)(=O)c2ccccc2)C1)c1ccc2[nH]nc(-c3ccncc3)c2c1]

Step 2. R)—N-(1-(Phenylsulfonyl)piperidin-3-yl)-3-(pyridin-4-yl)-1H-indazole-5-carboxamide (R)—N-(Piperidin-3-yl)-3-(pyridin-4-yl)-1H-indazole-5-carboxamide, bis TFA salt (45 mg, 0.082 mmol), DIPEA (0.050 mL, 0.287 mmol) and benzenesulfonyl chloride (0.013 mL, 0.098 mmol) were stirred in THF (0.8 mL) at room temperature for 20 hours. The solvent was removed in vacuo and the residue dissolved in 1 mL of DMF. This solution was purified by reverse phase mass triggered prep-HPLC. The product fraction was lyophilized to give the TFA salt of (R)—N-(1-(phenylsulfonyl)-piperidin-3-yl)-3-(pyridin-4-yl)-1H-indazole-5-carboxamide as a pale yellow solid. MS (APCI) calculated for C$_{24}$H$_{24}$N$_5$O$_3$S [M+H]$^+$, 462; found 462 (1.03 mins).

The following tables provide a comprehensive list of all of the individual compounds of the present invention prepared according to the aforementioned methods.

TABLE 1

| Structure | Kd TdF (nM) | cERK IC50 (nM) | aERK IC50 (nM) | M + H Calcd. | M + H Obs. | Retention Time minutes |
|---|---|---|---|---|---|---|
| (structure) | 106 | | | 416.2 | 416.1 | 2.4 |
| (structure) | 0.3 | 14.4 | 28.1 | 430.2 | 430.3 | 1.53 |
| (structure) | 0.6 | 16.6 | 32.5 | 412.2 | 412.3 | 1.51 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| (1H-indazole-3-(pyridin-4-yl)-5-carboxamide-N-(1-benzylpiperidin-3-yl)) | 118 | 303.5 | 485.1 | 412.2 | 412.03 | 2.04 |
| (1H-indazole-3-(pyridin-4-yl)-5-carboxamide-N-(1-(2-fluorobenzyl)piperidin-3-yl)) | 38 | 165.6 | 224.0 | 430.2 | 430.6 | 2.03 |
| (1H-indazole-3-(pyridin-4-yl)-5-carboxamide-N-(1-benzylpiperidin-3-yl), enantiomer) | 0.3 | 2.9 | 5.8 | 412.2 | 412.6 | 2.03 |
| (1H-indazole-3-(pyridin-4-yl)-5-carboxamide-N-(1-(2-fluorobenzyl)piperidin-3-yl), enantiomer) | 0.6 | 1.1 | 5.5 | 430.2 | 430.6 | 2.03 |
| (1H-indazole-3-(6-isopropoxypyridin-3-yl)-5-carboxamide-N-(1-(2-fluorobenzyl)piperidin-3-yl)) | 2.9 | 307.2 | 769.1 | 488.2 | 488.6 | 3.54 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| 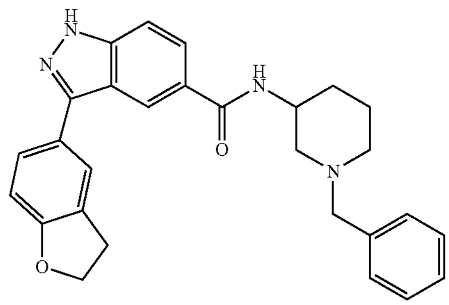 [SMILES: O=C(NC1CCCN(Cc2ccccc2)C1)c1ccc2[nH]nc(-c3ccc4c(c3)CCO4)c2c1] | 1.4 | 172.0 | 133.8 | 453.2 | 453.7 | 3.22 |
| 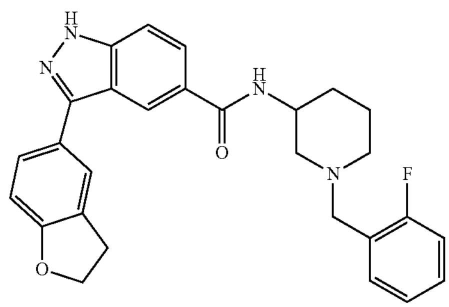 [SMILES: O=C(NC1CCCN(Cc2ccccc2F)C1)c1ccc2[nH]nc(-c3ccc4c(c3)CCO4)c2c1] | 2.6 | 230.9 | 283.7 | 471.2 | 471.7 | 3.2 |
| 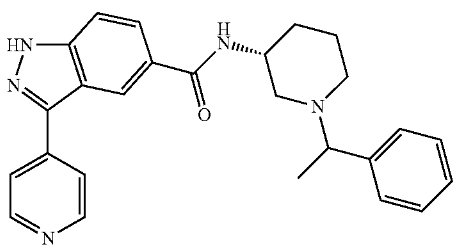 [SMILES: CC(c1ccccc1)N1CCC[C@@H](NC(=O)c2ccc3[nH]nc(-c4ccncc4)c3c2)C1] | 804 | 763.0 | 474.8 | 426.2 | 426.7 | 2.32 |
| 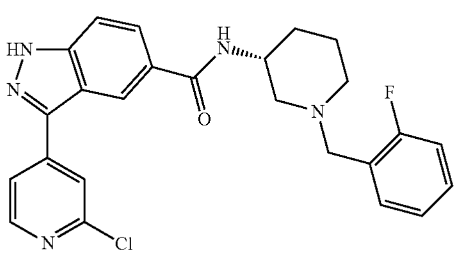 [SMILES: O=C(N[C@@H]1CCCN(Cc2ccccc2F)C1)c1ccc2[nH]nc(-c3ccnc(Cl)c3)c2c1] | 0.58 | 25.0 | 26.1 | 464.2 | 464.6 | 3.08 |
| 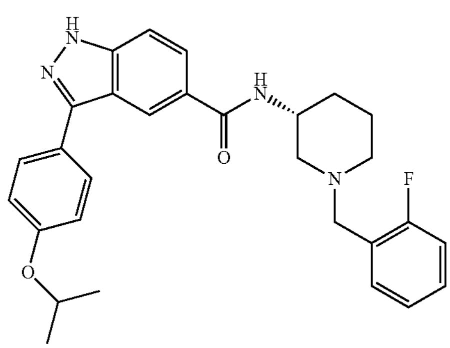 [SMILES: CC(C)Oc1ccc(-c2n[nH]c3ccc(C(=O)N[C@@H]4CCCN(Cc5ccccc5F)C4)cc23)cc1] | 1.2 | 442.6 | 275.1 | 487.2 | 487.7 | 3.7 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| 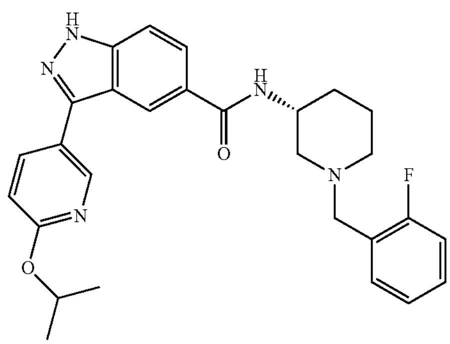 [SMILES: CC(C)Oc1ccc(-c2n[nH]c3ccc(C(=O)N[C@@H]4CCCN(Cc5ccccc5F)C4)cc23)cn1] | 2 | 124.1 | 77.9 | 488.2 | 488.7 | 3.49 |
| 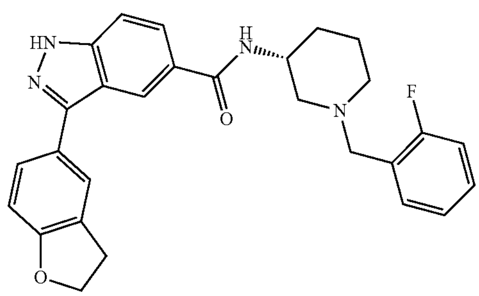 [SMILES: O=C(N[C@@H]1CCCN(Cc2ccccc2F)C1)c1ccc2[nH]nc(-c3ccc4c(c3)CCO4)c2c1] | 0.61 | 48.6 | 52.1 | 471.2 | 471.6 | 3.21 |
| 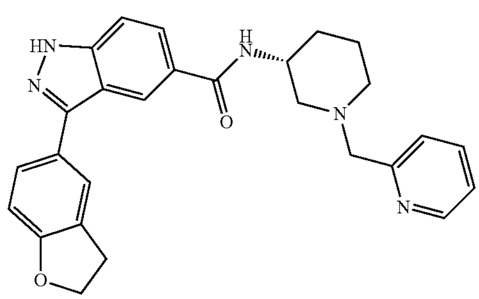 [SMILES: O=C(N[C@@H]1CCCN(Cc2ccccn2)C1)c1ccc2[nH]nc(-c3ccc4c(c3)CCO4)c2c1] | 9.2 | | 591 | 454.2 | 454.6 | 2.93 |
| 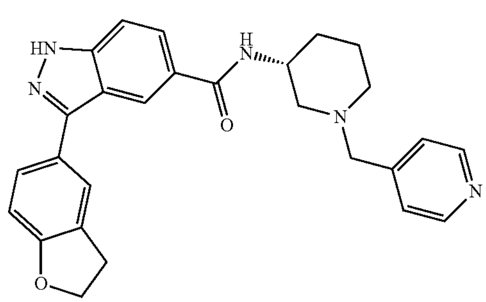 [SMILES: O=C(N[C@@H]1CCCN(Cc2ccncc2)C1)c1ccc2[nH]nc(-c3ccc4c(c3)CCO4)c2c1] | 76 | | 626 | 454.2 | 454.6 | 2.44 |
| 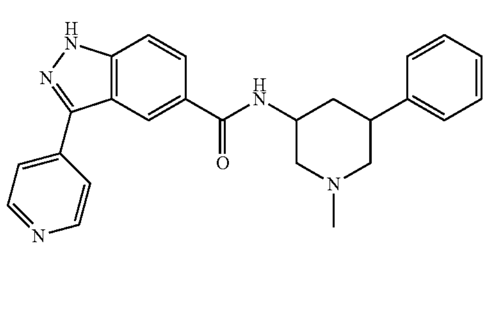 [SMILES: CN1CC(NC(=O)c2ccc3[nH]nc(-c4ccncc4)c3c2)CC(c2ccccc2)C1] | 1.4 | 7.4 | 2.6 | 412.2 | 412.6 | 2.3 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| | | | 23 | 439.5 | 439 | 3.35 |
| | | | 118.5 | 453.5 | 453 | 2.09 |
| | | | 27.1 | 441.5 | 441 | 2.06 |

TABLE 1-continued
| Structure | Kd TdF (nM) | cERK IC50 (nM) | aERK IC50 (nM) | M + H Calcd. | M + H Obs. | Retention Time minutes |
|---|---|---|---|---|---|---|
| 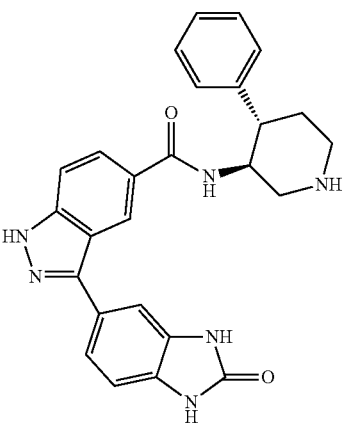 [SMILES: O=C(N[C@@H]1CNCC[C@H]1c1ccccc1)c1ccc2[nH]nc(-c3ccc4[nH]c(=O)[nH]c4c3)c2c1] | | | 50.1 | 453.5 | 453 | 2.68 |
| 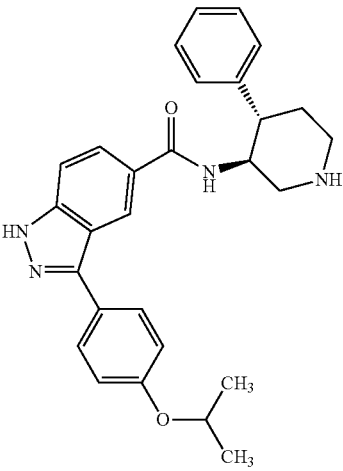 [SMILES: CC(C)Oc1ccc(-c2n[nH]c3ccc(C(=O)N[C@@H]4CNCC[C@H]4c4ccccc4)cc23)cc1] | | | 49.9 | 455.6 | 455 | 2.26 |
| 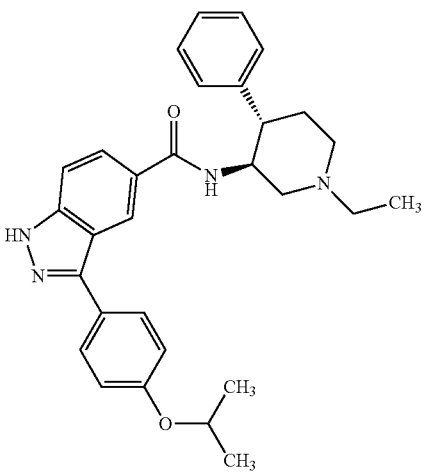 [SMILES: CCN1CC[C@@H](c2ccccc2)[C@H](NC(=O)c2ccc3[nH]nc(-c4ccc(OC(C)C)cc4)c3c2)C1] | | | 650 | 483.6 | 483 | 4.11 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| | | | 300 | 469.6 | 469 | 3.9 |
| | | | 84.9 | 456.6 | 456 | 3.72 |
| | | | 300 | 470.6 | 470 | 3.77 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| | | | 300 | 484.6 | 484 | 3.07 |
| | | | 300 | 472.6 | 472 | 3.63 |
| | | | 300 | 539.6 | 539 | 3.24 |

TABLE 1-continued

| Structure | Kd TdF (nM) | cERK IC50 (nM) | aERK IC50 (nM) | M + H Calcd. | M + H Obs. | Retention Time minutes |
|---|---|---|---|---|---|---|
| | | | 13.7 | 437.5 | 437 | 2.99 |
| | | | 141.3 | 456.6 | 456 | 1.76 |

TABLE 2

| Structure | Kd TdF (nM) | aERK IC50 (nM) | M + H Calcd. | M + H Obs. | Retention Time minutes |
|---|---|---|---|---|---|
| 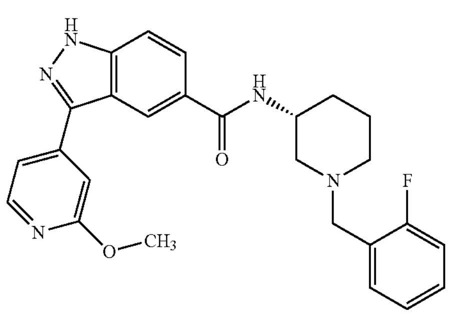 [SMILES: COc1cc(-c2n[nH]c3ccc(C(=O)N[C@@H]4CCCN(Cc5ccccc5F)C4)cc23)ccn1] | 0.81 | 111.79 | 460.2 | 460.7 | 3.31 |

TABLE 2-continued
| Structure | Kd TdF (nM) | aERK IC50 (nM) | M + H Calcd. | M + H Obs. | Retention Time minutes |
|---|---|---|---|---|---|
| 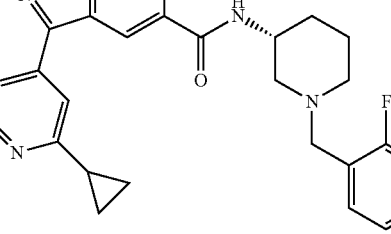 | 0.4 | 33.22 | 470.2 | 470.7 | 2.35 |
| 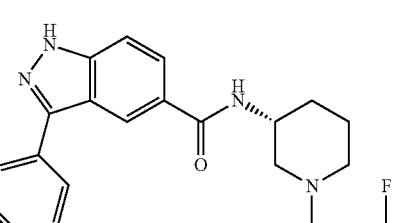 | 0.4 | 19.81 | 458.2 | 458.7 | 2.28 |
| 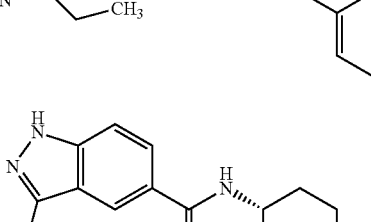 | 0.5 | 10.73 | 444.2 | 444.7 | 2.1 |
| 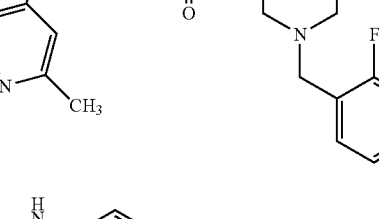 | 6.6 | 507.24 | 498.2 | 498.6 | 3.37 |
| 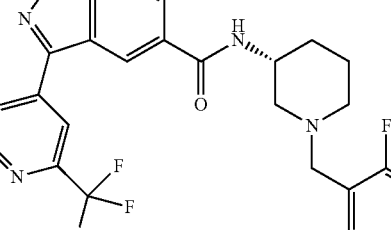 | 0.52 | 33.05 | 501.2 | 501.7 | 3.41 |

TABLE 2-continued
| Structure | Kd TdF (nM) | aERK IC50 (nM) | M + H Calcd. | M + H Obs. | Retention Time minutes |
|---|---|---|---|---|---|
| 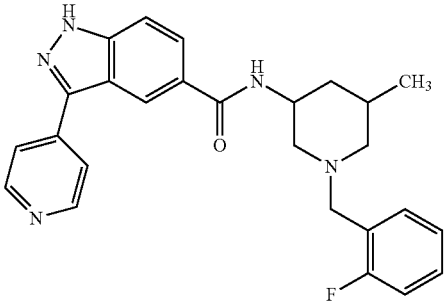 [SMILES: CC1CC(NC(=O)c2ccc3[nH]nc(-c4ccncc4)c3c2)CN(Cc2ccccc2F)C1] | 0.052 | 16.38 | 444.2 | 444.2 | 2.21 |
| 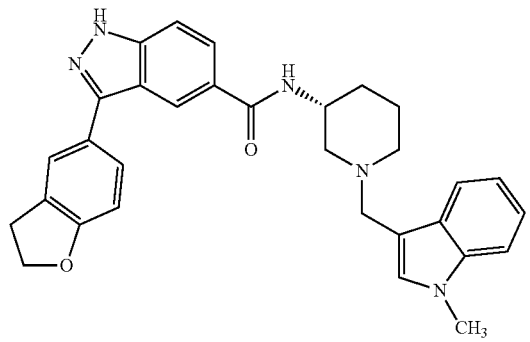 [SMILES: Cn1cc(CN2CCC[C@@H](NC(=O)c3ccc4[nH]nc(-c5ccc6c(c5)CCO6)c4c3)C2)c2ccccc21] | 11 | 158.46 | 506.2 | 506.2 | 3.56 |
| 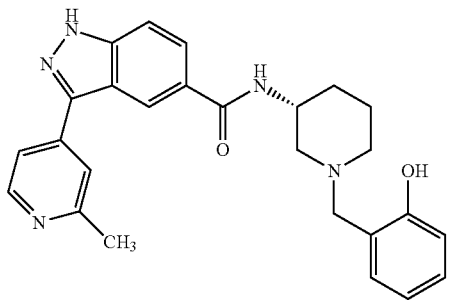 [SMILES: Cc1cc(-c2n[nH]c3ccc(C(=O)N[C@@H]4CCCN(Cc5ccccc5O)C4)cc23)ccn1] | 2.36 | 140.04 | 442.2 | 442.7 | 2.03 |
| 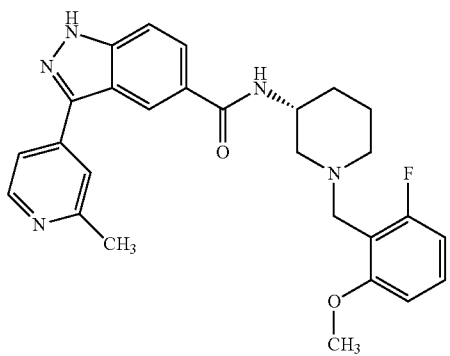 [SMILES: COc1cccc(F)c1CN1CCC[C@@H](NC(=O)c2ccc3[nH]nc(-c4ccnc(C)c4)c3c2)C1] | 0.22 | 4.98 | 474.2 | 474.7 | 2.29 |

TABLE 2-continued

| Structure | Kd TdF (nM) | aERK IC50 (nM) | M + H Calcd. | M + H Obs. | Retention Time minutes |
|---|---|---|---|---|---|
| 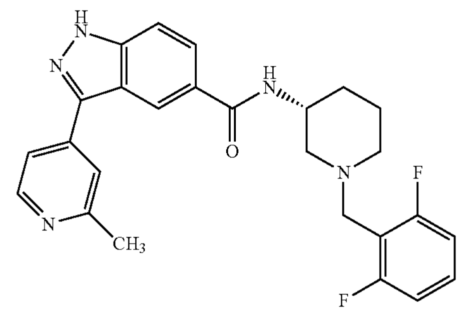 [SMILES: Cc1cc(-c2n[nH]c3ccc(C(=O)N[C@@H]4CCCN(Cc5c(F)cccc5F)C4)cc23)ccn1] | 0.51 | 29.7 | 462.2 | 462.7 | 2.09 |
| 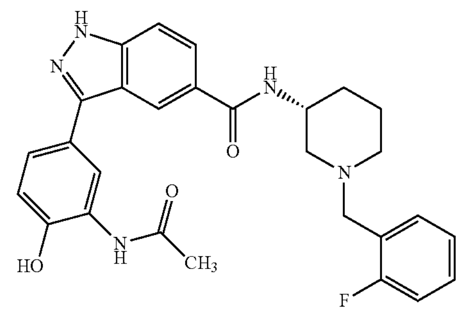 [SMILES: CC(=O)Nc1cc(-c2n[nH]c3ccc(C(=O)N[C@@H]4CCCN(Cc5ccccc5F)C4)cc23)ccc1O] | 0.48 | 74.73 | 502.2 | 502.3 | 2.08 |
| 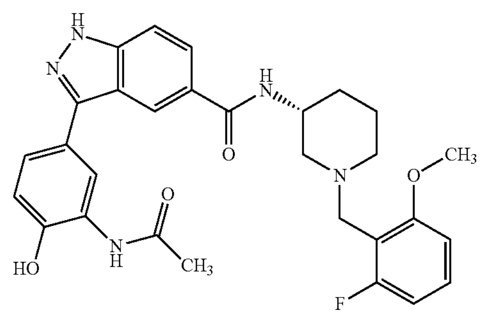 [SMILES: COc1cccc(F)c1CN1CCC[C@@H](NC(=O)c2ccc3[nH]nc(-c4ccc(O)c(NC(C)=O)c4)c3c2)C1] | 0.66 | 64.93 | 532.2 | 532.3 | 2.22 |
| 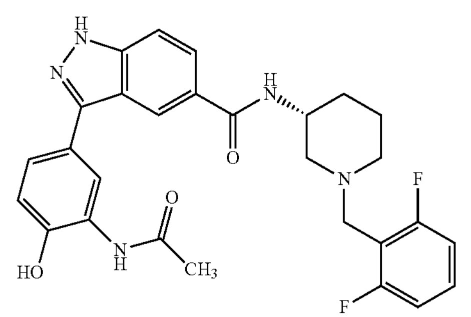 [SMILES: CC(=O)Nc1cc(-c2n[nH]c3ccc(C(=O)N[C@@H]4CCCN(Cc5c(F)cccc5F)C4)cc23)ccc1O] | 1.29 | 223.7 | 520.2 | 520.3 | 2.04 |

TABLE 2-continued

| Structure | Kd TdF (nM) | aERK IC50 (nM) | M + H Calcd. | M + H Obs. | Retention Time minutes |
|---|---|---|---|---|---|
| 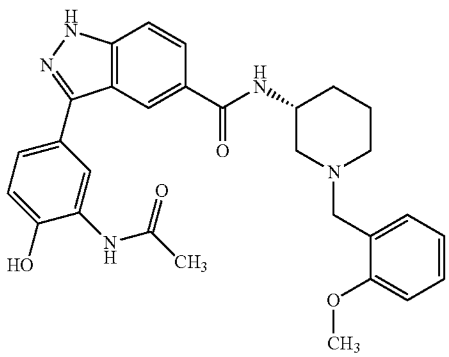 [SMILES: COc1ccccc1CN1CCC[C@@H](NC(=O)c2ccc3[nH]nc(-c4ccc(O)c(NC(C)=O)c4)c3c2)C1] | 1.29 | 253.61 | 514.2 | 514.3 | 2.214 |
| 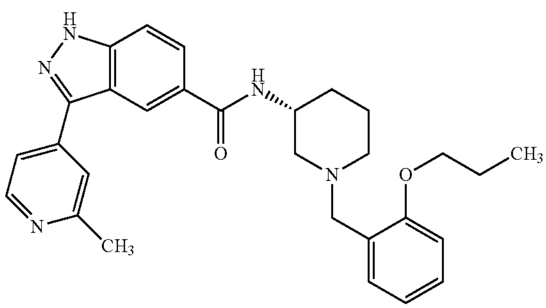 [SMILES: CCCOc1ccccc1CN1CCC[C@@H](NC(=O)c2ccc3[nH]nc(-c4ccnc(C)c4)c3c2)C1] | 1.72 | 245.55 | 484.3 | 484.7 | 2.72 |
| 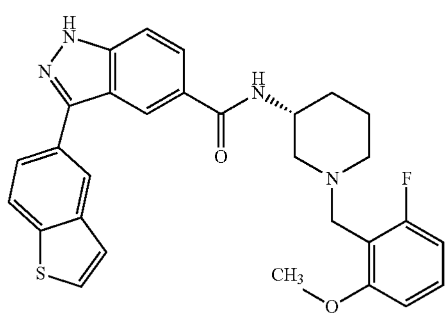 [SMILES: COc1cccc(F)c1CN1CCC[C@@H](NC(=O)c2ccc3[nH]nc(-c4ccc5sccc5c4)c3c2)C1] | 0.15 | 807.02 | 515.0 | 515 | 4.04 |
| 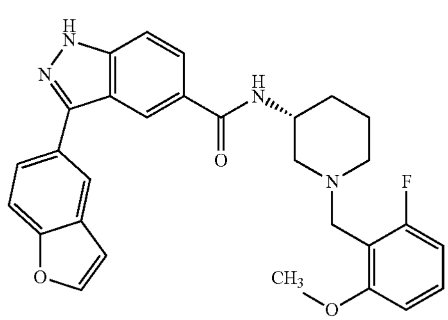 [SMILES: COc1cccc(F)c1CN1CCC[C@@H](NC(=O)c2ccc3[nH]nc(-c4ccc5occc5c4)c3c2)C1] | 0.21 | 495.27 | 499.2 | 499.1 | 3.79 |

TABLE 2-continued

| Structure | Kd TdF (nM) | aERK IC50 (nM) | M + H Calcd. | M + H Obs. | Retention Time minutes |
|---|---|---|---|---|---|
| *[structure]* | 0.27 | 162.9467 | 499.2 | 499.1 | 3.22 |
| *[structure]* | 2.63 | 359.41 | 566.2 | 566.1 | 3.58 |
| *[structure]* | 1.38 | 286.47 | 516.2 | 516.1 | 3.18 |
| *[structure]* | 0.9 | 189.47 | 501.2 | 501.1 | 3.49 |

TABLE 2-continued

| Structure | Kd TdF (nM) | aERK IC50 (nM) | M + H Calcd. | M + H Obs. | Retention Time minutes |
|---|---|---|---|---|---|
| 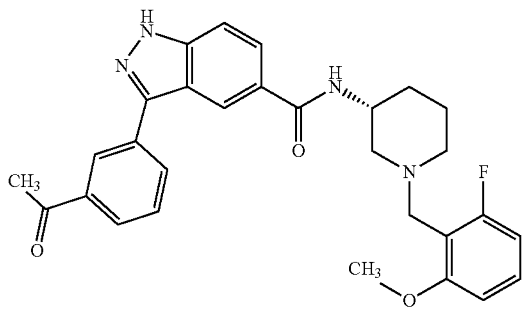 [SMILES: COc1cccc(F)c1CN1CCC[C@@H](NC(=O)c2ccc3[nH]nc(-c4cccc(C(C)=O)c4)c3c2)C1] | 2.01 | 608.66 | 501.2 | 501.1 | 3.54 |
| 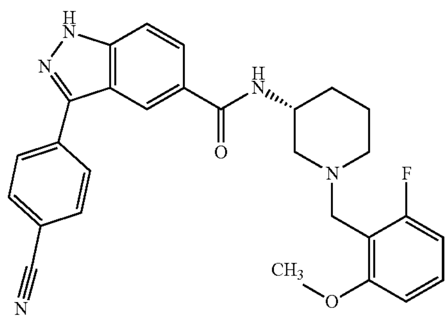 [SMILES: COc1cccc(F)c1CN1CCC[C@@H](NC(=O)c2ccc3[nH]nc(-c4ccc(C#N)cc4)c3c2)C1] | 0.24 | 155.3 | 484.2 | 484.1 | 3.58 |
| 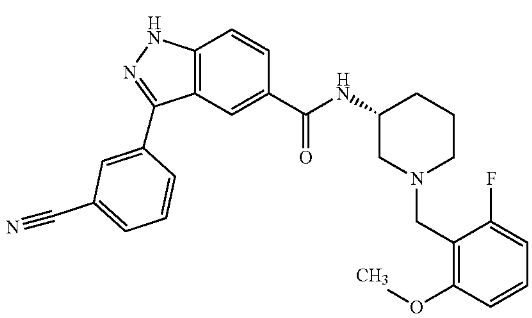 [SMILES: COc1cccc(F)c1CN1CCC[C@@H](NC(=O)c2ccc3[nH]nc(-c4cccc(C#N)c4)c3c2)C1] | 0.83 | 263.67 | 484.2 | 484.1 | 3.61 |
| 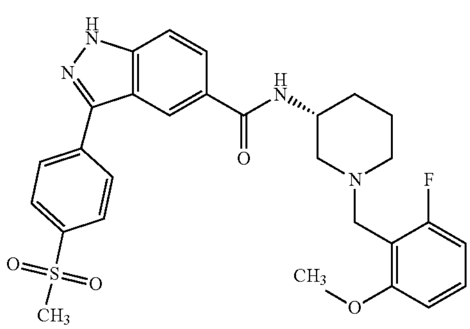 [SMILES: COc1cccc(F)c1CN1CCC[C@@H](NC(=O)c2ccc3[nH]nc(-c4ccc(S(C)(=O)=O)cc4)c3c2)C1] | 1.37 | 194.51 | 537.2 | 537.1 | 3.20 |

TABLE 2-continued

| Structure | Kd TdF (nM) | aERK IC50 (nM) | M + H Calcd. | M + H Obs. | Retention Time minutes |
|---|---|---|---|---|---|
| 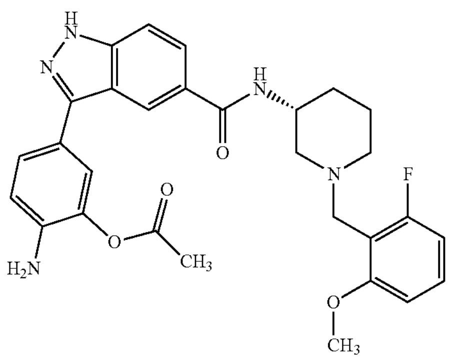 [SMILES: COc1cccc(F)c1CN1CCC[C@@H](NC(=O)c2ccc3[nH]nc(-c4ccc(N)c(OC(C)=O)c4)c3c2)C1] | 6.5 | 482.66 | 532.2 | 532.2 | 3.03 |
| 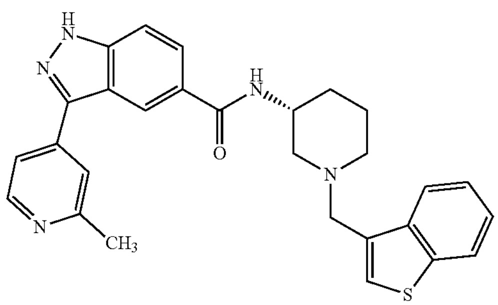 [SMILES: Cc1cc(-c2n[nH]c3ccc(C(=O)N[C@@H]4CCCN(Cc5csc6ccccc56)C4)cc23)ccn1] | 0.53 | 18.68 | 482.2 | 482.2 | 2.45 |
| 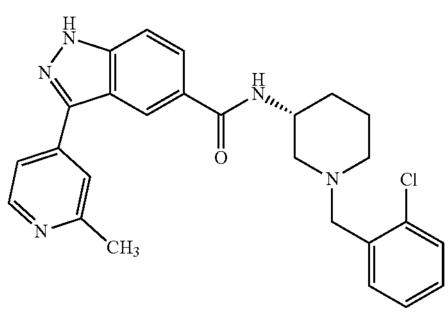 [SMILES: Cc1cc(-c2n[nH]c3ccc(C(=O)N[C@@H]4CCCN(Cc5ccccc5Cl)C4)cc23)ccn1] | 0.2 | 28.08 | 460.2 | 460.0 | 2.15 |
| 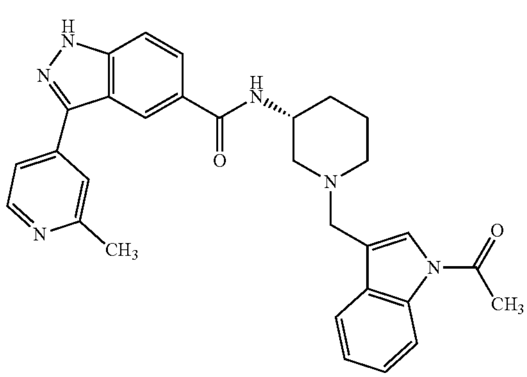 [SMILES: CC(=O)n1cc(CN2CCC[C@@H](NC(=O)c3ccc4[nH]nc(-c5ccnc(C)c5)c4c3)C2)c2ccccc21] | 1.95 | 153.73 | 507.2 | 507.0 | 2.34 |

TABLE 2-continued

| Structure | Kd TdF (nM) | aERK IC50 (nM) | M + H Calcd. | M + H Obs. | Retention Time minutes |
|---|---|---|---|---|---|
| 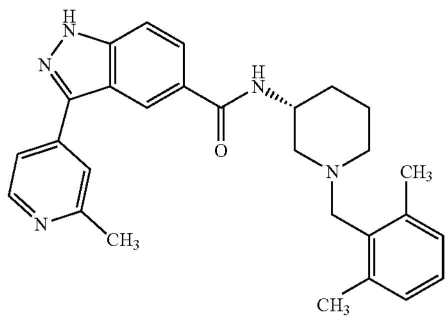 [SMILES: Cc1cc(-c2n[nH]c3ccc(C(=O)N[C@@H]4CCCN(Cc5c(C)cccc5C)C4)cc23)ccn1] | 0.13 | 89.04 | 454.3 | 454.0 | 2.7 |
| 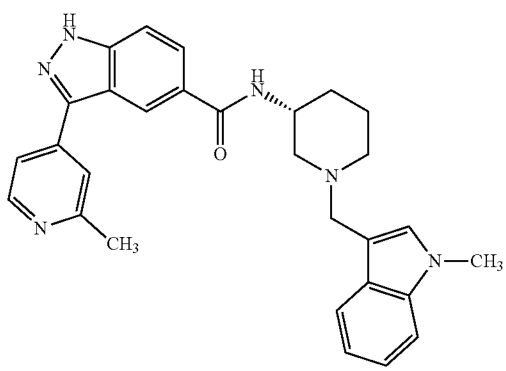 [SMILES: Cc1cc(-c2n[nH]c3ccc(C(=O)N[C@@H]4CCCN(Cc5cn(C)c6ccccc56)C4)cc23)ccn1] | 1.38 | 21.53 | 479.2 | 479.2 | 2.63 |
| 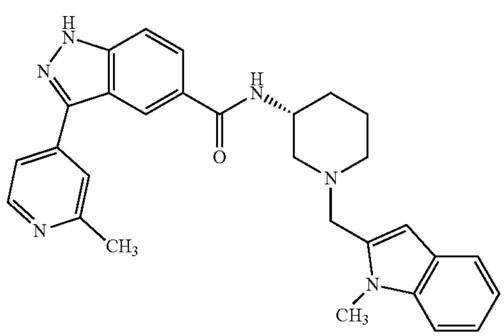 [SMILES: Cc1cc(-c2n[nH]c3ccc(C(=O)N[C@@H]4CCCN(Cc5cc6ccccc6n5C)C4)cc23)ccn1] | 0.21 | 41.71 | 479.2 | 479.2 | 2.72 |
| 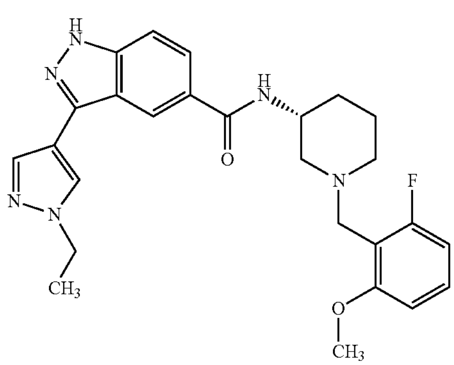 [SMILES: CCn1cc(-c2n[nH]c3ccc(C(=O)N[C@@H]4CCCN(Cc5c(F)cccc5OC)C4)cc23)cn1] | 1.59 | 113.71 | 477.2 | 477.0 | 3 |

TABLE 2-continued

| Structure | Kd TdF (nM) | aERK IC50 (nM) | M + H Calcd. | M + H Obs. | Retention Time minutes |
|---|---|---|---|---|---|
| | 0.1 | 4.02 | 499.2 | 499.0 | 2.38 |
| | 0.1 | 16.41 | 514.2 | 514.2 | 3.28 |
| 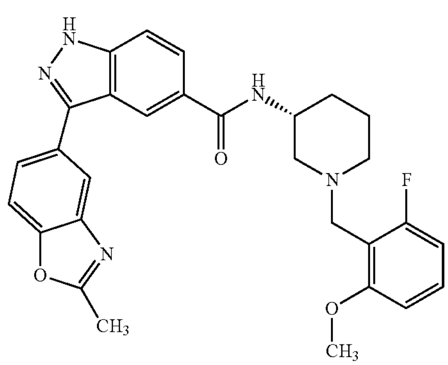 [SMILES: COc1cccc(F)c1CN1CCC[C@@H](NC(=O)c2ccc3[nH]nc(-c4ccc5oc(C)nc5c4)c3c2)C1] | 0.6 | 45.65 | 514.2 | 514.2 | 3.46 |
| 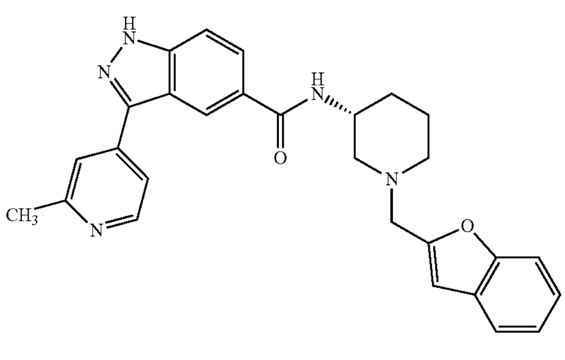 [SMILES: Cc1cc(-c2n[nH]c3ccc(C(=O)N[C@@H]4CCCN(Cc5cc6ccccc6o5)C4)cc23)ccn1] | 1.43 | 15.09 | 466.2 | 466.0 | 2.52 |

TABLE 2-continued

| Structure | Kd TdF (nM) | aERK IC50 (nM) | M + H Calcd. | M + H Obs. | Retention Time minutes |
|---|---|---|---|---|---|
| 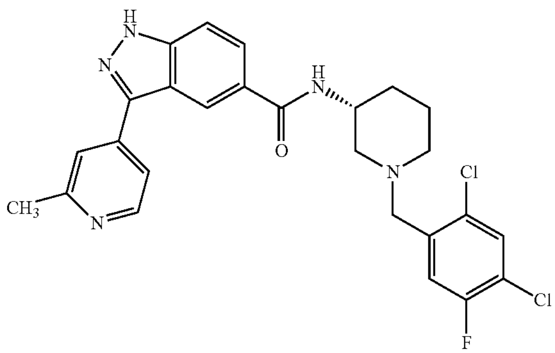 [SMILES: Cc1cc(-c2n[nH]c3ccc(C(=O)N[C@@H]4CCCN(Cc5cc(F)c(Cl)cc5Cl)C4)cc23)ccn1] | 9.76 | 659.9 | 512.1 | 511.8 | 2.75 |
| 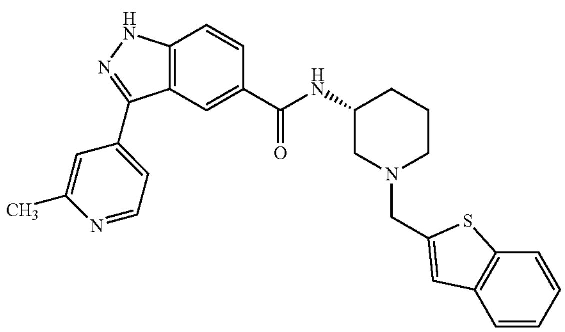 [SMILES: Cc1cc(-c2n[nH]c3ccc(C(=O)N[C@@H]4CCCN(Cc5cc6ccccc6s5)C4)cc23)ccn1] | 3.97 | 90.1 | 482.2 | 481.9 | 2.66 |
| 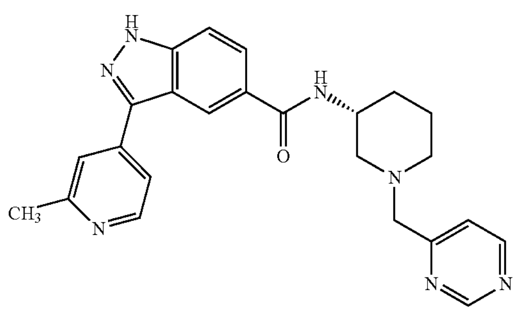 [SMILES: Cc1cc(-c2n[nH]c3ccc(C(=O)N[C@@H]4CCCN(Cc5ccncn5)C4)cc23)ccn1] | 20.5 | 506.7 | 428.2 | 427.9 | 1.82 |
| 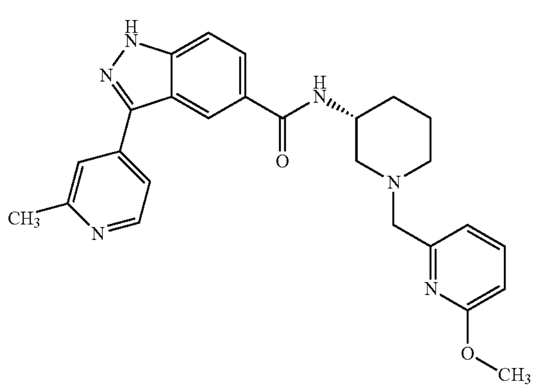 | 2.33 | 220.5 | 457.2 | 456.9 | 2.27 |

TABLE 2-continued
| Structure | Kd TdF (nM) | aERK IC50 (nM) | M + H Calcd. | M + H Obs. | Retention Time minutes |
|---|---|---|---|---|---|
| 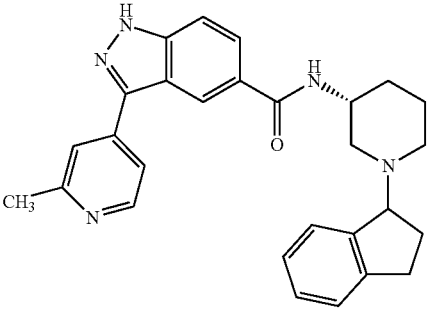 [SMILES: Cc1cc(-c2n[nH]c3ccc(C(=O)N[C@@H]4CCCN(C5CCc6ccccc65)C4)cc23)ccn1] | 0.28 | 65.4 | 452.2 | 452.0 | 2.43 |
| 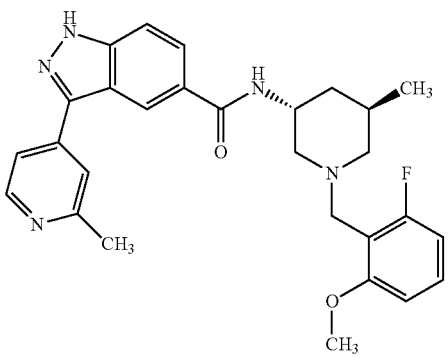 [SMILES: COc1cccc(F)c1CN1C[C@H](C)C[C@@H](NC(=O)c2ccc3[nH]nc(-c4ccnc(C)c4)c3c2)C1] | 3.33 | 203.9 | 488.2 | 488.0 | 2.65 |
| 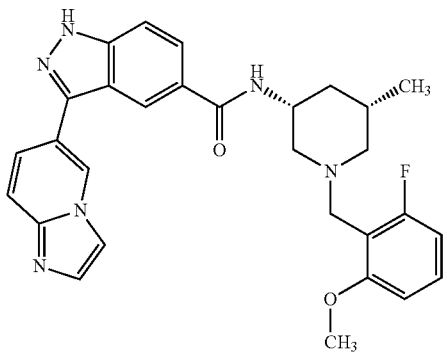 [SMILES: COc1cccc(F)c1CN1C[C@@H](C)C[C@@H](NC(=O)c2ccc3[nH]nc(-c4ccc5nccn5c4)c3c2)C1] | 0.01 | 5.84 | 513.2 | 513.2 | 1.72 |
| 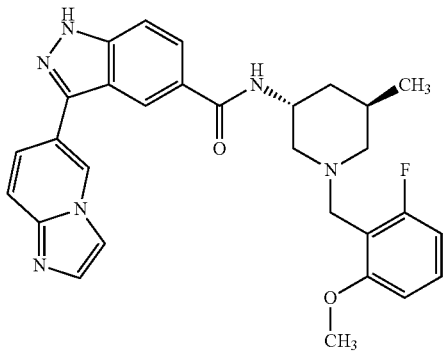 [SMILES: COc1cccc(F)c1CN1C[C@H](C)C[C@@H](NC(=O)c2ccc3[nH]nc(-c4ccc5nccn5c4)c3c2)C1] | 0.03 | 10.6 | 513.2 | 513.0 | 2.65 |

TABLE 2-continued

| Structure | Kd TdF (nM) | aERK IC50 (nM) | M + H Calcd. | M + H Obs. | Retention Time minutes |
|---|---|---|---|---|---|
| 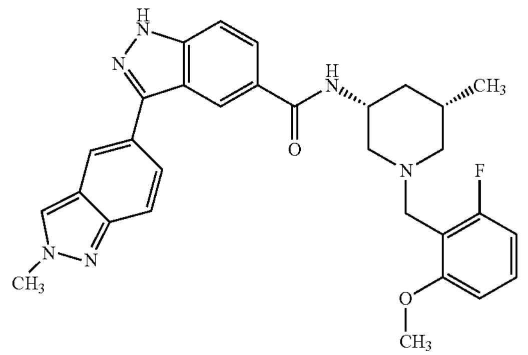 [SMILES: COc1cccc(F)c1CN1C[C@@H](C)C[C@@H](NC(=O)c2ccc3[nH]nc(-c4ccc5nn(C)cc5c4)c3c2)C1] | 0.02 | 6.1 | 527.2 | 527.3 | 2.17 |
| 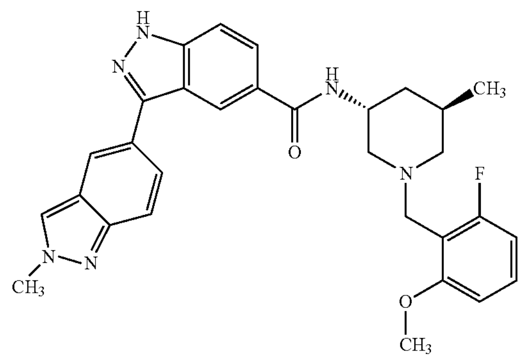 [SMILES: COc1cccc(F)c1CN1C[C@H](C)C[C@@H](NC(=O)c2ccc3[nH]nc(-c4ccc5nn(C)cc5c4)c3c2)C1] | 0.39 | 217.3 | 527.2 | 527.0 | 3.42 |
| 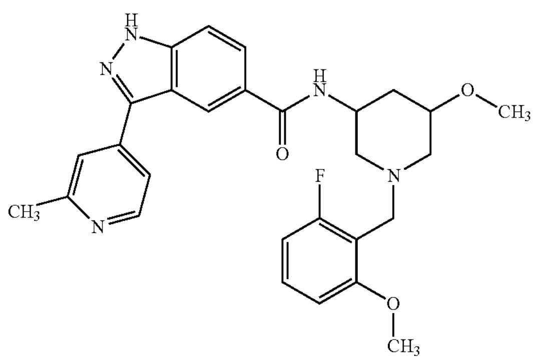 | 0.42 | 39.06 | 504.2 | 503.9 | 2.39 |
| 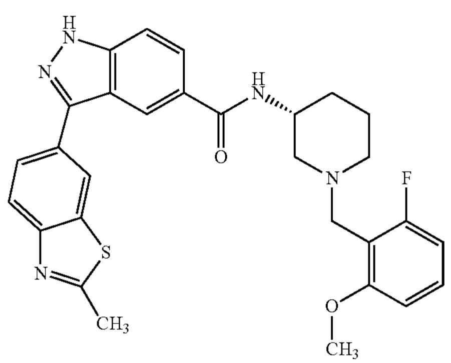 [SMILES: COc1cccc(F)c1CN1CCC[C@@H](NC(=O)c2ccc3[nH]nc(-c4ccc5nc(C)sc5c4)c3c2)C1] | 0.1 | 78.49 | 530.2 | 530.2 | 2.71 |

TABLE 2-continued

| Structure | Kd TdF (nM) | aERK IC50 (nM) | M + H Calcd. | M + H Obs. | Retention Time minutes |
|---|---|---|---|---|---|
| (structure) | 4.12 | 991.6 | 488.2 | 488.0 | 1.31 |
| (structure) | 17.66 | 663.12 | 513.2 | 513.1 | 1.31 |
| (structure) | 0.35 | 13.32 | 475.2 | 475.2 | 1.72 |
| (structure) | 3.79 | 146.17 | 532.2 | 532.2 | 1.13 |

TABLE 2-continued
| Structure | Kd TdF (nM) | aERK IC50 (nM) | M + H Calcd. | M + H Obs. | Retention Time minutes |
|---|---|---|---|---|---|
| 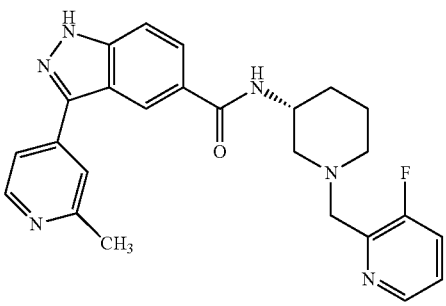 [SMILES: Cc1cc(-c2n[nH]c3ccc(C(=O)N[C@@H]4CCCN(Cc5ncccc5F)C4)cc23)ccn1] | 1.89 | 234.1 | 445.2 | 445.0 | 1.95 |
| 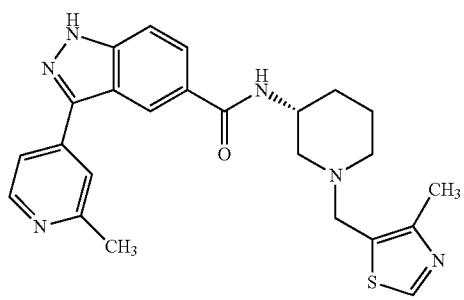 [SMILES: Cc1cc(-c2n[nH]c3ccc(C(=O)N[C@@H]4CCCN(Cc5scnc5C)C4)cc23)ccn1] | 20.34 | 874.7 | 447.2 | 446.8 | 1.8 |
| 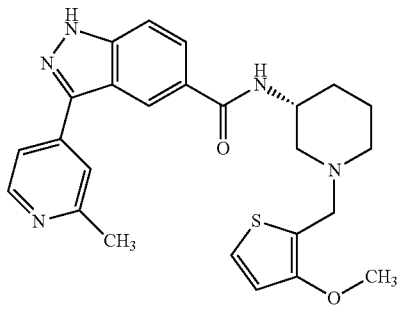 [SMILES: COc1ccsc1CN1CCC[C@@H](NC(=O)c2ccc3[nH]nc(-c4ccnc(C)c4)c3c2)C1] | 0.97 | 136.9 | 462.2 | 462.0 | 2.15 |
| 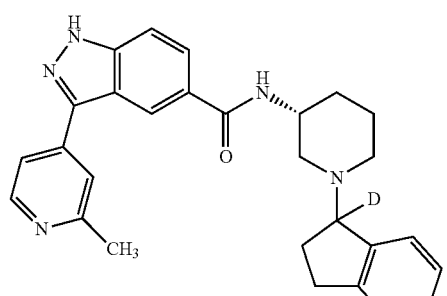 | 0.34 | 62.45 | 453.2 | 453.0 | 2.27 |

TABLE 2-continued
| Structure | Kd TdF (nM) | aERK IC50 (nM) | M + H Calcd. | M + H Obs. | Retention Time minutes |
|---|---|---|---|---|---|
| 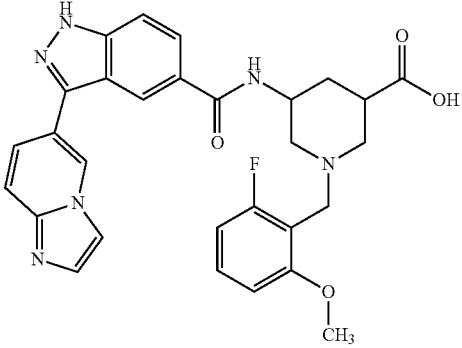 [SMILES: COc1cccc(F)c1CN1CC(NC(=O)c2ccc3[nH]nc(-c4ccc5nccn5c4)c3c2)CC(C(=O)O)C1] | 0.26 | 64.715 | 543.2 | 543.2 | 2.18 |
| 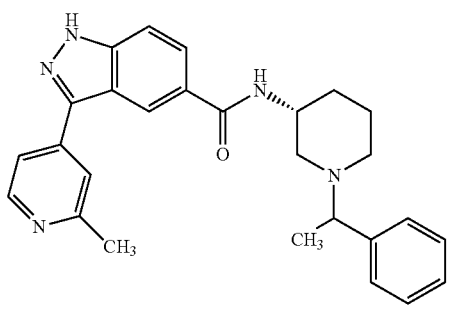 [SMILES: Cc1cc(-c2n[nH]c3ccc(C(=O)N[C@@H]4CCCN(C(C)c5ccccc5)C4)cc23)ccn1] | 4.4 | 128.26 | 440.2 | 440.0 | 2.25 |
| 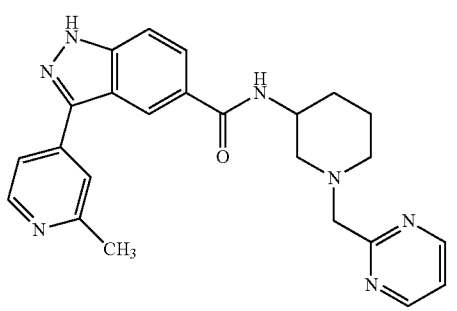 [SMILES: Cc1cc(-c2n[nH]c3ccc(C(=O)NC4CCCN(Cc5ncccn5)C4)cc23)ccn1] | 130 | 922.91 | 428.2 | 428.2 | 1.57 |
| 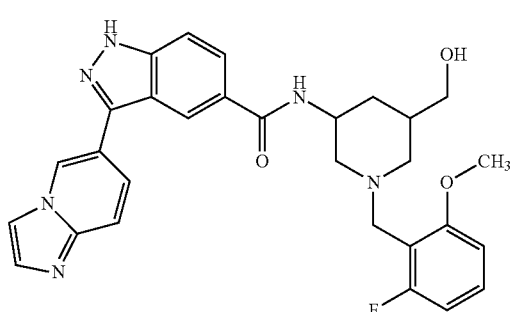 | 1.68 | 139.82 | 529.2 | 529.2 | 1.77 |

TABLE 2-continued
| Structure | Kd TdF (nM) | aERK IC50 (nM) | M + H Calcd. | M + H Obs. | Retention Time minutes |
|---|---|---|---|---|---|
| 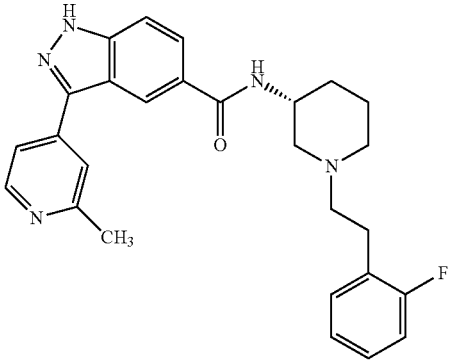 [SMILES: Cc1cc(-c2n[nH]c3ccc(C(=O)N[C@@H]4CCCN(CCc5ccccc5F)C4)cc23)ccn1] | 4.8 | 98.79 | 458.2 | 458.2 | 2.35 |
| 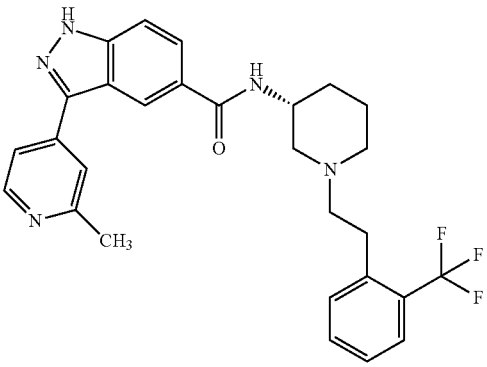 [SMILES: Cc1cc(-c2n[nH]c3ccc(C(=O)N[C@@H]4CCCN(CCc5ccccc5C(F)(F)F)C4)cc23)ccn1] | 2.2 | 86.92 | 508.2 | 508.0 | 2.7 |
| 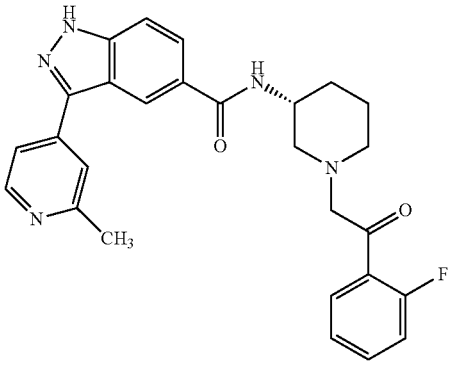 [SMILES: Cc1cc(-c2n[nH]c3ccc(C(=O)N[C@@H]4CCCN(CC(=O)c5ccccc5F)C4)cc23)ccn1] | 2.4 | 32.94 | 472.2 | 472.2 | 2.18 |
| 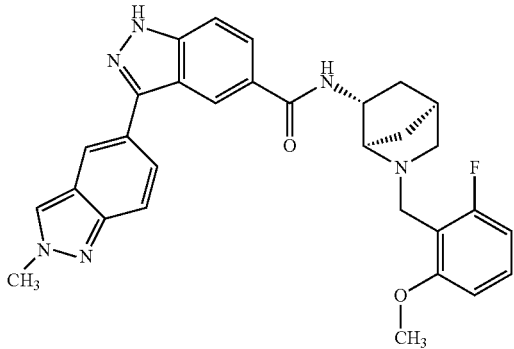 [SMILES: COc1cccc(F)c1CN1C[C@H]2C[C@@H]1[C@H](NC(=O)c1ccc3[nH]nc(-c4ccc5nn(C)cc5c4)c3c1)C2] | 85.24 | 526.83 | 525.2 | 525.0 | 2.97 |

TABLE 2-continued
| Structure | Kd TdF (nM) | aERK IC50 (nM) | M + H Calcd. | M + H Obs. | Retention Time minutes |
|---|---|---|---|---|---|
| 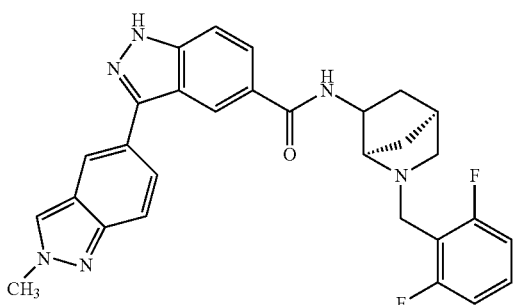 | 3.29 | 881.26 | 513.2 | 513.4 | 2.82 |
TABLE 3
| Structure | aERK IC50 nM | M + H Calcd. | M + H Obs. | Retention Time Min. |
|---|---|---|---|---|
| 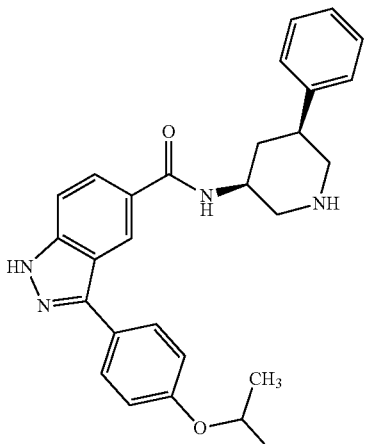 | 45.15 | 455.24 | 455.0 | 1.95 |
| 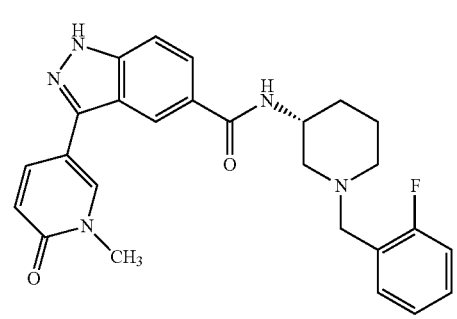 [SMILES: Cn1cc(-c2n[nH]c3ccc(C(=O)N[C@@H]4CCCN(Cc5ccccc5F)C4)cc23)ccc1=O] | 21.06 | 460.21 | 460.7 | 2.48 |
| 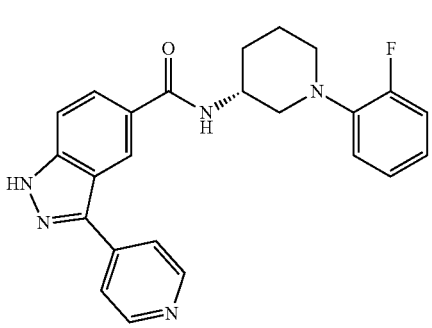 [SMILES: O=C(N[C@@H]1CCCN(c2ccccc2F)C1)c1ccc2[nH]nc(-c3ccncc3)c2c1] | 62.3 | 416.18 | 416.2 | 1.73 |

TABLE 3-continued

| Structure | aERK IC50 nM | M + H Calcd. | M + H Obs. | Retention Time Min. |
|---|---|---|---|---|
| 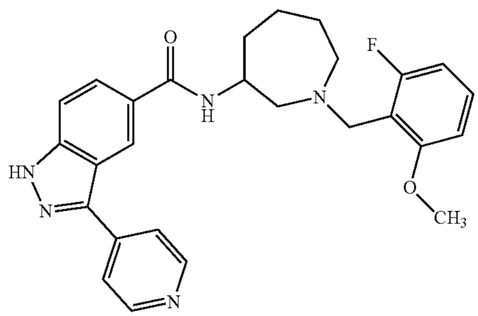 [SMILES: COc1cccc(F)c1CN1CCCCC(NC(=O)c2ccc3[nH]nc(-c4ccncc4)c3c2)C1] | 230.82 | 474.22 | 474.2 | 1.67 |
| 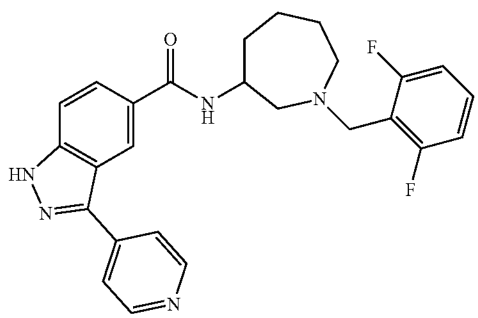 [SMILES: O=C(NC1CCCCN(Cc2c(F)cccc2F)C1)c1ccc2[nH]nc(-c3ccncc3)c2c1] | 148.04 | 462.20 | 462.2 | 1.63 |
| 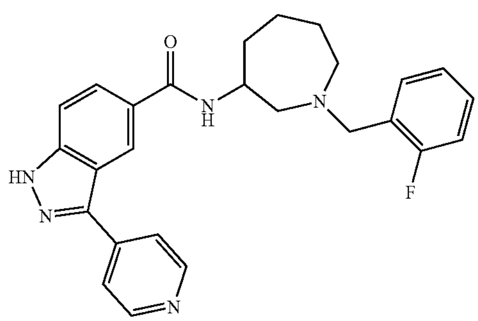 [SMILES: O=C(NC1CCCCN(Cc2ccccc2F)C1)c1ccc2[nH]nc(-c3ccncc3)c2c1] | 79.25 | 444.21 | 444.2 | 1.63 |
| 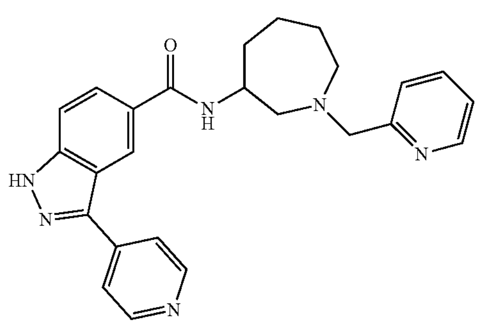 [SMILES: O=C(NC1CCCCN(Cc2ccccn2)C1)c1ccc2[nH]nc(-c3ccncc3)c2c1] | 369.19 | 427.22 | 427.2 | 1.41 |

TABLE 3-continued
| Structure | aERK IC50 nM | M + H Calcd. | M + H Obs. | Retention Time Min. |
|---|---|---|---|---|
| 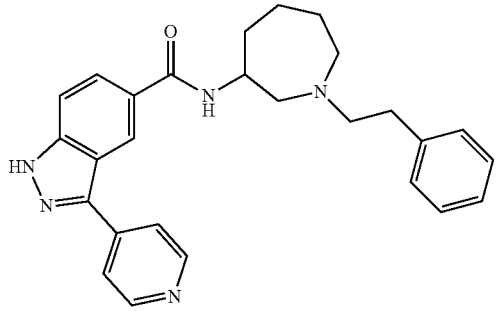 [SMILES: O=C(NC1CCCCN(CCc2ccccc2)C1)c1ccc2[nH]nc(-c3ccncc3)c2c1] | 8.725 | 440.24 | 440.3 | 1.61 |
| 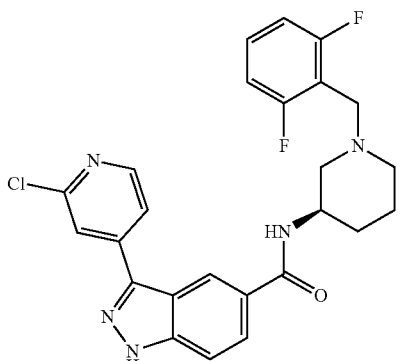 | 62.27 | 482.15 | 482.3 | 2.59 |
| 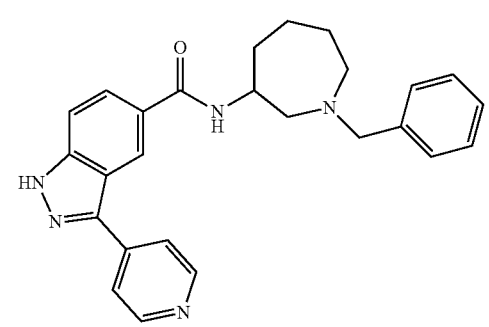 [SMILES: O=C(NC1CCCCN(Cc2ccccc2)C1)c1ccc2[nH]nc(-c3ccncc3)c2c1] | 249.4 | 426.22 | 426.3 | 1.56 |
| 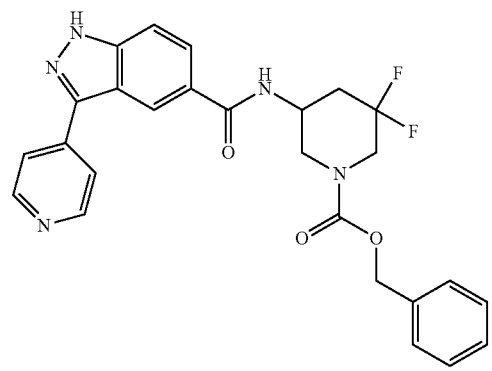 [SMILES: O=C(NC1CN(C(=O)OCc2ccccc2)CC(F)(F)C1)c1ccc2[nH]nc(-c3ccncc3)c2c1] | 104.88 | 492.18 | 492.0 | 0.85 |

TABLE 3-continued
| Structure | aERK IC50 nM | M + H Calcd. | M + H Obs. | Retention Time Min. |
|---|---|---|---|---|
| 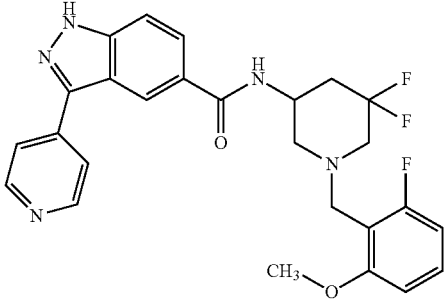 [SMILES: COc1cccc(F)c1CN1CC(NC(=O)c2ccc3[nH]nc(-c4ccncc4)c3c2)CC(F)(F)C1] | 17.35 | 496.19 | 496.2 | 1.68 |
| 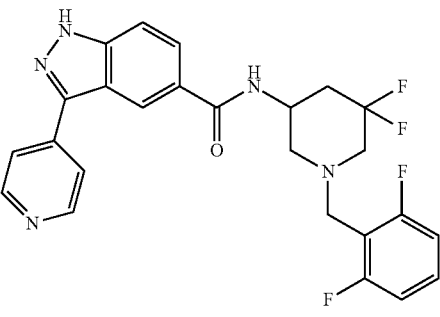 [SMILES: O=C(NC1CN(Cc2c(F)cccc2F)CC(F)(F)C1)c1ccc2[nH]nc(-c3ccncc3)c2c1] | 240.725 | 484.17 | 484.2 | 1.79 |
| 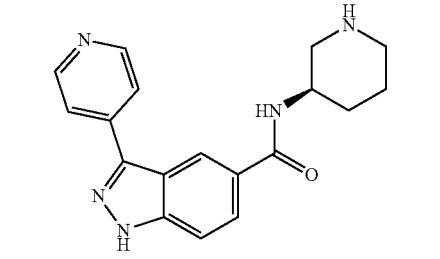 [SMILES: O=C(N[C@@H]1CCCNC1)c1ccc2[nH]nc(-c3ccncc3)c2c1] | 835.46 | 322.16 | 322.2 | 1.46 |
| 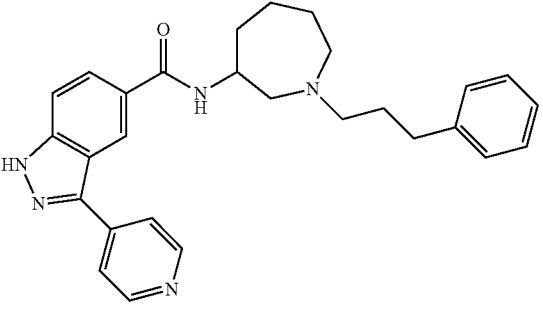 [SMILES: O=C(NC1CCCCN(CCCc2ccccc2)C1)c1ccc2[nH]nc(-c3ccncc3)c2c1] | 72.48 | 454.25 | 454.4 | 1.65 |
| 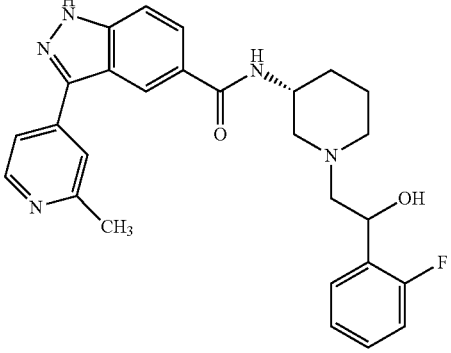 | 180.57 | 474.22 | 473.9 | 1.54 |

TABLE 3-continued

| Structure | aERK IC50 nM | M + H Calcd. | M + H Obs. | Retention Time Min. |
|---|---|---|---|---|
| 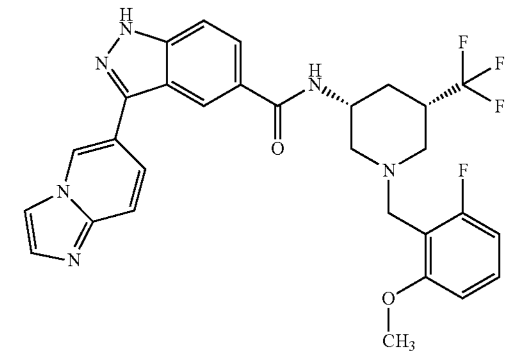 [SMILES: COc1cccc(F)c1CN1C[C@H](NC(=O)c2ccc3[nH]nc(-c4ccc5nccn5c4)c3c2)C[C@H](C(F)(F)F)C1] | 17.96 | 567.21 | 566.9 | 1.87 |
| 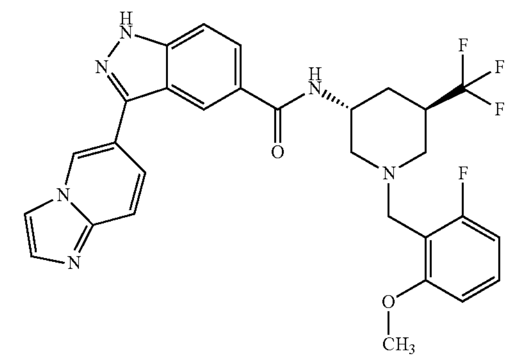 [SMILES: COc1cccc(F)c1CN1C[C@H](NC(=O)c2ccc3[nH]nc(-c4ccc5nccn5c4)c3c2)C[C@@H](C(F)(F)F)C1] | 180.6 | 567.21 | 567.2 | 2.04 |
| 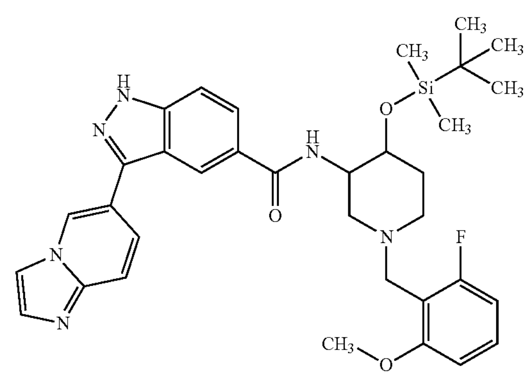 [SMILES: COc1cccc(F)c1CN1CCC(O[Si](C)(C)C(C)(C)C)C(NC(=O)c2ccc3[nH]nc(-c4ccc5nccn5c4)c3c2)C1] | 317.91 | 629.30 | 629.0 | 2.52 |
| 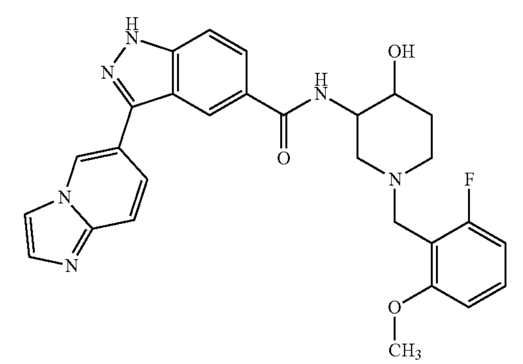 [SMILES: COc1cccc(F)c1CN1CCC(O)C(NC(=O)c2ccc3[nH]nc(-c4ccc5nccn5c4)c3c2)C1] | 42.13 | 515.21 | 514.9 | 1.54 |

TABLE 3-continued
| Structure | aERK IC50 nM | M + H Calcd. | M + H Obs. | Retention Time Min. |
|---|---|---|---|---|
| 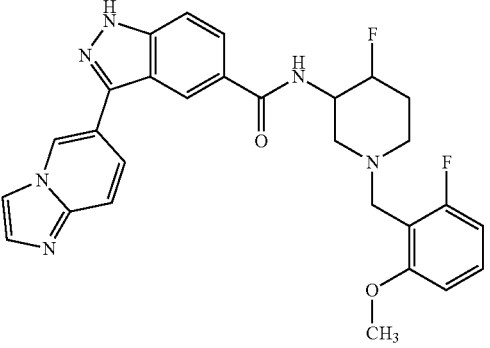 [SMILES: COc1cccc(F)c1CN1CCC(F)C(NC(=O)c2ccc3[nH]nc(-c4ccc5nccn5c4)c3c2)C1] | 16.26 | 517.21 | 517.0 | 1.65 |
| 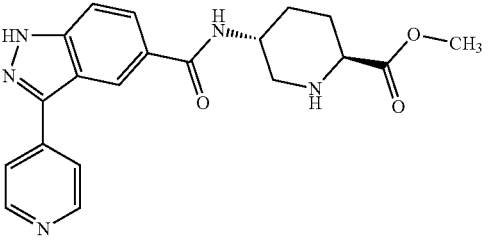 [SMILES: COC(=O)[C@@H]1CC[C@@H](NC(=O)c2ccc3[nH]nc(-c4ccncc4)c3c2)CN1] | 143.91 | 380.16 | 380.2 | 1.29 |
| 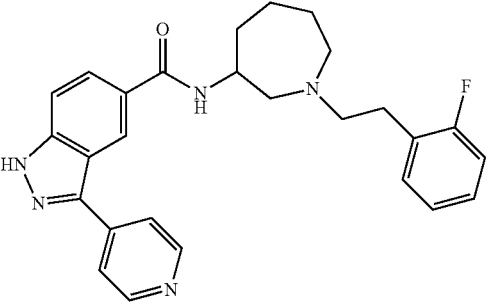 [SMILES: O=C(NC1CCCCN(CCc2ccccc2F)C1)c1ccc2[nH]nc(-c3ccncc3)c2c1] | 5 | 458.23 | 458.3 | 1.65 |
| 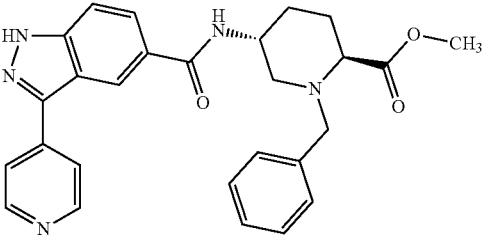 [SMILES: COC(=O)[C@@H]1CC[C@@H](NC(=O)c2ccc3[nH]nc(-c4ccncc4)c3c2)CN1Cc1ccccc1] | 40.68 | 470.21 | 470.2 | 1.60 |
| 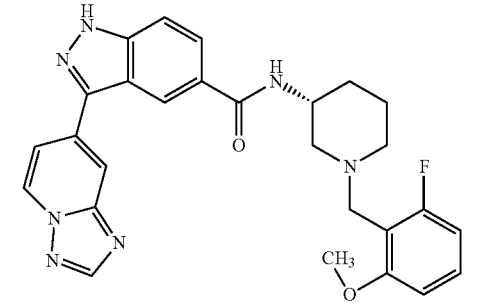 [SMILES: COc1cccc(F)c1CN1CCC[C@@H](NC(=O)c2ccc3[nH]nc(-c4ccn5ncnc5c4)c3c2)C1] | 68.94 | 500.21 | 500.0 | 2.00 |

TABLE 3-continued
| Structure | aERK IC50 nM | M + H Calcd. | M + H Obs. | Retention Time Min. |
|---|---|---|---|---|
| 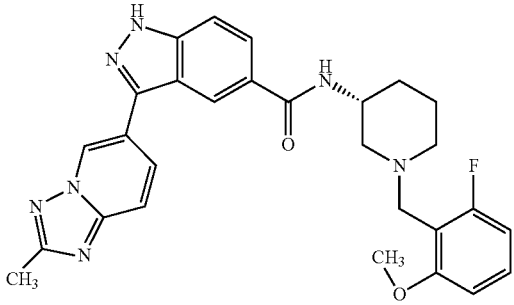 [SMILES: COc1cccc(F)c1CN1CCC[C@@H](NC(=O)c2ccc3[nH]nc(-c4ccc5nc(C)nn5c4)c3c2)C1] | 22.17 | 514.23 | 513.9 | 1.99 |
| 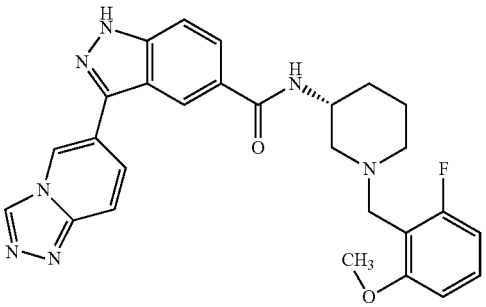 [SMILES: COc1cccc(F)c1CN1CCC[C@@H](NC(=O)c2ccc3[nH]nc(-c4ccc5nncn5c4)c3c2)C1] | 6.46 | 500.21 | 500.0 | 1.76 |
| 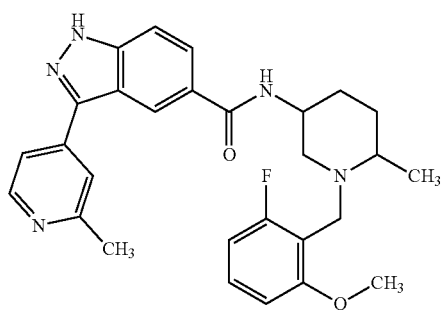 [SMILES: COc1cccc(F)c1CN1CC(NC(=O)c2ccc3[nH]nc(-c4ccnc(C)c4)c3c2)CCC1C] | 26.83 | 488.24 | 488.1 | 1.70 |
| 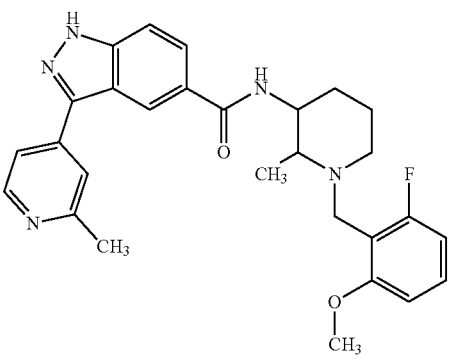 [SMILES: COc1cccc(F)c1CN1CCCC(NC(=O)c2ccc3[nH]nc(-c4ccnc(C)c4)c3c2)C1C] | 66.93 | 488.24 | 488.0 | 1.73 |

TABLE 3-continued

| Structure | aERK IC50 nM | M + H Calcd. | M + H Obs. | Retention Time Min. |
|---|---|---|---|---|
| (structure) | 169.65 | 494.21 | 494.0 | 1.85 |
| (structure) | 76.51 | 476.22 | 476.0 | 1.78 |
| (structure) | 12.87 | 490.25 | 490.2 | 0.77 |
| (structure) | 13.41 | 458.23 | 458.2 | 0.69 |

TABLE 3-continued
| Structure | aERK IC50 nM | M + H Calcd. | M + H Obs. | Retention Time Min. |
|---|---|---|---|---|
| 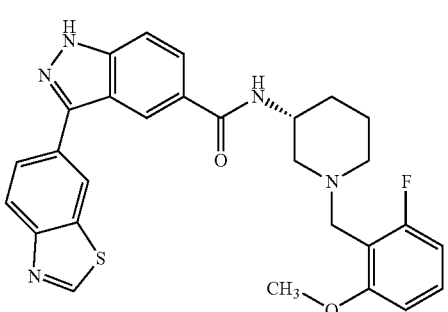 | 28.25 | 516.18 | 516.0 | 2.25 |
| 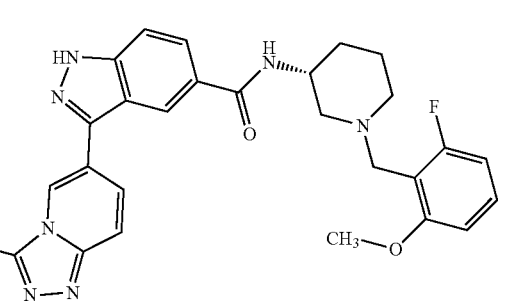 | 70.92 | 528.24 | 528.0 | 1.80 |
| 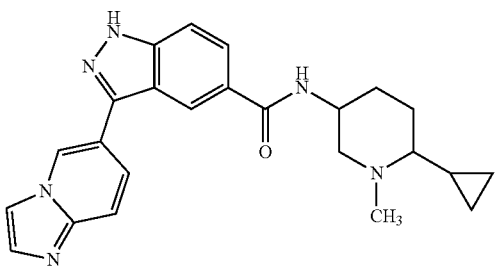 [SMILES: CN1CC(NC(=O)c2ccc3[nH]nc(-c4ccc5nccn5c4)c3c2)CCC1C1CC1] | 394.74 | 415.22 | 415.0 | 1.39 |
| 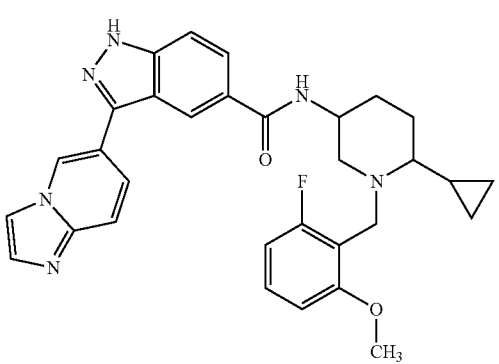 [SMILES: COc1cccc(F)c1CN1CC(NC(=O)c2ccc3[nH]nc(-c4ccc5nccn5c4)c3c2)CCC1C1CC1] | 49.32 | 539.25 | 539.1 | 1.89 |

TABLE 3-continued

| Structure | aERK IC50 nM | M + H Calcd. | M + H Obs. | Retention Time Min. |
|---|---|---|---|---|
| 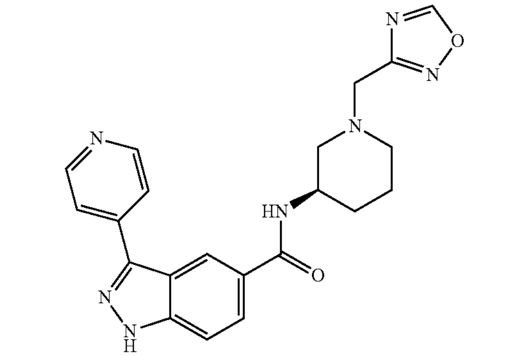 [SMILES: O=C(N[C@@H]1CCCN(Cc2ncon2)C1)c1ccc2[nH]nc(-c3ccncc3)c2c1] | 50.09 | 404.18 | 404.2 | 1.50 |
| 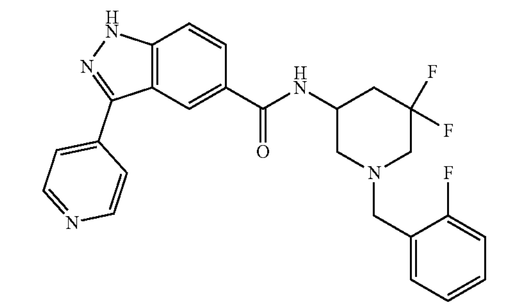 [SMILES: O=C(NC1CN(Cc2ccccc2F)CC(F)(F)C1)c1ccc2[nH]nc(-c3ccncc3)c2c1] | 126.56 | 466.18 | 466.2 | 0.76 |
| 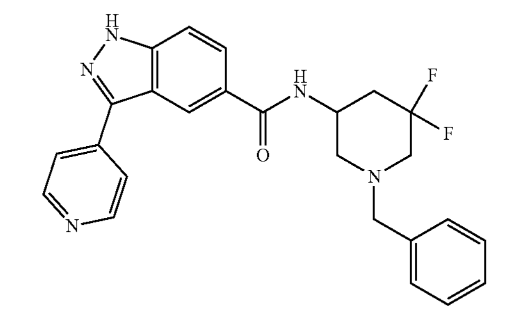 [SMILES: O=C(NC1CN(Cc2ccccc2)CC(F)(F)C1)c1ccc2[nH]nc(-c3ccncc3)c2c1] | 143.57 | 448.19 | 448.2 | 0.70 |
| 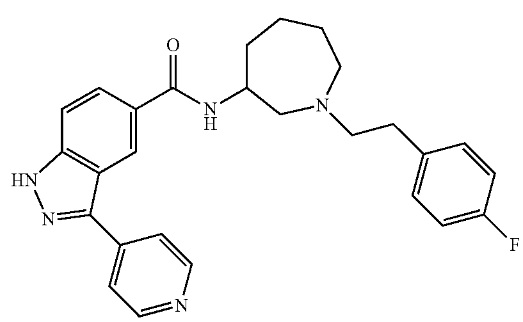 [SMILES: O=C(NC1CCCCN(CCc2ccc(F)cc2)C1)c1ccc2[nH]nc(-c3ccncc3)c2c1] | 98.08 | 458.23 | 458.2 | 0.70 |
| 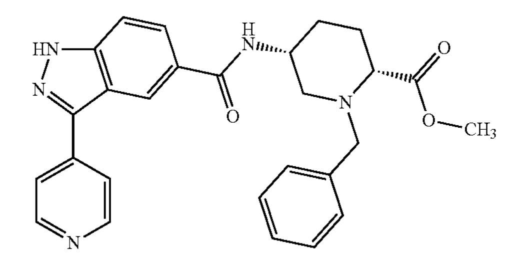 [SMILES: COC(=O)[C@H]1CC[C@@H](NC(=O)c2ccc3[nH]nc(-c4ccncc4)c3c2)CN1Cc1ccccc1] | 132.87 | 470.21 | 470.2 | 1.60 & 1.85 |

TABLE 3-continued

| Structure | aERK IC50 nM | M + H Calcd. | M + H Obs. | Retention Time Min. |
|---|---|---|---|---|
| 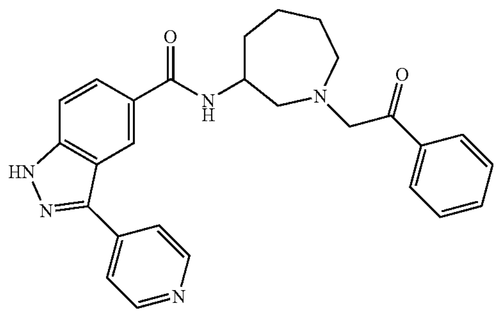 [SMILES: O=C(CN1CCCCC(NC(=O)c2ccc3[nH]nc(-c4ccncc4)c3c2)C1)c1ccccc1] | 34.84 | 454.22 | 454.2 | 0.67 |
| 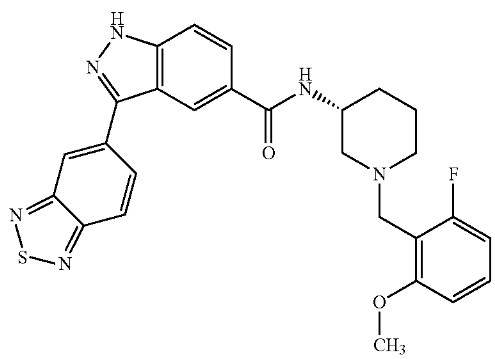 [SMILES: COc1cccc(F)c1CN1CCC[C@@H](NC(=O)c2ccc3[nH]nc(-c4ccc5nsnc5c4)c3c2)C1] | 175.42 | 517.17 | 516.9 | 2.48 |
| 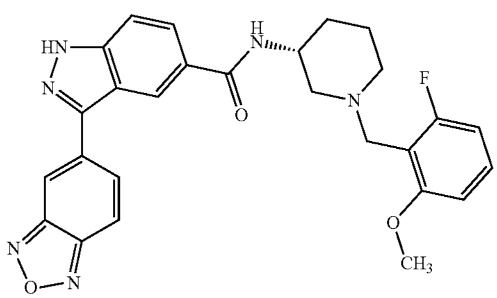 [SMILES: COc1cccc(F)c1CN1CCC[C@@H](NC(=O)c2ccc3[nH]nc(-c4ccc5nonc5c4)c3c2)C1] | 300.92 | 501.20 | 500.9 | 2.55 |
| 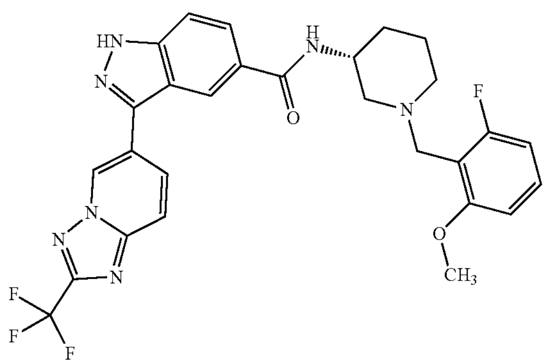 [SMILES: COc1cccc(F)c1CN1CCC[C@@H](NC(=O)c2ccc3[nH]nc(-c4ccc5nc(C(F)(F)F)nn5c4)c3c2)C1] | 822.31 | 568.20 | 568.2 | 2.58 |

TABLE 3-continued

| Structure | aERK IC50 nM | M + H Calcd. | M + H Obs. | Retention Time Min. |
|---|---|---|---|---|
| 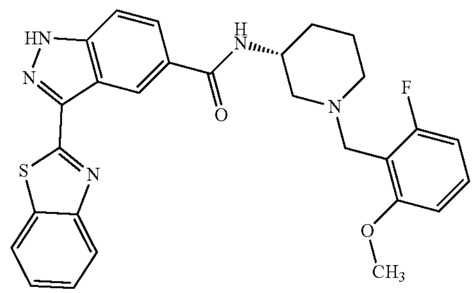 [SMILES: COc1cccc(F)c1CN1CCC[C@@H](NC(=O)c2ccc3[nH]nc(-c4nc5ccccc5s4)c3c2)C1] | 296.49 | 516.18 | 515.9 | 2.70 |
| 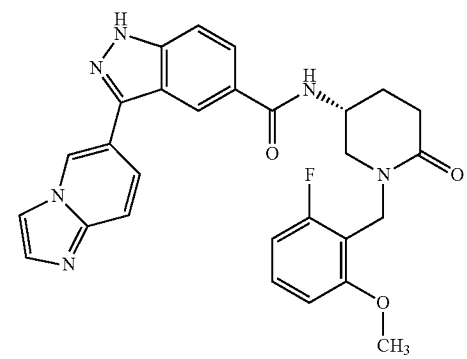 [SMILES: COc1cccc(F)c1CN1C[C@H](NC(=O)c2ccc3[nH]nc(-c4ccc5nccn5c4)c3c2)CCC1=O] | 69.19 | 513.20 | 513.0 | 2.04 |
| 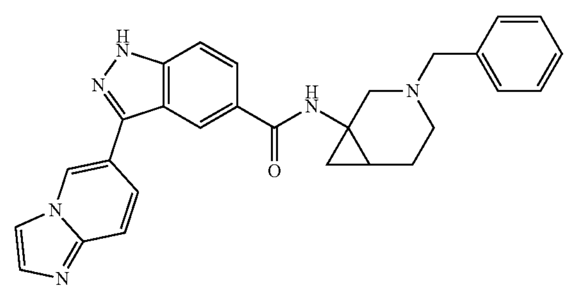 [SMILES: O=C(NC12CC1CCN(Cc1ccccc1)C2)c1ccc2[nH]nc(-c3ccc4nccn4c3)c2c1] | 199.625 | 463.22 | 463.0 | 1.58 |
| 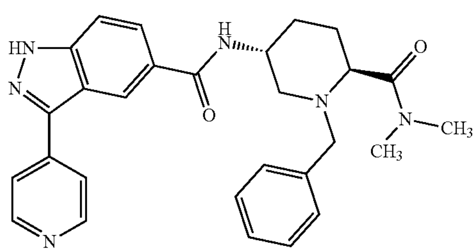 [SMILES: CN(C)C(=O)[C@@H]1CC[C@@H](NC(=O)c2ccc3[nH]nc(-c4ccncc4)c3c2)CN1Cc1ccccc1] | 51.31 | 483.24 | 483.3 | 1.54 |
| 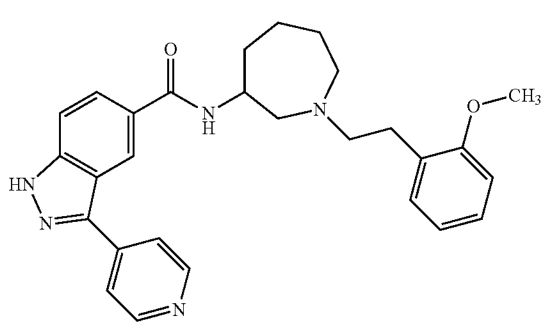 [SMILES: COc1ccccc1CCN1CCCCC(NC(=O)c2ccc3[nH]nc(-c4ccncc4)c3c2)C1] | 31.07 | 470.25 | 470.2 | 0.72 |

TABLE 3-continued

| Structure | aERK IC50 nM | M + H Calcd. | M + H Obs. | Retention Time Min. |
|---|---|---|---|---|
| 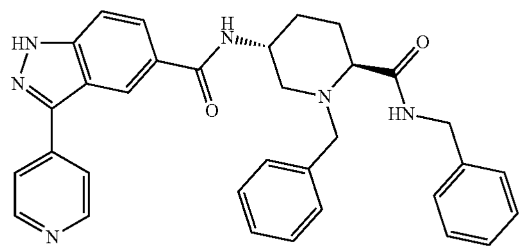 [SMILES: O=C(N[C@@H]1CC[C@@H](C(=O)NCc2ccccc2)N(Cc2ccccc2)C1)c1ccc2[nH]nc(-c3ccncc3)c2c1] | 47.53 | 545.26 | 545.3 | 1.72 |
| 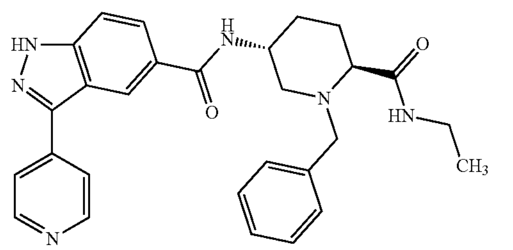 [SMILES: CCNC(=O)[C@@H]1CC[C@@H](NC(=O)c2ccc3[nH]nc(-c4ccncc4)c3c2)CN1Cc1ccccc1] | 48.34 | 483.24 | 483.0 | 1.60 |
| 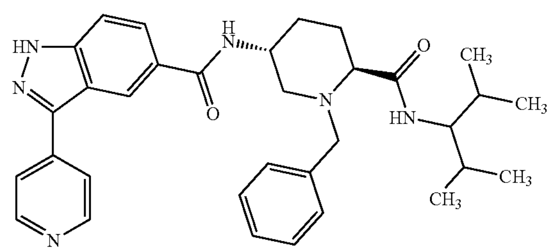 [SMILES: CC(C)C(NC(=O)[C@@H]1CC[C@@H](NC(=O)c2ccc3[nH]nc(-c4ccncc4)c3c2)CN1Cc1ccccc1)C(C)C] | 262.24 | 553.32 | 553.4 | 1.83 |
| 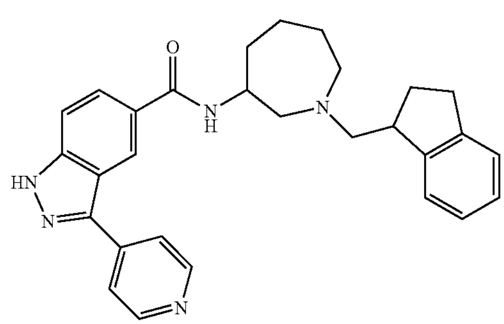 [SMILES: O=C(NC1CCCCN(CC2CCc3ccccc32)C1)c1ccc2[nH]nc(-c3ccncc3)c2c1] | 85.42 | 466.25 | 466.2 | 0.74 |
| 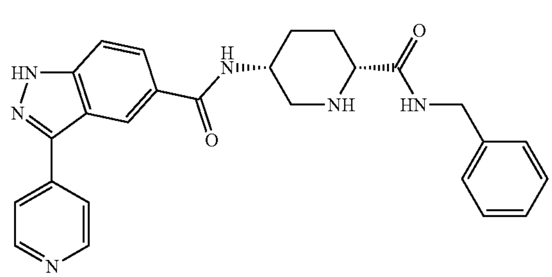 [SMILES: O=C(N[C@@H]1CC[C@H](C(=O)NCc2ccccc2)NC1)c1ccc2[nH]nc(-c3ccncc3)c2c1] | 371.03 | 455.21 | 455.2 | 1.59 |

TABLE 3-continued

| Structure | aERK IC50 nM | M + H Calcd. | M + H Obs. | Retention Time Min. |
|---|---|---|---|---|
| 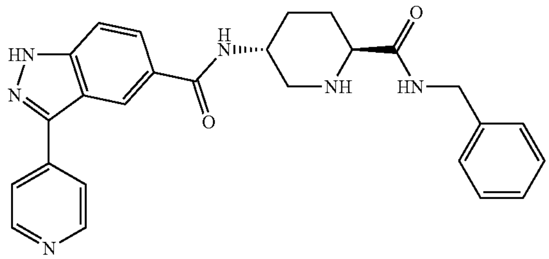 [SMILES: O=C(N[C@@H]1CC[C@@H](C(=O)NCc2ccccc2)NC1)c1ccc2[nH]nc(-c3ccncc3)c2c1] | 119.93 | 455.21 | 455.2 | 1.60 |
| 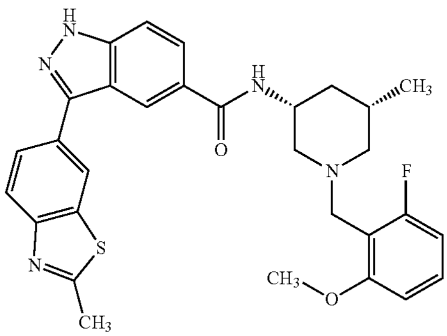 [SMILES: COc1cccc(F)c1CN1C[C@@H](C)C[C@@H](NC(=O)c2ccc3[nH]nc(-c4ccc5nc(C)sc5c4)c3c2)C1] | 3.67 | 544.21 | 544.2 | 2.67 |
| 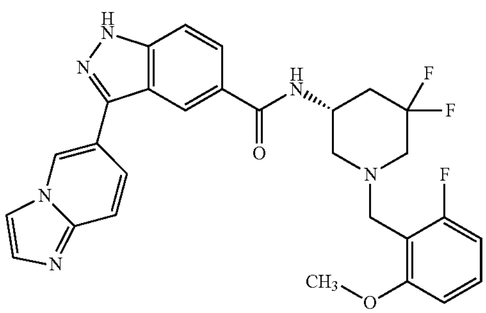 [SMILES: COc1cccc(F)c1CN1C[C@H](NC(=O)c2ccc3[nH]nc(-c4ccc5nccn5c4)c3c2)CC(F)(F)C1] | 23.91 | 535.20 | 534.9 | 2.04 |
| 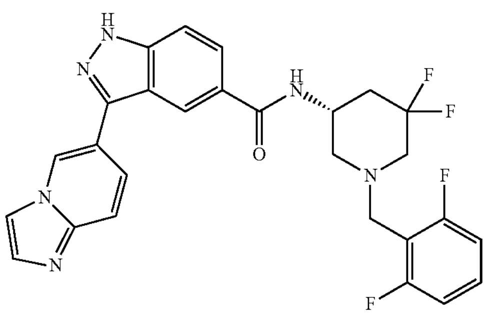 [SMILES: O=C(N[C@H]1CN(Cc2c(F)cccc2F)CC(F)(F)C1)c1ccc2[nH]nc(-c3ccc4nccn4c3)c2c1] | 234.47 | 523.18 | 523.2 | 2.41 |
| 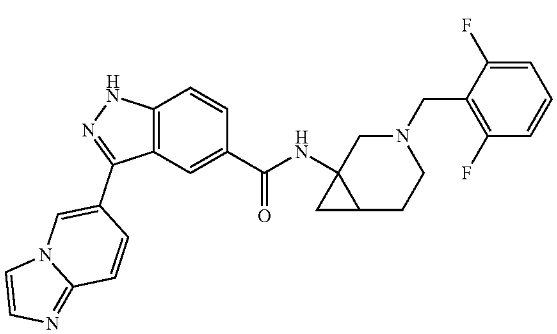 [SMILES: O=C(NC12CC1CCN(Cc1c(F)cccc1F)C2)c1ccc2[nH]nc(-c3ccc4nccn4c3)c2c1] | 136.21 | 499.20 | 499.0 | 1.56 |

TABLE 3-continued
| Structure | aERK IC50 nM | M + H Calcd. | M + H Obs. | Retention Time Min. |
|---|---|---|---|---|
| 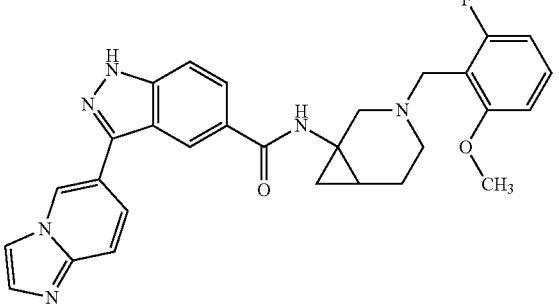 | 86.04 | 511.22 | 511.0 | 1.71 |
| 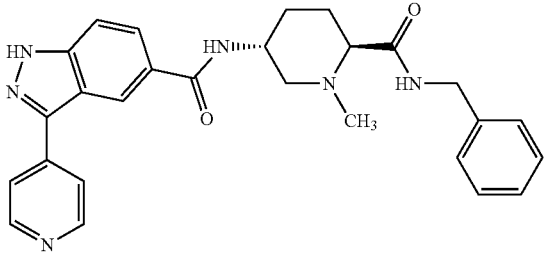 [SMILES: CN1C[C@H](NC(=O)c2ccc3[nH]nc(-c4ccncc4)c3c2)CC[C@H]1C(=O)NCc1ccccc1] | 350.19 | 469.23 | 469.2 | 1.60 |
| 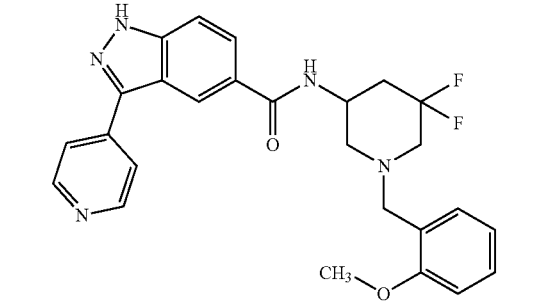 [SMILES: COc1ccccc1CN1CC(NC(=O)c2ccc3[nH]nc(-c4ccncc4)c3c2)CC(F)(F)C1] | 167.2 | 478.20 | 478.0 | 0.71 |
| 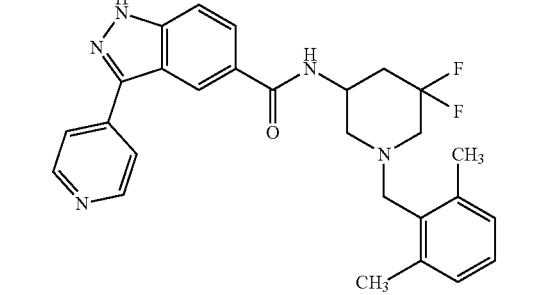 | 456.88 | 476.22 | 476.0 | 0.90 |
| 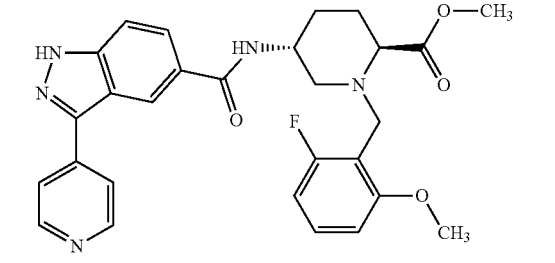 [SMILES: COC(=O)[C@@H]1CC[C@@H](NC(=O)c2ccc3[nH]nc(-c4ccncc4)c3c2)CN1Cc1c(F)cccc1OC] | 40.53 | 518.21 | 518.2 | 1.64 |

TABLE 3-continued

| Structure | aERK IC50 nM | M + H Calcd. | M + H Obs. | Retention Time Min. |
|---|---|---|---|---|
| (structure) | 15.23 | 530.20 | 529.9 | 2.38 |
| (structure) | 39.84 | 569.20 | 568.9 | 2.56 |
| (structure) | 374.85 | 569.20 | 568.9 | 2.56 |
| (structure) | 3.58 | 490.22 | 490.2 | 1.00 & 1.01 |
| (structure) | 36.17 | 448.19 | 448.0 | 1.44 |

TABLE 3-continued
| Structure | aERK IC50 nM | M + H Calcd. | M + H Obs. | Retention Time Min. |
|---|---|---|---|---|
| 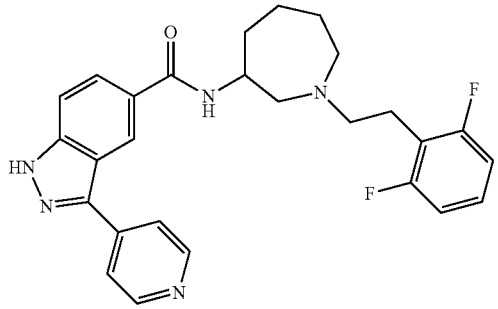 [SMILES: O=C(NC1CCCCN(CCc2c(F)cccc2F)C1)c1ccc2[nH]nc(-c3ccncc3)c2c1] | 43.29 | 476.22 | 476.0 | 0.70 |
| 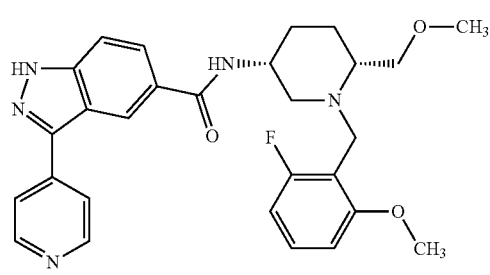 [SMILES: COC[C@H]1CC[C@@H](NC(=O)c2ccc3[nH]nc(-c4ccncc4)c3c2)CN1Cc1c(F)cccc1OC] | 455.92 | 504.23 | 504.2 | 1.63 |
| 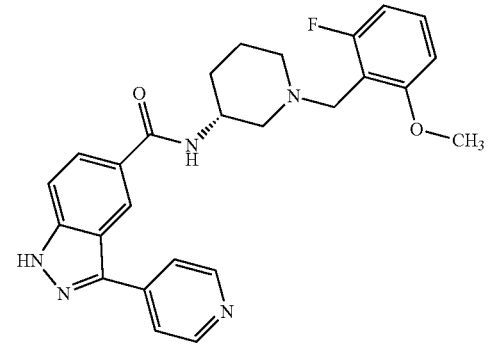 [SMILES: COc1cccc(F)c1CN1CCC[C@@H](NC(=O)c2ccc3[nH]nc(-c4ccncc4)c3c2)C1] | 13.91 | 460.21 | 460.2 | 1.63 |
| 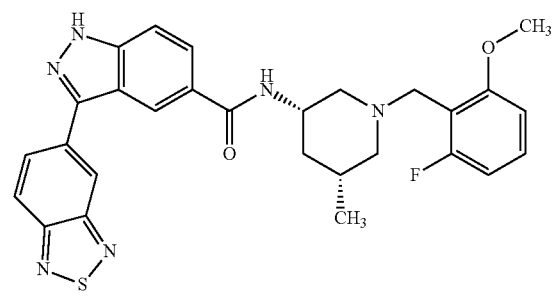 [SMILES: COc1cccc(F)c1CN1C[C@H](C)C[C@H](NC(=O)c2ccc3[nH]nc(-c4ccc5nsnc5c4)c3c2)C1] | 73.64 | 531.19 | 531.1 | 2.79 |
| 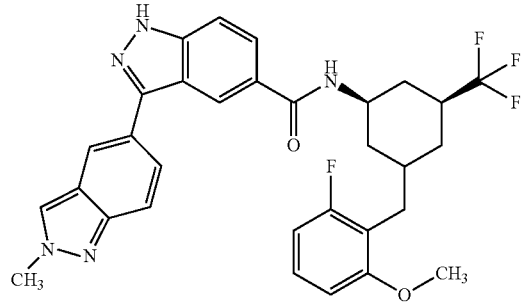 [SMILES: COc1cccc(F)c1CC1C[C@@H](NC(=O)c2ccc3[nH]nc(-c4ccc5nn(C)cc5c4)c3c2)C[C@@H](C(F)(F)F)C1] | 809.77 | 581.22 | 581.2 | 2.56 |

TABLE 3-continued

| Structure | aERK IC50 nM | M + H Calcd. | M + H Obs. | Retention Time Min. |
|---|---|---|---|---|
| (structure) | 4.455 | 567.21 | 567.2 | 1.87 |
| (structure) | 15.14 | 514.23 | 514.0 | 2.11 |
| (structure) | 127.795 | 515.21 | 515.2 | 2.66 |
| (structure) | 61.33 | 530.20 | 530.0 | 2.81 |

TABLE 3-continued

| Structure | aERK IC50 nM | M + H Calcd. | M + H Obs. | Retention Time Min. |
|---|---|---|---|---|
| 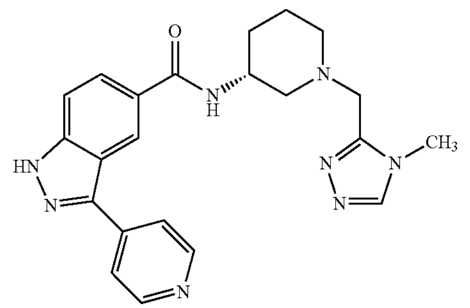 [SMILES: Cn1cnnc1CN1CCC[C@@H](NC(=O)c2ccc3[nH]nc(-c4ccncc4)c3c2)C1] | 231.01 | 417.21 | 417.0 | 1.06 |
| 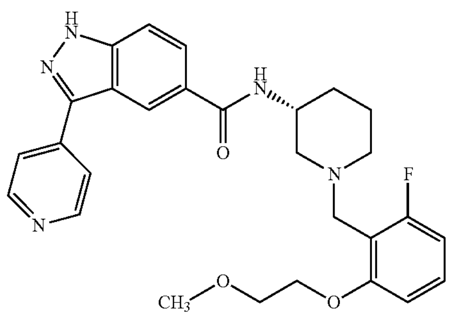 [SMILES: COCCOc1cccc(F)c1CN1CCC[C@@H](NC(=O)c2ccc3[nH]nc(-c4ccncc4)c3c2)C1] | 16.95 | 504.23 | 504.0 | 1.62 |
| 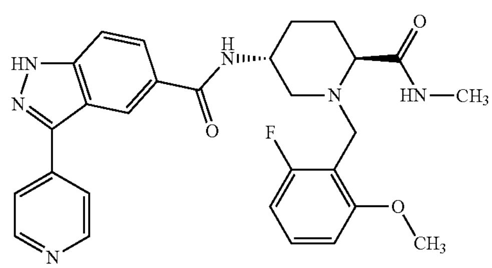 [SMILES: CNC(=O)[C@@H]1CC[C@@H](NC(=O)c2ccc3[nH]nc(-c4ccncc4)c3c2)CN1Cc1c(F)cccc1OC] | 2.41 | 517.23 | 517.2 | 1.58 |
| 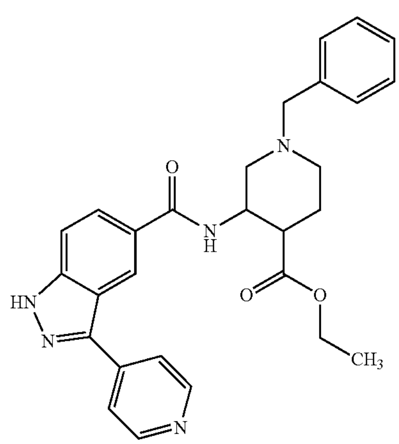 [SMILES: CCOC(=O)C1CCN(Cc2ccccc2)CC1NC(=O)c1ccc2[nH]nc(-c3ccncc3)c2c1] | 191.34 | 484.23 | 484.0 | 1.60 |

TABLE 3-continued
| Structure | aERK IC50 nM | M + H Calcd. | M + H Obs. | Retention Time Min. |
|---|---|---|---|---|
| 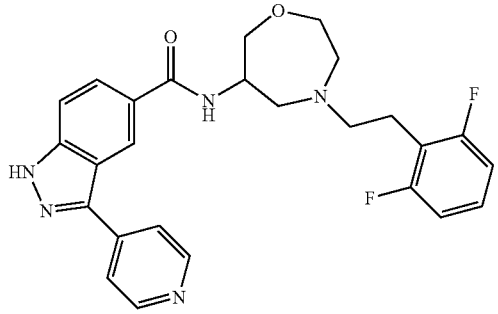 [SMILES: O=C(NC1COCCN(CCc2c(F)cccc2F)C1)c1ccc2[nH]nc(-c3ccncc3)c2c1] | 20.76 | 478.20 | 478.0 | 0.66 |
| 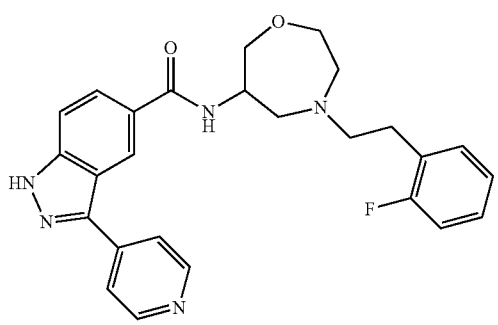 [SMILES: O=C(NC1COCCN(CCc2ccccc2F)C1)c1ccc2[nH]nc(-c3ccncc3)c2c1] | 9.84 | 460.21 | 460.0 | 0.66 |
| 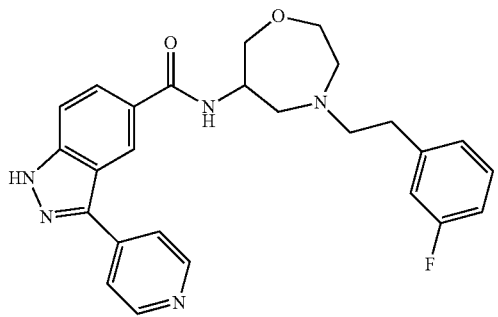 [SMILES: O=C(NC1COCCN(CCc2cccc(F)c2)C1)c1ccc2[nH]nc(-c3ccncc3)c2c1] | 61.6 | 460.21 | 460.0 | 0.66 |
| 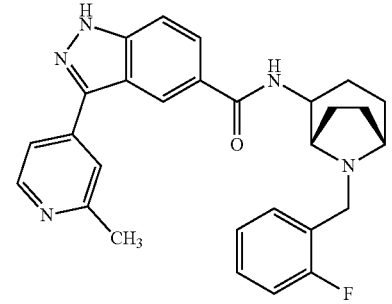 [SMILES: Cc1cc(-c2n[nH]c3ccc(C(=O)NC4CC[C@H]5CC[C@@H]4N5Cc4ccccc4F)cc23)ccn1] | 9.1 | 470.23 | 470.0 | 1.59 |

TABLE 3-continued

| Structure | aERK IC50 nM | M + H Calcd. | M + H Obs. | Retention Time Min. |
|---|---|---|---|---|
| (structure shown) | 20.4 | 500.24 | 500.0 | 1.67 |

20

The compounds in the following table were made following procedures similar to those described above.

| Structure | aErk2 Ic50 | M + H Calcd. | M + H Obs. | Retention Time minutes |
|---|---|---|---|---|
| (structure shown) N-[(3R,6S)-1-(2-fluoro-6-methoxybenzyl)-6-(methylcarbamoyl)piperidin-3-yl]-3-pyridin-4-yl-1H-indazole-5-carboxamide | 3.2 | 517.58 | 517.2 | 1.57 |
| (structure shown, Chiral) N-[(3R,6S)-6-(dimethylcarbamoyl)-1-(2-fluoro-6-methoxybenzyl)piperidin-3-yl]-3-pyridin-4-yl-1H-indazole-5-carboxamide | 18.2 | 531.61 | 531.2 | 1.61 |

-continued

| Structure | aErk2 Ic50 | M + H Calcd. | M + H Obs. | Retention Time minutes |
|---|---|---|---|---|
| N-[(3R,6S)-1-benzyl-6-(benzylcarbamoyl)piperidin-3-yl]-3-pyridin-4-yl-1H-indazole-5-carboxamide | 47.5 | 545.66 | 545.3 | 1.73 |
| N-[(3R,6S)-1-benzyl-6-(ethylcarbamoyl)-piperidin-3-yl]-3-pyridin-4-yl-1H-indazole-5-carboxamide | 48.3 | 483.59 | 483.2 | 1.60 |
| N-[(3R,6S)-6-carbamoyl-1-(2-fluoro-6-methoxybenzyl)piperidin-3-yl]-3-pyridin-4-yl-1H-indazole-5-carboxamide | 1.7 | 503.55 | 503 | 0.64 |

-continued

| Structure | aErk2 Ic50 | M + H Calcd. | M + H Obs. | Retention Time minutes |
|---|---|---|---|---|
| Chiral 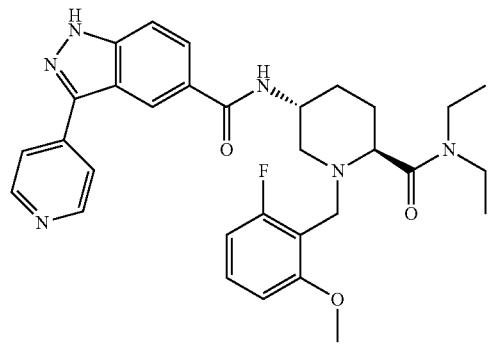 N-[(3R,6S)-6-(diethylcarbamoyl)-1-(2-fluoro-6-methoxybenzyl)piperidin-3-yl]-3-pyridin-4-yl-1H-indazole-5-carboxamide | 18.4 | 559.66 | 559 | 0.76 |
| Chiral 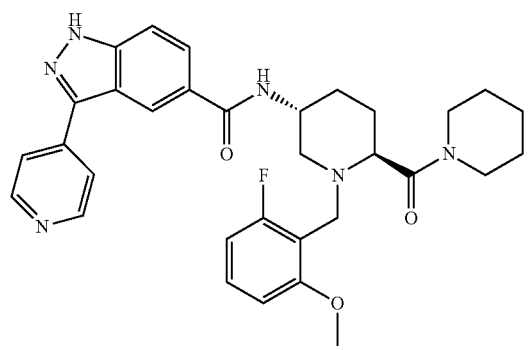 N-[(3R,6S)-1-(2-fluoro-6-methoxybenzyl)-6-(piperidin-1-ylcarbonyl)piperidin-3-yl]-3-pyridin-4-yl-1H-indazole-5-carboxamide | 59.9 | 571.67 | 571 | 0.77 |
| Chiral 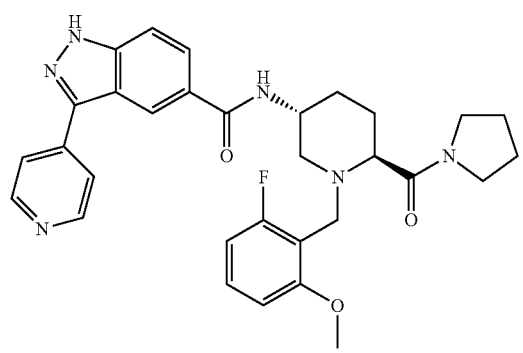 N-[(3R,6S)-1-(2-fluoro-6-methoxybenzyl)-6-(pyrrolidin-1-ylcarbonyl)piperidin-3-yl]-3-pyridin-4-yl-1H-indazole-5-carboxamide | 35.5 | 557.65 | 557 | 0.72 |

-continued

| Structure | aErk2 Ic50 | M + H Calcd. | M + H Obs. | Retention Time minutes |
|---|---|---|---|---|
| Chiral | 35.0 | 607.65 | 607 | 0.66 |

N-[(3R,6S)-6-[(4,4-difluoropiperidin-1-yl)carbonyl]-1-(2-fluoro-6-methoxybenzyl)-piperidin-3-yl]-3-pyridin-4-yl-1H-indole-5-carboxamide

| | 37.8 | 545.63 | 545 | 0.68 |

N-[(3R,6S)-6-(dimethylcarbamoyl)-1-(2-fluoro-6-methoxybenzyl)piperidin-3-yl]-3-(2-methylpyridin-4-yl)-1H-indazole-5-carboxamide

| | 16.2 | 572.69 | 573 | 1.73 |

N-[(3R,6S)-6-(diethylcarbamoyl)-1-(2-fluoro-6-methoxybenzyl)piperidin-3-yl]-3-(2-methylpyridin-4-yl)-1H-indazole-5-carboxamide -continued

| Structure | aErk2 Ic50 | M + H Calcd. | M + H Obs. | Retention Time minutes |
|---|---|---|---|---|
| 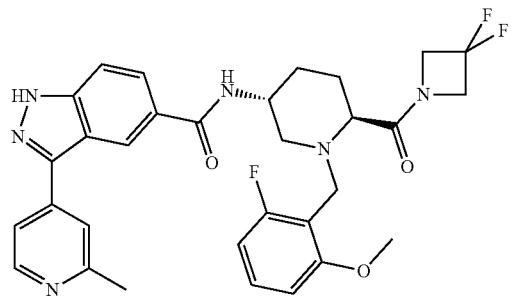 N-[(3R,6S)-6-[(3,3-difluoroazetidin-1-yl)carbonyl]-1-(2-fluoro-6-methoxybenzyl)-piperidin-3-yl]-3-(2-methylpyridin-4-yl)-1H-indazole-5-carboxamide (Chiral) | 14.8 | 593.63 | 593 | 1.68 |
| 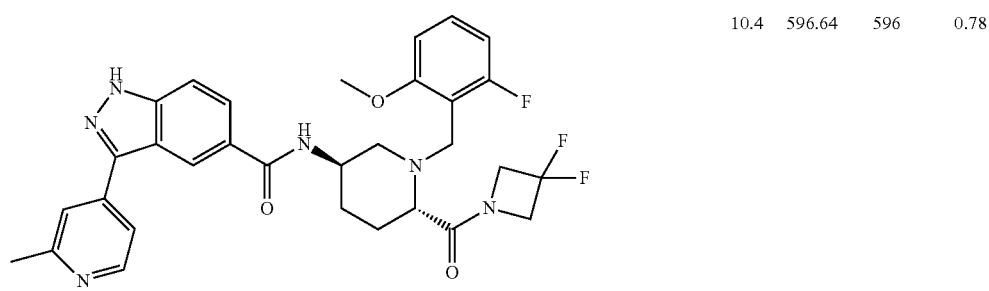 N-[(3R,6S)-6-[(3,3-difluoroazetidin-1-yl)carbonyl]-1-(2-fluoro-6-methoxybenzyl)-piperidin-3-yl]-3-(2-methylpyridin-4-yl)-1H-indazole-5-carboxamide | 10.4 | 596.64 | 596 | 0.78 |
| 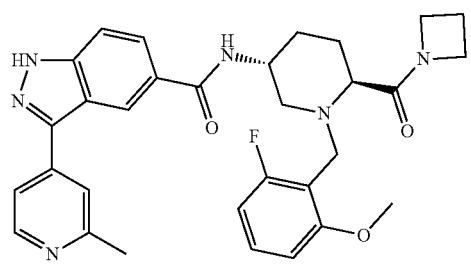 N-[(3R,6S)-6-(azetidin-1-ylcarbonyl)-1-(2-fluoro-6-methoxybenzyl)piperidin-3-yl]-3-(2-methylpyridin-4-yl)-1H-indazole-5-carboxamide (Chiral) | 34.9 | 557.65 | 557 | 1.60 |

-continued

| Structure | aErk2 Ic50 | M + H Calcd. | M + H Obs. | Retention Time minutes |
|---|---|---|---|---|
| N-[(3R,6S)-1-(2-fluoro-6-methoxybenzyl)-6-(morpholin-4-ylcarbonyl)piperidin-3-yl]-3-(2-methylpyridin-4-yl)-1H-indazole-5-carboxamide | 18.2 | 587.67 | 587 | 1.62 |
| N-[(3R,6S)-6-{[2-(benzyloxy)ethyl]-carbamoyl}-1-(2-fluoro-6-methoxybenzyl)-piperidin-3-yl]-3-(2-methylpyridin-4-yl)-1H-indazole-5-carboxamide | 120.6 | 651.76 | 651 | 1.79 |
| N-{(3R,6S)-1-(2-fluoro-6-methoxybenzyl)-6-[(2-methoxyethyl)carbamoyl]piperidin-3-yl}-3-(2-methylpyridin-4-yl)-1H-indazole-5-carboxamide | 56.7 | 575.66 | 575 | 1.64 |

| Structure | aErk2 Ic50 | M + H Calcd. | M + H Obs. | Retention Time minutes |
|---|---|---|---|---|
| [Chiral] N-{(3R,6S)-1-(2-fluoro-6-methoxybenzyl)-6-[(1-methylethyl)carbamoyl]piperidin-3-yl}-3-(2-methylpyridin-4-yl)-1H-indazole-5-carboxamide | 46.5 | 559.66 | 559 | 0.74 |
| [Chiral] N-[(3R,6S)--6-(cyclopentylcarbamoyl)-1-(2-fluoro-6-methoxybenzyl)piperidin-3-yl]-3-(2-methylpyridin-4-yl)-1H-indazole-5-carboxamide | 105.0 | 585.70 | 585 | 0.79 |
| [Chiral] N-{(3R,6S)-1-(2-fluoro-6-methoxybenzyl)-6-[(2-hydroxyethyl)carbamoyl]piperidin-3-yl}-3-(2-methylpyridin-4-yl)-1H-indazole-5-carboxamide | 5.6 | 561.63 | 561 | 1.57 |

| Structure | aErk2 Ic50 | M + H Calcd. | M + H Obs. | Retention Time minutes |
|---|---|---|---|---|
| 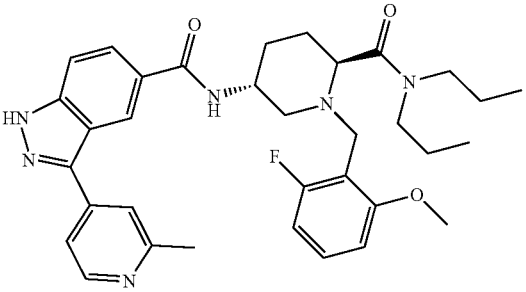 [SMILES: CCCN(C)C(=O)[C@@H]1CC[C@@H](NC(=O)c2ccc3[nH]nc(-c4ccnc(C)c4)c3c2)CN1Cc1c(F)cccc1OC] N-[(3R,6S)-6-(dipropylcarbamoyl)-1-(2-fluoro-6-methoxybenzyl)piperidin-3-yl]-3-(2-methylpyridin-4-yl)-1H-indazole-5-carboxamide | 141.4 | 601.74 | 601 | 2.20 |
| 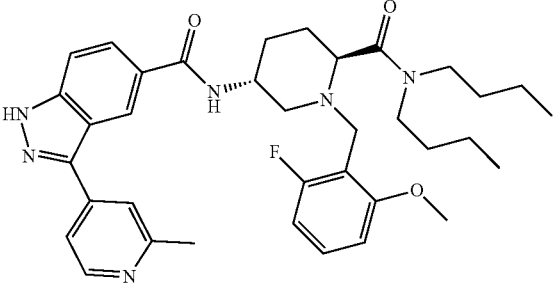 N-[(3R,6S)-6-(dibutylcarbamoyl)-1-(2-fluoro-6-methoxybenzyl)piperidin-3-yl]-3-(2-methylpyridin-4-yl)-1H-indazole-5-carboxamide | 502.0 | 629.80 | 629 | 2.93 |
| 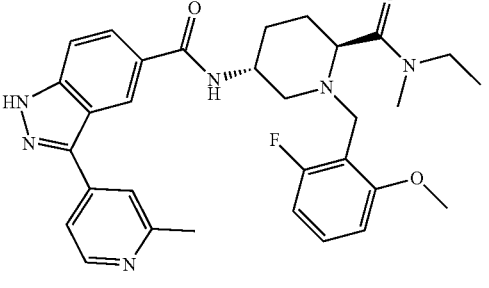 N-[(3R,6S)-6-[ethyl(methyl)carbamoyl]-1-(2-fluoro-6-methoxybenzyl)piperidin-3-yl]-3-(2-methylpyridin-4-yl)-1H-indazole-5-carboxamide | 21.8 | 559.66 | 559 | 1.67 |

| Structure | aErk2 Ic50 | M + H Calcd. | M + H Obs. | Retention Time minutes |
|---|---|---|---|---|
| N-{(3R,6S)-1-(2-fluoro-6-methoxybenzyl)-6-[methyl(propyl)carbamoyl]piperidin-3-yl}-3-(2-methylpyridin-4-yl)-1H-indazole-5-carboxamide | 57.0 | 573.69 | 573 | 1.71 |
| N-[(3R,6S)-6-(diethylcarbamoyl)-1-(2,6-difluorobenzyl)piperidin-3-yl]-3-(2-methylpyridin-4-yl)-1H-indazole-5-carboxamide (Chiral) | 80.7 | 561.55 | 561 | 1.67 |
| N-[(3R,6S)-1-(2,6-difluorobenzyl)-6-(dimethylcarbamoyl)piperidin-3-yl]-3-(2-methylpyridin-4-yl)-1H-indazole-5-carboxamide (Chiral) | 74.0 | 533.60 | 533 | 1.57 |

| Structure | aErk2 Ic50 | M + H Calcd. | M + H Obs. | Retention Time minutes |
|---|---|---|---|---|
| N-[(3R,6S)-6-[(3,3-difluoroazetidin-1-yl)carbonyl]-1-(2,6-difluorobenzyl)piperidin-3-yl]-3-(2-methylpyridin-4-yl)-1H-indazole-5-carboxamide | 96.5 | 581.59 | 581 | 1.62 |
| N-[(3R,6S)-6-(dimethylcarbamoyl)-1-(2-fluorobenzyl)piperidin-3-yl]-3-(2-methylpyridin-4-yl)-1H-indazole-5-carboxamide | 39.4 | 515.61 | 515 | 1.59 |
| N-[(3R,6S)-6-(diethylcarbamoyl)-1-(2-fluorobenzyl)piperidin-3-yl]-3-(2-methylpyridin-4-yl)-1H-indazole-5-carboxamide | 20.1 | 543.66 | 543 | 1.68 |

| Structure | aErk2 Ic50 | M + H Calcd. | M + H Obs. | Retention Time minutes |
|---|---|---|---|---|
| N-[(3R,6S)-6-[(3,3-difluoroazetidin-1-yl)carbonyl]-1-(2-fluorobenzyl)piperidin-3-yl]-3-(2-methylpyridin-4-yl)-1H-indazole-5-carboxamide | 56.6 | 563.60 | 563 | 1.64 |
| N-[(3R,6S)-6-(dimethylcarbamoyl)-1-(thiophen-2-ylmethyl)piperidin-3-yl]-3-(2-methylpyridin-4-yl)-1H-indazole-5-carboxamide | 14.4 | 503.64 | 503 | 1.55 |
| N-[(3R,6S)-6-[(3,3-difluoroazetidin-1-yl)carbonyl]-1-(thiophen-2-ylmethyl)-piperidin-3-yl]-3-(2-methylpyridin-4-yl)-1H-indazole-5-carboxamide | 25.8 | 551.64 | 551 | 1.62 |

| Structure | aErk2 Ic50 | M + H Calcd. | M + H Obs. | Retention Time minutes |
|---|---|---|---|---|
| N-[(3R,6S)-1-(diethylcarbamoyl)-1-(thiophen-2-ylmethyl)piperidin-3-yl]-3-(2-methylpyridin-4-yl)-1H-indazole-5-carboxamide | 28.2 | 531.70 | 531 | 1.66 |
| Chiral<br>N-[(3R,6S)-6-(dimethylcarbamoyl)-1-(2-fluoro-6-methoxybenzyl)piperidin-3-yl]-2'-methyl-1H,2'H,3,5'-biindazole-5-carboxamide | 15.9 | 584.67 | 584 | 1.78 |
| Chiral<br>N-[(3R,6S)-6-(diethylcarbamoyl)-1-(2-fluoro-6-methoxybenzyl)piperidin-3-yl]-2'-methyl-1H,2'H,3,5'-biindazole-5-carboxamide | 39.4 | 612.73 | 612 | 1.82 |

-continued

| Structure | aErk2 Ic50 | M + H Calcd. | M + H Obs. | Retention Time minutes |
|---|---|---|---|---|
| Chiral
N-[(3R,6S)-6-[(3,3-difluoroazetidin-1-yl)carbonyl]-1-(2-fluoro-6-methoxybenzyl)-piperidin-3-yl]-2'-methyl-1H,2'H,3,5'-biindazole-5-carboxamide | 22.8 | 632.66 | 632 | 1.83 |
| Chiral
N-[(3R,6S)-6-(dimethylcarbamoyl)-1-(2-fluoro-6-methoxybenzyl)piperidin-3-yl]-3-(2-methyl-1,3-benzothiazol-6-yl)-1H-indazole-5-carboxamide | 48.0 | 601.72 | 601 | 1.87 |

| Structure | aErk2 Ic50 | M + H Calcd. | M + H Obs. | Retention Time minutes |
|---|---|---|---|---|
| Chiral 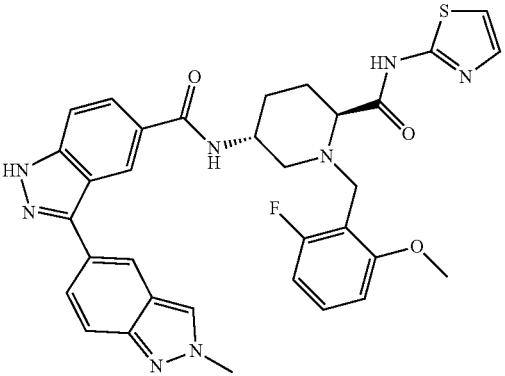 N-[(3R,6S)-1-(2-fluoro-6-methoxybenzyl)-6-(1,3-thiazol-2-ylcarbamoyl)piperidin-3-yl]-2'-methyl-1H,2'H,3,5'-biindazole-5-carboxamide | 112.7 | 639.73 | 639 | 1.83 |
| Chiral 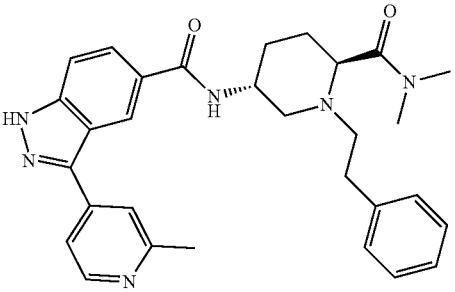 N-[(3R,6S)-6-(dimethylcarbamoyl)-1-(2-phenylethyl)piperidin-3-yl]-3-(2-methylpyridin-4-yl)-1H-indazole-5-carboxamide | 131.3 | 511.64 | 511 | 1.65 |
| Chiral 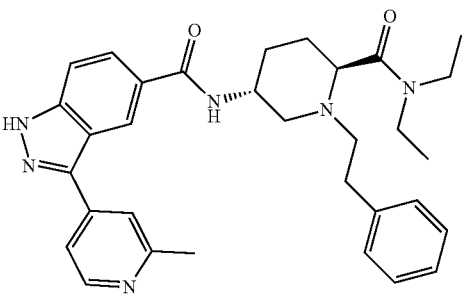 N-[(3R,6S)-6-(diethylcarbamoyl)-1-(2-phenylethyl)piperidin-3-yl]-3-(2-methylpyridin-4-yl)-1H-indazole-5-carboxamide | 157.8 | 539.70 | 539 | 1.72 |

-continued

| Structure | aErk2 Ic50 | M + H Calcd. | M + H Obs. | Retention Time minutes |
|---|---|---|---|---|
| Chiral<br><br>N-[(3R,6S)-6-[(3,3-difluoroazetidin-1-yl)carbonyl]-1-(2-phenylethyl)piperidin-3-yl]-3-(2-methylpyridin-4-yl)-1H-indazole-5-carboxamide | 232.2 | 559.64 | 559 | 1.70 |
| Chiral<br><br>3-(2-methylpyridin-4-yl)-N-[(3R,6S)-1-(2-phenylethyl)-6-(1,3-thiazol-2-ylcarbamoyl)-piperidin-3-yl]-1H-indazole-5-carboxamide | 132.7 | 566.70 | 566 | 1.71 |
| Chiral<br><br>N-[(3R,6S)-6-(diethylcarbamoyl)-1-(2-fluoro-6-methoxybenzyl)piperidin-3-yl]-3-(2-methyl-1,3-benzothiazol-6-yl)-1H-indazole-5-carboxamide | 32.9 | 629.78 | 629 | 1.95 |

| Structure | aErk2 Ic50 | M + H Calcd. | M + H Obs. | Retention Time minutes |
|---|---|---|---|---|
| 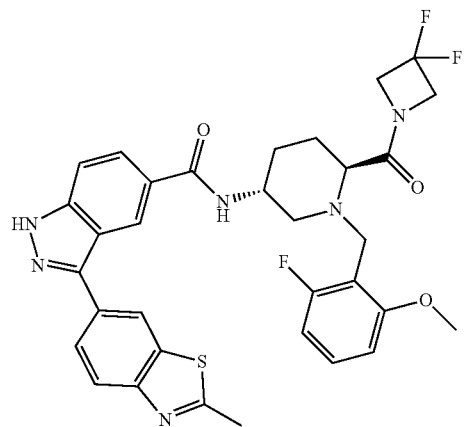 Chiral<br>N-[(3R,6S)-6-[(3,3-difluoroazetidin-1-yl)carbonyl]-1-(2-fluoro-6-methoxybenzyl)-piperidin-3-yl]-3-(2-methyl-1,3-benzothiazol-6-yl)-1H-indazole-5-carboxamide | 47.4 | 649.71 | 648.8 | 1.91 |
| 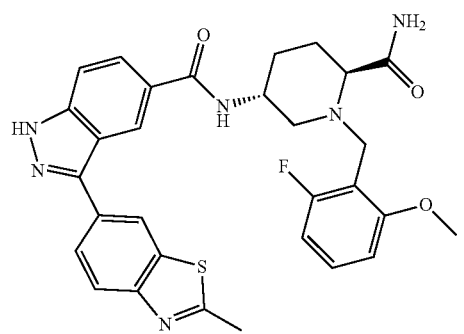 Chiral<br>N-[(3R,6S)-6-carbamoyl-1-(2-fluoro-6-methoxybenzyl)piperidin-3-yl]-3-(2-methyl-1,3-benzothiazaol-6-yl)-1H-indazole-5-carboxamide | 3.6 | 573.67 | 573 | 1.83 |

-continued

| Structure | aErk2 Ic50 | M + H Calcd. | M + H Obs. | Retention Time minutes |
|---|---|---|---|---|
| N-[(3R,6S)-6-carbamoyl-1-{2-fluoro-6-[(~2~H_3_)methyloxy]benzyl}piperidin-3-yl]-3-(2-methyl-1,3-benzothiazol-6-yl)-1H-indazole-5-carboxamide | 3.4 | 576.69 | 576 | 1.83 |
| N-[(3R,6S)-6-carbamoyl-1-(2-fluoro-6-methoxybenzyl)piperidin-3-yl]-3-(2-methylpyridin-4-yl)-1H-indazole-5-carboxamide | 1.0 | 517.58 | 517 | 1.58 |
| N-[(3R,6S)-1-(2-fluoro-6-methoxybenzyl)-6-(hydrazinocarbonyl)piperidin-3-yl]-3-(2-methylpyridin-4-yl)-1H-indazole-5-carboxamide | 1.0 | 532.60 | 532 | 1.56 |

-continued

| Structure | aErk2 Ic50 | M + H Calcd. | M + H Obs. | Retention Time minutes |
|---|---|---|---|---|
| [Chiral] N-[(3R,6S)-6-[(2,2-dimethylhydrazino)carbonyl]-1-(2-fluoro-6-methoxybenzyl)piperidin-3-yl]-3-(2-methylpyridin-4-yl)-1H-indazole-5-carboxamide | 12.2 | 560.65 | 560 | 1.60 |
| [Chiral] tert-butyl 4-{[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}piperazine-1-carboxylate | 7.0 | 686.81 | 686 | 1.79 |
| [Chiral] N-[(3R,6S)-6-[(3-chloropropyl)carbamoyl]-1-(2-fluoro-6-methoxybenzyl)piperidin-3-yl]-3-(2-methylpyridin-4-yl)-1H-indazole-5-carboxamide | 11.8 | 593.24 | 593 | 1.70 |

| Structure | aErk2 Ic50 | M + H Calcd. | M + H Obs. | Retention Time minutes |
|---|---|---|---|---|
| Chiral N-[(3R,6S)-6-[(4-chloropiperidin-1-yl)carbonyl]-1-(2-fluoro-6-methoxybenzyl)-piperidin-3-yl]-3-(2-methylpyridin-4-yl)-1H-indazole-5-carboxamide | 48.3 | 620.15 | 619 | 1.74 |
| Chiral N-{(3R,6S)-1-(2-fluoro-6-methoxybenzyl)-6-[methoxy(methyl)carbamoyl]piperidin-3-yl}-3-(2-methylpyridin-4-yl)-1H-indazole-5-carboxamide | 11.2 | 561.63 | 561 | 1.64 |
| Chiral N-{(3R,6S)-1-(2-fluoro-6-methoxybenzyl)-6-[(2-methylhydrazino)carbonyl]piperidin-3-yl}-3-(2-methylpyridin-4-yl)-1H-indazole-5-carboxamide | 20.2 | 546.62 | 546 | 1.61 |

| Structure | aErk2 Ic50 | M + H Calcd. | M + H Obs. | Retention Time minutes |
|---|---|---|---|---|
| Chiral<br><br>N-{(3R,6S)-1-(2-fluoro-6-methoxybenzyl)-6-[(2-methylhydrazino)carbonyl]piperidin-3-yl}-3-(2-methylpyridin-4-yl)-1H-indazole-5-carboxamide | 30.0 | 586.69 | 586 | 1.62 |
| Chiral<br><br>N-[(3R,6S)-6-{[4-(ethylcarbamoyl)piperazin-1-yl]carbonyl}-1-(2-fluoro-6-methoxybenzyl)piperidin-3-yl]-3-(2-methylpyridin-4-yl)-1H-indazole-5-carboxamide | 16.4 | 656.77 | 657 | 1.64 |
| Chiral<br><br>N-[(3R,6S)-1-(2-fluoro-6-methoxybenzyl)-6-(methylcarbamoyl)piperidin-3-yl]-3-(2-methylpyridin-4-yl)-1H-indazole-5-carboxamide | 2.7 | 530.61 | 531 | 1.61 |

-continued

| Structure | aErk2 Ic50 | M + H Calcd. | M + H Obs. | Retention Time minutes |
|---|---|---|---|---|
| N-[(3R,6S)-1-(2-fluoro-6-methoxybenzyl)-6-{[2-(methylcarbamothioyl)hydrazino]-carbonyl}piperidin-3-yl]-3-(2-methylpyridin-4-yl)-1H-indazole-5-carboxamide | 1.0 | 605.71 | 605 | 1.62 |
| N-[(3R,6S)-6-(dimethylcarbamoyl)-1-(2-fluoro-6-methoxybenzyl)piperidin-3-yl]-3-pyridazin-4-yl-1H-indazole-5-carboxamide | 136.6 | 532.60 | 532 | 1.70 |
| N-[(3R,6S)-6-[(2-fluoroethyl)carbamoyl]-1-(2-fluoro-6-methoxybenzyl)piperidin-3-yl]-3-(2-methylpyridin-4-yl)-1H-indazole-5-carboxamide | 9.0 | 563.63 | 563 | 1.64 |

| Structure | aErk2 Ic50 | M + H Calcd. | M + H Obs. | Retention Time minutes |
|---|---|---|---|---|
| N-{(3R,6S)-1-(2-fluoro-6-methoxybenzyl)-6-[(2,2,2-trifluoroethyl)carbamoyl]piperidin-3-yl}-3-(2-methylpyridin-4-yl)-1H-indazole-5-carboxamide | 46.5 | 599.61 | 599 | 1.72 |
| tert-butyl 4-{[(2S,5R)-1-{2-fluoro-6-[(~2~H_3_)methyloxy]benzyl}-5-({[3-(2-methyl-1,3-benzothiazol-6-yl)-1H-indazol-5-yl]carbonyl}amino)piperidin-2-yl]carbonyl}piperazine-1-carboxylate | 72.8 | 745.91 | 745 | 2.01 |

| Structure | aErk2 Ic50 | M + H Calcd. | M + H Obs. | Retention Time minutes |
|---|---|---|---|---|
| N-[(3R,6S)-6-[(4-acetylpiperazin-1-yl)carbonyl]-1-{2-fluoro-6-[(~2~H_3_)methyloxy]benzyl}piperidin-3-yl]-3-(2-methyl-1,3-benzothiazol-6-yl)-1H-indazole-5-carboxamide | 63.1 | 687.83 | 687 | 0.82 |
| N-[(3R,6S)-6-(diethylcarbamoyl)-1-(2-fluoro-6-methoxybenzyl)piperidin-3-yl]-3-pyridazin-4-yl-1H-indazole-5-carboxamide | 136.7 | 560.63 | 560.0 | 1.80 |
| N-[(3R,6S)-6-[(3,3-difluoroazetidin-1-yl)carbonyl]-1-(2-fluoro-6-methoxybenzyl)-piperidin-3-yl]-3-pyridazin-4-yl-1H-indazole-5-carboxamide | 61.2 | 580.57 | 580.0 | 1.73 |

-continued

| Structure | aErk2 Ic50 | M + H Calcd. | M + H Obs. | Retention Time minutes |
|---|---|---|---|---|
| N-[(3R,6S)-1-(2-fluoro-6-methoxybenzyl)-6-(isoxazolidin-2-ylcarbonyl)piperidin-3-yl]-3-(2-methylpyridin-4-yl)-1H-indazole-5-carboxamide | 10.5 | 573.63 | 573.0 | 1.64 |
| N-[(3R,6S)-1-(2-fluoro-6-methoxybenzyl)-6-(1,2-oxazinan-2-ylcarbonyl)piperidin-3-yl]-3-(2-methylpyridin-4-yl)-1H-indazole-5-carboxamide | 9.6 | 587.66 | 587.3 | 1.69 |
| N-{(3R,6S)-1-(2-fluoro-6-methoxybenzyl)-6-[(4-methylpiperazin-1-yl)carbonyl]piperidin-3-yl}-3-(2-methylpyridin-4-yl)-1H-indazole-5-carboxamide | 32.5 | 600.70 | 600.4 | 1.49 |
| N-[(3R,6S)-6-[(4-acetylpiperazin-1-yl)carbonyl]-1-(2-fluoro-6-methoxybenzyl)-piperidin-3-yl]-3-(2-methylpyridin-4-yl)-1H-indazole-5-carboxamide | 19.1 | 628.71 | 628.4 | 1.61 |

| Structure | aErk2 Ic50 | M + H Calcd. | M + H Obs. | Retention Time minutes |
|---|---|---|---|---|
| methyl 4-{[(2S,5R)-1-(2-fluoro-6-methoxy-benzyl)-5-({[3-(2-methylpyridin-4-yl)-1H-indazol-5-yl]carbonyl}amino)piperidin-2-yl]carbonyl}piperazine-1-carboxylate | 17.9 | 644.71 | 644.3 | 1.66 |
| ethyl 4-{[(2S,5R)-1-(2-fluoro-6-methoxy-benzyl)-5-({[3-(2-methylpyridin-4-yl)-1H-indazol-5-yl]carbonyl}amino)piperidin-2-yl]carbonyl}piperazine-1-carboxylate | 20.5 | 658.73 | 658.3 | 1.71 |
| tert-butyl 4-{[(2S,5R)-1-{2-fluoro-6-[(~2~H_3_)methyloxy]benzyl}-5-({[3-(2-methylpyridin-4-yl)-1H-indazol-5-yl]carbonyl}amino)piperidin-2-yl]carbonyl}piperazine-1-carboxylate | 12.2 | 689.81 | 689.4 | 1.79 |

| Structure | aErk2 Ic50 | M + H Calcd. | M + H Obs. | Retention Time minutes |
|---|---|---|---|---|
| tert-butyl [2-({[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}amino)ethyl]carbamate | 18.9 | 660.75 | 660.4 | 1.74 |
| tert-butyl [3-({[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}amino)propyl]carbamate | 16.9 | 674.78 | 674.4 | 1.75 |
| 1-methylcyclopropyl 4-{[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}piperazine-1-carboxylate | 22.1 | 684.77 | 684.4 | 1.76 |

-continued

| Structure | aErk2 Ic50 | M + H Calcd. | M + H Obs. | Retention Time minutes |
|---|---|---|---|---|
| 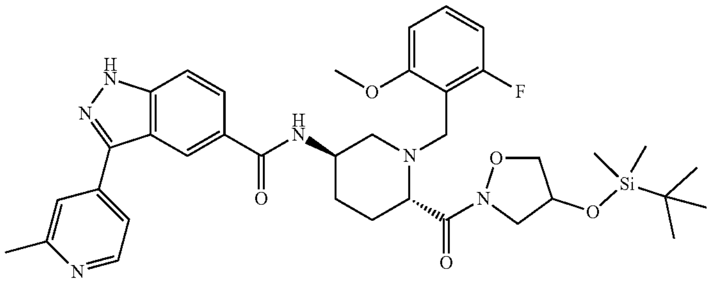 [SMILES: COc1cccc(F)c1CN1C[C@H](NC(=O)c2ccc3[nH]nc(-c4ccnc(C)c4)c3c2)CC[C@H]1C(=O)N1CC(O[Si](C)(C)C(C)(C)C)CO1] | 72.5 | 703.89 | 703.4 | 1.98 |

N-[(3S,6R)-6-[(4-{[tert-butyl(dimethyl)silyl]oxy}isoxazolidin-2-yl)carbonyl]-1-(2-fluoro-6-methoxybenzyl)-piperidin-3-yl]-3-(2-methylpyridin-4-yl)-1H-indazole-5-carboxamide

| | 144.1 | 703.89 | 703.4 | 2.00 |
|---|---|---|---|---|

N-[(3S,6R)-6-[(4-{[tert-butyl(dimethyl)silyl]oxy}isoxazolidin-2-yl)carbonyl]-1-(2-fluoro-6-methoxybenzyl)-piperidin-3-yl]-3-(2-methylpyridin-4-yl)-1H-indazole-5-carboxamide

| | 26.2 | 589.67 | 589.4 | 1.70 |
|---|---|---|---|---|

N-[(3R,6S)-6-(tert-butoxycarbamoyl)-1-(2-fluoro-6-methoxybenzyl)piperidin-3-yl]-3-(2-methylpyridin-4-yl)-1H-indazole-5-carboxamide -continued

| Structure | aErk2 Ic50 | M + H Calcd. | M + H Obs. | Retention Time minutes |
|---|---|---|---|---|
| tert-butyl {4-[{[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}(methyl)amino]butyl}carbamate | 90.3 | 702.83 | 702.4 | 1.83 |
| cyclopentyl 4-{[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}piperazine-1-carboxylate | 31.0 | 698.80 | 698.3 | 1.81 |
| 1-methylethyl 4-{[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}piperazine-1-carboxylate | 19.1 | 672.76 | 672.4 | 1.77 |

-continued
| Structure | aErk2 Ic50 | M + H Calcd. | M + H Obs. | Retention Time minutes |
|---|---|---|---|---|
| 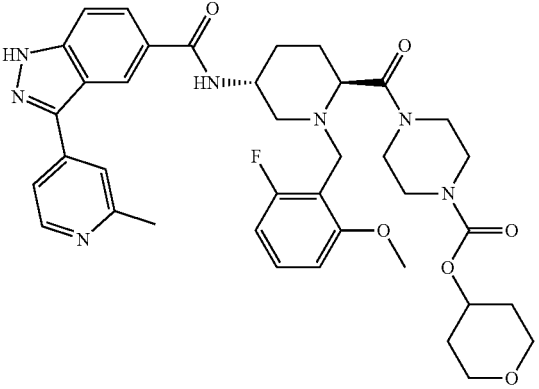 [SMILES: COc1cccc(F)c1CN1C[C@H](NC(=O)c2ccc3[nH]nc(-c4ccnc(C)c4)c3c2)CC[C@H]1C(=O)N1CCN(C(=O)OC2CCOCC2)CC1] tetrahydro-2H-pyran-4-yl 4-{[(2S,5R)-1-(2-fluoro-6-methoxybenzyl)-5-({[3-(2-methylpyridin-4-yl)-1H-indazol-5-yl]carbonyl}amino)piperidin-2-yl]carbonyl}piperazine-1-carboxylate | 18.8 | 714.80 | 714.3 | 1.72 |
TABLE 4
| Structure | aERK IC50 nM | M + H Calcd. | M + H Obs. | Retention Time min. |
|---|---|---|---|---|
| 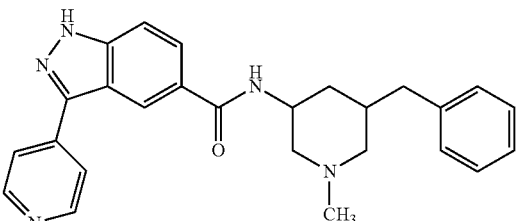 | 8.34 | 426.22 | 426.0 | 2.36 |
| 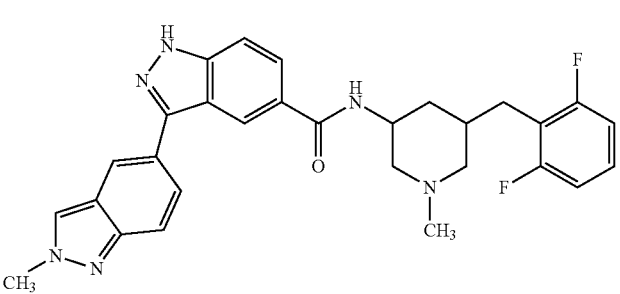 [SMILES: CN1CC(Cc2c(F)cccc2F)CC(NC(=O)c2ccc3[nH]nc(-c4ccc5nn(C)cc5c4)c3c2)C1] | 1.395 | 515.23 | 515.2 | 2.23 |

TABLE 4-continued
| Structure | aERK IC50 nM | M + H Calcd. | M + H Obs. | Retention Time min. |
|---|---|---|---|---|
| 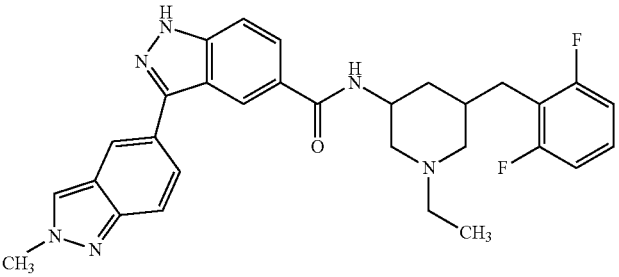 [SMILES: CCN1CC(Cc2c(F)cccc2F)CC(NC(=O)c2ccc3[nH]nc(-c4ccc5nn(C)cc5c4)c3c2)C1] | 3.09 | 529.25 | 529.2 | 2.52 |
| 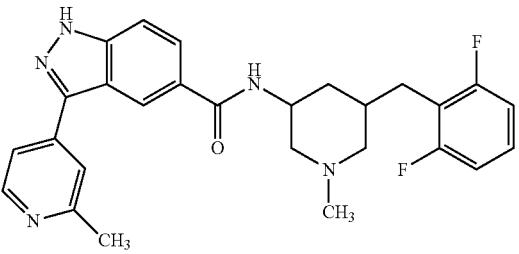 [SMILES: Cc1cc(-c2n[nH]c3ccc(C(=O)NC4CC(Cc5c(F)cccc5F)CN(C)C4)cc23)ccn1] | 4.805 | 476.22 | 476.0 | 1.8 |
| 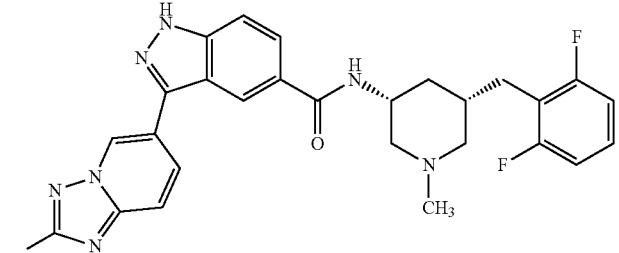 | 1.45 | 516.22 | 516.2 | 2.32 |
| 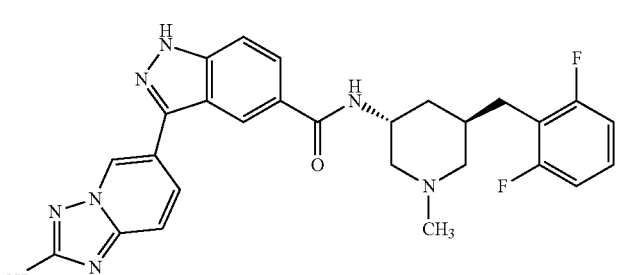 | 47.6 | 516.22 | 516.2 | 2.3 |
| 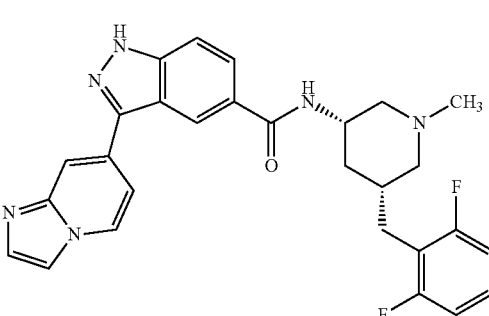 | 1.59 | 501.21 | 501.2 | 1.89 |
| 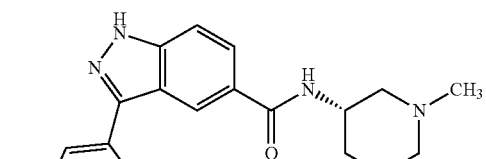 | 149.95 | 501.21 | 501.1 | 1.88 |

The fourth compound of Table 4 was prepared according to the procedures set forth below. The remaining compounds were made using the same general methodology.

Synthesis of 5-(2,6-difluorobenzyl)-1-methylpiperidin-3-amine

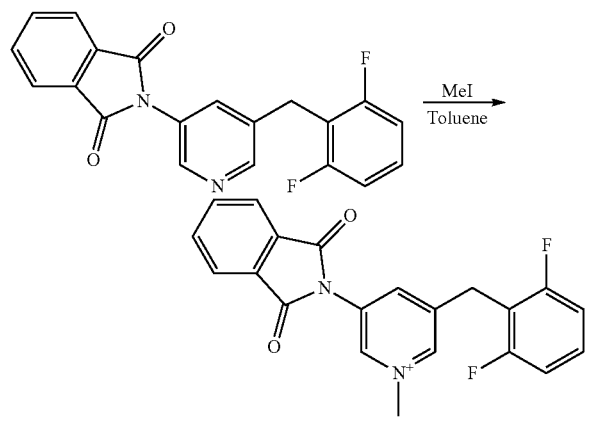

To 2-(5-(2,6-difluorobenzyl)pyridin-3-yl)isoindoline-1,3-dione (300 mg, 0.86 mmol) was added iodomethane (17 mmol, 1.1 ml) and toluene (1 ml). The reaction mixture was stirred at 80° C. overnight. The mixture was then filtered, and the remaining solid was put on the lyophilizer. The product was used in the next step without purification.

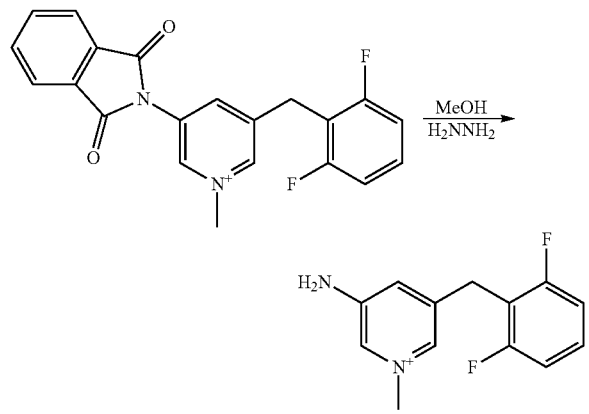

To 100 mg (0.27 mmol) of starting material was added methanol (3 ml) and hydrazine (27 mmol, 86 ul). The reaction mixture was stirred at room temperature overnight. The reaction was filtered, dried on vacuo and used in the next step without purification.

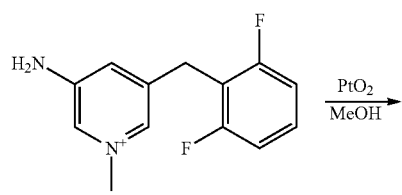

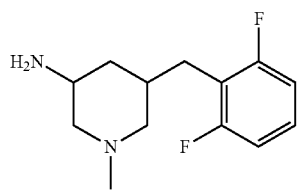

To the starting material was added methanol (10 ml) and platinum oxide (100 mg). The reaction mixture was stirred at 60° C. overnight under H$_2$. The mixture was then filtered through celite and dried on vacuo to afford the desired product.

3-bromo-N-(5-(2,6-difluorobenzyl)-1-methylpiperidin-3-yl)-1-trityl-1H-indazole-5-carboxamide 2-(7-Aza-1H-benzotriazole-1-yl)-1,1,3,3-tetramethyluronium hexafluorophosphate (HATU) (3.1 mmol) was added to a suspension of 3-bromo-1-trityl-1H-indazole-5-carboxylic acid (1 g, 2.07 mmol) in DMF (5 mL) and was stirred at room temperature for 15 minutes. A solution of 5-(2,6-difluorobenzyl)-1-methylpiperidin-3-amine (511 mg, 2.13 mmol) in DMF (5 mL) was added to the reaction and followed by diisopropyl ethyl amine (DIEA) (0.72 mL). The mixture was stirred at room temperature for an additional 30 minutes. The reaction was quenched with water (50 mL) and extracted with ethyl acetate (3×100 mL). The extracts were combined, dried using anhydrous sodium sulfate, filtered, and concentrated in vacuum. The crude product was progressed to the next step without purification.

Synthesis of N-(5-(2,6-difluorobenzyl)-1-methylpiperidin-3-yl)-3-(2-methylpyridin-4-yl)-1-trityl-1H-indazole-5-carboxamide

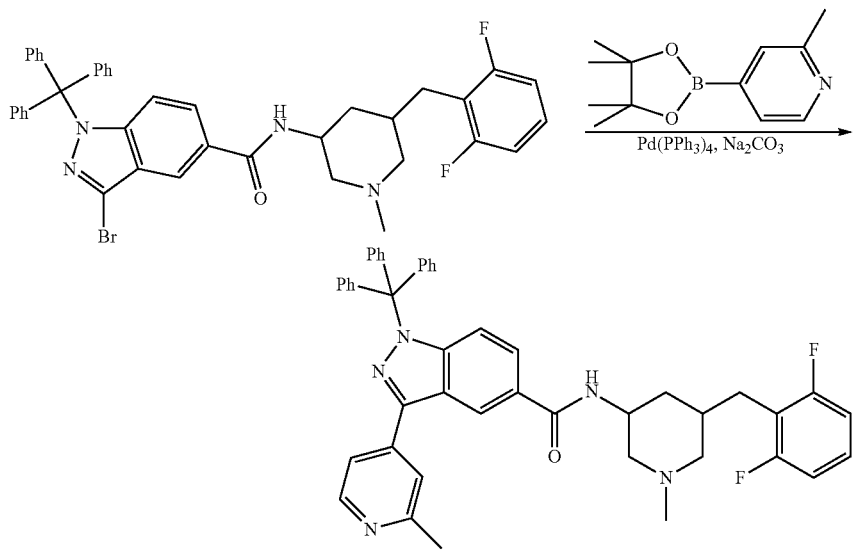

3-bromo-N-(5-(2,6-difluorobenzyl)-1-methylpiperidin-3-yl)-1-trityl-1H-indazole-5-carboxamide (0.050 g, 0.0716 mmol), [1,1'-Bis(diphenylphosphino)ferrocene]-dichloropalladium(II) (0.0052 g, 0.00716 mmol), Potassium phosphate tribasic (0.046 g, 0.215 mmol) and 2-methyl-4-(4,4,5,5-tetramethyl-1,3,2-dioxaborolan-2-yl)pyridine (0.018 g, 0.0788 mmol) was added into a flask. After purging the reaction vessel with nitrogen gas, dioxane (0.215 mL) and water (0.043 mL) was added. The reaction was allowed to stir at 80° C. for 16 hrs. The reaction was quenched with water (1 mL) and extracted with dichloromethane (3×1 mL). The extracts were combined, dried using sodium sulfate, filtered through celite, and concentrated under vacuo. The crude product was progressed to the next step without further purification. LC-MS found 718.2, calcd M+H 718.3.

Synthesis of N-(5-(2,6-difluorobenzyl)-1-methylpiperidin-3-yl)-3-(2-methylpyridin-4-yl)-1H-indazole-5-carboxamide

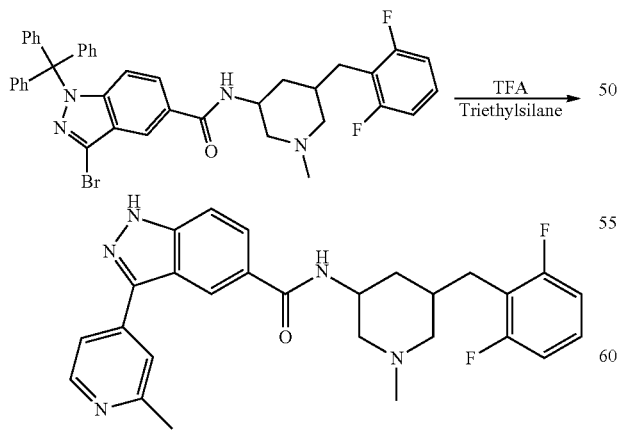

To the crude product from previous step was added TFA (0.5 mL) followed by triethylsilane (83 mg, 0.72 mmol). After stirring about 20 minutes, excess TFA was removed under vacuum and the residue was purified by prep-HPLC to give the desired product (12 mg). LC-MS found 475.98, calcd M+H, 476.22

N—((R)-1-((S or R)-2-Amino-1-(2-fluorophenyl)-2-oxoethyl)piperidin-3-yl)-3-(pyridin-4-yl)-1H-indazole-5-carboxamide

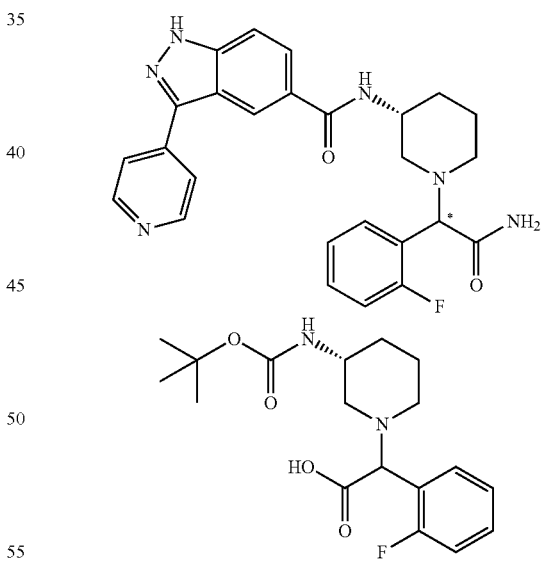

Step 1. 2-((R)-3-(tert-Butoxycarbonylamino)piperidin-1-yl)-2-(2-fluorophenyl)acetic acid tert-Butyl (3R)-piperidin-3-ylcarbamate (0.1 g, 0.499 mmol), (2-fluorophenyl)boronic acid (0.070 g, 0.499 mmol) and glyoxilic acid monohydrate (0.045 g, 0.499 mmol) were taken up in DCM (2.25 mL)/HFIP (0.25 mL) in a 5 mL microwave vial. The reaction mixture was heated to 120° C. for 15 minutes under microwave irradiation. The solvent was removed in vacuo to give 2-((R)-3-(tert-butoxycarbonylamino)piperidin-1-yl)-2-(2-fluorophenyl)acetic acid as a 1:1 mixture of diastereoisomers.

MS (APCI) calculated for $C_{18}H_{26}FN_2O_4$ [M+H]$^+$, 353; found 353 (1.76 mins).

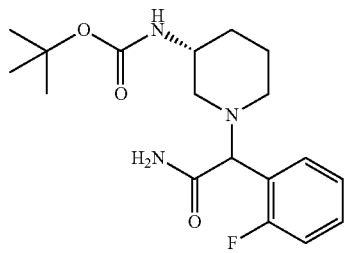 [SMILES: CC(C)(C)OC(=O)N[C@@H]1CCCN(C(C(N)=O)c2ccccc2F)C1]

Step 2. tert-Butyl (3R)-1-(2-amino-1-(2-fluorophenyl)-2-oxoethyl)piperidin-3-ylcarbamate 2-((R)-3-(tert-Butoxycarbonylamino)piperidin-1-yl)-2-(2-fluorophenyl)acetic acid (174 mg, 0.494 mmol), ammonium chloride (79 mg, 1.481 mmol), DIPEA (0.431 mL, 2.469 mmol), EDC (142 mg, 0.741 mmol) and HOBT (113 mg, 0.741 mmol) were stirred in DMF (5 mL) at room temperature for 3 days. Saturated NaHCO$_3$ was added and the products extracted into EtOAc (×2). The combined organic extracts were washed with brine, dried over Na$_2$SO$_4$, filtered and concentrated in vacuo. Purification of the residue by MPLC (12-100% EtOAc-hexanes) gave tert-butyl (3R)-1-(2-amino-1-(2-fluorophenyl)-2-oxoethyl)piperidin-3-ylcarbamate as a mixture of diastereoisomers.

MS (APCI) calculated for $C_{18}H_{27}FN_3O_3$ [M+H]$^+$, 352; found 352 (0.99 mins).

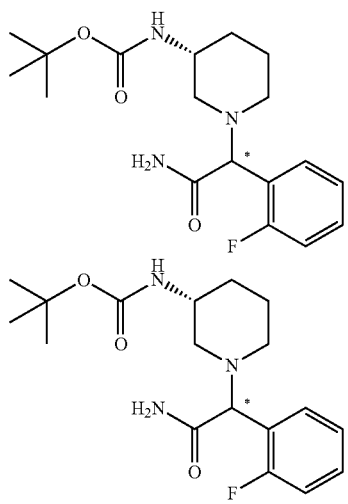

Step 3. tert-Butyl (R)-1-[((R or S)-2-amino-1-(2-fluorophenyl)-2-oxoethyl)piperidin-3-ylcarbaniate and tert-butyl (R)-1-((S or R)-2-amino-1-(2-fluorophenyl)-2-oxoethyl]piperidin-3-ylcarbamate The diastereoisomers of tert-butyl (3R)-1-(2-amino-1-(2-fluorophenyl)-2-oxoethyl)piperidin-3-ylcarbamate (90 mg, 0.256 mmol) were separated by chiral SFC (Berger Multigram II, Chiral Technology IA-H 2.1×25 cm, 5 uM, 20% 80% Methanol/CO$_2$, 70 mL/Min, 5 min run time) to give tert-butyl (R)-1-((R or S)-2-amino-1-(2-fluorophenyl)-2-oxoethyl)piperidin-3-ylcarbamate and tert-butyl (R)-1-((S or R)-2-amino-1-(2-fluorophenyl)-2-oxoethyl)piperidin-3-ylcarbamate.

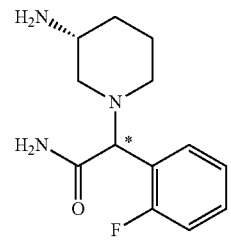 [SMILES: NC(=O)C(c1ccccc1F)N1CCC[C@@H](N)C1]

Step 4. (R)-2-((S or R)-3-Aminopiperidin-1-yl)-2-(2-fluorophenyl)acetamide tert-Butyl (R)-1-((S or R)-2-amino-1-(2-fluorophenyl)-2-oxoethyl)piperidin-3-ylcarbamate (35 mg, 0.100 mmol) was stirred in 3 M HCl in MeOH (2 mL) at 70° C. for 1 hour. The solvent was removed in vacuo to give the bis HCl salt of (R)-2-((S or R)-3-aminopiperidin-1-yl)-2-(2-fluorophenyl)acetamide as a pale green solid.

MS (APCI) calculated for $C_{13}H_{19}FN_3O$ [M+H]$^+$, 252; found 252 (0.82 mins).

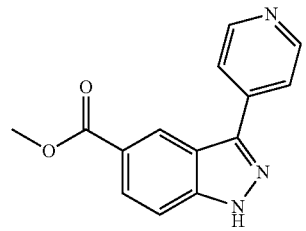 [SMILES: COC(=O)c1ccc2[nH]nc(-c3ccncc3)c2c1]

Step 5. Methyl 3-pyridin-4-yl-1H-indazole-5-carboxylate 4-(4,4,5,5-Tetramethyl-1,3,2-dioxaborolan-2-yl)pyridine (0.965 g, 4.70 mmol), PdCl$_2$(dppf)-CH$_2$Cl$_2$ (0.256 g, 0.314 mmol), sodium carbonate (3.14 mL, 6.27 mmol) and methyl 3-bromo-1H-indazole-5-carboxylate (0.8 g, 3.14 mmol) were taken up in 1,4-dioxane (15 mL). The flask was evacuated and back-filled with N$_2$ (×3) before stirring at 100° C. for 24 hours. Room temperature was attained, the reaction mixture was diluted with MeOH, filtered through Celite and concentrated in vacuo. Purification of the residue by MPLC (12-100% EtOAc-hexanes) gave methyl 3-pyridin-4-yl-1H-indazole-5-carboxylate as a yellow solid.

MS (APCI) calculated for $C_{14}H_{12}N_3O_2$ [M+H]$^+$, 254; found 254 (0.92 mins).

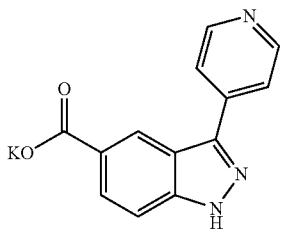

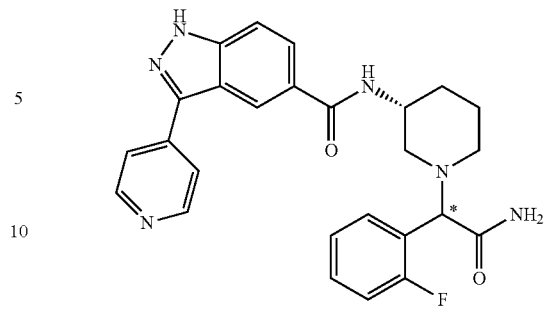

Step 6. Potassium 3-(pyridin-4-yl)-1H-indazole-5-carboxylate

Methyl 3-pyridin-4-yl-1H-indazole-5-carboxylate (305 mg, 1.204 mmol) and KOH (88 mg, 1.566 mmol) were stirred in THF (9 mL)/MeOH (1.5 mL)/water (1.5 mL) at 70° C. for 24 hours. Additional KOH (87 mg, 1.551 mmol) was added and stirring at 70° C. continued for 20 hours. Room temperature was attained and the solvent was removed in vacuo to give potassium 3-(pyridin-4-yl)-1H-indazole-5-carboxylate as a brown solid (~67 wt %).

MS (APCI) calculated for $C_{13}H_{10}N_3O_2$ [M+H]+, 240; found 240 (0.88 mins).

Step 7. N—((R)-1-((S or R)-2-Amino-4-(2-fluorophenyl)-2-oxoethyl)piperidin-3-yl)-3-(pyridin-4-yl)-1H-indazole-5-carboxamide The bis HCl salt of (R)-2-((S or R)-3-aminopiperidin-1-yl)-2-(2-fluorophenyl)acetamide (32 mg, 0.099 mmol), potassium 3-pyridin-4-yl-1H-indazole-5-carboxylate (24 mg, 0.087 mmol), EDC (33.2 mg, 0.173 mmol), HOBT (26.5 mg, 0.173 mmol) and DIPEA (0.060 mL, 0.346 mmol) were stirred in DMF (1 mL) at room temperature for 20 hours. Saturated NaHCO₃ was added and the products extracted into EtOAc (×2). The combined organic extracts were washed with brine, dried over Na₂SO₄, filtered and concentrated in vacuo. The residue was purified by mass triggered reverse phase prep-HPLC to give the bis TFA salt of N—((R)-1-((S or R)-2-amino-1-(2-fluorophenyl)-2-oxoethyl)piperidin-3-yl)-3-(pyridin-4-yl)-1H-indazole-5-carboxamide as a pale yellow solid.

MS (APCI) calculated for $C_{26}H_{26}FN_6O_2$ [M+H]+, 473; found 473 (0.88 mins).

The compounds in the table below were made using the same general methodology.

| Structure | IUPAC name | ExactMass [M + H]+ Retention time (min) | aERK IC$_{50}$ (nM)[b] |
|---|---|---|---|
| (structure) | N-((R)-1-((R or S)-2-amino-1-(2-fluorophenyl)-2-oxoethyl)-piperidin-3-yl)-3-(pyridin-4-yl)-1H-indazole-5-carboxamide | Calc'd 473, found 473 (0.88 mins) | 72.2 |
| (structure) | N-((R)-1-((R or S)-1-(2-fluorophenyl)-2-(methyl-amino)-2-oxoethyl)piperidin-3-yl)-3-(pyridin-4-yl)-1H-indazole-5-carboxamide | Calc'd 487, found 487 (0.82 mins) | 174.9 |

-continued

| Structure | IUPAC name | ExactMass [M + H]+ Retention time (min) | aERK IC$_{50}$, (nM)[b] |
|---|---|---|---|
| 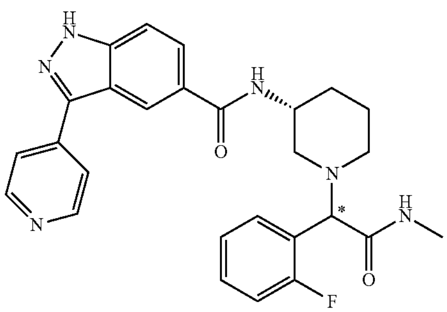 [SMILES: CNC(=O)C(c1ccccc1F)N1CCC[C@@H](NC(=O)c2ccc3[nH]nc(-c4ccncc4)c3c2)C1] | N-((R)-1-((S or R)-1-(2-fluorophenyl)-2-(methyl-amino)-2-oxoethyl)piperidin-3-yl)-3-(pyridin-4-yl)-1H-indazole-5-carboxamide | Calc'd 487, found 487 (0.94 mins) | 4.6 |
| 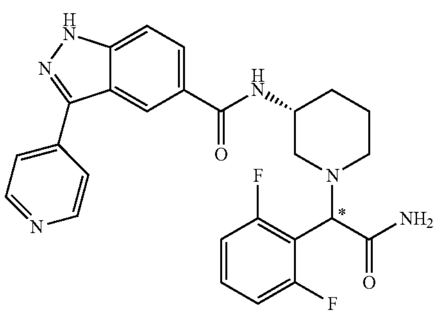 [SMILES: NC(=O)C(c1c(F)cccc1F)N1CCC[C@@H](NC(=O)c2ccc3[nH]nc(-c4ccncc4)c3c2)C1] | N-((R)-1-((R or S)-2-amino-1-(2,6-difluorophenyl)-2-oxoethyl)piperidin-3-yl)-3-(pyridin-4-yl)-1H-indazole-5-carboxamide | Calc'd 491, found 491 (0.93 mins) | 222.5 |
| 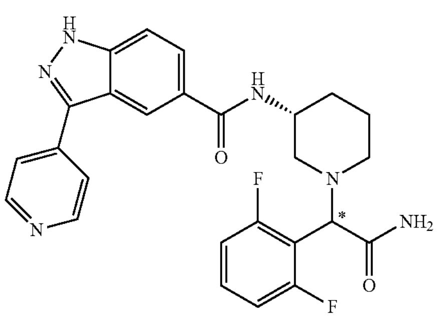 [SMILES: NC(=O)C(c1c(F)cccc1F)N1CCC[C@@H](NC(=O)c2ccc3[nH]nc(-c4ccncc4)c3c2)C1] | N-((R)-1-((S or R)-2-amino-1-(2,6-difluorophenyl)-2-oxoethyl)piperidin-3-yl)-3-(pyridin-4-yl)-1H-indazole-5-carboxamide | Calc'd 491, Found 491 (0.89 mins) | 35.3 |
| 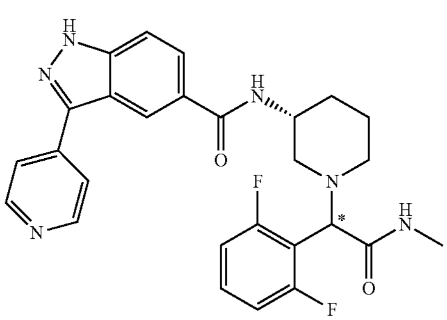 [SMILES: CNC(=O)C(c1c(F)cccc1F)N1CCC[C@@H](NC(=O)c2ccc3[nH]nc(-c4ccncc4)c3c2)C1] | N-((R)-1-((R or S)-1-(2,6-difluorophenyl)-2-(methylamino)-2-oxoethyl)-piperidin-3-yl)-3-(pyridin-4-yl)-1H-indazole-5-carboxamide | Calc'd 505, found 505 (1.33 mins) | 450.8 |
| 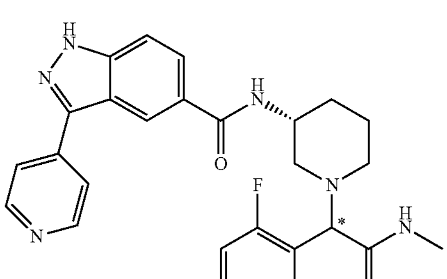 | N-((R)-1-((S or R)-1-(2,6-difluorophenyl)-2-(methylamino)-2-oxoethyl) piperidin-3-yl)-3-(pyridin-4-yl)-1H-indazole-5-carboxamide | Calc'd 505, found 505 (1.32 mins) | 20.8 |

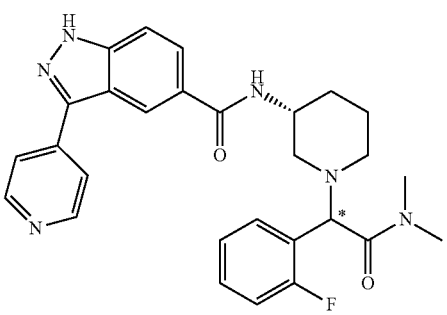 [SMILES: CN(C)C(=O)C(c1ccccc1F)N1CCC[C@@H](NC(=O)c2ccc3[nH]nc(-c4ccncc4)c3c2)C1]

N—((R)-1-((S or R)-2-(Dimethylamino)-1-(2-fluorophenyl)-2-oxoethyl)piperidin-3-yl)-3-(pyridin-4-yl)-1H-indazole-5-carboxamide

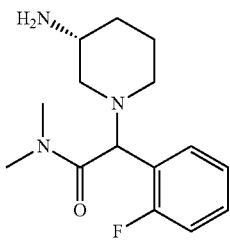 [SMILES: CN(C)C(=O)C(c1ccccc1F)N1CCC[C@@H](N)C1]

Step 1. 2-((R)-3-Aminopiperidin-1-yl)-2-(2-fluorophenyl)-N,N-dimethylacetamide tert-Butyl (3R)-1-(2-(dimethylamino)-1-(2-fluorophenyl)-2-oxoethyl)piperidin-3-ylcarbamate (302 mg, 0.796 mmol), prepared according to the procedures described for tert-butyl (3R)-1-(2-amino-1-(2-fluorophenyl)-2-oxoethyl)piperidin-3-ylcarbamate, was stirred in 3 M HCl in MeOH (8 mL) at 50° C. for 5 hours. The solvent was removed in vacuo to give the bis HCl salt of 2-((R)-3-aminopiperidin-1-yl)-2-(2-fluorophenyl)-N,N-dimethylacetamide as a ~1:1 mixture of diastereoisomers.

MS (APCI) calculated for $C_{15}H_{23}FN_3O$ [M+H]$^+$, 280; found 280 (0.87 mins).

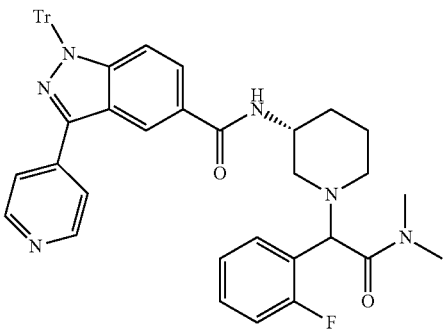

Step 2. N-((3R)-1-(2-(Dimethylamino)-1-(2-fluorophenyl)-2-oxoethyl)piperidin-3-yl)-3-(pyridin-4-yl)-1-trityl-4H-indazole-5-carboxamide 3-(Pyridin-4-yl)-1-trityl-1H-indazole-5-carboxylic acid (120 mg, 0.249 mmol), 2-((R)-3-aminopiperidin-1-yl)-2-(2-fluorophenyl)-N,N-dimethylacetamide, bis HCl salt (105 mg, 0.299 mmol), HOBT (57.2 mg, 0.374 mmol), EDC (71.7 mg, 0.374 mmol) and DIPEA (0.174 mL, 0.997 mmol) were stirred in DMF (2.5 mL) at room temperature for 18 hours. Saturated NaHCO$_3$ was added and the products extracted into EtOAc (×2). The combined organic extracts were washed with brine, dried over Na$_2$SO$_4$, filtered and concentrated in vacuo. Purification of the residue by MPLC (0-10% MeOH-EtOAc) gave N-((3R)-1-(2-(dimethylamino)-1-(2-fluorophenyl)-2-oxoethyl)piperidin-3-yl)-3-(pyridin-4-yl)-1-trityl-1H-indazole-5-carboxamide as a white solid.

MS (APCI) calculated for $C_{47}H_{44}FN_6O_2$ [M+H], 743; found 743 (1.20 mins).

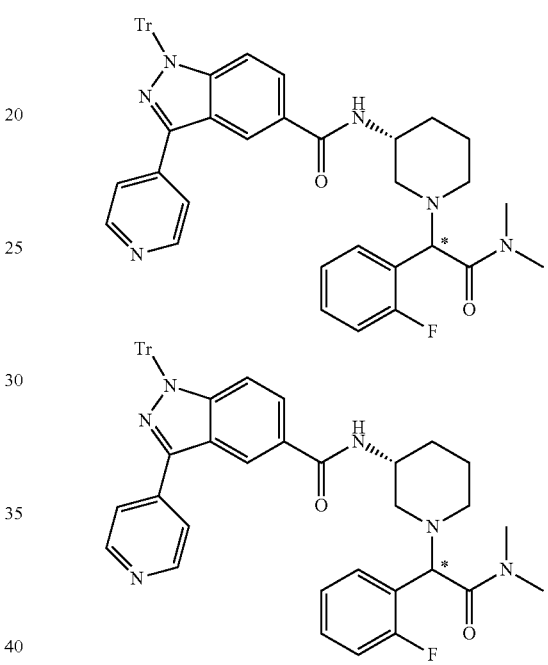

Step 3. N—((R)-1-((R or S)-2-(Dimethylamino)-1-(2-fluorophenyl)-2-oxoethyl)piperidin-3-yl)-3-(pyridin-4-yl)-1-trityl-4H-indazole-5-carboxamide and N—((R)-1-((S or R)-2-(dimethylamino)-1-(2-fluorophenyl)-2-oxoethyl)piperidin-3-yl)-3-(pyridin-4-yl)-1-trityl-1H-indazole-5-carboxamide The diastereoisomers of N-((3R)-1-(2-(dimethylamino)-1-(2-fluorophenyl)-2-oxoethyl)piperidin-3-yl)-3-(pyridin-4-yl)-1-trityl-1H-indazole-5-carboxamide (170 mg, 0.229 mmol) were separated by chiral SFC (Berger Multigram II, Chiral Technology AS-H 2.1×25 cm, 5 uM, 30%/70% IPA/CO$_2$, 60 mL/Min, 14 min run time) to give N—((R)-1-((R or S)-2-(dimethylamino)-1-(2-fluorophenyl)-2-oxoethyl)piperidin-3-yl)-3-(pyridin-4-yl)-1-trityl-1H-indazole-5-carboxamide and N—((R)-1-((S or R)-2-(dimethylamino)-1-(2-fluorophenyl)-2-oxoethyl)piperidin-3-yl)-3-(pyridin-4-yl)-1-trityl-1H-indazole-5-carboxamide.

R,R or S-MS (APCI) calculated for $C_{47}H_{44}FN_6O_2$ [M+H]$^+$, 743; found 743 (1.43 mins).

R,S or R-MS (APCI) calculated for $C_{47}H_{44}FN_6O_2$ [M+H]$^+$, 385; found 385 (1.27 mins).

333

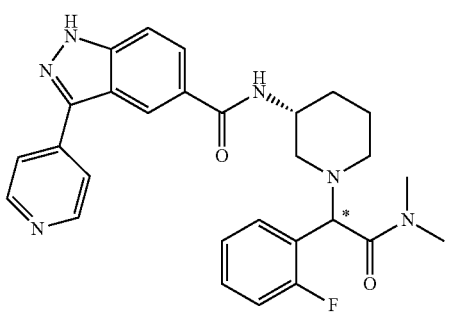 [SMILES: CN(C)C(=O)C(c1ccccc1F)N1CCC[C@@H](NC(=O)c2ccc3[nH]nc(-c4ccncc4)c3c2)C1]

Step 4. N—((R)-1-((S or R)-2-(Dimethylamino)-1-(2-fluorophenyl)-2-oxoethyl)piperidin-3-yl)-3-(pyridin-4-yl)-1H-indazole-5-carboxamide N—((R)-1-((S or R)-2-(Dimethylamino)-1-(2-fluorophenyl)-2-oxoethyl)piperidin-3-yl)-3-(pyridin-4-yl)-1-trityl-1H-indazole-5-carboxamide (53 mg, 0.071 mmol) was stirred in TFA (0.5 mL) at room temperature for 30 minutes. triethylsilane (0.015 mL, 0.093 mmol) was added and the reaction mixture diluted with DMF (1 mL). The solution was purified by reverse-phase, mass-triggered prep-HPLC. The product fraction was lyophilized to give the bis TFA salt of N—((R)-1-((S or R)-2-(dimethylamino)-1-(2-fluorophenyl)-2-oxoethyl)piperidin-3-yl)-3-(pyridin-4-yl)-1H-indazole-5-carboxamide as a white solid.

MS (APCI) calculated for C28H30FN6O2 [M+H]$^+$, 501; found 501 (1.34 mins).

334

(S)-Methyl 2-(2,6-difluorophenyl)-2-((R)-3-(3-(pyridin-4-yl)-1H-indazole-5-carboxamido)piperidin-1-yl)acetate

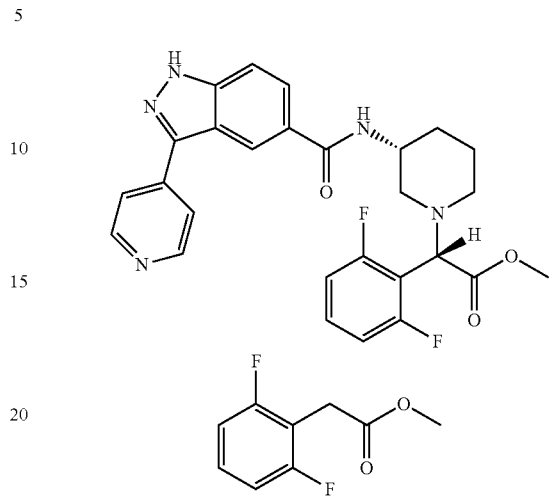

Step 1. Methyl 2,6-difluorophenylacetate 2,6-Difluorophenylacetic acid (2.61 g, 15.16 mmol) was taken up in THF (52 mL)/MeOH (13 mL). TMS-Diazomethane, 2 M in Et$_2$O (8.5 mL, 17.00 mmol) was added and the resulting mixture was stirred at room temperature for 2 hours. The solvent was removed in vacuo and the residue

| Structure | IUPAC name | ExactMass [M + H]+ Retention time (min) | aERK IC$_{50}$ (nM)$^b$ |
|---|---|---|---|
| ![structure] | N-((R)-1-((R or S)-2-(dimethylamino)-1-(2-fluorophenyl)-2-oxoethyl)piperidin-3-yl)-3-(pyridin-4-yl)-1H-indazole-5-carboxamide | Calc'd 501, found 501 (1.34 mins) | 26.4 |

$^b$aERK assay condition 2 purified by MPLC (2-20% EtOAc-hexanes) to give methyl 2,6-difluorophenylacetate as a colourless oil.

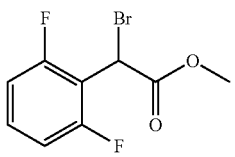

Step 2. Methyl bromo(2,6-difluorophenyl)acetate

Methyl 2,6-difluorophenylacetate (2.141 g, 11.50 mmol), NBS (2.6 g, 14.61 mmol) and AIBN (0.057 g, 0.345 mmol) were taken up in CCl₄ (45 mL). The reaction mixture was stirred at reflux for 18 hours. Additional NBS (1.433 g, 8.05 mmol) and AIBN (0.038 g, 0.230 mmol) were added and stirring at reflux continued for 24 hours. Room temperature was attained and the reaction mixture filtered through Celite, washing with DCM. The filtrate was concentrated in vacuo and the residue purified by MPLC (0-10% EtOAc-hexanes) to give methyl bromo(2,6-difluorophenyl)-acetate as a pale yellow oil.

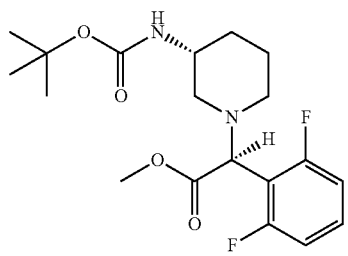

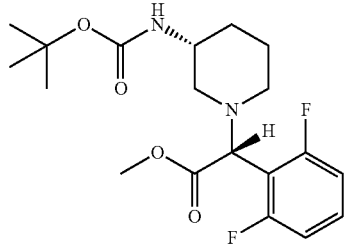

Step 3. (S)-Methyl 2-((R)-3-(tert-butoxycarbonylamino)piperidin-1-yl)-2-(2,6-difluorophenyl)acetate and (R)-methyl 2-((R)-3-(tert-butoxycarbonylamino)piperidin-1-yl)-2-(2,6-difluorophenyl)acetate tert-Butyl (3R)-piperidin-3-ylcarbamate (0.234 g, 1.168 mmol), methyl bromo(2,6-difluorophenyl)acetate (0.434 g, 1.636 mmol) and DIPEA (0.612 mL, 3.51 mmol) were taken up in MeCN (11 mL) in a 20 mL microwave vial. The reaction was stirred at 90° C. for 18 hours. Room temperature was attained, and the solvent removed in vacuo. Purification of the residue by MPLC (6-50% EtOAc-hexanes) gave (S)-methyl 2-((R)-3-(tert-butoxycarbonylamino)piperidin-1-yl)-2-(2,6-difluorophenyl)-acetate as a yellow gum and (R)-methyl 2-((R)-3-(tert-butoxycarbonylamino)piperidin-1-yl)-2-(2,6-difluorophenyl)acetate as a yellow gum (R,R).

S,R-MS (APCI) calculated for $C_{19}H_{27}F_2N_2O_4$ [M+H]⁺, 385; found 385 (2.11 mins).

R,R-MS (APCI) calculated for $C_{19}H_{27}F_2N_2O_4$ [M+H]⁺, 385; found 385 (2.10 mins).

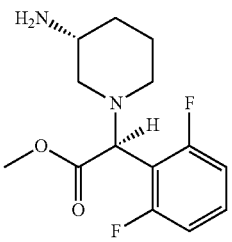 [SMILES: COC(=O)[C@H](c1c(F)cccc1F)N1CCC[C@@H](N)C1]

Step 4. (S)-Methyl 2-((R)-3-aminopiperidin-1-yl)-2-(2,6-difluorophenyl)acetate (S)-Methyl 2-((R)-3-(tert-butoxycarbonylamino)piperidin-1-yl)-2-(2,6-difluorophenyl)acetate (185 mg, 0.481 mmol) was stirred in 3 M HCl in MeOH (5 mL) at room temperature for 24 hours and at 50° C. for 5 hours. The solvent was removed in vacuo to give the bis HCl salt of (S)-methyl 2-((R)-3-aminopiperidin-1-yl)-2-(2,6-difluorophenyl)acetate as a beige solid.

MS (APCI) calculated for $C_{14}H_{19}F_2N_2O_2$ [M+H]⁺, 285; found 285 (0.98 mins).

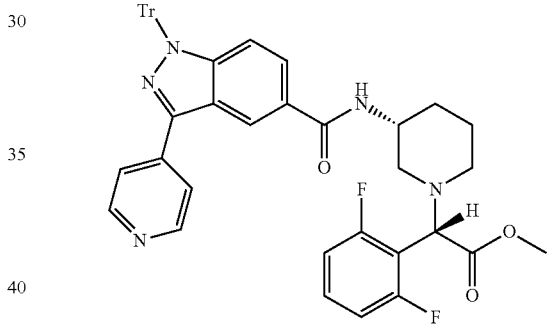

Step 5. (S)-Methyl 2-(2,6-difluorophenyl)-2-(R)-3-(3-(pyridin-4-yl)-1-trityl-1H-indazole-5-carboxamido)piperidin-1-yl)acetate 3-(Pyridin-4-yl)-1-trityl-1H-indazole-5-carboxylic acid (50 mg, 0.104 mmol), (S)-methyl 2-((R)-3-aminopiperidin-1-yl)-2-(2,6-difluorophenyl)acetate, bis HCl salt (44.5 mg, 0.125 mmol), HOBT (23.85 mg, 0.156 mmol), EDC (29.9 mg, 0.156 mmol) and DIPEA (0.073 mL, 0.415 mmol) were stirred in DMF (1 mL) at room temperature for 18 hours. Saturated NaHCO₃ was added and the resulting precipitate collected by filtration and washed with water to give (S)-methyl 2-(2,6-difluorophenyl)-2-(R)-3-(3-(pyridin-4-yl)-1-trityl-1H-indazole-5-carboxamido)piperidin-1-yl)acetate as a white solid.

MS (APCI) calculated for $C_{46}H_{40}F_2N_5O_3$ [M+H]⁺, 748; found 748 (1.47 mins).

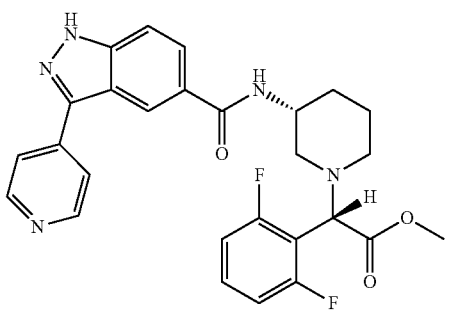 [SMILES: COC(=O)[C@H](c1c(F)cccc1F)N1CCC[C@@H](NC(=O)c2ccc3[nH]nc(-c4ccncc4)c3c2)C1]

Step 6. (S)-Methyl 2-(2,6-difluorophenyl)-2-(R)-3-(3-(pyridin-4-yl)-1H-indazole-5-carboxamido)piperidin-1-yl)acetate (S)-Methyl 2-(2,6-difluorophenyl)-2-(R)-3-(3-(pyridin-4-yl)-1-trityl-1H-indazole-5-carboxamido)piperidin-1-yl)acetate (68 mg, 0.091 mmol) was stirred in TFA (0.5 mL) at room temperature for 30 minutes. Triethylsilane (0.019 mL, 0.118 mmol) was added and the reaction mixture diluted with DMF (1 mL). The solution was then purified by reverse-phase, mass-triggered prep-HPLC to give the bis TFA salt of (S)-methyl 2-(2,6-difluorophenyl)-2-(R)-3-(3-(pyridin-4-yl)-1H-indazole-5-carboxamido)piperidin-1-yl)acetate as a yellow solid.

MS (APCI) calculated for $C_{27}H_{26}F_2N_5O_3$ [M+H]$^+$, 506; found 506 (1.17 mins).

added into the 96-well PCR plate, where it consisted of 3 μM ERK protein and 15, 50 or 100 μM compound (depending on compound's solubility) in buffer (25 mM HEPES, 150 mM NaCl, pH=7.5 and 1 mM DTT) incorporated with Sypro Orange dye (5× final concentration). Final percentage of DMSO resided in the sample was 2%. The sample plate was heated from 30° C. to 90° C. with thermal ramping rate of 1° C./min. The fluorescence signals were acquired with excitation and emission wavelengths centered at 490 and 560 nm respectively. The instrument thermal stability was ±0.2° C. The melting temperatures ($T_m$) for ERK protein under aforementioned conditions occurred at 61.0±0.2° C. and 64.8±02° C. respectively.

Theoretical Basis for TdF-Based Ligand Binding Affinity Constant

The derivation of TdF-based ligand binding affinity constant ($K_d$) followed closely those previously formulated by Brandts and Lin [2]. In brief, the binding constant of the ligand at the $T_m$ is expressed as below:

$$K_L(T_m) = \frac{\left\{\exp\left\{\begin{array}{l}-(\Delta H_u(T_0)/R)(1/T_m - 1/T_0) + \\ (\Delta C p_u/R)[\ln(T_m/T_0) + (T_0/T_m) - 1]\end{array}\right\} - 1\right\}}{[L_{Tm}]}$$

where $T_0$ is the midpoint of unfolding for unliganded protein and $T_m$ is the midpoint of unfolding in presence of ligand. $[L_{Tm}]$ is free ligand at $T_m$. The $\Delta H_u$ and $\Delta C p_u$ are the enthalpy of unfolding and heat capacity change of unfolding for the protein respectively. Following algorithm derived by Winsor

| Structure | IUPAC name | ExactMass [M + H]+ Retention time (min) | aERK IC$_{50}$ (nM)$^b$ |
|---|---|---|---|
| 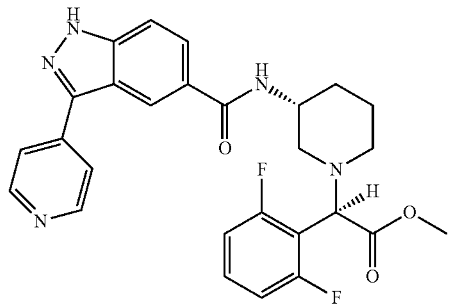 [SMILES: COC(=O)[C@@H](c1c(F)cccc1F)N1CCC[C@@H](NC(=O)c2ccc3[nH]nc(-c4ccncc4)c3c2)C1] | (R)-methyl 2-(2,6-difluorophenyl)-2-((R)-3-(3-(pyridin-4-yl)-1H-indazole-5-carboxamido)piperidin-1-yl)acetate | Calc'd 506, found 506 (0.96 mins) | 2205 |

$^b$aERK assay condition 2

Assays:
TdF Assay for ERK

The SAR (Structure Activity Relationship) for ERK ligands covered by this invention was interrogated using the TdF (Temperature Dependence Fluorescence) assay or best known as thermal shift assay [1]. The TdF assay was mainly conducted in the 96-well based CHROMO-4 real time fluorescence plate reader (BioRad). The Sypro Orange (Sigma-Aldrich), environmentally sensitive fluorescence dye, was used to monitor the protein folding-unfolding transition. Protein-ligand binding was gauged by the change (or shift) in the unfolding transition temperature ($\Delta T_m$) acquired at protein alone with respect to protein in the presence of ligand of interest.

Compound of interest was first prepared in DMSO stock (typical concentration: 10 mM). Sample of 20 μL was then and coworker [3], the $T_0$, $\Delta H_u$ and $\Delta C p_u$ can be determined separately from nonlinear regression fitting the protein alone melting curve:

$$F(T) = \frac{(Y_n + m_n(T)) + (Y_u + m_u(T))\exp\left\{-\left(\frac{\Delta H_u}{RT}\right)\left(1 - \frac{T}{T_0}\right) + \left(\frac{\Delta C p_u}{RT}\right)\left(T\ln\left(\frac{T}{T_0}\right) + T_0 - T\right)\right\}}{1 + \exp\left\{-\left(\frac{\Delta H_u}{RT}\right)\left(1 - \frac{T}{T_0}\right) + \left(\frac{\Delta C p_u}{RT}\right)\left(T\ln\left(\frac{T}{T_0}\right) + T_0 - T\right)\right\}}$$

Where F(T) is the observed fluorescence intensity at any temperature T, $Y_n$ and $Y_u$ are the predicted fluorescence intensities for fully folded and unfolded protein, respectively; $m_n$ and $m_u$ are slope correction for changes in $Y_n$ and $Y_u$ with respect to changes in temperature (analogously replace $T_0$ with $T_m$ in the above equation for liganded protein to yield $T_m$).

Finally, the ligand binding affinity constant at any temperature T (i.e. 25° C.) can be thermodynamically connected to the preceding $K_L(T_m)$ via [2,3]

$$K_L(T) = K_L(T_m) \exp\left\{\left(\frac{-\Delta H_L(T)}{R}\right)\left(\frac{1}{T} - \frac{1}{T_m}\right) + \left(\frac{\Delta C_{P_L}}{R}\right)\left[\ln\frac{T}{T_m} + 1 - \frac{T}{T_m}\right]\right\}$$

where $\Delta H_L$ (T) is the van't Hoff enthalpy of ligand binding at temperature T and $\Delta C_{P_L}$ is the heat capacity upon ligand binding. For simplicity, the $\Delta C_{P_L}$ and $\Delta H_L$ (T) were set to zero and −7 kcal/mol respectively. The uncertainty in the calculated ligand binding affinity constant was estimated to be ±50%.

REFERENCES

1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as ageneral strategy for drug discovery, *J. Biomol. Screen* 6 (2001) 429-440
2. J. F. Brandts, L.-N. Lin, Study of strong to ultratight protein interactions using differential scanning calorimetry, *Biochemistry* 29 (1990) 6927-6940
3. Mayhood, T. W., Windsor, W. T., Ligand binding affinity determined by temperature-dependent circular dichroism: Cyclin-dependent kinase 2 inhibitors, *Analytical Biochemistry* 345 (2005) 187-197

Coupled ERK2 (cERK) Assay:

Activity of compounds against inactive ERK2 was tested in a coupled MEK1/ERK2 IMAP assay as follows: Compounds were diluted to 25× final test concentration in 100% DMSO. 14 µl of kinase buffer (10 mM Tris.HCl pH 7.2, 10 mM MgCl$_2$, 0.01% Tween-20, 1 mM DTT) containing 0.4 ng unphosphorylated Mouse ERK2 protein was added to each well of a black 384-well assay plate. 1 µl of 25× compound was added to each well and incubated at room temperature for 30 minutes to allow an opportunity for the compound to bind to the inactive enzyme. DMSO concentration during initial incubation is 6.7%. ERK2 activity was determined to be insensitive to DMSO concentrations up to 20%. ERK2 was then activated and it's kinase activity measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPTTPITTTYFFFK-CONH2 and 100 nM IPTTPITTTYFFFK(5-carboxyfluorescein)-CONH2) and 30 µM ATP. DMSO concentration during ERK activation was 4%. After one hour, reactions were terminated by addition of 60 µl IMAP detections beads in binding buffer (Molecular Devices). Binding was allowed to equilibrate for 30 minutes before reading the plate on an LJL Analyst Fluorescence Polarization plate reader. Compound inhibition was calculated relative to DMSO and fully inhibited standards. Active compounds were reconfirmed in an independent assay.

Active ERK2 (aERK) Assay: (Unless Indicated Otherwise, the Data Provided for aERK was obtained using Condition 1)

Condition 1 (aERK Assay)

Activated ERK2 activity was also determined in the IMAP assay format using the procedure outlined above. 1 µl of 25× compound was added to 140 of kinase buffer containing 0.25 ng fully phosphorylated, active Mouse ERK2 protein. Following a 30 minute incubation, the reactions were initiated by addition of 10 µl of kinase buffer containing 1 µM ERK2 IMAP substrate peptide (0.9 µM unlabeled IPTTPITTTY-FFFK-CONH2 and 100 nM IPTTPITTTYFFFK(5-carboxyfluorescein)-CONH2) and 30 µM ATP. Reactions proceeded for 30 minutes before termination by addition of 60 µl IMAP detection beads in binding buffer. Plates were read as above after 30 minute binding equilibration. Active compounds were reconfirmed in an independent assay.

Condition 2 (aERK Assay)

Activated ERK2 activity was determined in an IMAP-FP assay (Molecular Devices). Using this assay format, the potency (IC$_{50}$) of each compound was determined from a 10 point (1:3 serial dilution, 3 µM starting compound concentration) titration curve using the following outlined procedure. 7.5 mL of compound (3333 fold dilution in final assay volume of 25 µL) was added to 15 µL of kinase buffer containing 0.0133 ng/mL (0.316 nM) of fully phosphorylated, mouse aERK2 enzyme. Following a 15 minute incubation, each reaction was initiated by the addition of 10 µL kinase buffer containing 2.45 µM ERK2 IMAP substrate peptides (2.25 µM-unlabeled IPTTPITTTYFFFK-COOH and 200 nM-labeled IPTTPITTTYFFFK-5FAM (5-carboxyfluorescein)-COOH), and 75 µM ATP. The final reaction in each well of 25 µL consists of 0.19 nM mouse ERK2, 900 nM unlabeled peptide, 80 nM labeled-peptide, and 30 uM ATP. Phosphorylation reactions were allowed to proceed for 40-45 minutes and were immediately quenched by the addition of 60 µL IMAP detection beads (1:1000 dilutions) in IMAP binding buffer. Plates were read on EnVision reader after 30 minutes binding equilibration.

Values for Kd TdF (nM), cERK IC50 (nM) and aERK 1050 (nM) for individual compounds have been set forth above in Tables 1-4. In one embodiment, the compounds of the present invention have aERK 1050 values of from about 0.05 nM to 1 µM; and in a preferred embodiment, less than 100 nM (<100 nM); and in a more preferred embodiment less than 10 nM (<10 nM).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

Each and every reference publication referred to hereinabove is incorporated herein by reference in its entirety for all purposes.

What is claimed is:

1. A compound of Formula I

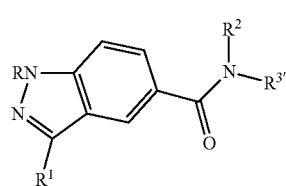

Formula I or a pharmaceutically acceptable salt thereof, wherein:
R is selected from the group consisting of: H, alkyl and hydroxylalkyl;
$R^1$ is selected from the group consisting of heterocyclyl, heterocycloalkenyl, aryl and heteroaryl, wherein when said heterocyclyl, heterocycloalkenyl, aryl or heteroaryl has two substituents on adjacent ring atoms, said substituents together with the ring atoms to which they are attached, optionally form a five- or six-membered heterocyclyl, aryl or heteroaryl;

$R^2$ is H or alkyl;

$R^{3'}$ is selected from the group consisting of:

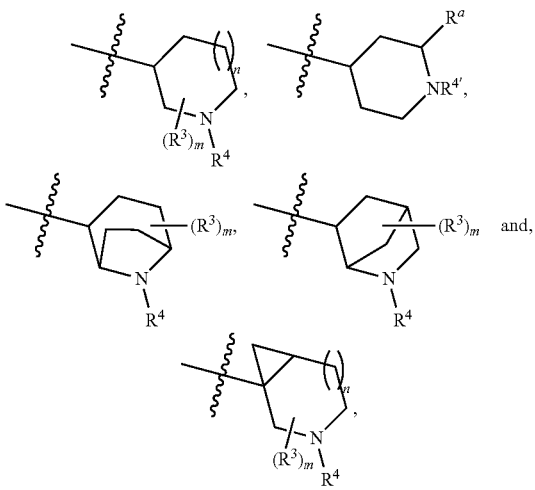

each $R^3$ independently is selected from the group consisting of —C(=O)—O-alkyl, halo, haloalkyl, —OSi(alkyl)$_3$, —C(=O)—OH, —C(O)NR$^B$R$^C$—C(O)NH-alkyl-NR$^D$R$^E$, —C(O)NH-alkyl-O-alkyl-aryl, —C(O)R$^F$, —C(O)NH—NHR$^G$, —C(O)NH—Oalkyl, —C(O)NH—O-alkyl-cycloalkyl, alkyl, hydroxyl, alkoxy, alkenyl, cycloalkyl, cycloalkenyl, alkynyl, heterocyclyl, heterocyclenyl, aryl, and heteroaryl; or wherein two $R^3$ groups together with the carbon atom to which both $R^3$ groups are attached form —C(=O)—;

$R^B$ and $R^C$ are each independently selected from the group consisting of: H, alkyl, cycloalkyl, cycloalkylalkyl-, heteroaryl, aryl, heterocycloalkyl, benzyl, and alkoxy, wherein said alkyl, cycloalkyl, cycloalkylalkyl-, heteroaryl, aryl, heterocycloalkyl, benzyl, and alkoxy groups are optionally substituted with 1 to 3 substitutents independently selected from the group consisting of: —OH, alkyl, alkoxy, hydroxyalkyl-, halo, and —C(O)Oalkyl;

$R^D$ and $R^E$ are each independently selected from the group consisting of: H, alkyl, and —C(O)Oalkyl;

$R^F$ is a heterocycloalkyl optionally substituted with 1-3 substitutents independently selected from the group consisting of: —OH, halo, —C(O)Oalkyl, —C(O)NH-alkyl, —C(O)alkyl, alkyl, —C(O)Ocycloalkyl, —O—Si(alkyl)$_2$ (wherein each alkyl is independently selected), and —C(O)Oheterocycloalkyl;

$R^G$ is selected from the group consisting of: H, alkyl, and —C(=S)—NH-alkyl;

each m independently is 0, 1, 2 or 3;

n independently is 1;

Each $R^4$ is independently selected from the group consisting of: H, alkyl, cycloalkyl, aryl, heteroaryl, —SO$_2$-aryl, —C(O)—O-alkyl, —C(O)—O-alkylaryl, and —(CR$^5$R$^6$)$_p$R$^7$, wherein p is 1 or 2; wherein when said $R^4$ cycloalkyl has two substituents on adjacent carbon atoms, said substituents together with the carbon atoms to which they are attached, optionally form a five- or six-membered ring selected from the group consisting of heterocyclyl, aryl and heteroaryl;

$R^{4'}$ is selected from the group consisting of H and alkyl;

$R^a$ is alkyl;

$R^5$ and $R^6$ independently are selected from the group consisting of H, D, halo, —OH, —C(O)NR$^H$R$^2$, —C(O)—O-alkyl, and alkyl; or wherein one —CR$^5$R$^6$— is —C(=O)—;

$R^H$ is selected from the group consisting of H and alkyl; and $R^7$ is selected from the group consisting of H, —O-alkyl-aryl, aryl and heteroaryl, wherein when said aryl or heteroaryl has two substituents on adjacent carbon atoms, said substituents together with the carbon atoms to which they are attached, optionally form a five- or six-membered ring selected from the group consisting of cycloalkylheterocyclyl, aryl or heteroaryl.

2. The compound of claim 1, wherein R is H.

3. The compound of claim 1, wherein $R^1$ is selected from the group consisting of:

(a) heteroaryl, wherein said heteroaryl optionally with said five- or six-membered heterocyclyl, aryl or heteroaryl is selected from the group consisting of imidazo[1,2-a]pyridinyl, pyridyl, pyrazolyl, [1,2,4]triazolo[1,5-a]pyridinyl, and [1,2,4]triazolo[4,3-]pyridinyl, each of which is independently unsubstituted or substituted with at least one substituent independently selected from the group consisting of alkyl, cycloalkyl, haloalkyl, alkoxy and halo;

(b) aryl, wherein when said aryl has two substituents on adjacent carbon atoms, said substituents together with the carbon atoms to which they are attached, optionally form a five- or six-membered ring selected from the group consisting of heterocyclyl, aryl and heteroaryl; wherein said aryl optionally with said five- or six-membered heterocyclyl, aryl and heteroaryl is independently unsubstituted or substituted with at least one substitutent selected from the group consisting of alkyl, alkoxy, hydroxy, —NH—C(=O)-alkyl, —S(=O)$_2$—N(alkyl)$_2$, —C(=O)-alkyl, cyano, —S(=O)$_2$-alkyl, —NH$_2$, and —OC(=O)alkyl, (c) aryl, optionally with said five- or six-membered heterocyclyl, aryl and heteroaryl selected from the group consisting of phenyl, benzo[c][1,2,5]thiadiazolyl, benzo[c][1,2,5]oxadiazolyl, 2H-indazolyl, benzotetrahydrofuranyl, benzothiophenyl, benzopyrrolyl, benzopyrazolyl, benzothiazolyl, benzofuranyl, and benzoxazolyl, each of which independently is unsubstituted or substituted with at least one substituent selected from the group consisting of alkyl, alkoxy, hydroxy, —NH—C(=O)-alkyl, —S(=O)$_2$—N(alkyl)$_2$, —C(=O)-alkyl, cyano, —S(=O)$_2$-alkyl, —NH$_2$, and —OC(=O)alkyl; and (d) heterocyclyl, wherein said heterocyclyl optionally with said five- or six-membered heterocyclyl, aryl and heteroaryl is selected from the group consisting of:

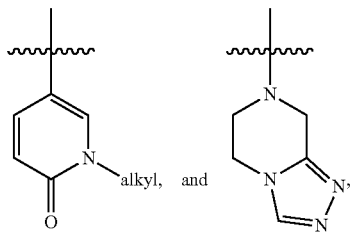

wherein the second structure is unsubstituted or substituted with a cycloalkyl group.

4. The compound of claim 1 wherein $R^1$ is selected from the group consisting of: phenyl, pyridyl, methylpyridyl, methylindazolyl, methylbenzothiazolyl, pyridazinyl, dihydropyran, dioxidodihydrothiopyran, dioxidotetrahydrothiopyran, imidazolyl, teterahydropyran, benzofuranyl, indazolyl, pyridazinyl, indazolyl, imidazopyridly, benzooxazolyl, benzothiadiazolyl, benzooxadiazolyl, benzothiazolyl, pyridine-one, triazolopyridinyl, dihydrobenzoimidazolyl, benzohydrofuranyl; and wherein said $R^1$ is optionally substituted with 1 or more substitutents independently selected from the group consisting of: =O, —OH, alkyl, cycloalkyl, haloalkyl, alkoxy, halo, —NH—C(=O)-alkyl, —S(=O)$_2$—N(alkyl)$_2$, —C(=O)-alkyl, cyano, —S(=O)$_2$-alkyl, —NH$_2$, and —OC(=O)alkyl.

5. The compound of claim 1, wherein said $R^2$ is alkyl, which is unsubstituted or substituted with at least one aryl.

6. The compound of claim 1, wherein $R^{3'}$ is

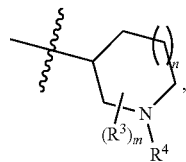

wherein n is 1.

7. The compound of claim 6, wherein:
(a) n is 1; or
(b) n is 1 and m is 0, 1 or 2; or
(c) n is 1, m is 1 or 2, and $R^3$ is selected from the group consisting of halo, haloalkyl, —OSi(alkyl)$_3$, hydroxyl, alkyl, cycloalkyl, alkoxy, aryl, —C(=O)OH, —C(=O)—O-alkyl, —C(=O)N(alkyl)$_3$, —C(=O)NH-alkyl; or wherein two $R^3$ groups together with the carbon atom to which both $R^3$ groups are attached form —C(=O)—.

8. The compound of claim 1 wherein:
(1) $R^3$ is selected from the group consisting of
(a) —C(O)NR$^B$R$^C$, wherein R$^B$ and R$^C$ are each independently selected from the group consisting of (1) H, (2) $C_1$-$C_6$ alkyl, (3) $C_3$-$C_6$ cycloalkyl, (4) $C_3$-$C_6$cycloalkyl-$C_1$-$C_6$alkyl-, (5) 5-6 membered heteroaryl comprising 1 to 3 heteroatoms selected from the group consisting of N, O, and S, (6) $C_6$-$C_{10}$aryl, (7) benzyl, (8) $C_1$-$C_2$ alkoxy; wherein each of said R$^B$ and R$^C$ is optionally substituted with 1 to 3 substitutents independently selected from the group consisting of: —OH, $C_1$-$C_4$alkyl, —$C_1$-$C_4$alkoxy, -hydroxy($C_1$-$C_3$)alkyl-, halo, —C(O)OC$_1$-$C_4$alkyl, and the optional substitution of R$^B$ is independent of the optional substitution of R$^C$;

(b) —C(O)NH-alkyl-NR$^D$R$^E$, and R$^D$ and R$^E$ are independently selected from the group consisting of: H, $C_1$-$C_4$alkyl and —C(O)OC$_1$-$C_4$alkyl;
(c) —C(O)—NH—$C_1$-$C_2$alkyl-O—$C_1$-$C_2$alkyl-phenyl,
(d) —C(O)R$^F$ wherein R$^F$ is selected from the group consisting of pyrrolidinyl, piperidinyl, piperazinyl, azetidinyl, morpholinyl, and isoxazolidinyl, and said R$^F$ group is optionally substituted with 1-3 substitutents independently selected from the group consisting of: —OH, halo, —C(O)OC$_1$-$C_4$alkyl, —C(O)NH—$C_1$-$C_4$alkyl, —C(O)$C_1$-$C_4$alkyl, —C(O)OC$_3$-$C_6$cycloalkyl, —O—Si($C_1$-$C_4$alkyl)$_2$ wherein each alkyl is independently selected, and —C(O)Oheterocycloalkyl wherein said heterocycloalkyl moiety is a 5 to 6 membered ring comprising 1 to 3 heteroatoms selected from the group consisting of O, N and S;
(e) —C(O)—NH—NHR$^G$ wherein R$^G$ is selected from the group consisting of: H, $C_1$-$C_4$alkyl, and —C(=S)—NH—$C_1$-$C_4$alkyl;
(f) —C(O)NH—O—$C_1$-$C_4$alkyl;
(g) —C(=O)—N(alkyl)$_2$, wherein each alkyl group is independently selected;
(h) —C(=O)—NHalkyl;
(i) phenyl;
(j) —C(O)NH—O—$C_1$-$C_2$alkyl-$C_3$-$C_5$cycloalkyl;
(2) $R^{3'}$ is

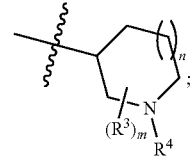

(3) m is 1; and
(4) n is 1.

9. The compound of claim 6 wherein $R^4$ is selected from the group consisting of:
(a) H;
(b) cycloalkyl, wherein when said $R^4$ cycloalkyl has two substituents on adjacent carbon atoms, said substituents together with the carbon atoms to which they are attached, optionally form a six-membered aryl; and
(c) —(CR$^5$R$^6$)$_{1-2}$R$^7$, wherein each of R$^5$ and R$^6$ independently is H or alkyl, or wherein one —CR$^5$R$^6$— together is —C(=O)— and R$^7$ is selected from the group consisting of H, cycloalkyl, heterocyclyl, —O-alkyl-aryl, aryl and heteroaryl, wherein when each of said R$^7$ cycloalkyl, heterocyclyl, aryl and heteroaryl has two substituents on adjacent carbon atoms, said substituents together with the carbon atoms to which they are attached, optionally form a five- or six-membered cycloalkyl, heterocyclyl, aryl or heteroaryl.

10. The compound of claim 1 wherein $R^4$ is selected from the group consisting of: phenyl, quinolinyl, —SO$_2$-phenyl, —CH$_2$-phenyl, di-F-phenyl, F-phenyl, —CH$_2$-thienyl, —(CH$_2$)$_2$-phenyl, —CH$_2$-(D$_3$CO—, F-phenyl), —CH(C(O)NH$_2$)(F-phenyl), —CH(C(O)NHCH$_3$)(F-phenyl), —CH(C(O)NH$_2$)(di-F-phenyl), —CH(C(O)NHCH$_3$)(di-F-phenyl), —CH(C(O)N(CH$_3$)$_2$)(di-F-phenyl), —CH(C(O)N(CH$_3$)$_2$)(F-phenyl), and —CH(C(O)OCH$_3$)(di-F-phenyl).

11. The compound of claim 1, wherein $R^{3'}$ is selected from the group consisting of:

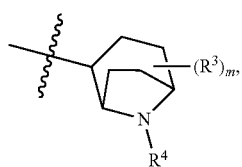
wherein m is 0, and R⁴ is —CR⁵R⁶R⁷;
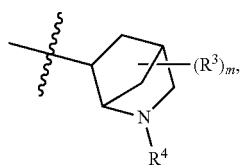
wherein m is 0, and R⁴ is —CR⁵R⁶R⁷;
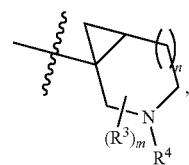
wherein n is 1, m is 0, and R⁴ is —CR⁵R⁶R⁷; and
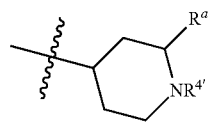
wherein R⁴' is H, and Rᵃ is alkyl which is unsubstituted or substituted with an aryl substituent.
12. The compound of claim 1 selected from the group consisting of:
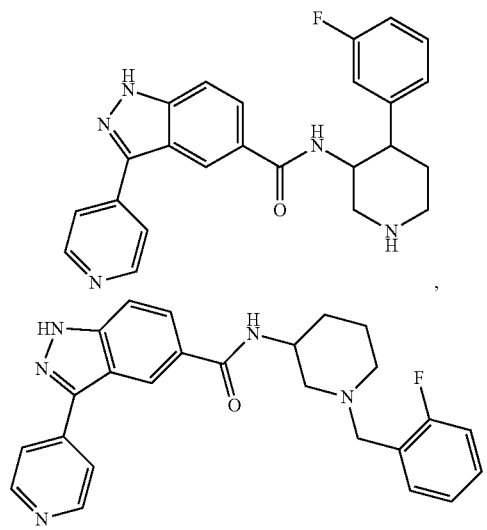
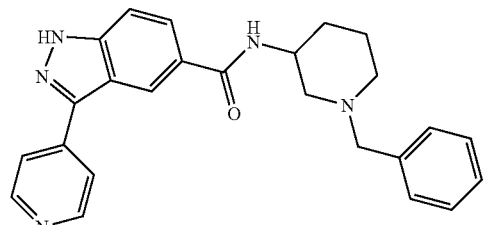
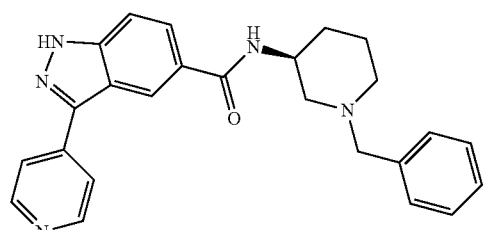
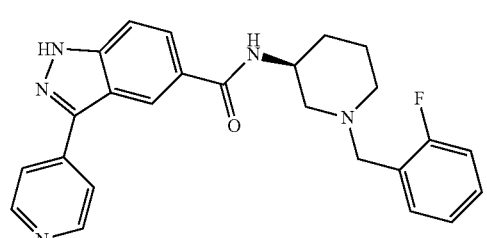
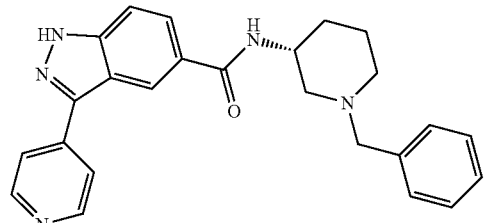
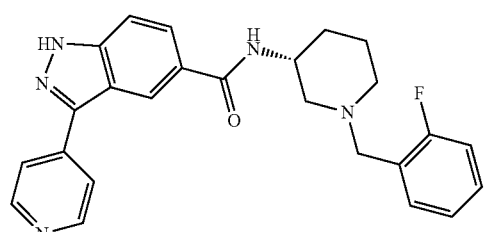
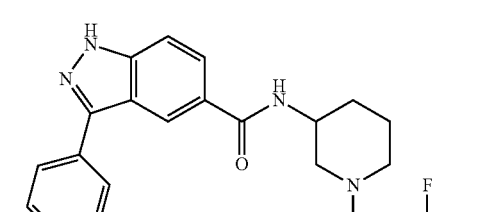

347
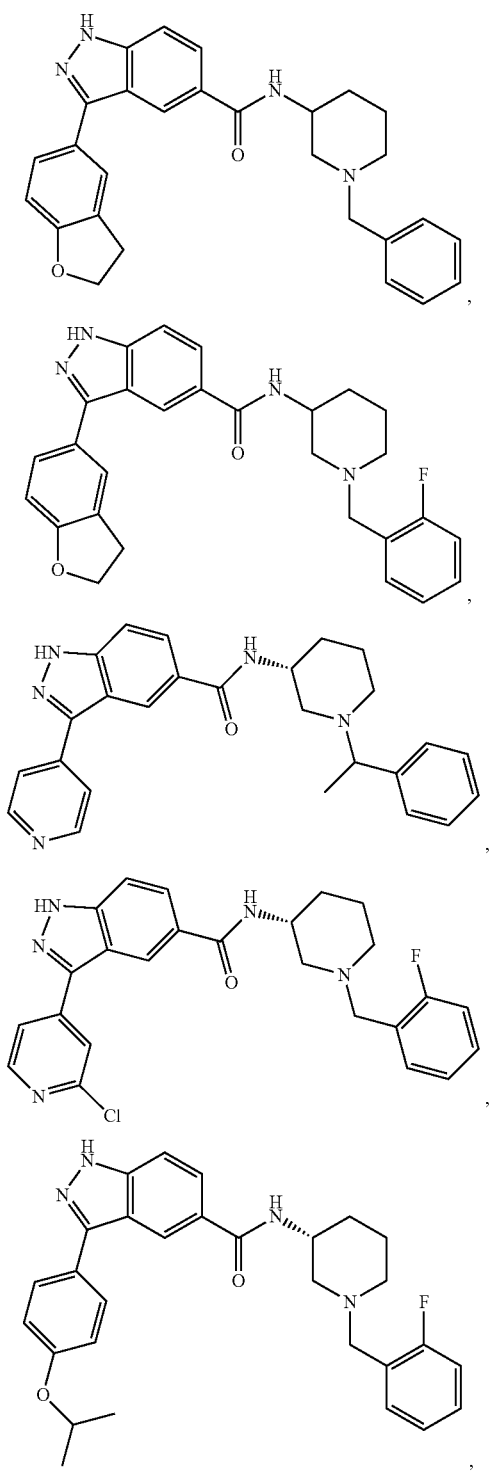
348
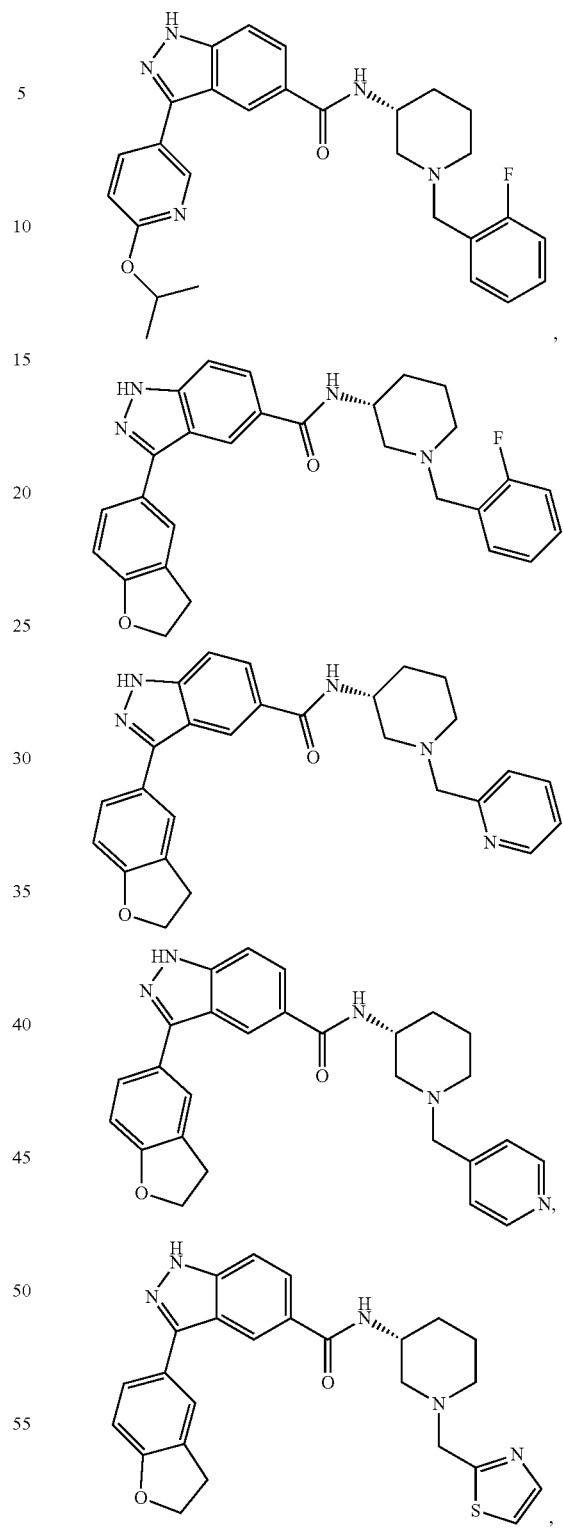

349
-continued
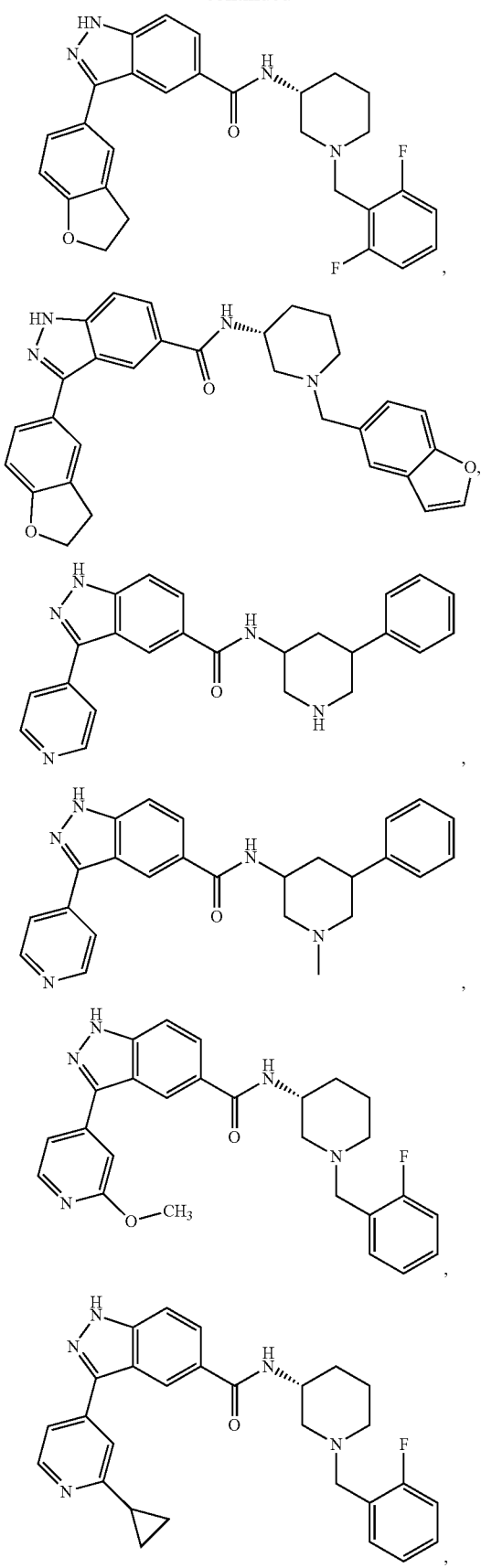
350
-continued
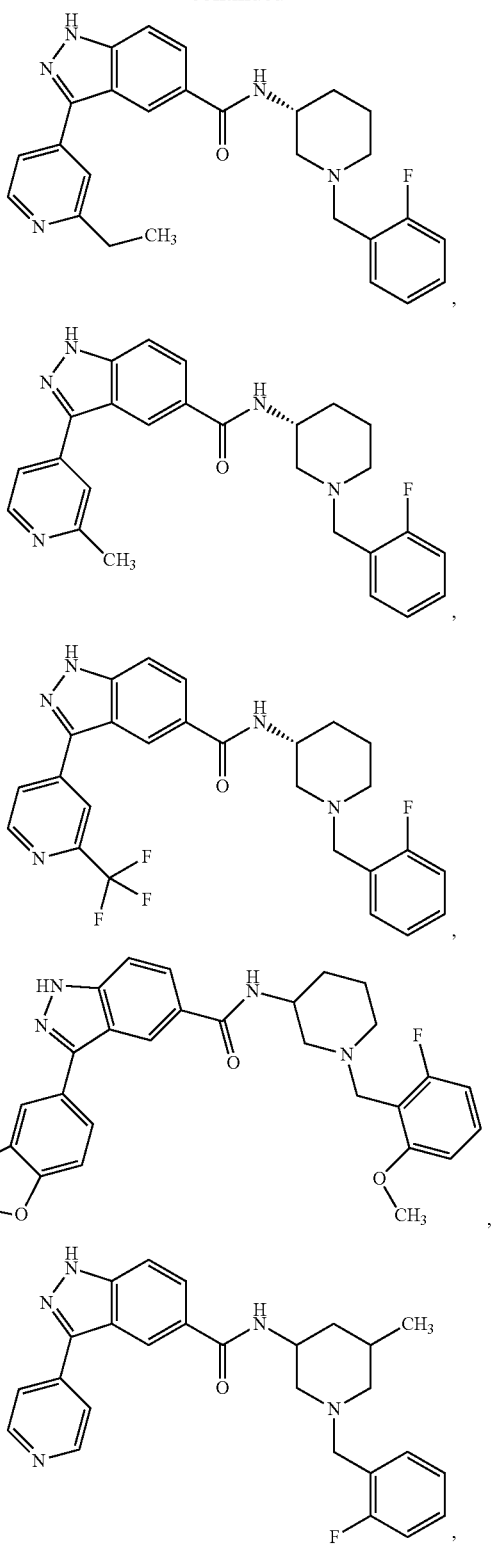

351
-continued
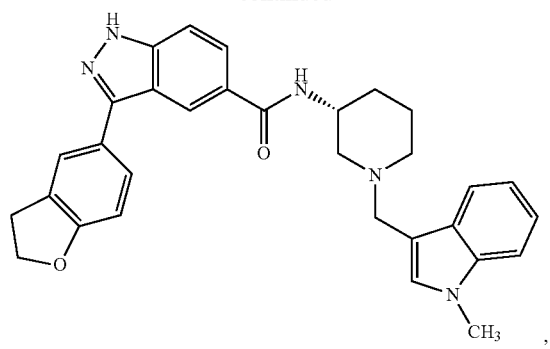
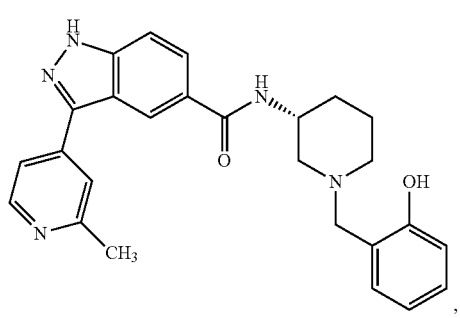
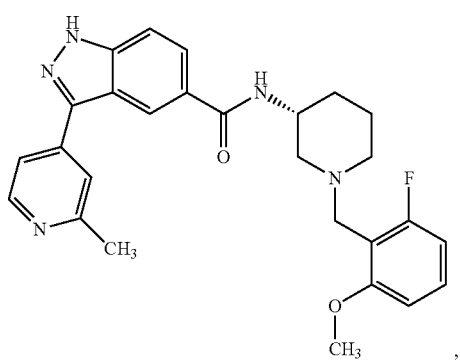
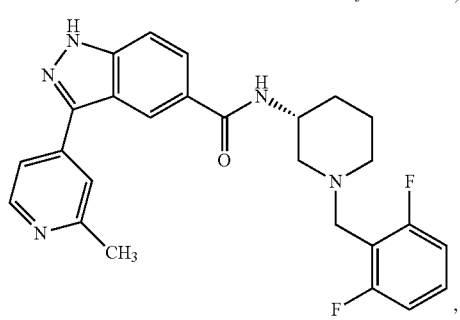
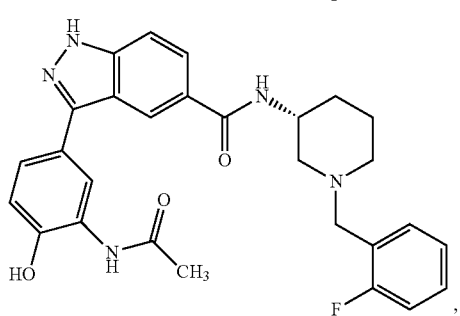
352
-continued
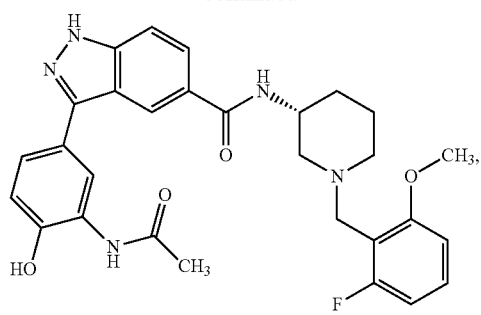
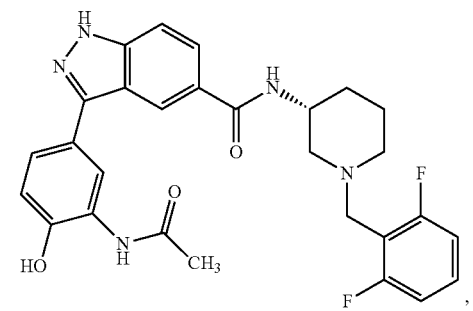
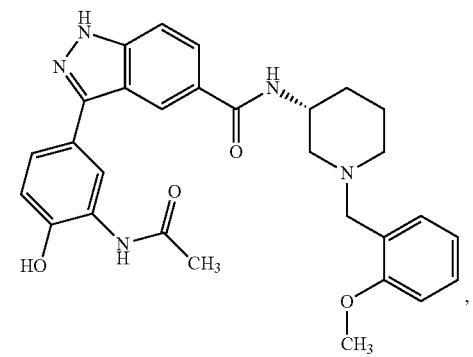
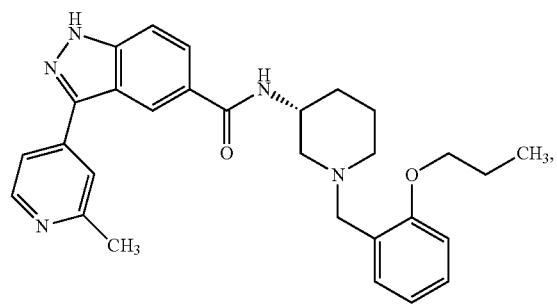
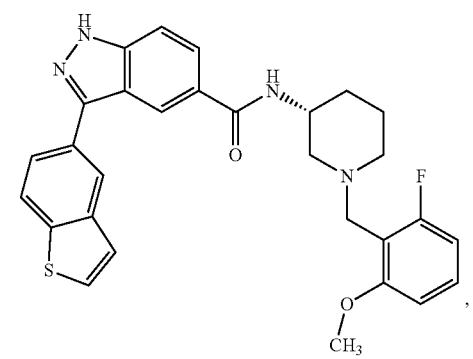

353
-continued
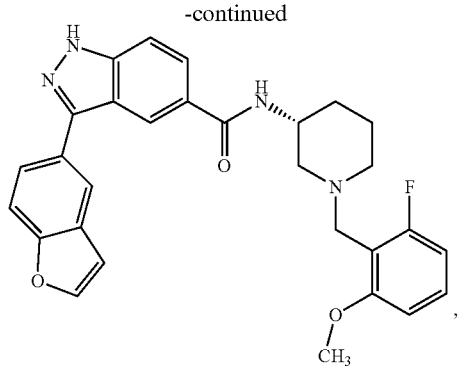
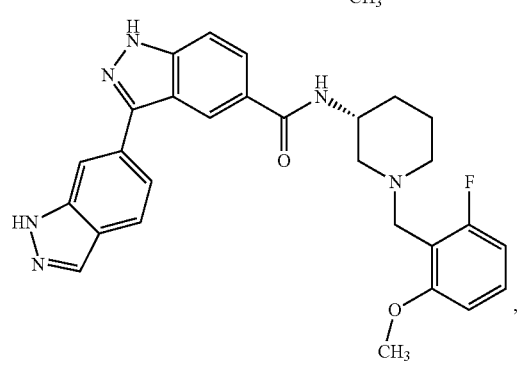
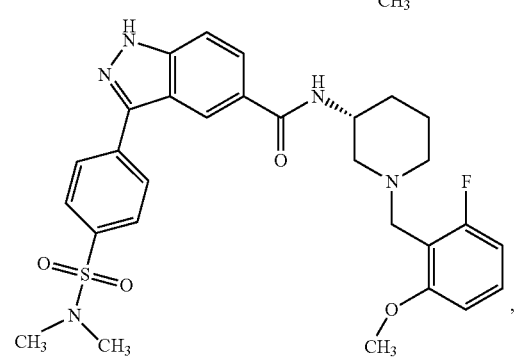
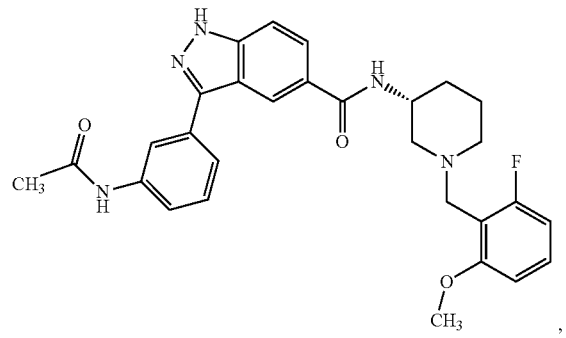
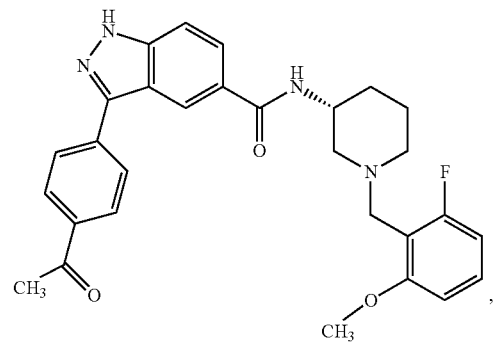
354
-continued
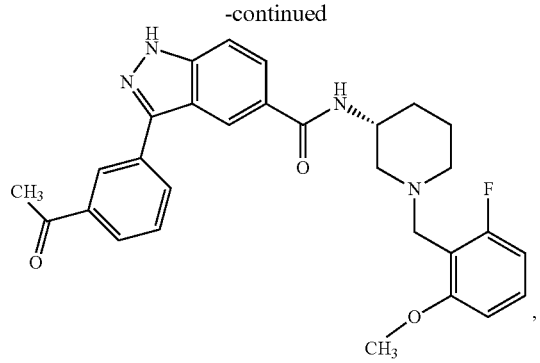
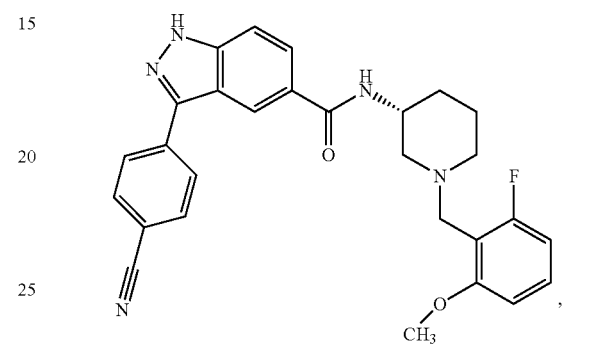
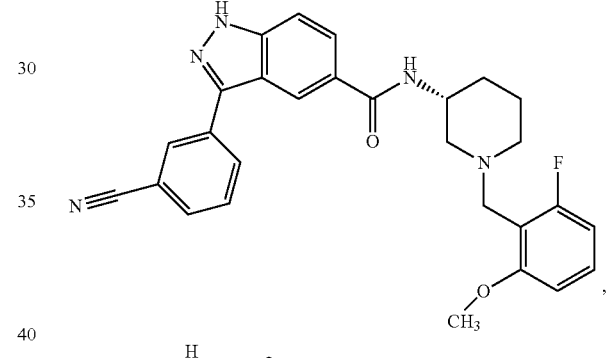
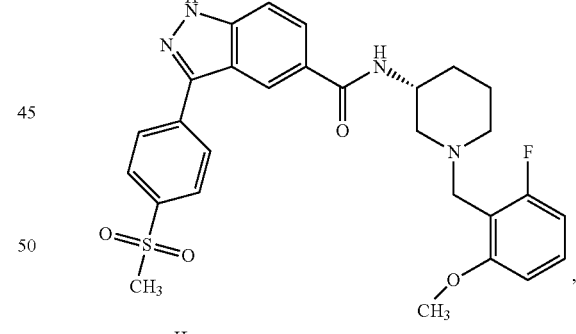
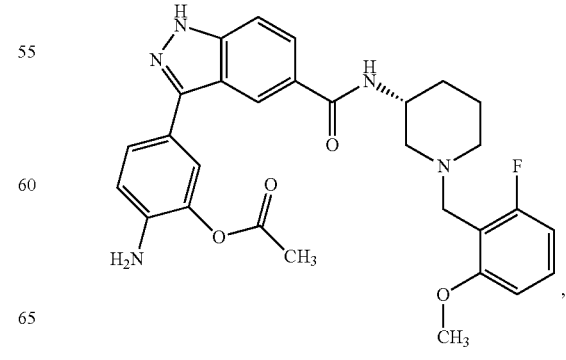

355
-continued
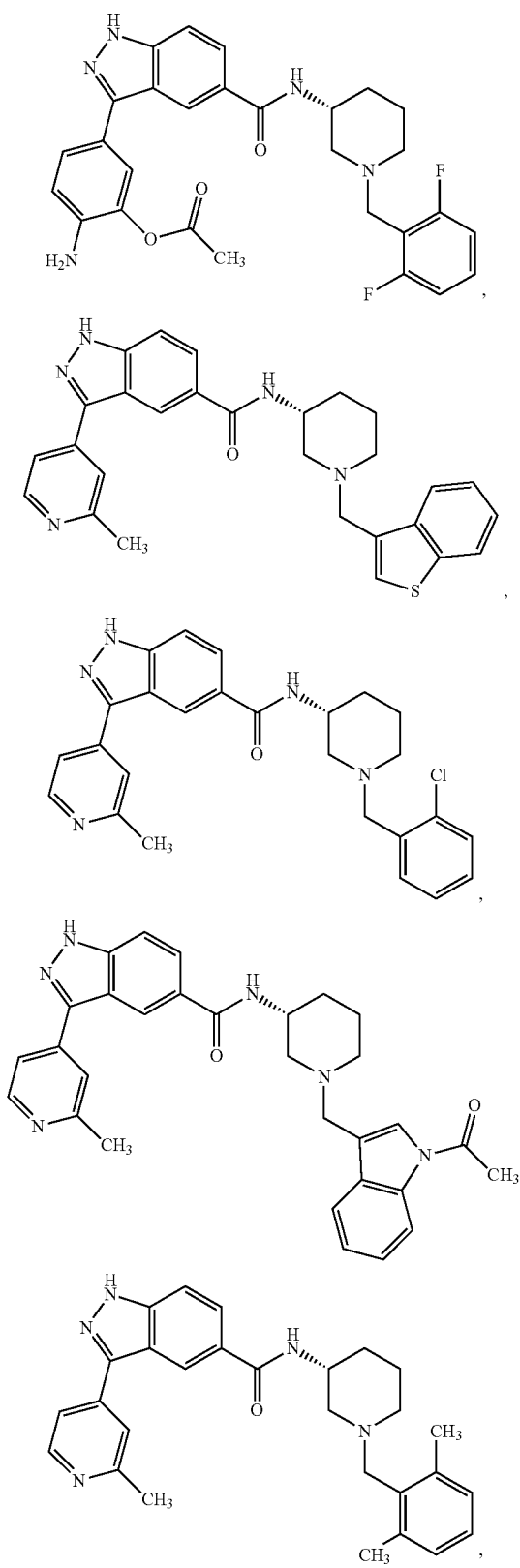
356
-continued
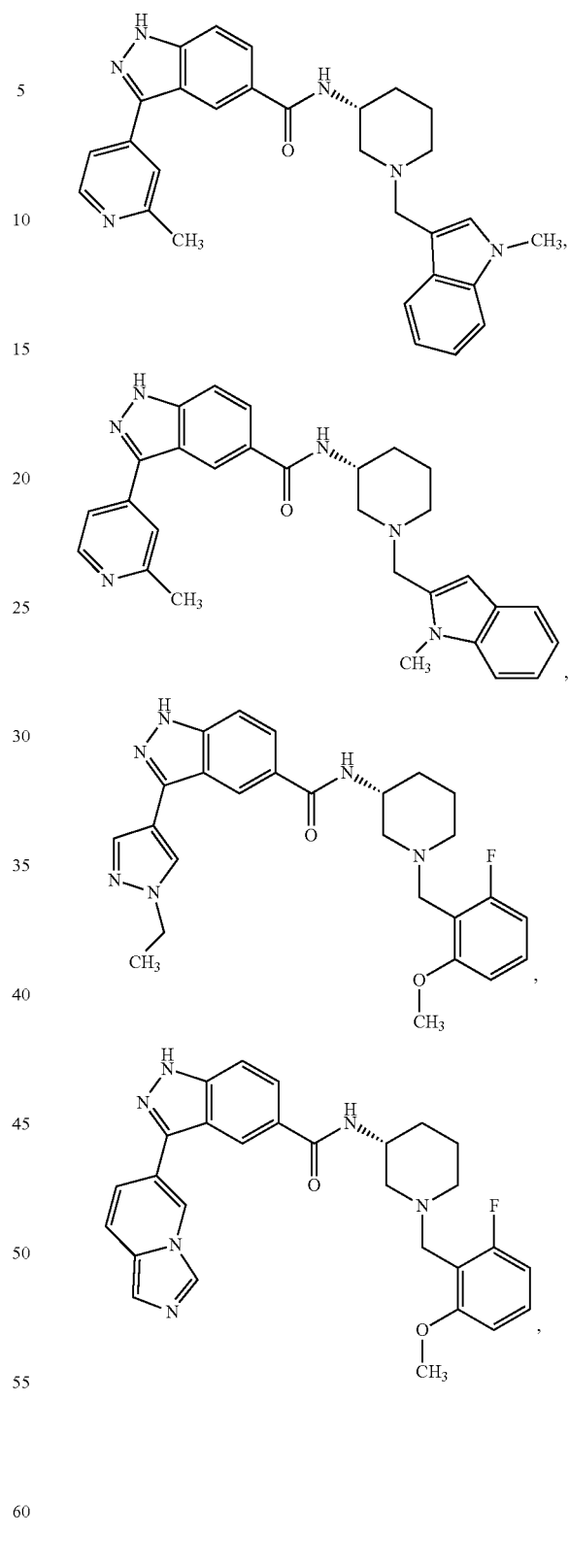

357
-continued
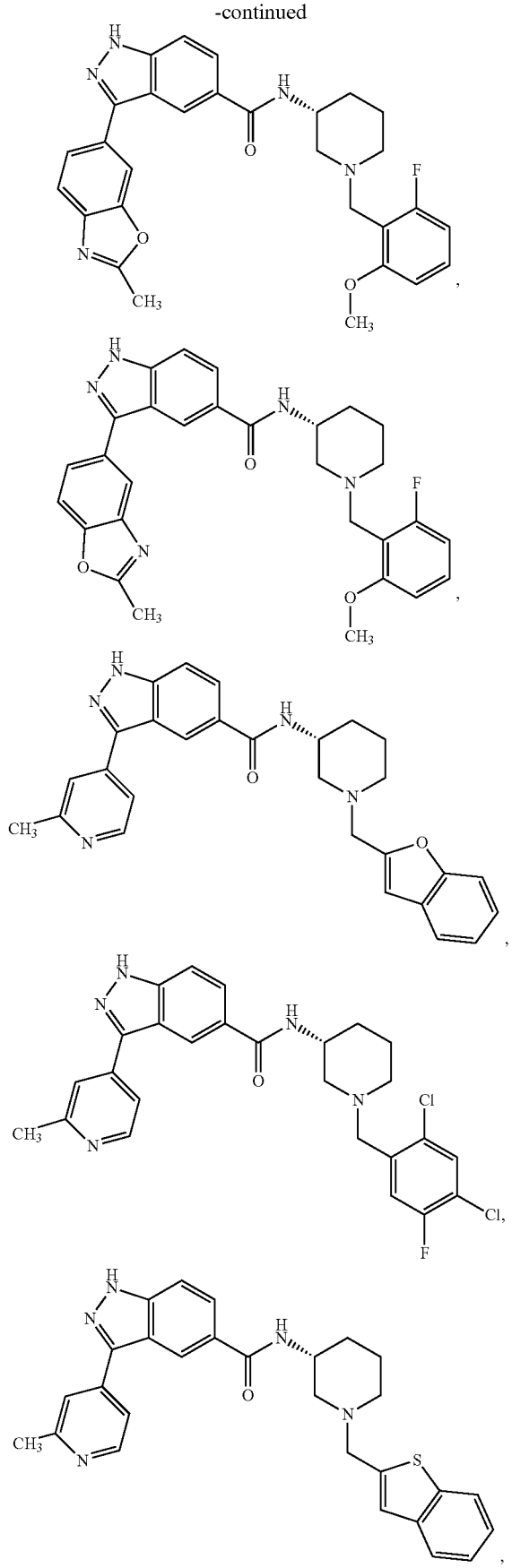
358
-continued
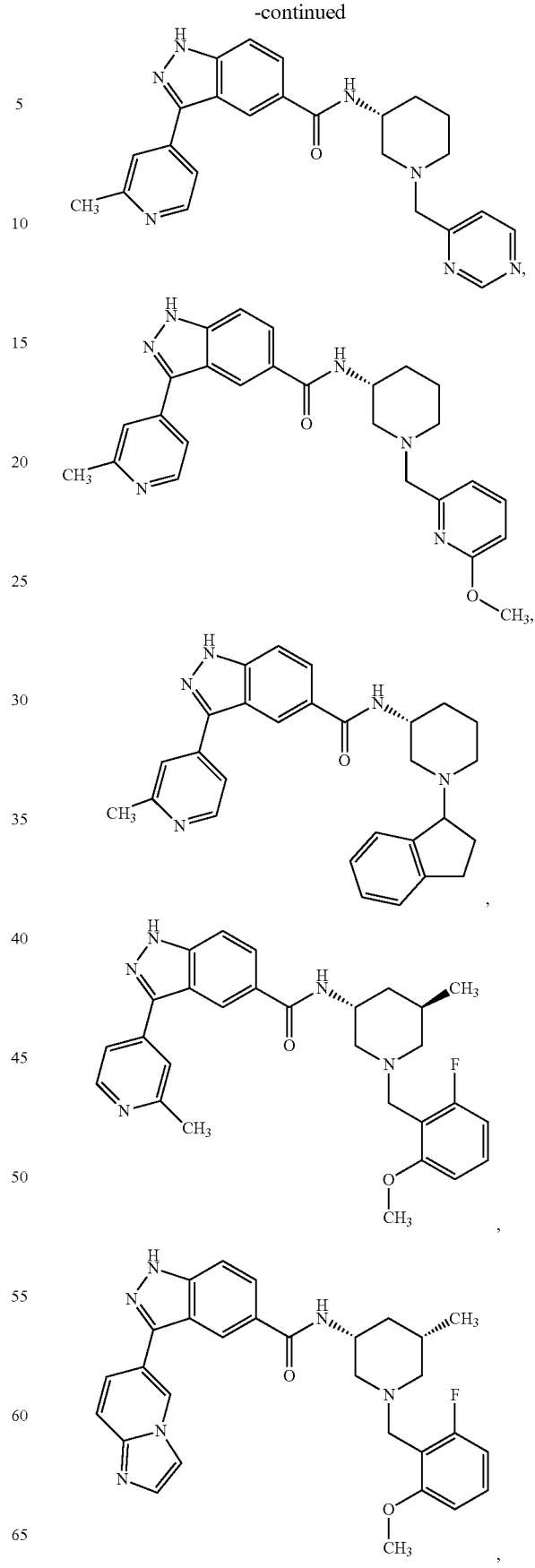

359
-continued
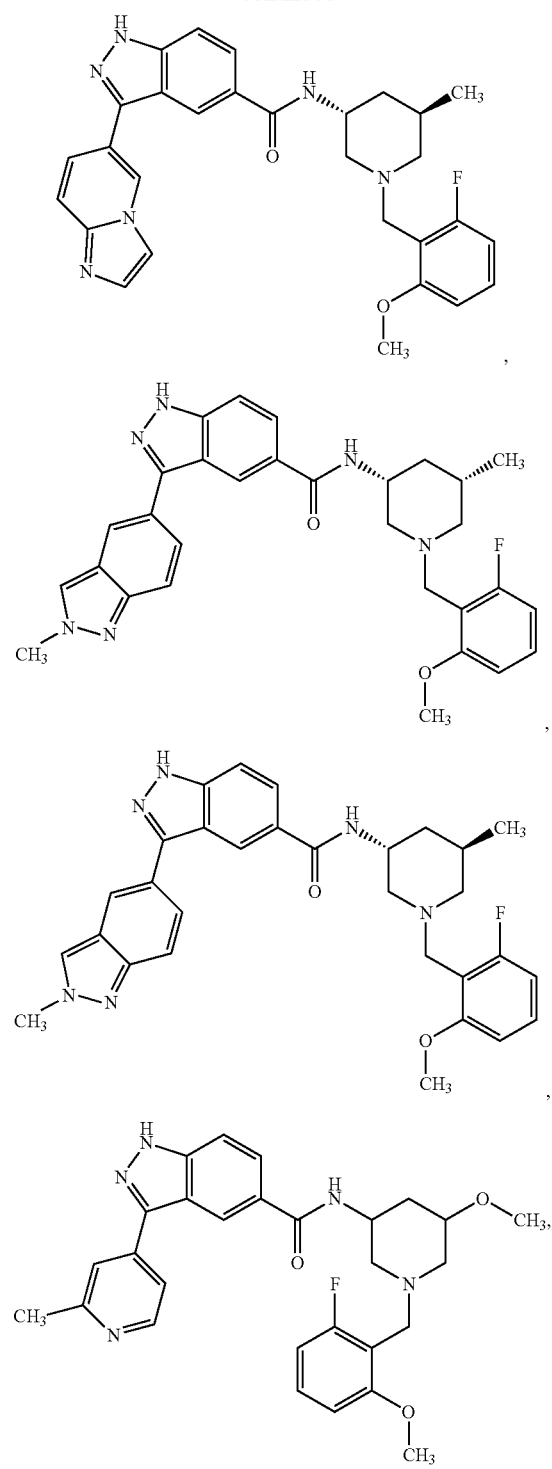
360
-continued
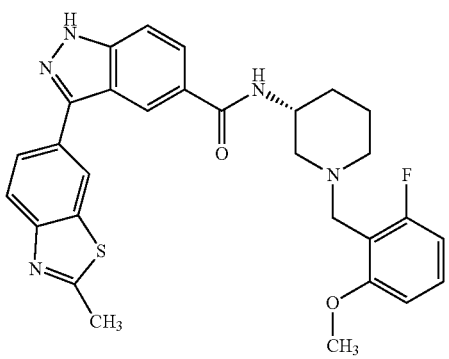
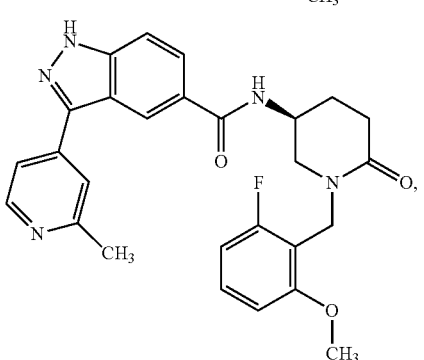
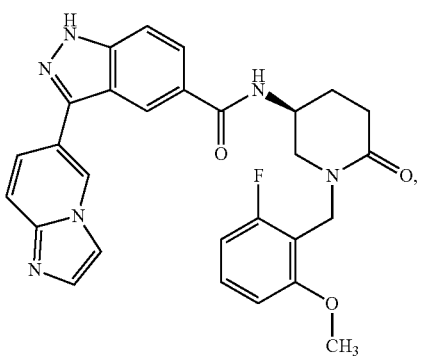

361
-continued
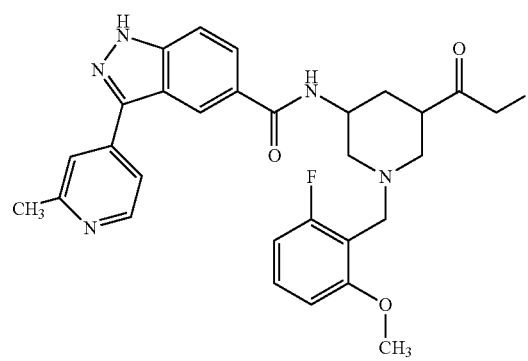
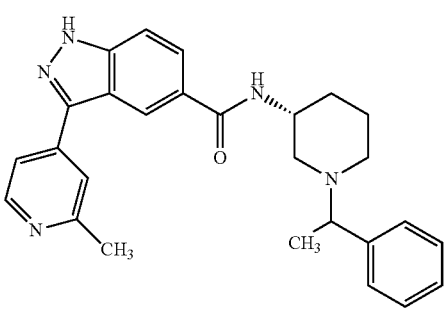
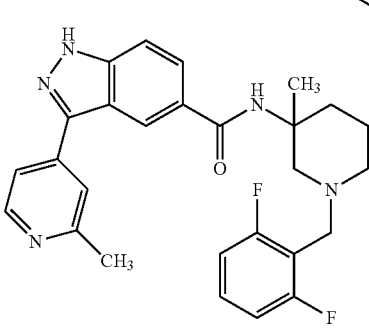
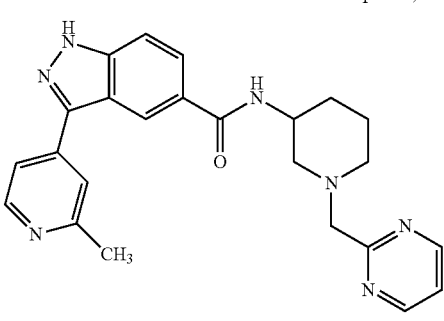
362
-continued
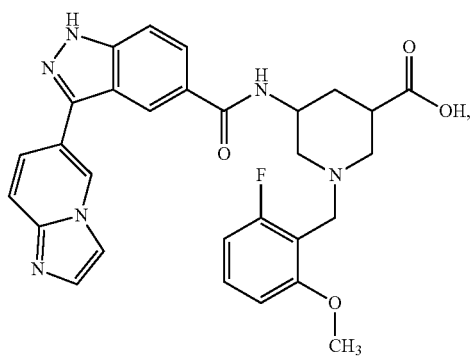
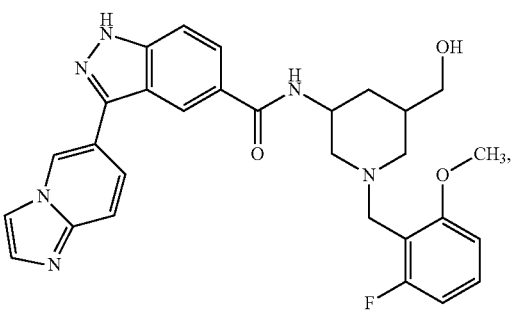

363
-continued
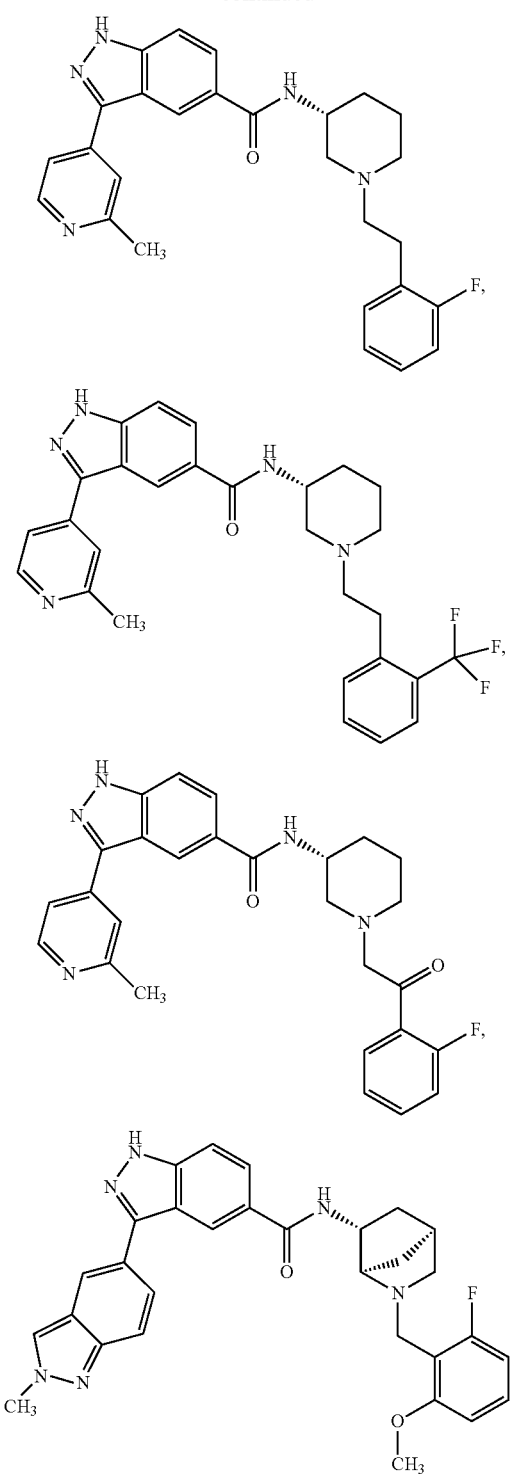
364
-continued
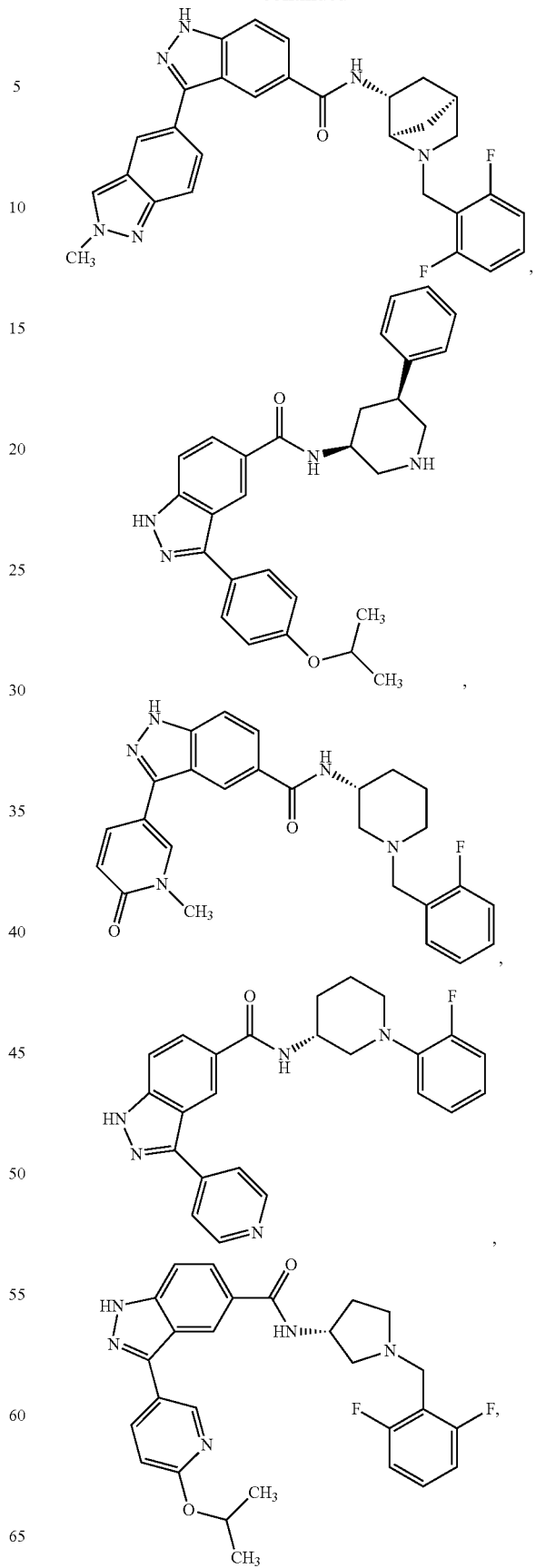

365
-continued
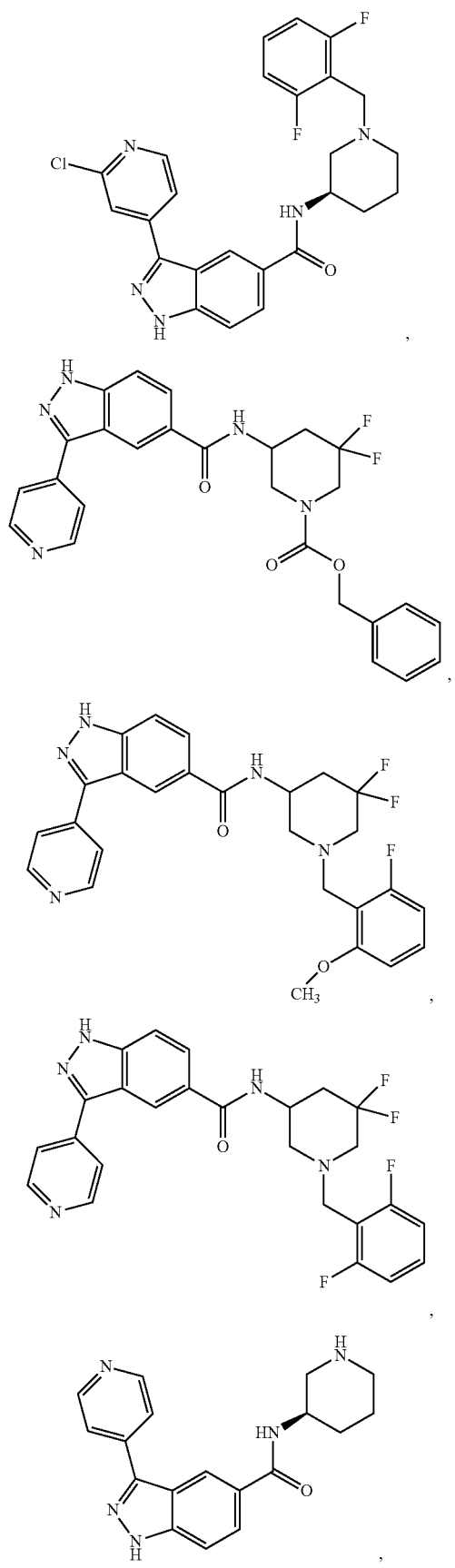
366
-continued
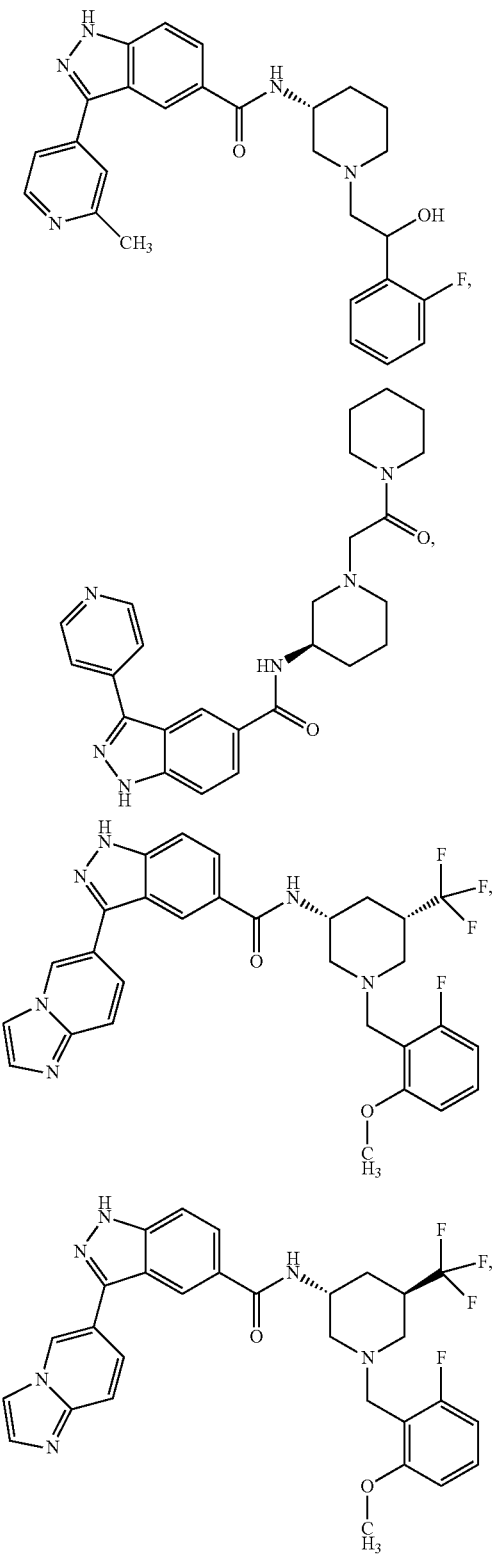

367
-continued
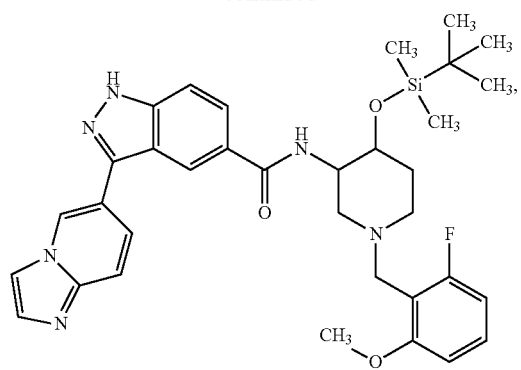
368
-continued
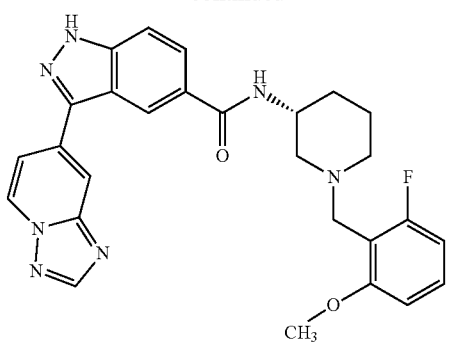
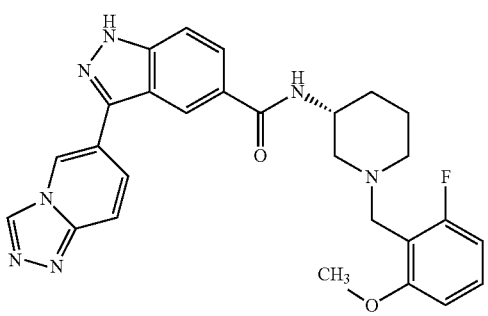
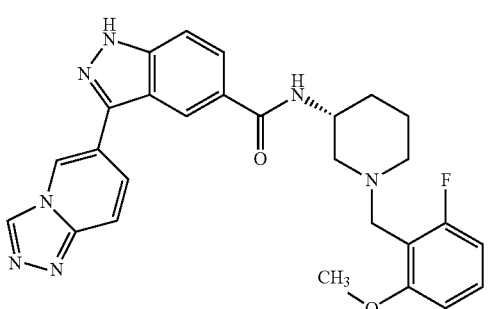
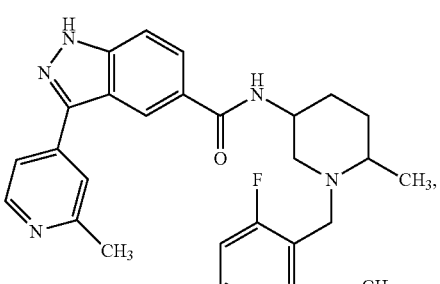
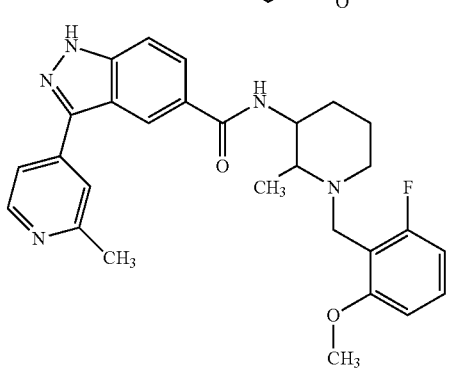

369
-continued
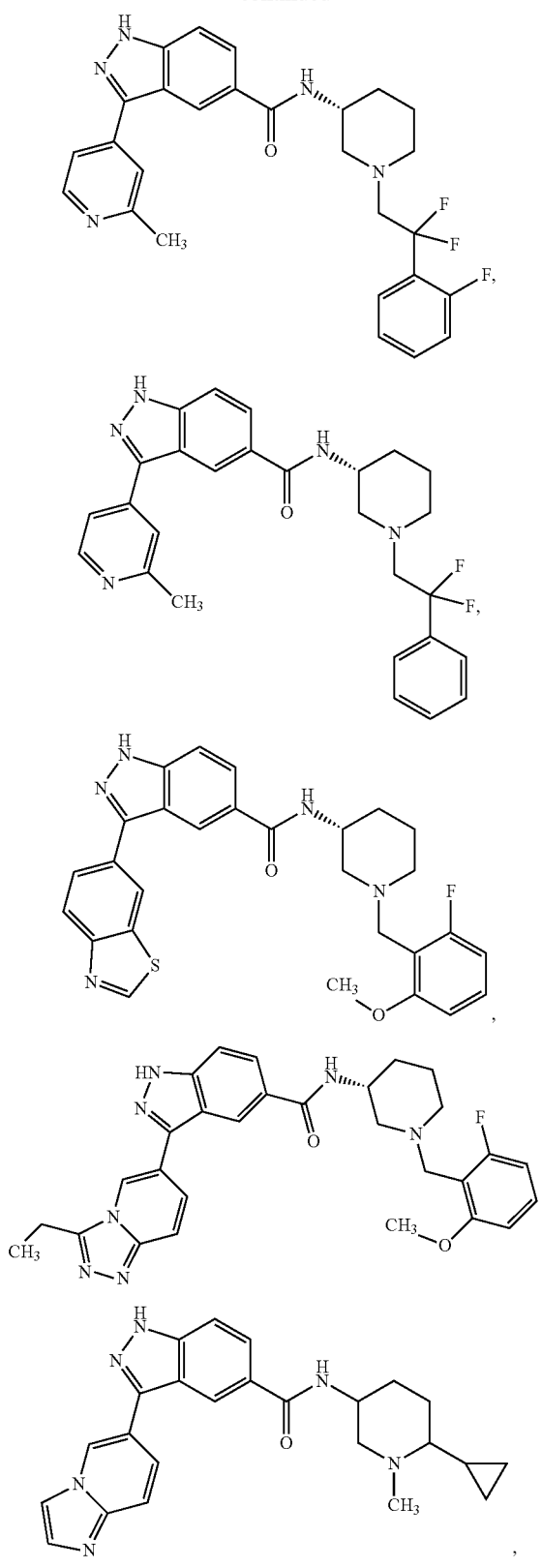
370
-continued
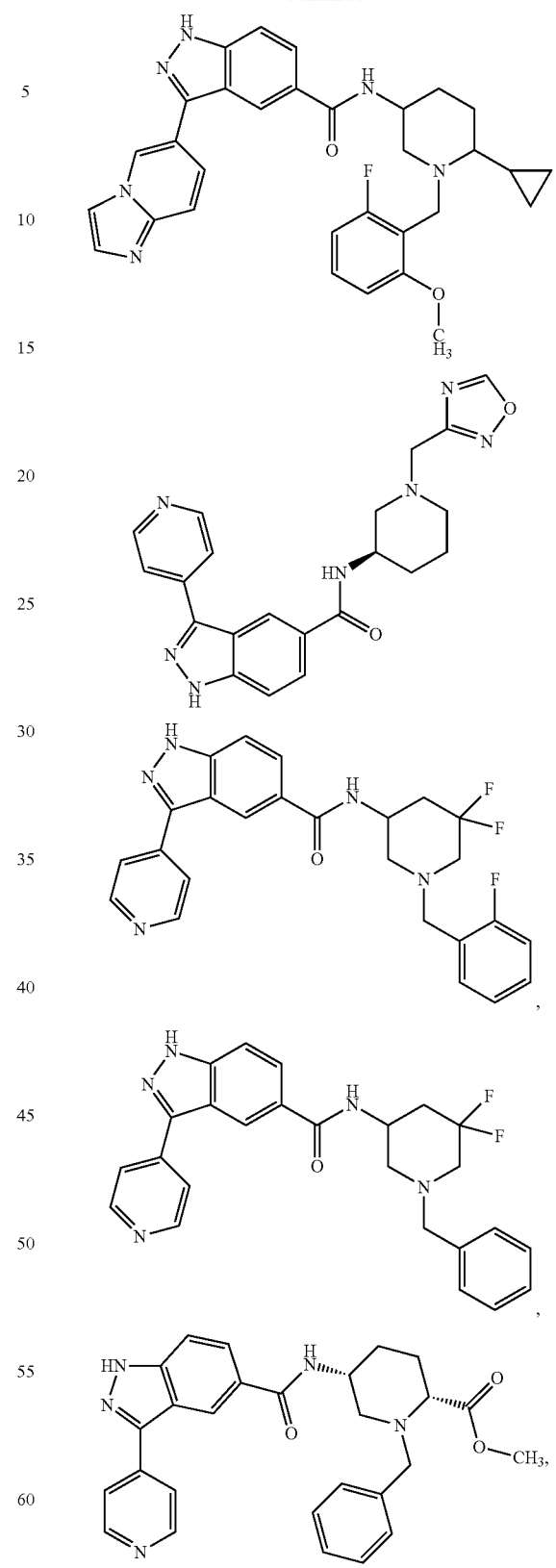

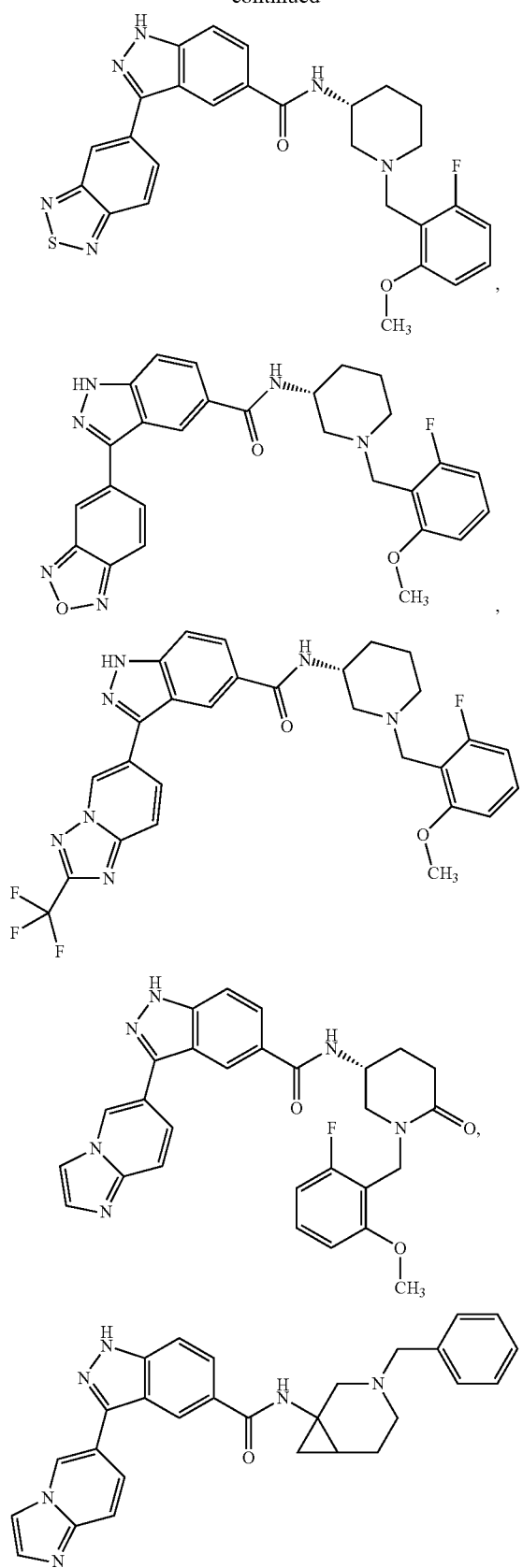
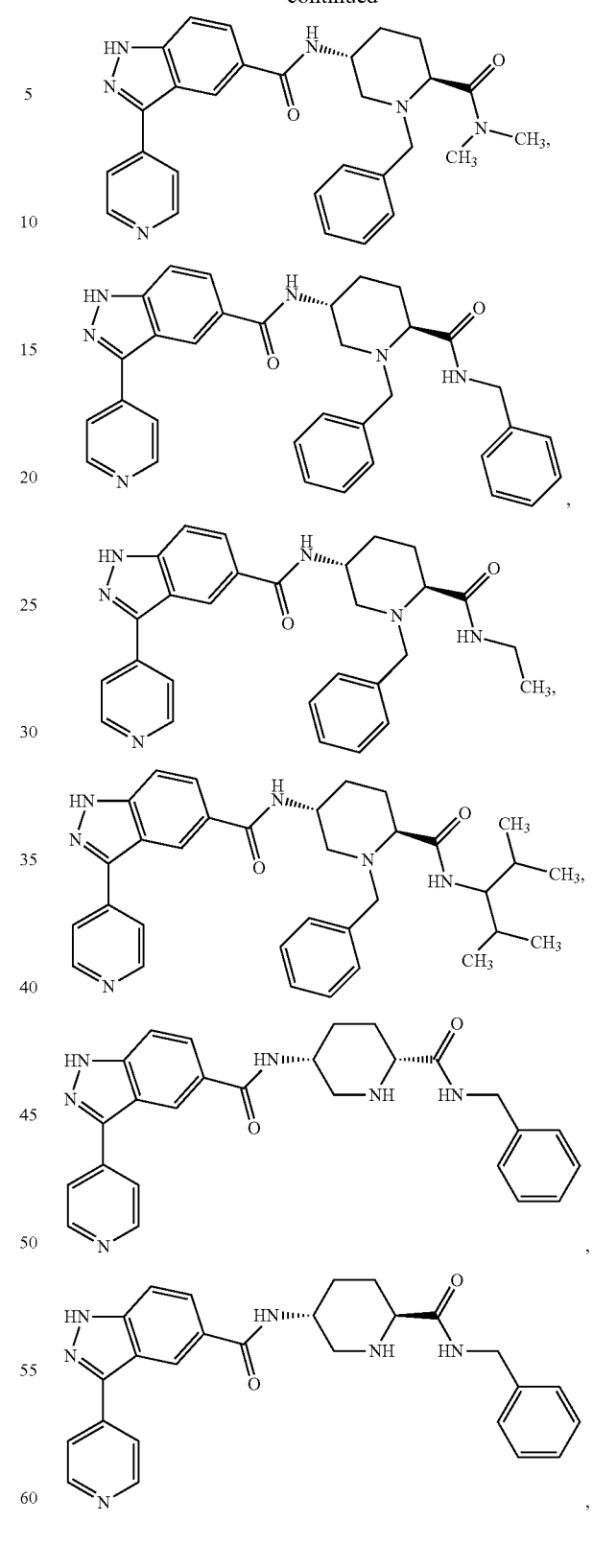

373
-continued
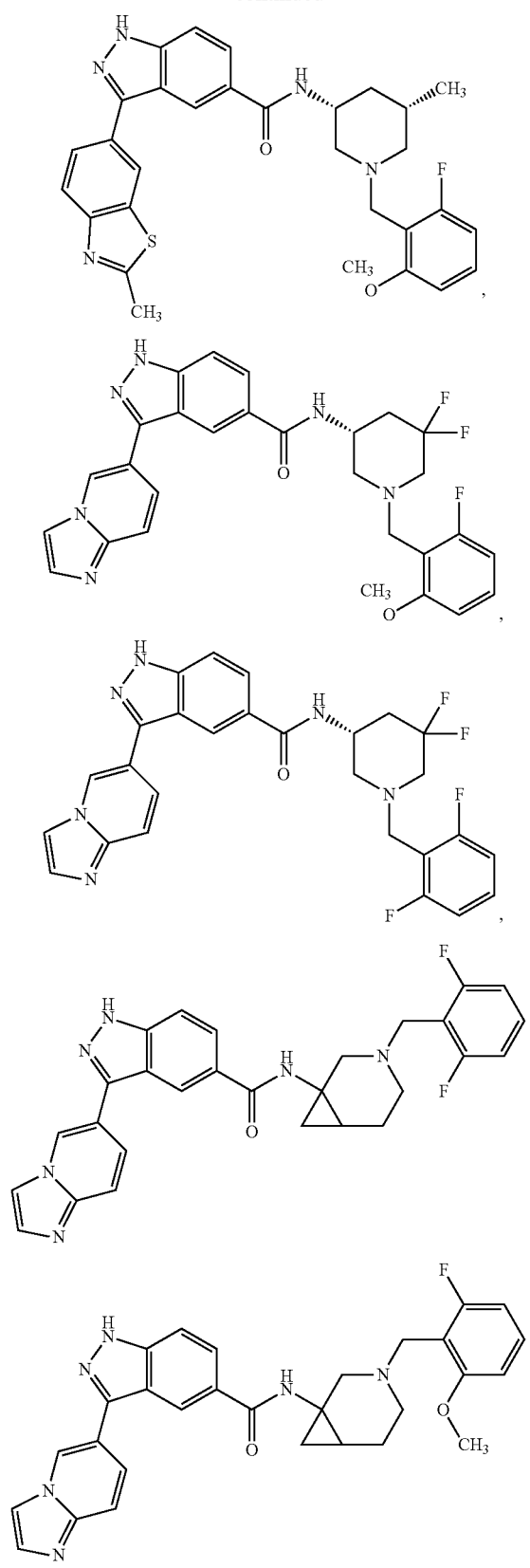
374
-continued
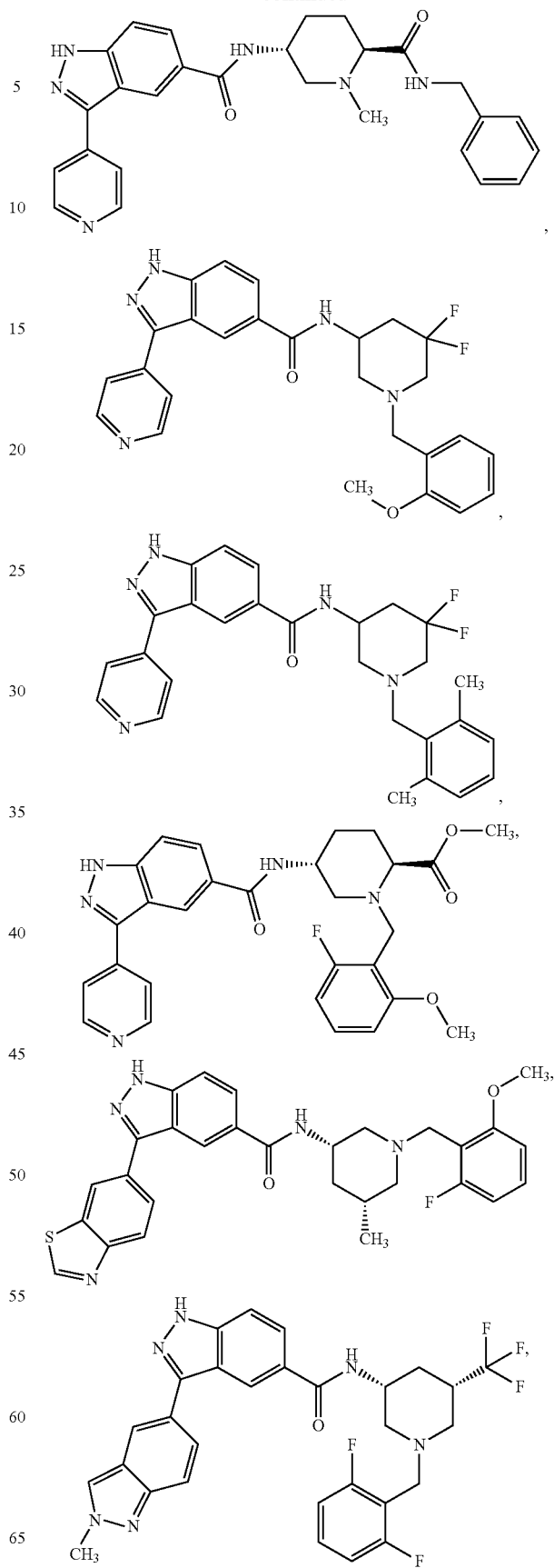

375
-continued
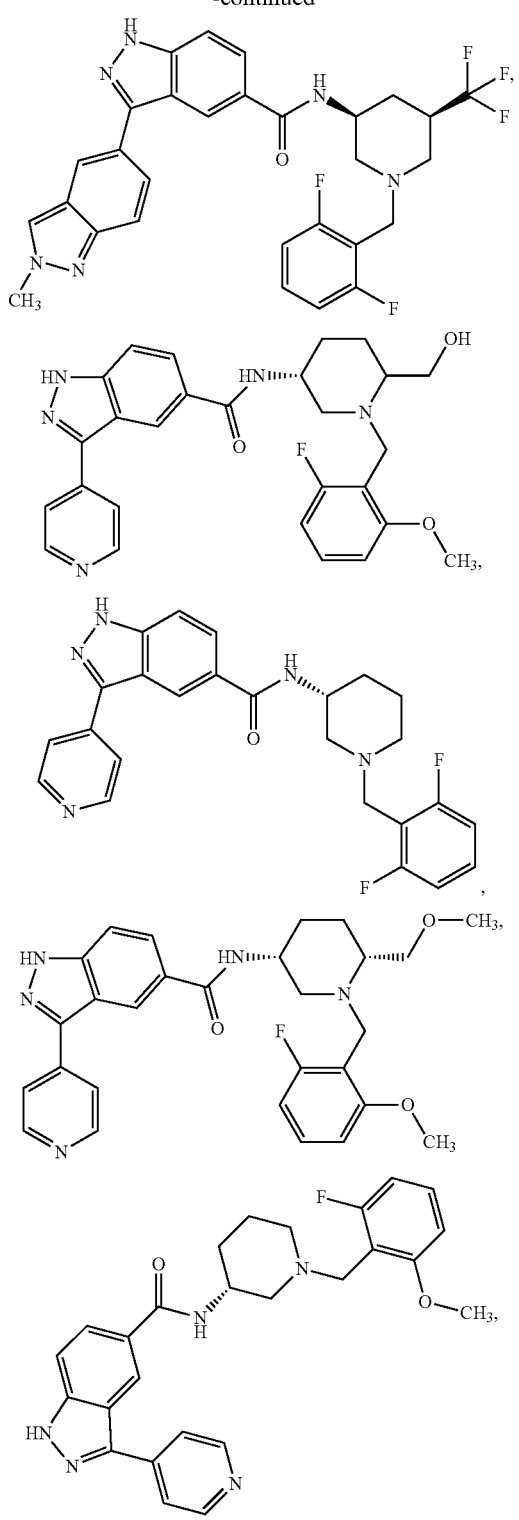
376
-continued
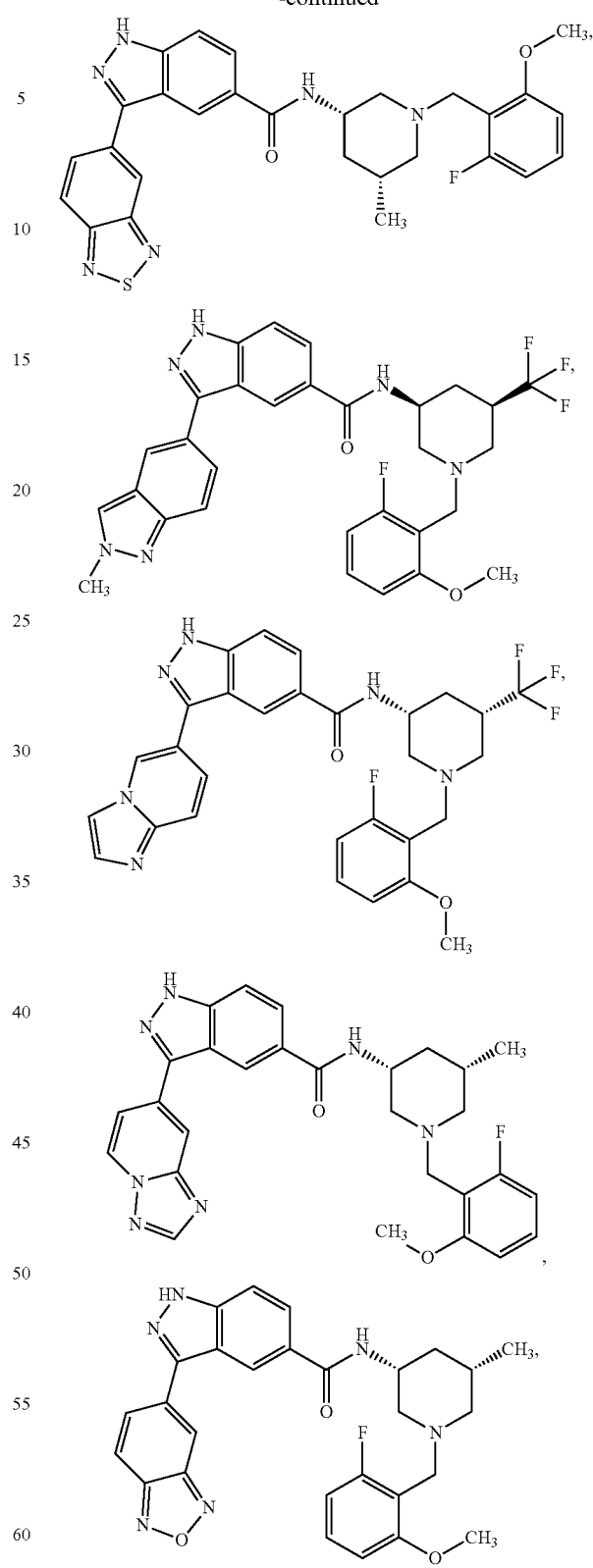

377
-continued
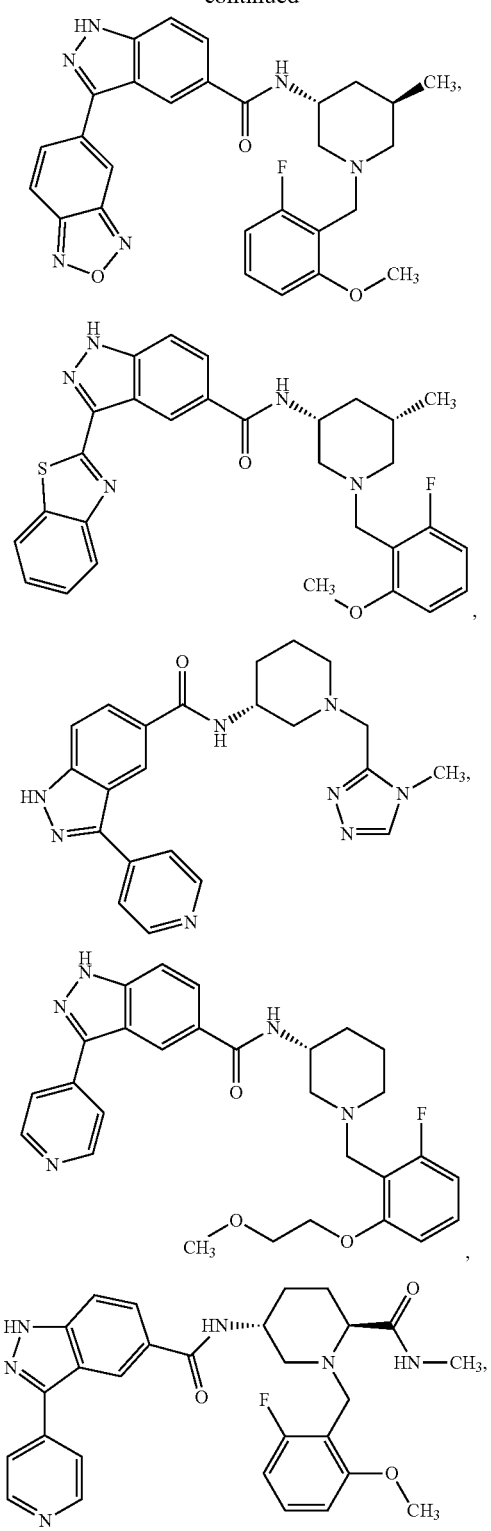
378
-continued
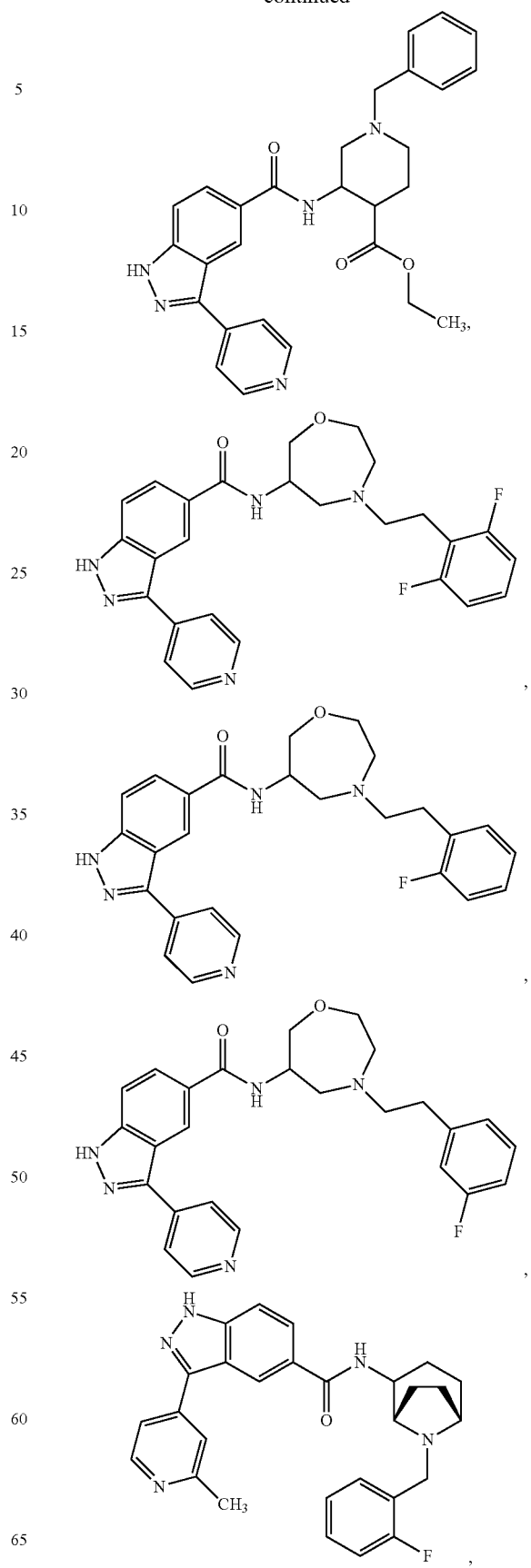

379
-continued
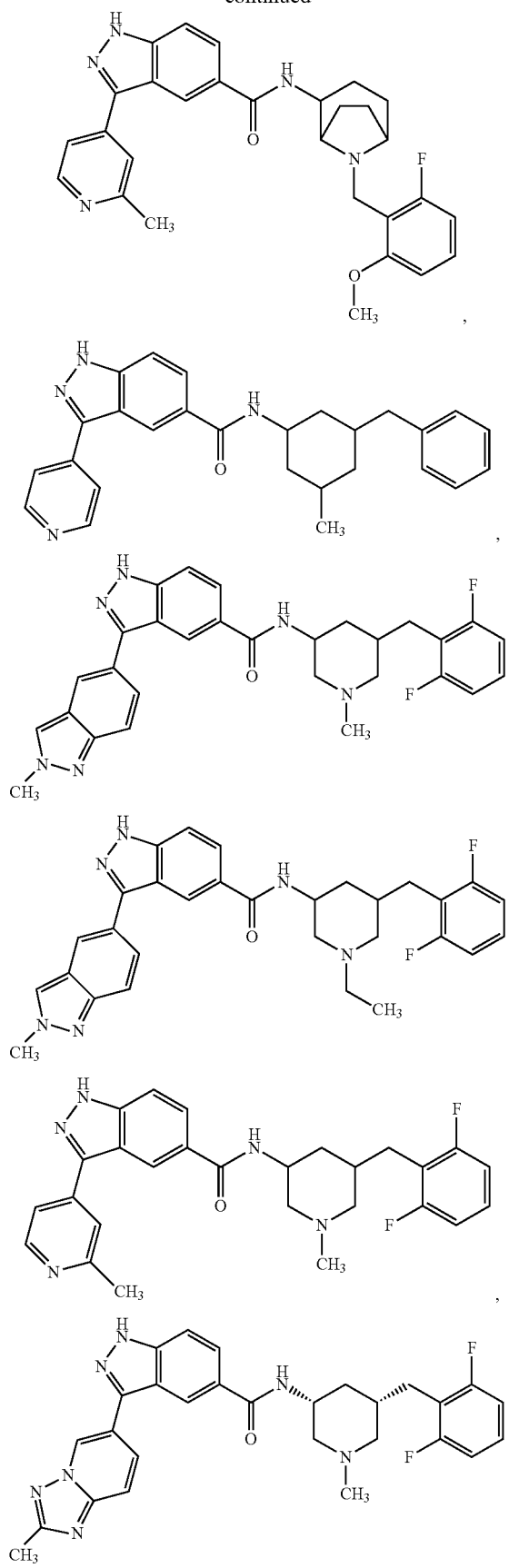
380
-continued
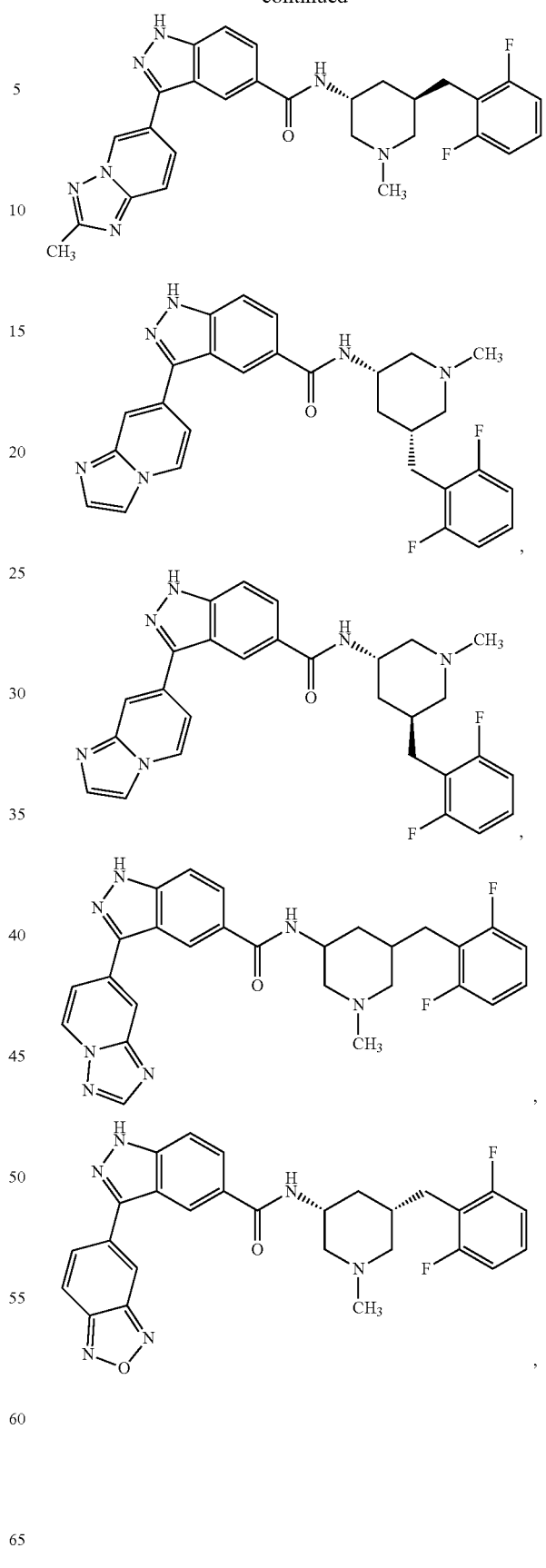

381
-continued
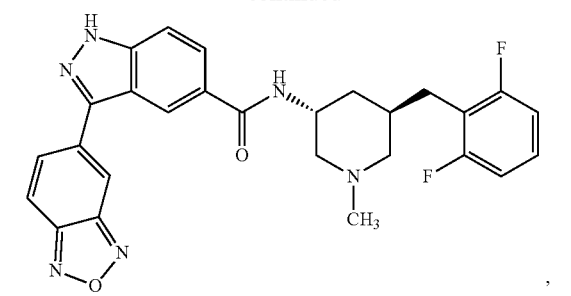
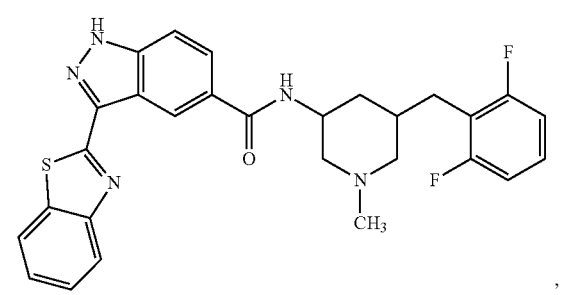
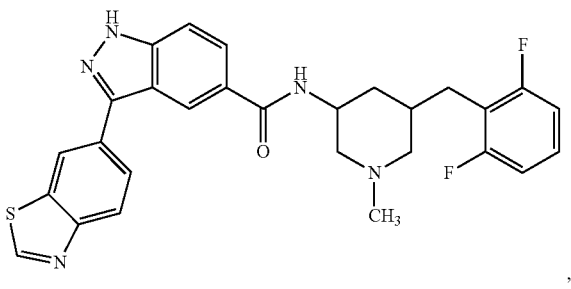
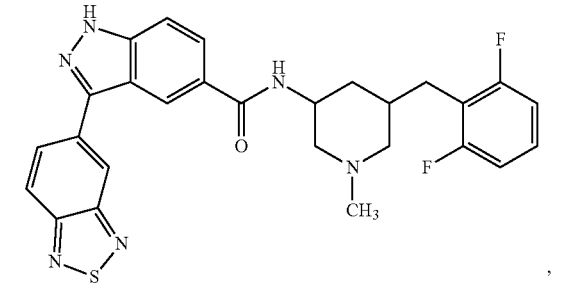
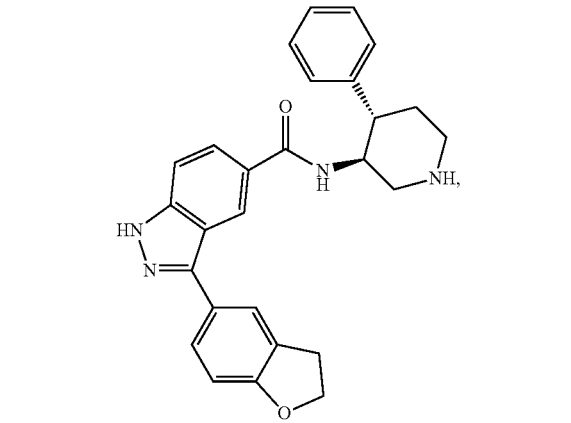
382
-continued
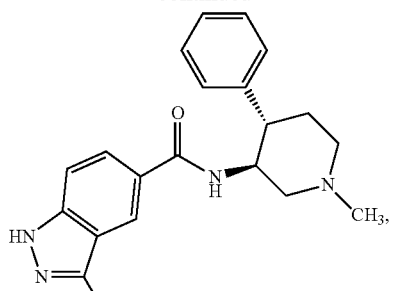
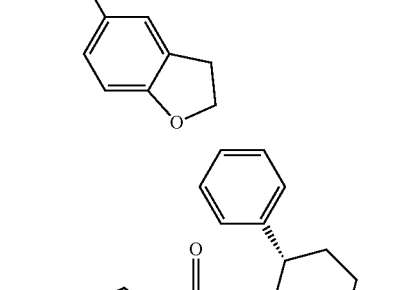
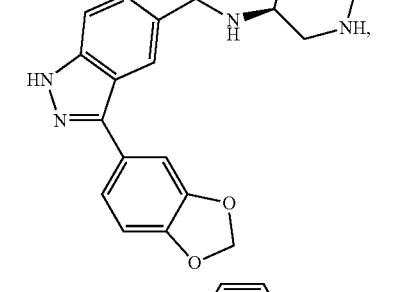
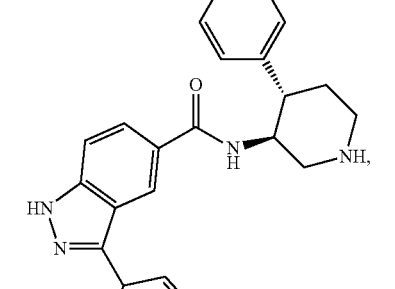
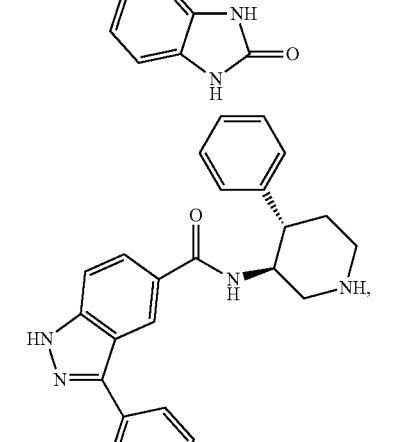

383
-continued
384
-continued
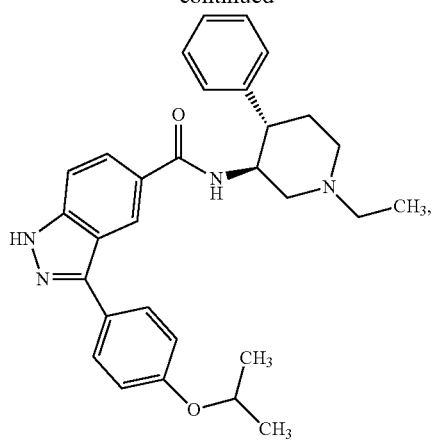
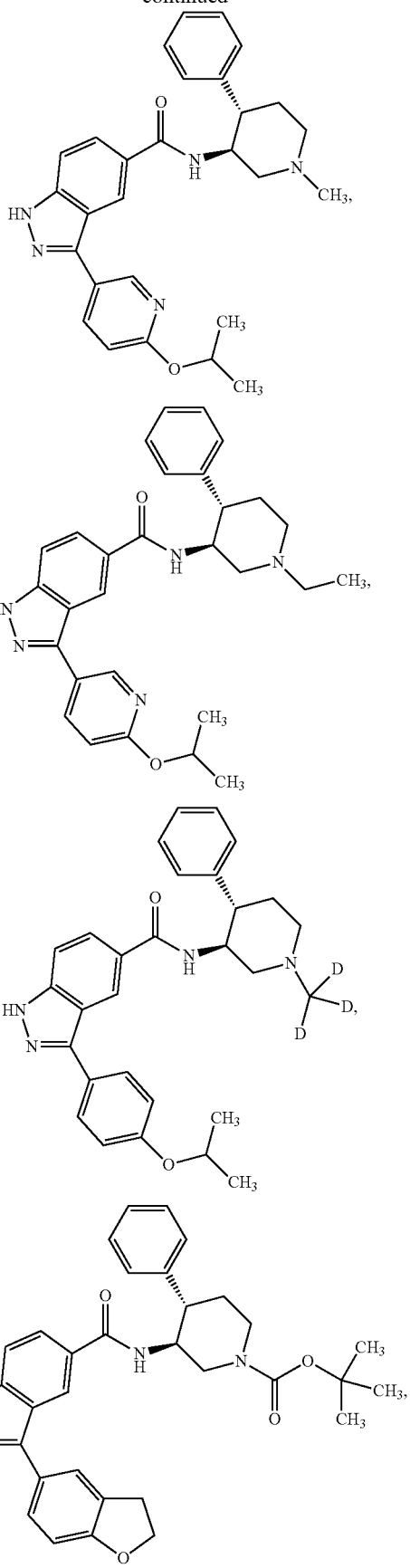

385
-continued
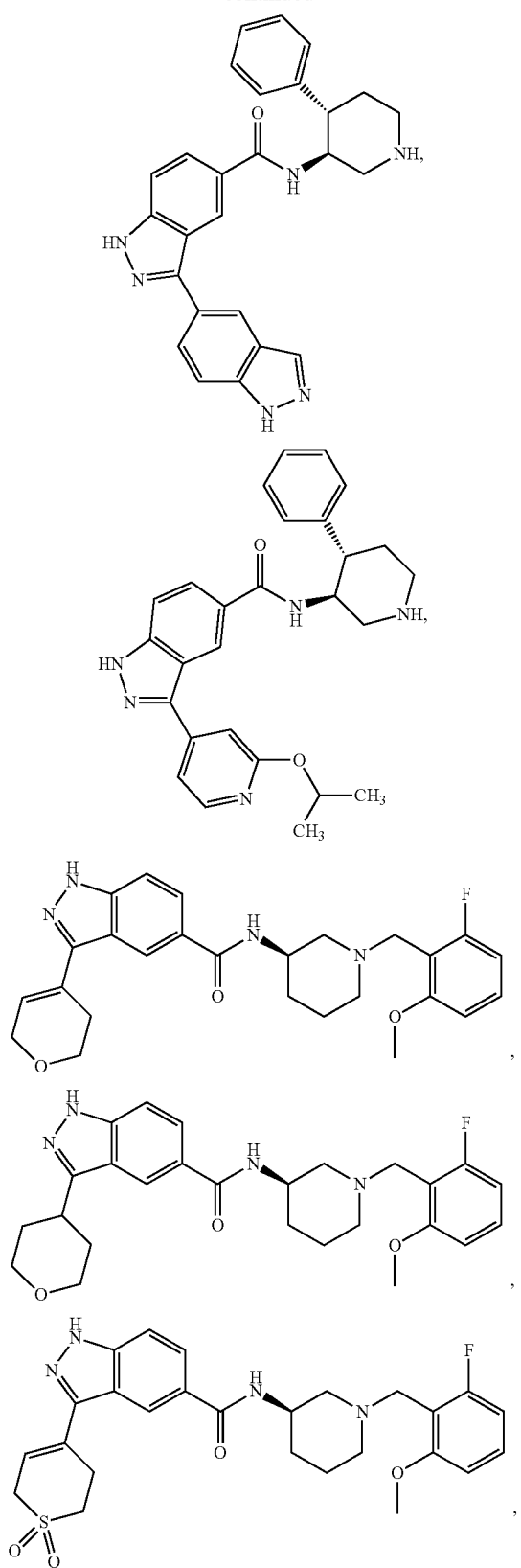
386
-continued
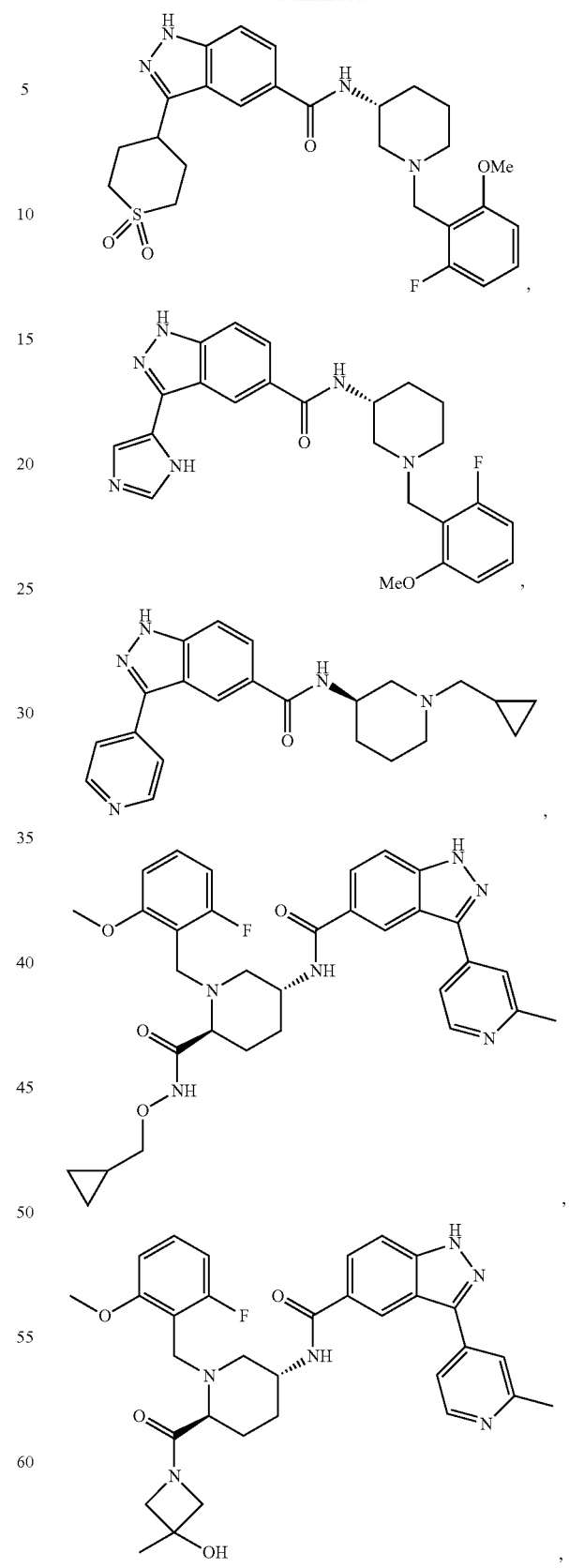

387
-continued
388
-continued
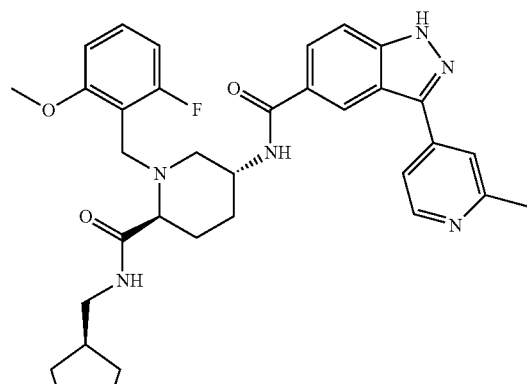
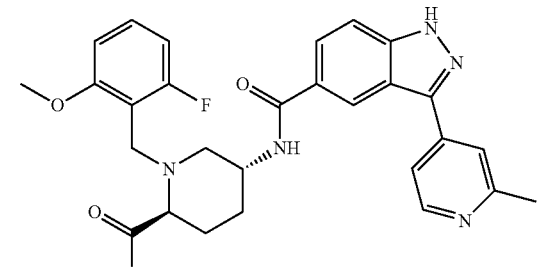

389
-continued
390
-continued
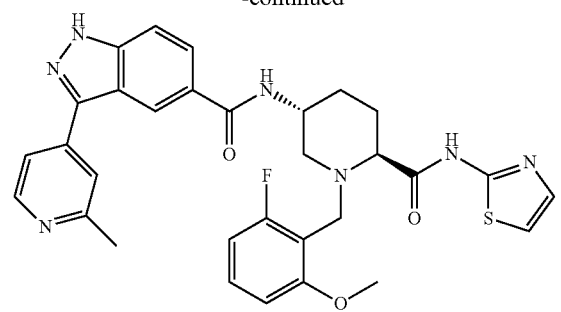
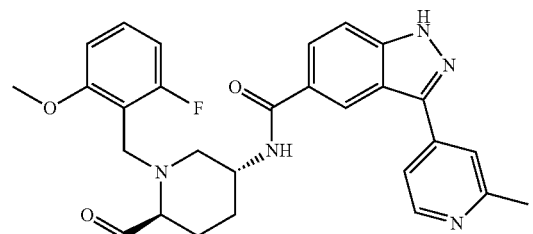

391
-continued
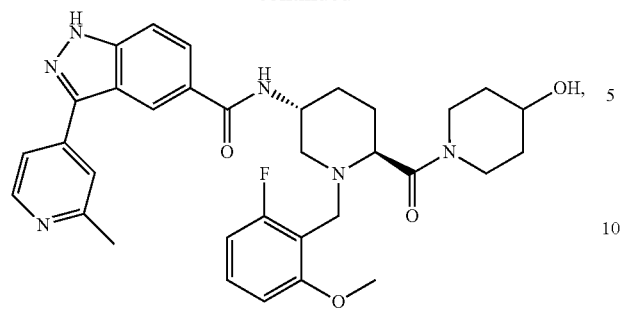
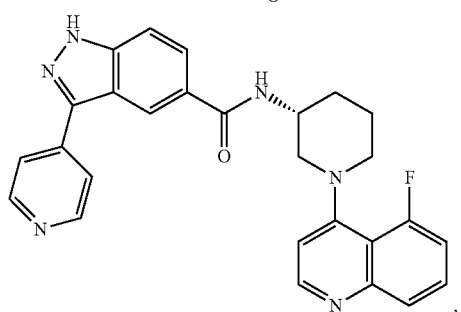
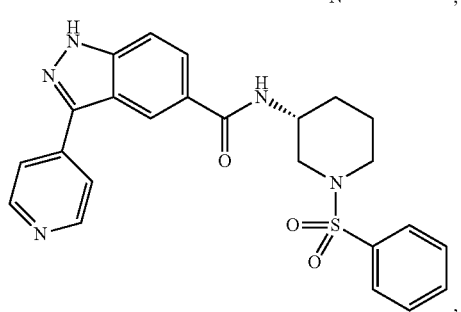
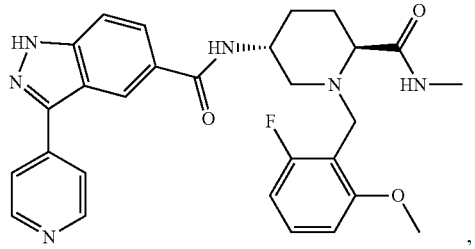
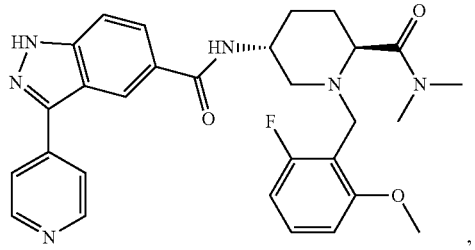
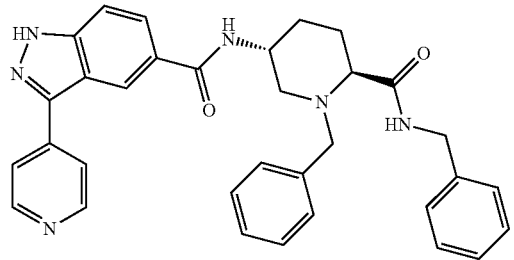
392
-continued
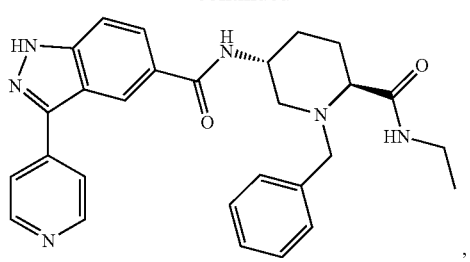
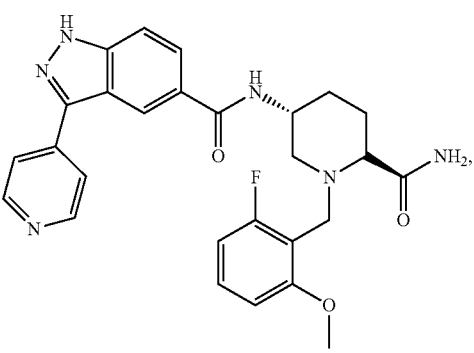
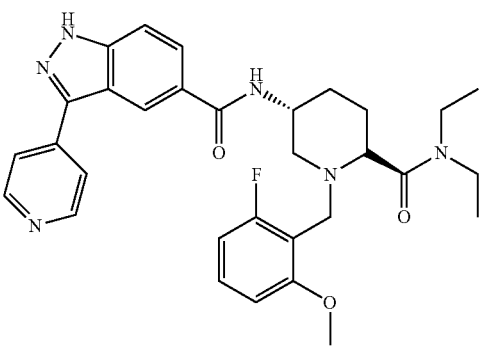
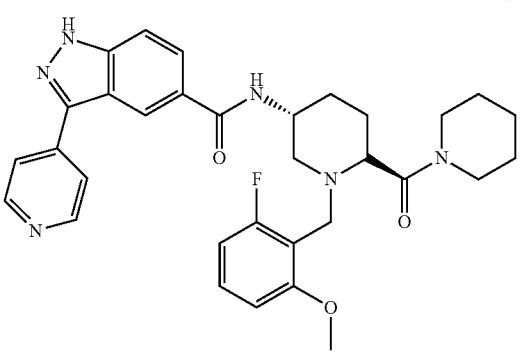
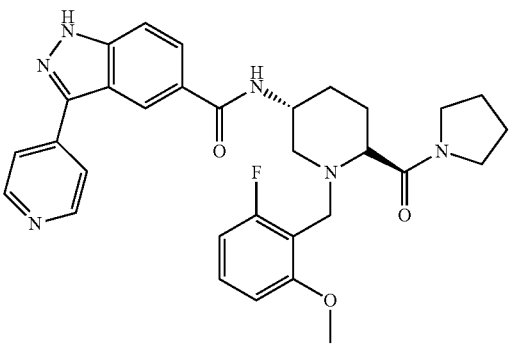

393
-continued
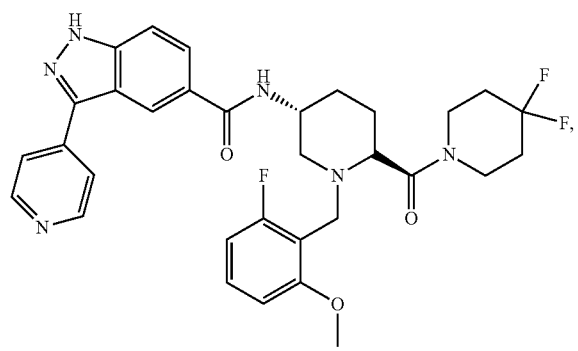
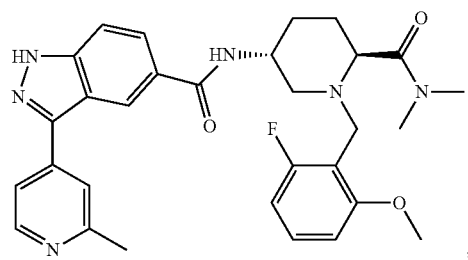
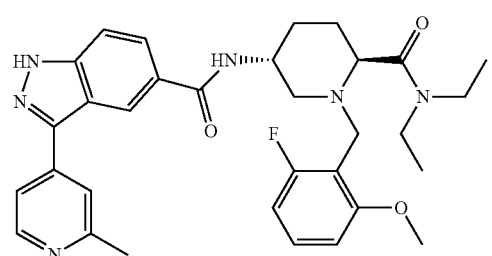
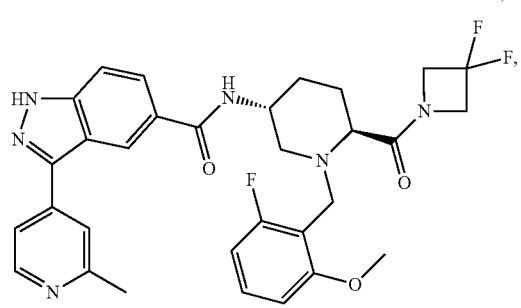
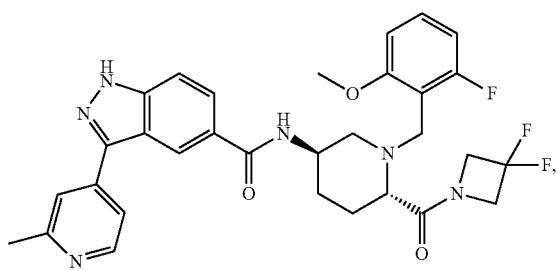
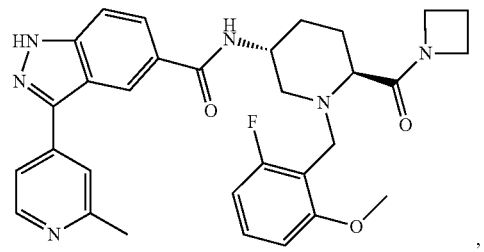
394
-continued
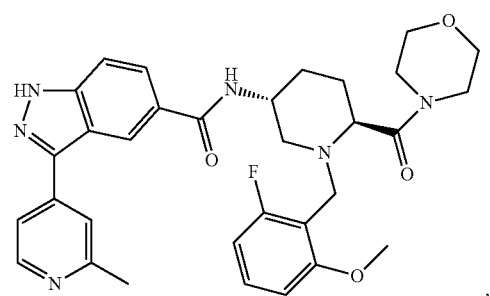
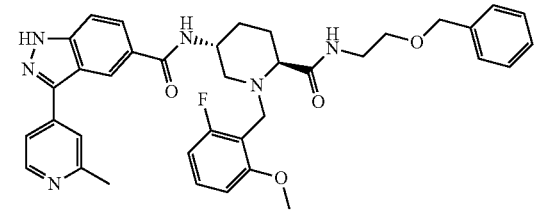
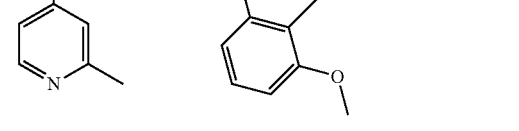
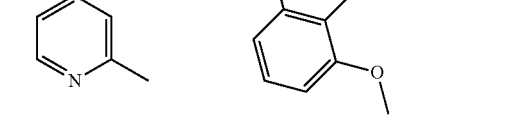
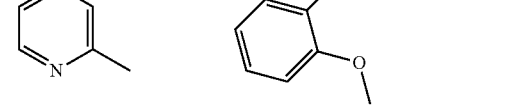
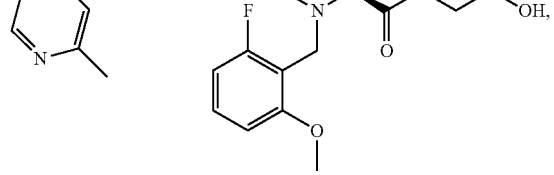

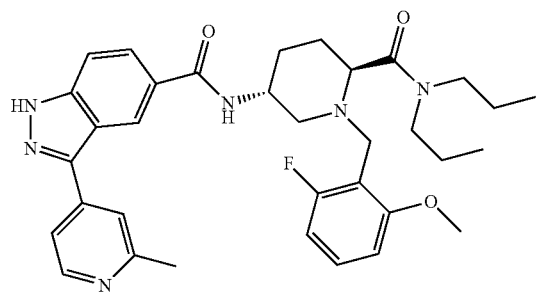
,
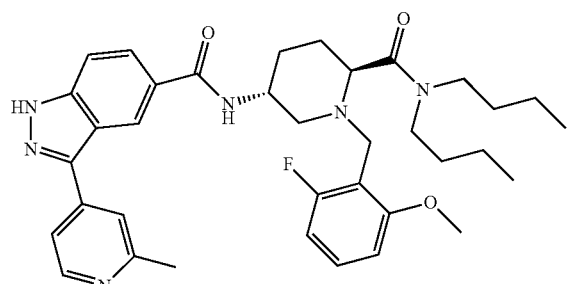
,
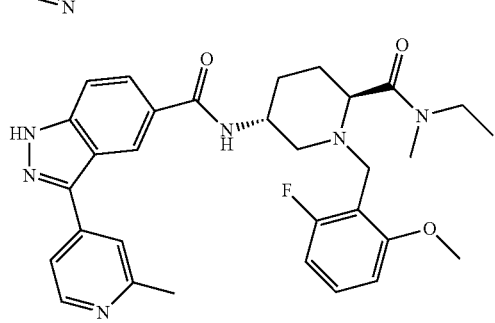
,
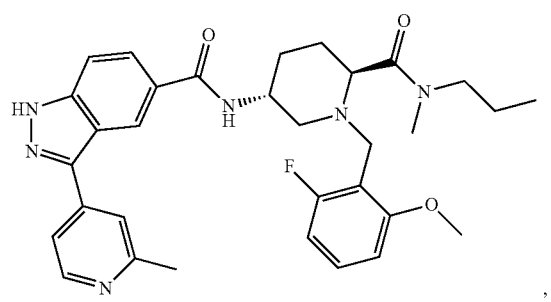
,
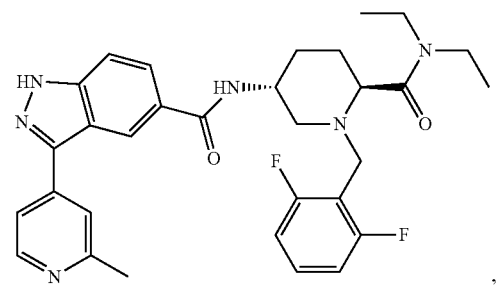
,
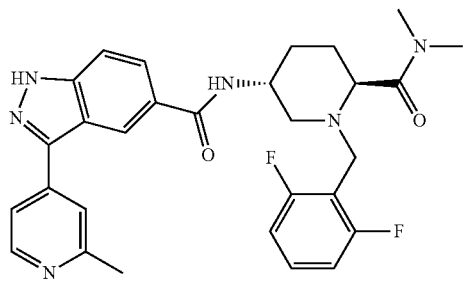
,
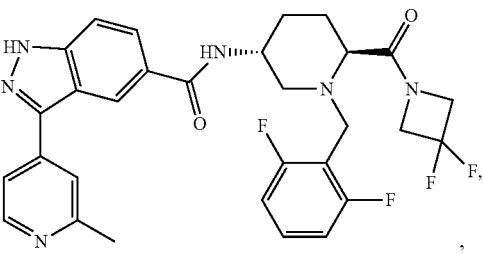
,
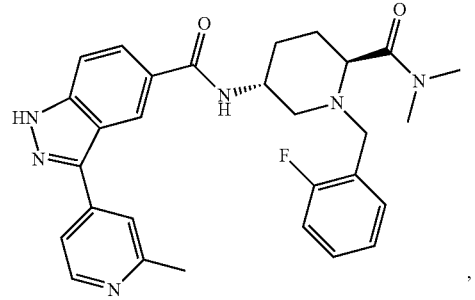
,
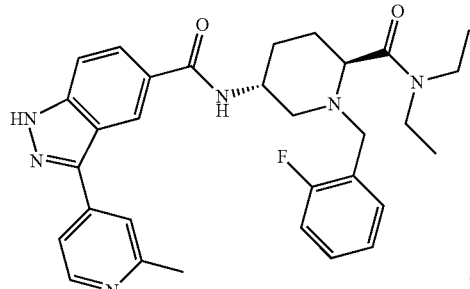
,
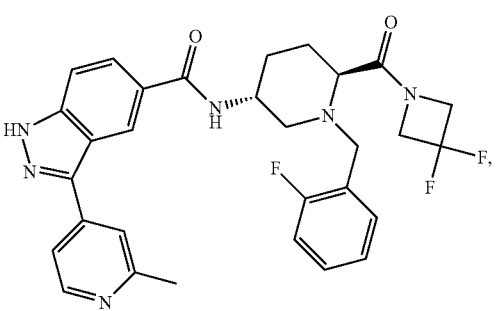
, 397
-continued
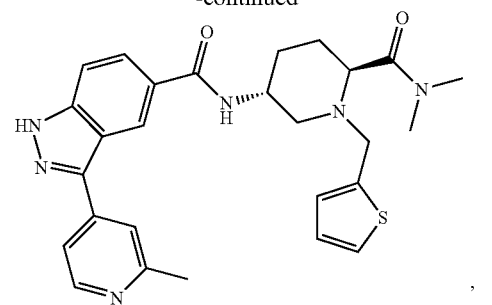
,
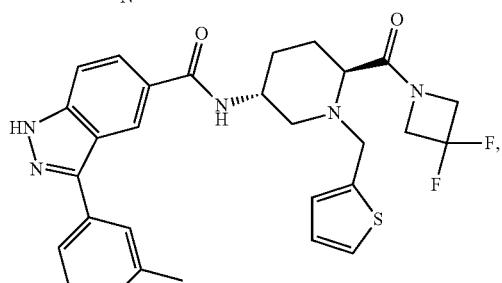
,
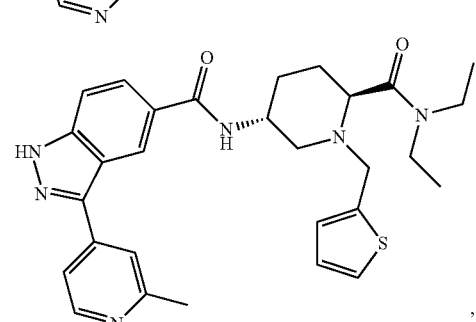
,
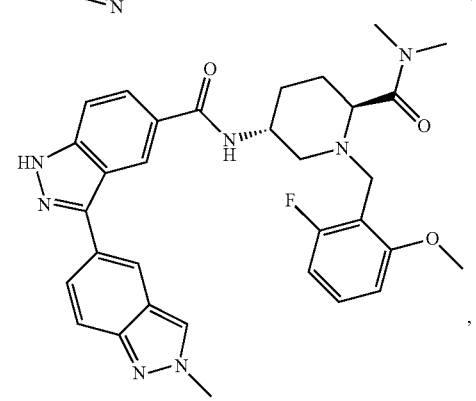
,
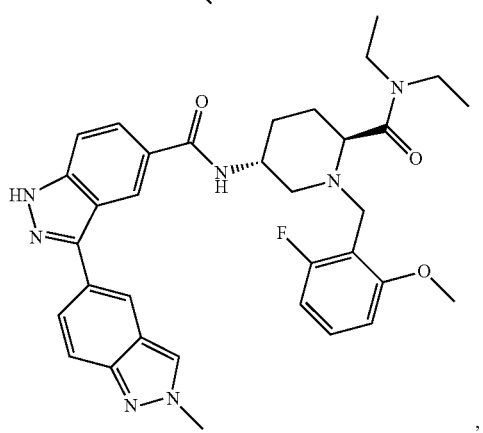
,
398
-continued
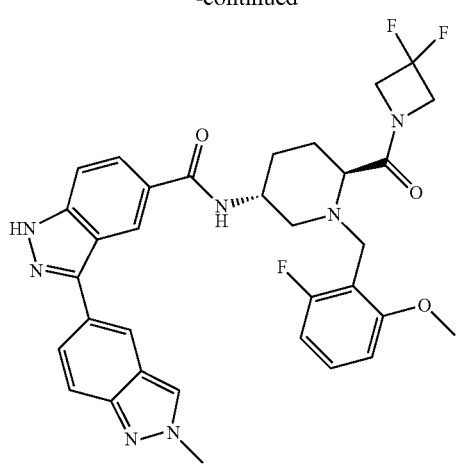
,
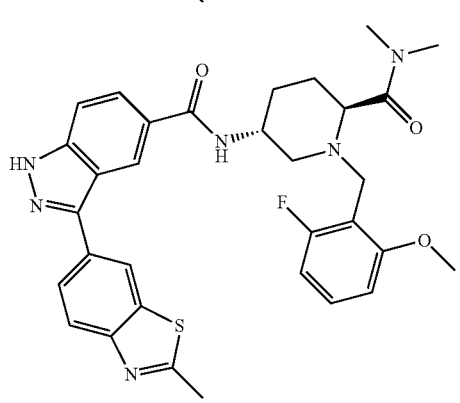
,
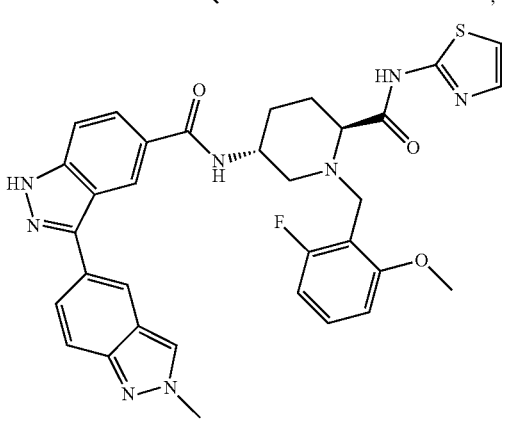
,
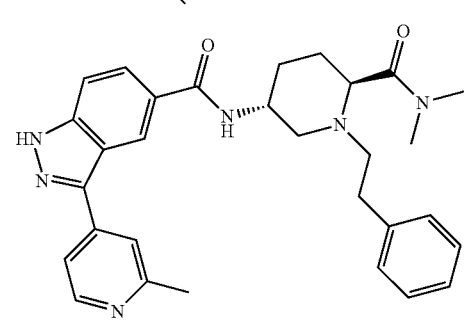
, 399
-continued
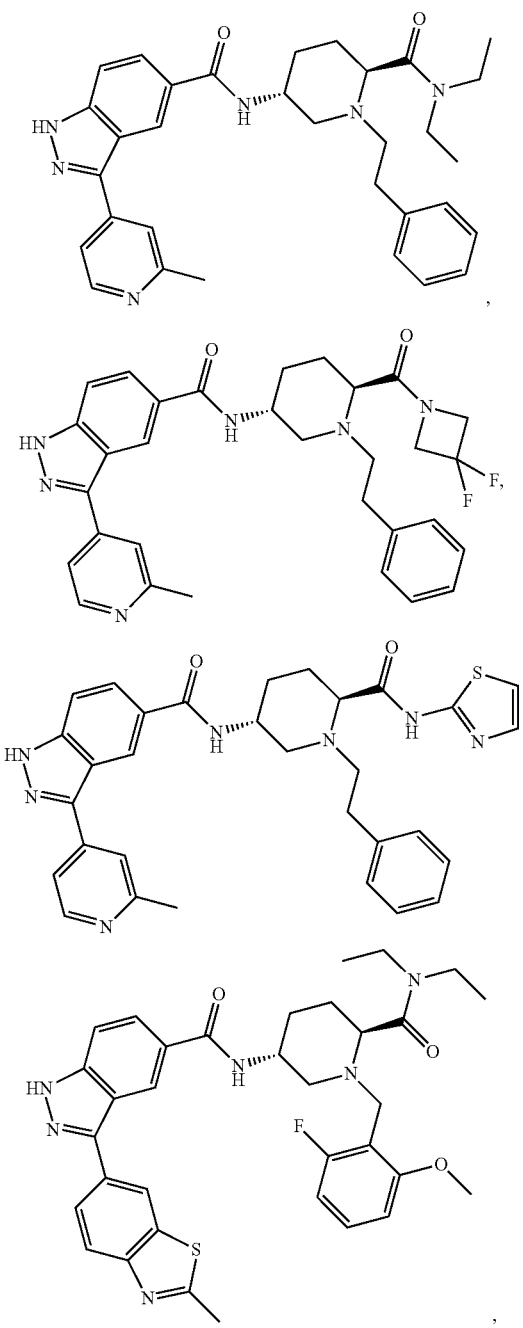
400
-continued
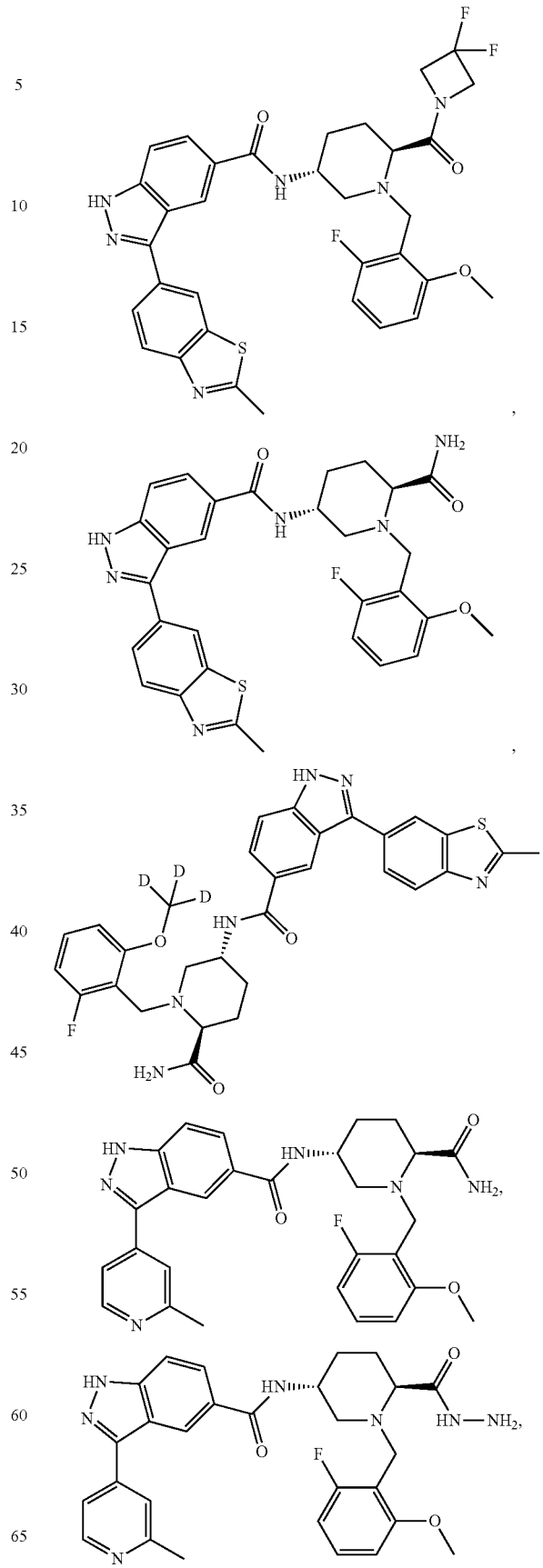

401
-continued
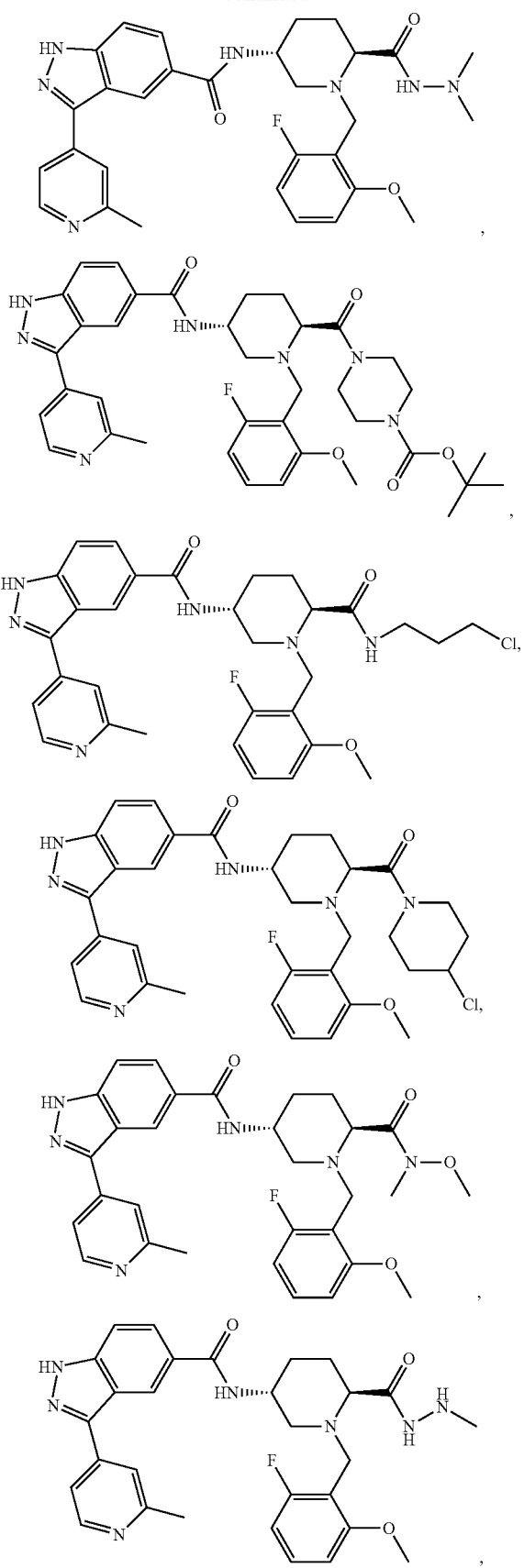
402
-continued
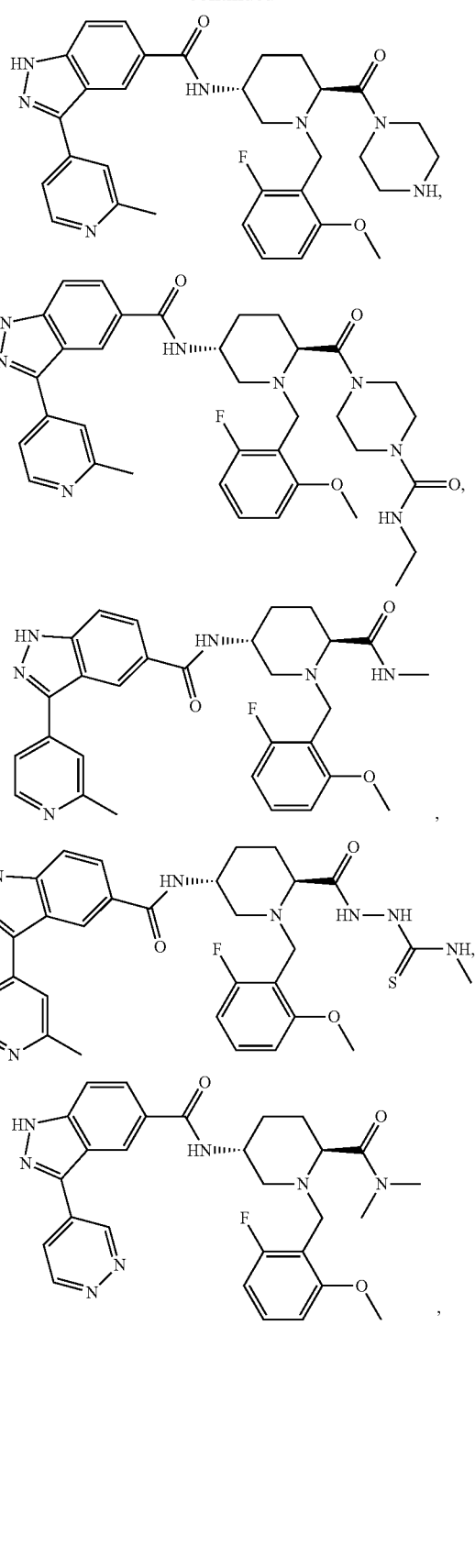

403
-continued
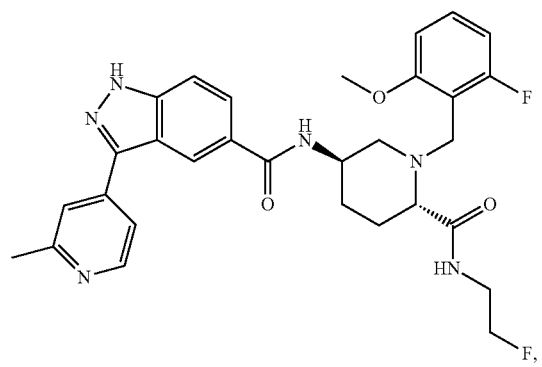
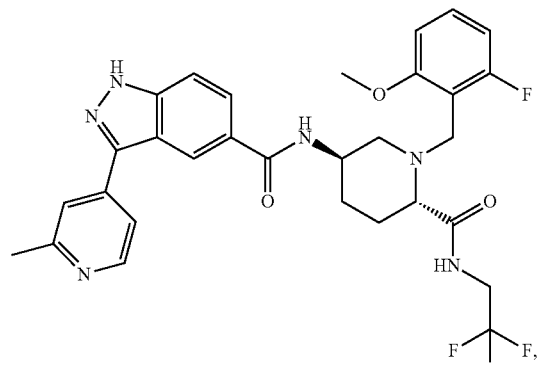
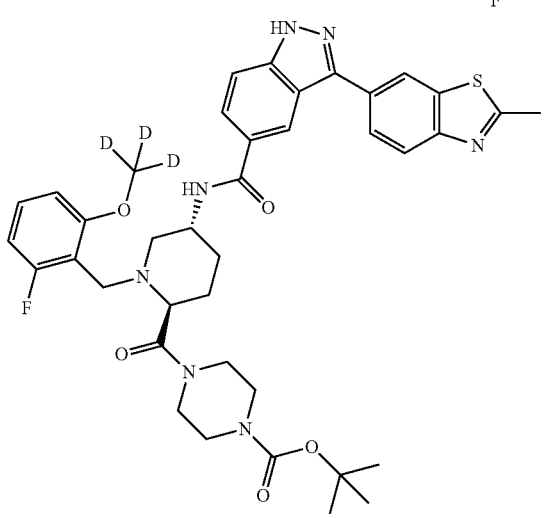
404
-continued
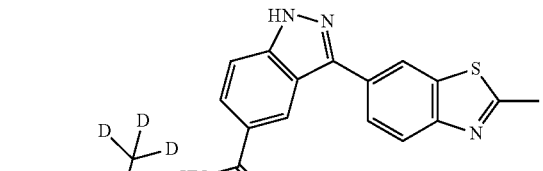
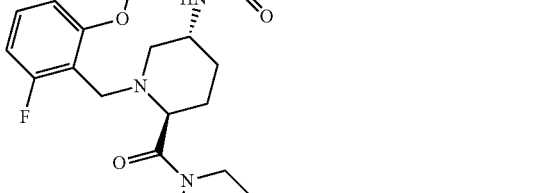
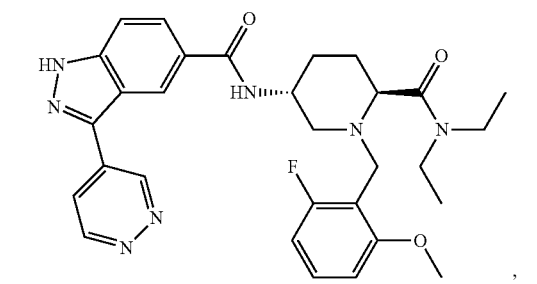
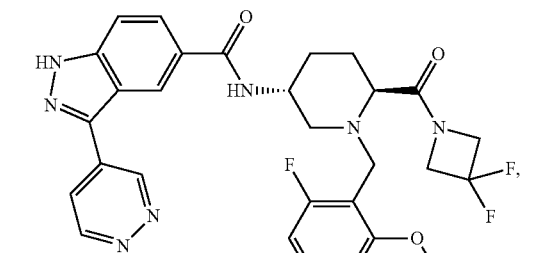
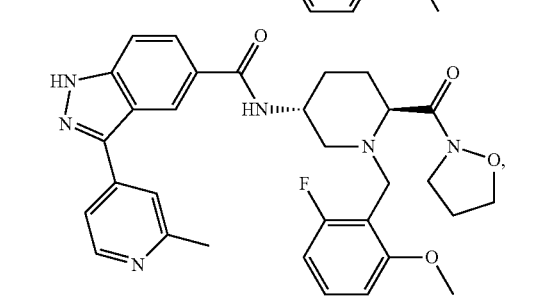
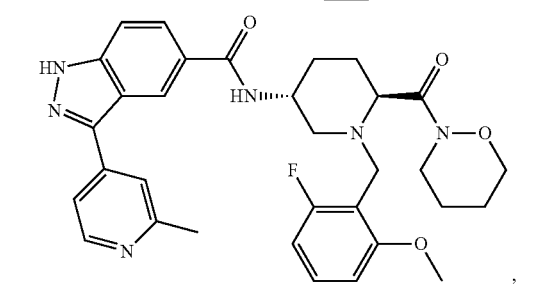

405
-continued
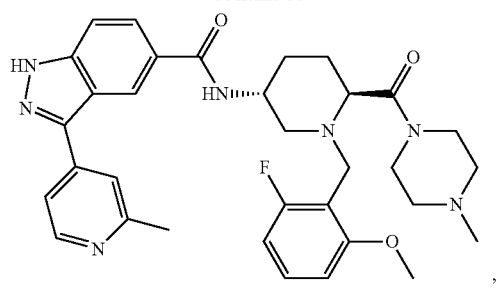
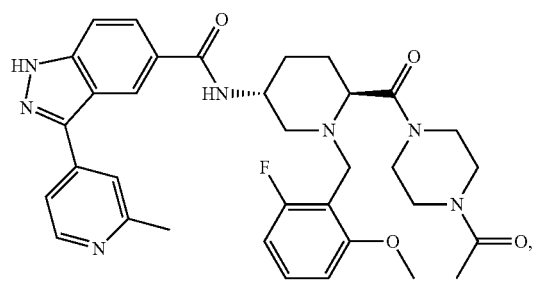
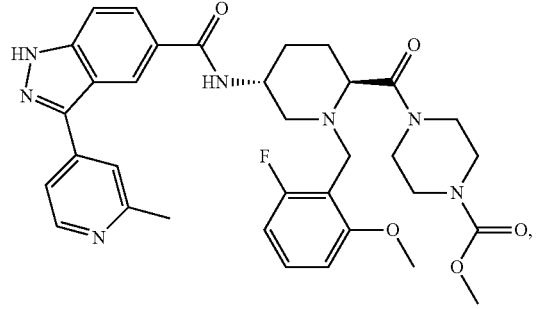
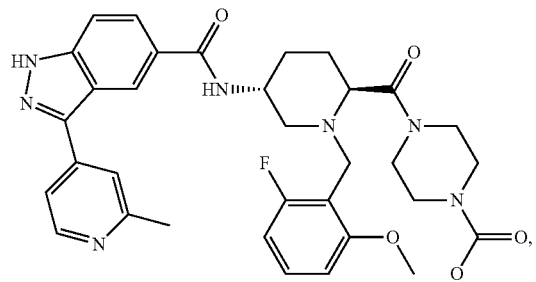
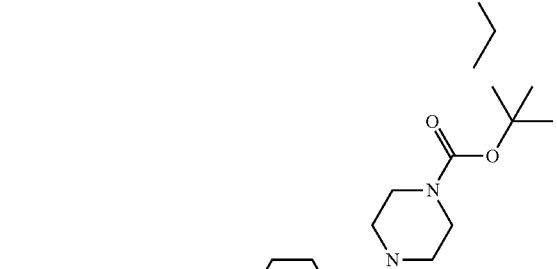
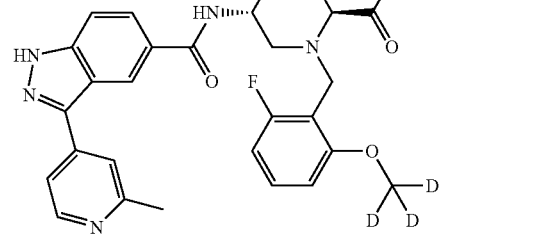
406
-continued
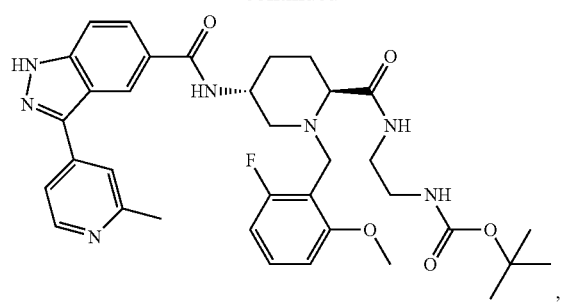
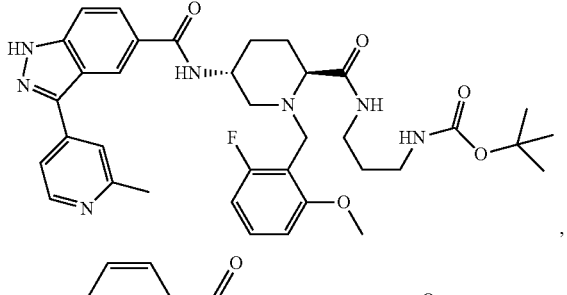
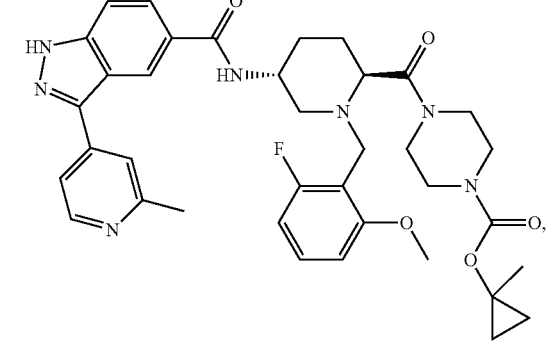
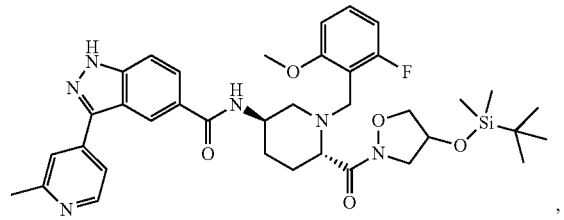
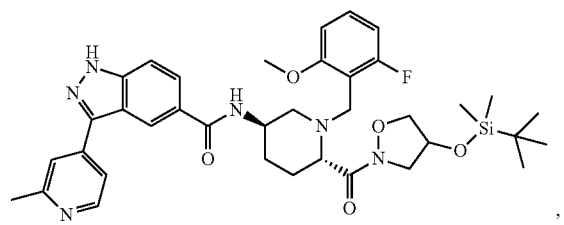
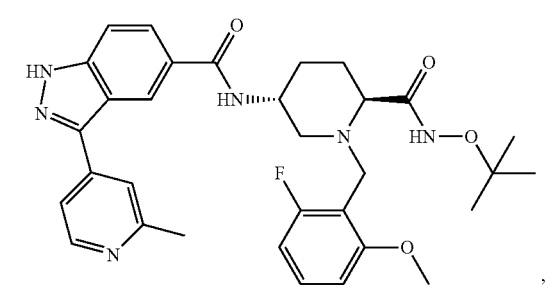

407
-continued
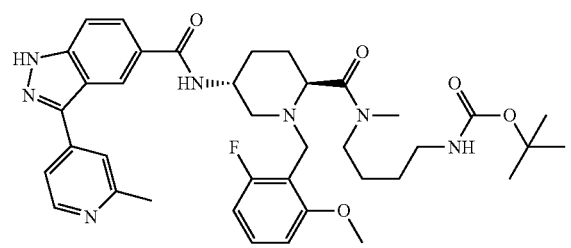
,
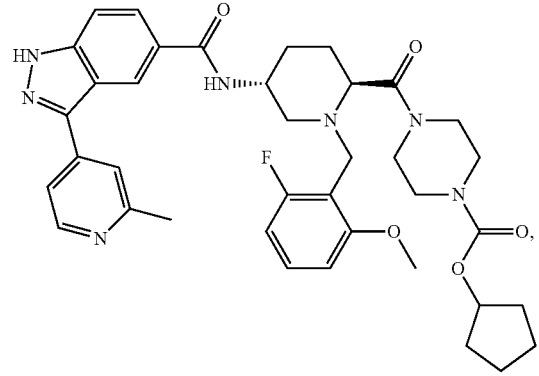
,
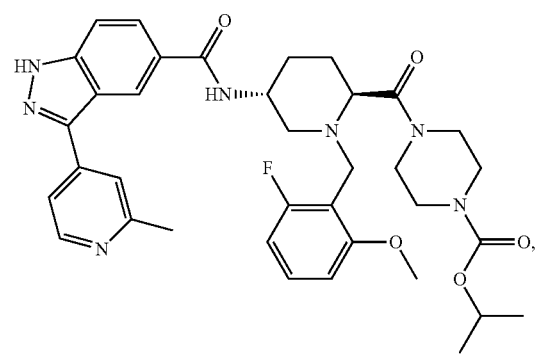
,
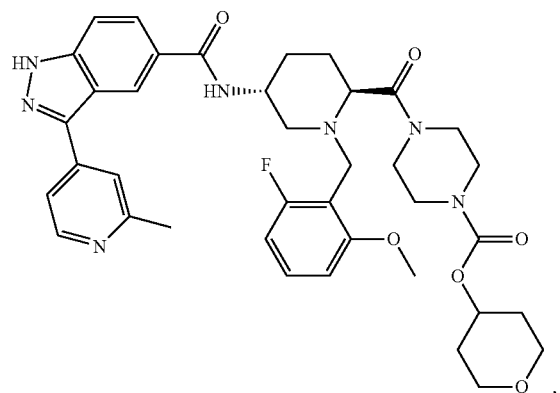
,
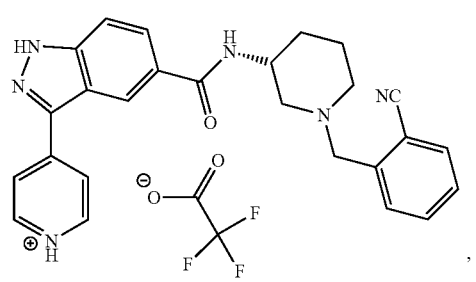
,
408
-continued
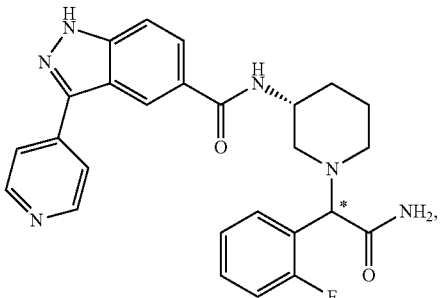
,
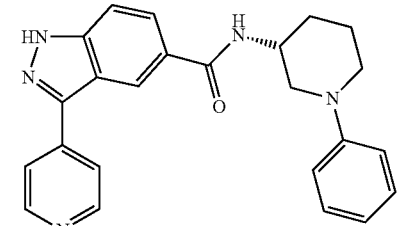
,
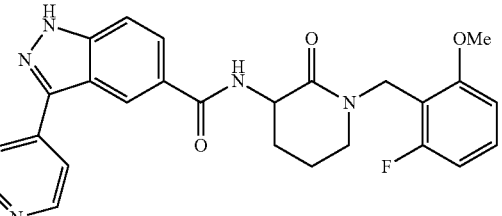
,
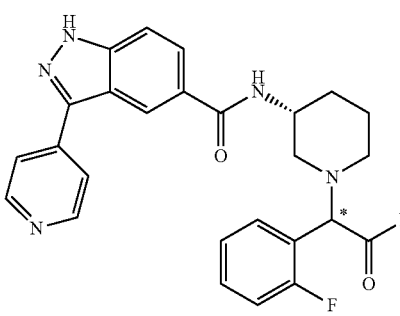
,
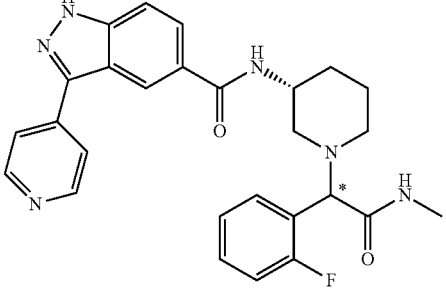
,
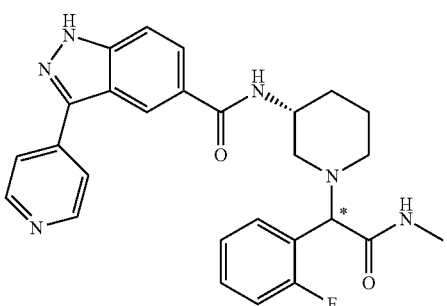
, or a pharmaceutically acceptable salt, solvate or ester thereof.

13. A pharmaceutical composition comprising at least one compound of claim 1, or a pharmaceutically acceptable salt, solvate or ester thereof, and a pharmaceutically acceptable carrier.

14. A compound of claim 1, or a pharmaceutically acceptable salt, thereof, for use in inhibiting ERK.
15. A compound selected from the group consisting of
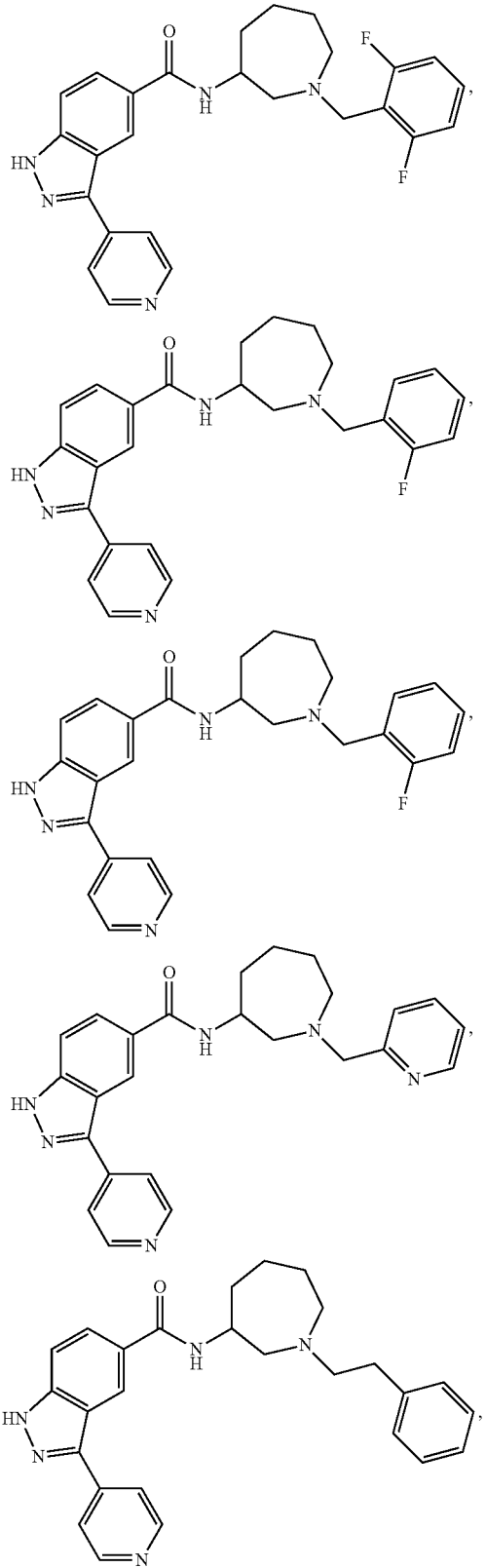
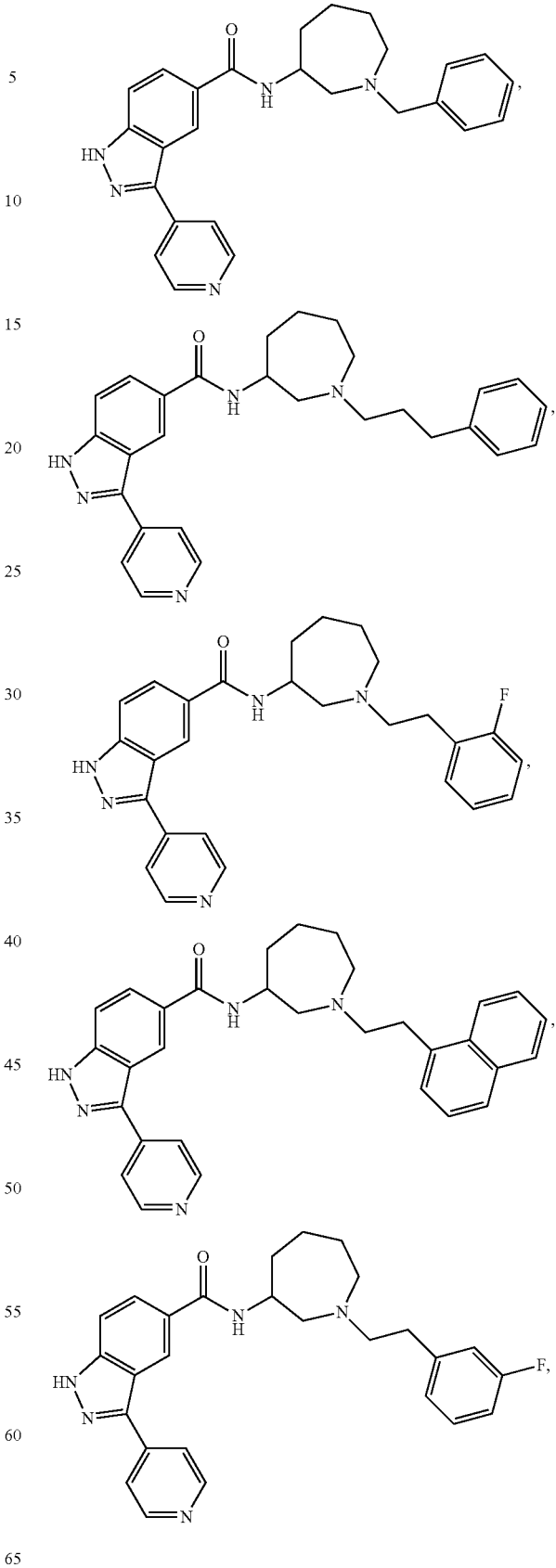

-continued
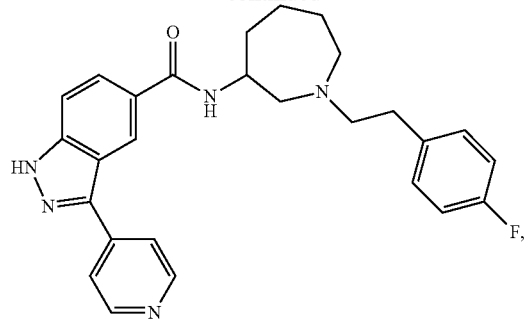
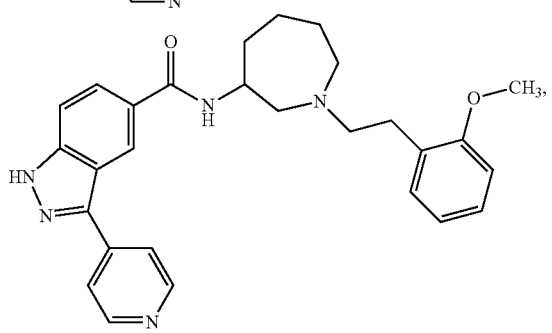
-continued
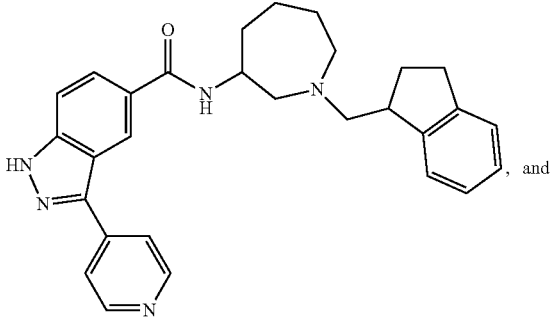, and
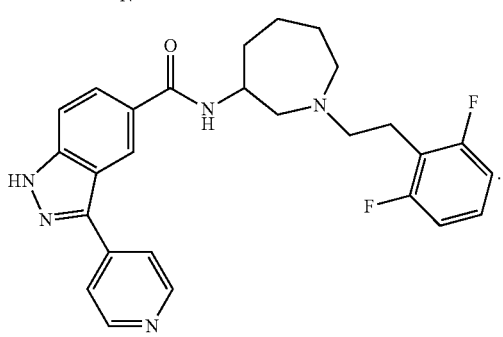.
* * * * *